US008088918B2

(12) United States Patent
Barbeau

(10) Patent No.: US 8,088,918 B2
(45) Date of Patent: Jan. 3, 2012

(54) NONCARDIOTOXIC PHARMACEUTICAL COMPOUNDS

(75) Inventor: Donald L. Barbeau, Evanston, IL (US)

(73) Assignee: Williamsburg Holdings LLC, Evanston, IL (US)

( * ) Notice: Subject to any disclaimer, the term of this patent is extended or adjusted under 35 U.S.C. 154(b) by 1475 days.

(21) Appl. No.: 11/199,866

(22) Filed: Aug. 9, 2005

(65) Prior Publication Data

US 2006/0035863 A1   Feb. 16, 2006

Related U.S. Application Data

(60) Provisional application No. 60/600,699, filed on Aug. 11, 2004, provisional application No. 60/673,545, filed on Apr. 21, 2005.

(51) Int. Cl.
*C07D 491/00* (2006.01)
*C07D 291/08* (2006.01)
*C07D 223/18* (2006.01)

(52) U.S. Cl. ................... 540/557; 540/587; 540/550

(58) Field of Classification Search .............. 540/550, 540/557, 587
See application file for complete search history.

(56) References Cited

U.S. PATENT DOCUMENTS

| | | | |
|---|---|---|---|
| 2,832,786 A * | 4/1958 | Tilford et al. ................ 546/21 |
| 2,994,638 A | 8/1961 | Malz et al. | |
| 3,058,879 A | 10/1962 | Malz et al. | |
| 3,188,309 A | 6/1965 | Mukaiyama et al. | |
| 4,126,442 A | 11/1978 | Shen et al. | |
| 4,493,931 A | 1/1985 | Chekroun et al. | |
| 4,584,132 A | 4/1986 | Albrecht et al. | |
| 5,070,082 A * | 12/1991 | Murdock et al. ............ 514/105 |
| 5,077,283 A * | 12/1991 | Murdock et al. ............ 514/94 |
| 5,116,827 A * | 5/1992 | Murdock et al. ............ 514/82 |
| 5,212,291 A * | 5/1993 | Murdock et al. ............ 536/6.4 |
| 5,334,741 A | 8/1994 | Quin et al. | |
| 5,387,748 A * | 2/1995 | Demuth et al. .......... 514/253.08 |
| 5,512,570 A | 4/1996 | Dorn et al. | |
| 5,631,256 A * | 5/1997 | Demuth et al. .......... 514/253.04 |
| 5,646,163 A * | 7/1997 | Demuth et al. ............ 514/312 |
| 5,672,600 A * | 9/1997 | Demuth et al. ............ 514/224.5 |
| 5,688,955 A * | 11/1997 | Kruse et al. ............ 546/276.4 |
| 5,691,336 A | 11/1997 | Dorn et al. | |
| 5,807,846 A | 9/1998 | Roark et al. | |
| 5,958,905 A | 9/1999 | Chan et al. | |
| 6,521,605 B1 | 2/2003 | Arnold et al. | |
| 6,593,374 B2 | 7/2003 | Pinney et al. | |
| 6,746,794 B2 * | 6/2004 | Mandal et al. ............ 429/62 |
| 6,956,054 B2 * | 10/2005 | Pero et al. ............ 514/419 |
| 7,001,926 B2 | 2/2006 | Pinney et al. | |

FOREIGN PATENT DOCUMENTS

| | | | |
|---|---|---|---|
| EP | 0 671 389 | | 9/1995 |
| ES | 2006099 | * | 4/1999 |
| SU | 1786037 | * | 5/1991 |
| WO | WO 99/02531 | | 1/1999 |
| WO | WO 2006026395 | | 9/2006 |

OTHER PUBLICATIONS

McCarty et al. Journal of Organic Chemistry (1961), 26, 4084.*
Kaszubska et al. Journal of Environmental Science and Health, Part B: Pesticides, Food Contaminants, and Agricultural Wastes (1983), B18(4-5), 515-27.*
Gajda et al. Polish Journal of Chemistry (2000), 74(10), 1385-1387.*
Hemenway et al Journal of organic chemistry (1999) 64(17), 6312-6318.*
Cates et al. Journal of Pharmaceutical sciences, 1966, 55(12), 1400-1405.*
Sakhibullina et al. US Zhurnal Obshchei Khimii (1991), 61(11), 2419-20.*
Basarab et al. Bioorganic & Medicinal Chemistry (2002), 10(12),4143-4154.*
Goument et al. STN Accession No. 1994:244208, Document No. 120:244208, Abstract of Bulletin de la Societe Chimique de France (1993), 130(4),450-8.*
Gazaliev et al. Khimiya Prirodnykh Soedinenii (1989), (4), 584-5.*
Q. Xiao et al., "Facile Synthesis of 3B-Cholesterol H-Phosphonates," Chemistry Letters vol. 32 No. 6 (2003), pp. 522-523.
M.S. Hemenway et al., "Syntheses of New Phosphorus-Containing Azabicycloalkanes and Their Microbial Hydroxylation Using *Beauveria bassiana*," J. Org. Chem. 1999 64, 6312-6318.
Y.W. Wu et al., "Sythesis, In Vitro Anticancer Evaluation, and Interference with Cell Cyle Progression . . . ," Nucl., Nucleos. & Nucl. Acid., 23, 2004, 1797-1811.
M.P. Gamble et al., "A Novel Phosphinamide Catalyst for the Assymetric Reduction of Ketones by Borane," J. Org. Chem. 1998, 63, pp. 6068-6071.
G.S. Basarab et al., "Design of Inhibitors of Scytalone Dehydratase: Probing Interactions with an Asparagine Carboxamide," Bioorganic & Medicinal Chemistry 10 (2002), 4143-54.
Caplus English Abstract, DN 134:28996, T. Gajda et al., See RN #118132-91-5, 2000.
Caplus English Abstract, DN 56:45951, M.G. Campen et al., See RN #95159-07-2, 1961.

(Continued)

*Primary Examiner* — Nizal S Chandrakumar
(74) *Attorney, Agent, or Firm* — Schiff Hardin LLP

(57) ABSTRACT

The present invention relates to novel noncardiotoxic compounds and pharmaceutical compositions useful in the treatment of a variety of disorders including the treatment of depression, allergies, psychoses, cancer and gastrointestinal disorders. In particular, the present invention describes pharmaceutical compositions that mitigate life-threatening arrhythmias such as torsade de pointes. Torsade de pointes is a particular cardiac problem associated with many therapeutic agents and has been implicated as a possible cause of sudden death, particularly in those individuals with a past history of disturbances of cardiac rhythm, myocardial infarction, congenital repolarization abnormalities and cardiac risk factors such as hyperlipidemia and age. This arrhythmia is a variant of paroxysmal ventricular tachycardia associated with a prolonged QTc interval or prominent U waves on the ECG. Torsade de pointes is potentially lethal because it can progress to ventricular fibrillation, life-threatening arrhythmias or precipitate sudden death.

7 Claims, 3 Drawing Sheets

OTHER PUBLICATIONS

Caplus English Abstract, DN 99:207981, J. Kaszubska et al., See RN #87834-89-7, 1983.

Caplus English Abstract, DN 113:40732, L. Molina et al., ES 2006099, 1989.

Lindley A. Cates & Noel M. Ferguson, Phosporus-Nitrogen Compounds V. Some Guanidine and 2-Aminopyrimidine Derivatives, Journal of Pharmaceutical Sciences, vol. 55, No. 9, Sep. 1966, pp. 966-969.

Lindley A. Cates & Ven-Shun Li, Phosphorus-Nitrogen Compounds XXIII: Oncolytic Phosphorylated Imines, Journal of Pharmaceutical Sciences, vol. 71, No. 3, Mar. 1982, pp. 308-311.

Lindley A. Cates & Noel M. Ferguson, Phosphorus-Nitrogen Compounds IV. Some 2-Aminopyridine Derivatives, Journal of Pharmaceutical Sciences, vol. 54, No. 3, Mar. 1965, pp. 465-466.

L. A. Cates, W. H. Lawrence, & R. J. McClain, Phosphorus-Nitrogen Compounds VI: Some Phenethylamine Derivatives, Journal of Pharmaceutical Sciences, vol. 55, No. 12, Dec. 1966, pp. 1400-1405.

Lindley A. Cates, Ven-Shun Li, & Sharathchandra S. Hegde, Phosphorus-Nitrogen Compounds. 31. N-Phosphinylamino-1,2,5,6-tetrahydropyridines: Analgesic Activity and Effect on Blood Glucose, Pharmaceutical Research, vol. 6, No. 8, 1989, pp. 737-739.

Lindley A. Cates, Phosphorus-Nitrogen Compounds. XI. Phosphamidase Studies. I. Unsubstituted Amides, Journal of Medicinal Chemistry, vol. 13, No. 2, 1970, p. 301-302.

Lindley A. Cates, Phosphorus-Nitrogen Compounds. IX. Hydroxylamine Derivatives, Journal of Medicinal Chemistry, vol. 11, No. 2, 1968, pp. 382-383.

L.A. Cates, R.L. Gallio, & M.B. Cramer, Phosphorus-Nitrogen Compounds XV: N-1-Adamantylphosphoramidic Dichloride and Dimethyl and Diphenyl N-1-Adamantylphosphoramidate, Journal of Pharmaceutical Sciences, vol. 62, No. 10, Oct. 1973, pp. 1719-1720.

Lindley A. Cates, Phosphorus-Nitrogen Compounds. 12. Phosphamidase Studies. 2. N-Alkylphosphoramidic Acids, Journal of Medicinal Chemistry, 1971, vol. 14, No. 7, pp. 647-649.

Keiko Kitagishi & Keitaro Hiromi, Binding Between Thermolysin and its Specific Inhibitor, N-Phosphoryl-L-Leucyl-L-Tryptophan (PLT), J. Biochem., vol. 99, No. 1., 1986, pp. 191-197.

M.T. Garcia-Lopez, R. Gonzalez Muniz, R. Herranz, H. Bravo, J.R. Naranjo, & J. Del Rio, Synthesis and Analgesic Properties of N-Phosphorylated Derivatives of Phe-Ala and Phe-Gly, Int. J. Peptide Protein Res. vol. 26, 1985, pp. 174-178.

Hugo Garrido-Hernandez, Kyung D. Moon, Robert L. Geahlen, & Richard F. Borch, Design and Synthesis of Phosphotyrosine Peptidomimetic Prodrugs, Journal of Medicinal Chemistry, 2006, vol. 49, No. 11, pp. 3368-3376.

Jeffrey J. Hale, et al., Phosphorylated Morpholine Acetal Human Neurokinin-1 Receptor Antagonists as Water-Soluble Prodrugs, Journal of Medicinal Chemistry, 2000, vol. 43, No. 6, pp. 1234-1241.

Su-Er W. Huskey, et al., Substance P Receptor Antagonist I: Conversion of Phosphoramidate Prodrug After I.V. Administration to Rats and Dogs, Drug Metabolism and Disposition, vol. 27, No. 11, 1999, pp. 1367-1373.

H. J. Lee, W. S. Fillers, & M.R. Iyengar, Phosphocreatine, an Intracellular High-Energy Compound, Is Found in the Extracellular Fluid of the Seminal Vesicles in Mice and Rats, Proc. Natl. Acad. Sci., vol. 85, Oct. 1988, pp. 7265-7269.

K.C. Murdock, et al., N-Phosphoryl Derivatives of Bisantrene. Antitumor Prodrugs with Enhanced Solubility and Reduced Potential for Toxicity, Journal of Medicinal Chemistry, 1993, vol. 36, No. 15, pp. 2098-2101.

Nguyen-Hai Nam, et al., Water Soluble Prodrugs of the Antitumor Agent 3-[(3-Amino-4-methoxy) phenyl]-2-(3,4,5,-trimethoxyphenypcyclopent-2-ene-1-one, Bioorganic & Medicinal Chemistry, vol. 11, 2003, pp. 1021-1029.

Dasu Ramaswami & Ernst R. Kirch, Anticonvulsant and Growth Inhibitory Effects of Some Organophosphorus Compounds, Journal of the American Pharmaceutical Association, vol. XLII, No. 8, Aug. 1953, pp. 495-497.

F.D. Tattersall, et al., The Novel NK1 Receptor Antagonist MK-0869 (L-754,030) and its Water Soluble Phosphoryl Prodrug, L-758,298, Inhibit Acute and Delayed Cisplatin-Induced Emesis in Ferrets, Neuropharmacology, vol. 39, 2000, pp. 652-663.

Victor D. Warner, Dale B. Mirth, & Adrienne S. Dey, Synthesis of Diethyl N-Dodecylphosphoramidate Analogs as Potential Inhibitors of Dental Plaque, Journal of Medicinal Chemistry, vol. 16, No. 10, 1973, pp. 1185-1186.

Chemical Abstract, CAS registry No. 22700-45-4.
Chemical Abstract, CAS registry No. 22767-82-4.
Chemical Abstract, CAS registry No. 22846-97-5.
Chemical Abstract, CAS registry No. 25627-01-4.
Chemical Abstract, CAS registry No. 26245-77-2.
Chemical Abstract, CAS registry No. 3848-51-9.
Chemical Abstract, CAS registry No. 4972-36-5.
Chemical Abstract, CAS registry No. 6345-18-2.
Chemical Abstract, CAS registry No. 90008-29-0.
Chemical Abstract, CAS registry No. 51287-66-2.
Chemical Abstract, CAS registry No. 5786-71-0.
Chemical Abstract, CAS registry No. 1892-18-8.
Chemical Abstract, CAS registry No. 52670-78-7.
PubChem, Compound Identification No. 267208.
PubChem, Compound Identification No. 2302418.
PubChem, Compound Identification No. 263590.
PubChem, Compound Identification No. 2272818.
PubChem, Compound Identification No. 2305281.
PubChem, Compound Identification No. 605821.

G. Halliwell et al., A Comparison of Imipramine, Chlorpromazine and Related Drugs in Various Tests Involving Autonomic Functions and Antagonism of Reserpine, 23 Brit. J. Pharmacol. 330, 330 (1964).

John Hinton, Psychotropic Drugs, 44 Postgrad. Med. J. 286, 292 (1968).

Julian R.A. Wooltorton & Alistair Mathie, Block of Potassium Currents in Rat Isolated Sympathetic Neurones by Tricyclic Antidepressants and Structurally Related Compounds, 110 Br. J. Pharmacol. 1126 (1993).

* cited by examiner

NONCARDIOTOXIC PHARMACEUTICAL COMPOUNDS

CROSS-REFERENCE TO RELATED APPLICATIONS

This patent application claims the benefit of prior filed copending provisional application Nos. 60/600,699 filed Aug. 11, 2004, and 60/673,545 filed Apr. 21, 2005 each titled Noncardiotoxic Pharmaceutical Compositions, which are hereby incorporated by reference in their entirety.

BACKGROUND OF THE INVENTION

The present invention relates to novel noncardiotoxic compounds and pharmaceutical compositions useful in the treatment of a variety of disorders including the treatment of depression, allergies, psychoses, infection, cancer and gastrointestinal disorders. The compounds and pharmaceutical compositions of the present invention are useful in the prevention and/or reduction of severe cardiac conductance and cardiac rhythm disturbances and the cardiac arrhythmias such as torsade de pointes that lead to sudden cardiac death.

The annual incidence of sudden cardiac death is estimated to be greater than 400,000 persons in the United States alone, and accounts for approximately 50% of all deaths from cardiovascular disease (Chugh et al. Journal American College of Cardiology 44: 1268-1275 (2004); U.S. Centers for Disease Control; Chugh et al. Circulation 102:649-654 (2000)). Although the occurrence of sudden cardiac death in the general population is high, the incidence (as a percent of the total) in patients over 64 years of age and in patients with cardiovascular disease is considerably higher (Huikuri et al. New England Journal of Medicine 345(2):1473-1482 (2001); Morbidity and Mortality: 2004 Chart Book on Cardiovascular, Lung and Blood Diseases, National Institutes of Health (May 2004); and Myerburg et al. Annals of Internal Medicine 119:1187-1197 (1993)). According to the World Health Organization, the non-cardiovascular drugs most commonly associated with torsade de pointes between 1983 and 1999 are gastrointestinal, antiinfective, antidepressant, antihistaminic and antipsychotic agents. Moreover, antipsychotic, antidepressant and cardiovascular drugs account for over 40% of fatalities for all pharmaceutical agents (The 2002 Annual Report of the American Association of Poison Control Centers Toxic Exposure Surveillance System (AAPCC-TESS)).

It has been reported that the incidence of sudden cardiac death is clearly associated with increasing amounts of antidepressant and antipsychotic drugs at therapeutically relevant doses (Ray, A R et al. Clinical Pharmacology and Therapeutics 75(3): 234-241 (2004); Ray, A R et al. Archives General Psychiatry 58: 1162-1167 (2001)). Although low therapeutic doses of these types of drugs (<100 mg daily) are not associated with sudden cardiac death, moderate and high therapeutic doses of these drugs ($\geq$100 mg daily) are clearly associated with sudden cardiac death. Not only is the incidence of sudden death in patients with cardiovascular disease and treated with these drugs considerably higher than patients without cardiovascular disease, the incidence of sudden death in these patients is clearly correlated with the severity of cardiovascular disease (Ray, A R et al. Archives General Psychiatry 58: 1162-1167 (2001)).

Antipsychotics primarily antagonize central dopaminergic $D_2$ receptor neurotransmission, although they also have antagonist effects at muscarinic, serotonergic, $\alpha_1$-adrenergic, and $H_1$-histaminergic receptors. Because antipsychotics are also are used as sedatives, as antiemetics, to control hiccups, to treat migraine headaches, and as antidotes for drug-induced psychosis, the adverse effects of antipsychotics are not confined to psychiatric patients. Antipsychotics are capable of causing orthostatic and severe hypotension, as well as prolongation of the QTc interval and QRS which can result in arrhythmias. Antipsychotics account for about 18 % of moderate (pronounced) toxicity, over 20% of life-threatening toxicity and 17% of the fatalities of all pharmaceuticals.

Tricyclic antidepressants cause the overwhelming majority of antidepressant poisoning in the United States resulting in morbidity and mortality; the most severe toxicity occurs in the cardiovascular system. Antidepressants account for about 15 % of moderate (pronounced) toxicity and 18% of life-threatening toxicity of the fatalities of all pharmaceuticals.

Antidepressants affect the prolongation of the QTc interval causing cardiotoxicity that result from direct myocardial depression, cardiac conduction disturbances, effects on peripheral vasomotor tone, and changes in the autonomic nervous system. The interactions of tricyclic antidepressants with fast sodium channels in cardiac tissue results in slowed cardiac conduction (e.g. prolonged QRS on the ECG), impaired cardiac contractility and possible ventricular dysrhythmias and inhibition of repolarization in His-Purkinje myocytes (e.g. prolonged QTc on the ECG).

Torsade de pointes is a particular cardiac problem associated with many therapeutic agents and has been implicated as a possible cause of sudden death, particularly in those individuals with a past history of disturbances of cardiac rhythm, myocardial infarction, congenital repolarization abnormalities and cardiac risk factors such as hyperlipidemia and age. This arrhythmia is a variant of paroxysmal ventricular tachycardia associated with a prolonged QTc interval or prominent U waves on the ECG. Although torsade de pointes might remit spontaneously, it is potentially lethal because it can progress to ventricular fibrillation, life-threatening arrhythmias or precipitate sudden death.

Drug-induced QTc interval prolongation may be clinically important even if the mean increase is not very large. For example, the drug terodiline was withdrawn after causing QTc interval prolongation, torsade de pointes, and sudden death. In healthy volunteers, therapeutic plasma concentrations of terodiline are associated with increases in mean QTc of only 23 ms, which are similar to the increases associated with quinidine and prenylamine. Nevertheless, much larger increases occurred in a minority of patients who developed arrhythmias. These included those predisposed by existing problems such as heart disease and congenital repolarization abnormalities. Thus, benign QTc interval prolongation in one subject may indicate that another more susceptible patient might develop extreme QTc interval prolongation and arrhythmias with the same drug at the same dose. Furthermore, small increases in QTc interval might increase the risk of ventricular fibrillation/torsade de pointes over a large population. The number of excess cases of sudden death in the large numbers of patients with minor QTc interval prolongation might actually exceed those in the small numbers of patients with extreme QTc interval prolongation. Nevertheless, the potential of a drug to cause QTc interval prolongation is currently believed to be the lower threshold of determining the cardiotoxicity of a therapeutic drug.

To date, the understanding of QTc interval prolongation has focused on defective repolarization of the heart through blockade of $K^+$ channels, either alone or in combination with $Na^+$ channel modulation. Prevailing theories also suggest that the arrhythmogenic potential of drugs is based on elevated plasma levels of parent drug that are not metabolized. Despite attempts to correlate the blockade of human cardiac $K^+$ channels, such as the Herg channel, with torsade de pointes and sudden cardiac death, very little evidence exists to support this correlation. In fact, a number of severely cardiotoxic drugs that have been withdrawn from the market or denied approval by the FDA have insignificant effects on the Herg channel.

Although data has existed for decades that demonstrates adverse conductance changes and arrhythmias in patients having higher than normal plasma concentrations of drug metabolites, the cardiotoxic effects of these metabolites have received relatively little attention. These observed adverse cardiac conductance changes reflect significant changes in cardiac depolarization (QRS interval prolongation and dispersion) and atrial block (PR interval prolongation) that were correlated with elevated plasma levels of hydroxylated drug metabolites in clinical studies (Kutcher S P et al. British Journal of Psychiatry 148: 676-679 (1986); Stern S L et al. Journal of Clinical Pharmacology 11: 93-98 (1991); Vozeh S et al. American Journal of Cardiology 59: 681-684 (1987); Vozeh S et al. Clinical Pharmacology and Therapeutics 37:575-581 (1985); Drayer D E et al. Clinical Pharmacology and Therapeutics 24: 31-39 (1978)); in isolated perfused heart studies (Uematsu T et al. Archives of International Pharmacodynamics 297: 29-38 (1989); Uematsu T. et al. Journal of Pharmacological Methods 18: 179-185 (1987); and in animal studies (Pollock B G Ph.D. Dissertation University of Pittsburgh 1987; Pollack B G and Perel J M Psychopharmacology 109: 57-62 (1992); Jandhyala H S et al. European Journal of Pharmacology 42: 403-410 (1977)). Hydroxylated drug metabolites have also been reported to be responsible for severe cardiotoxic effects in vitro (Chem. Res. Toxicology (17: 623-632 (2004)).

A considerable number of cardiovascular and noncardiovascular therapeutic agents rely on secondary and tertiary amine structural motifs in their chemical structure that are responsible for their pharmacological activity. Many cardiovascular drugs, including antiarrhythmics, calcium channel antagonists, adrenergics and P-blockers contain essential secondary and tertiary amines in their chemical structure. Entire therapeutic classes of non-cardiovascular drugs, including antidepressants, antihistamines and antipsychotics rely on the secondary and tertiary amine functionality for their primary activity. Others, such as gastrointestinal and antiinfective drugs do not necessarily rely on the secondary and tertiary amine group for their primary activity; but, include this structural motif as part of their chemical structure. Cardiotoxicity associated with the therapeutic use of secondary and tertiary amine-containing drugs is reflected in a variety of cardiac disturbances, including notable changes in ECG, polymorphic ventricular tachycardia, negative inotropism, drops in blood pressure, orthostatic hypotension and depressed cardiac contractility resulting in acute cardiac arrest.

Serious cardiac arrhythmias (both fatal and non-fatal) including tachycardia, ventricular fibrillation, torsade de pointes, and QTc interval prolongation have been reported in patients taking individual secondary and tertiary amine-containing drugs that are oxidized by cytochrome P450 2D6 or combinations of secondary and tertiary amine-containing drugs that inhibit cytochrome P450 3A4. Drugs known to inhibit metabolism of secondary and tertiary amine-containing drugs by cytochrome P450 3A4 include, inter alia, ketoconazole, itraconazole, micoconazole, troleandomycin, erythromycin, fluconazole and clarithromycin. It is generally believed that inhibition of a drug's metabolism by cytochrome P450 3A4 increases the plasma concentration of the parent amine-containing drug to toxic levels; however, this view has not been supported by rigorous examination and discrimination between plasma levels of the parent drugs and their metabolites. An alternate explanation is that inhibition of cytochrome P450 3A4 by inhibitors administered concomitantly "switches" the metabolism of the parent compound from one involving both cytochrome P450 3A4 and cytochrome P450 2D6 to the metabolism of the parent drug primarily by cytochrome P450 2D6.

Cisapride (Propulsid®), shown below, was commonly used to treat nocturnal heartburn as well as a variety of other gastrointestinal disorders:

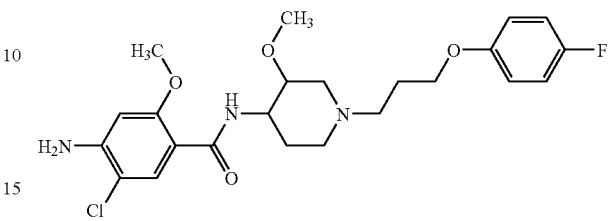

Cisapride (Propulsid®) was recently removed from the market by the FDA because of the QTc interval prolongation and life-threatening ventricular arrhythmias such as torsade de pointes which produced sudden cardiac death. These cardiotoxic effects are believed to be due to cardiac conduction delays such as the specific and potent blockade of human cardiac K⁺ channels, particularly the HERG channels. The specific, high affinity block of the human cardiac K⁺ channel HERG by cisapride ($IC_{50}$ of 0.045 µM) is similar to that observed for the class III antiarrhythmic agent dofetilide ($IC_{50}$ of 0.010 µM) and the nonsedating antihistamines astemizole ($IC_{50}$) of 0.001 µM) and terfenadine ($IC_{50}$) of 0.213 µM). It is further believed that this blockade of human cardiac K⁺ channels underlies the proarrhythmic effects of the drug observed under certain clinical settings. In guinea pig ventricular myocytes cisapride elicited a concentration-dependent block ($IC_{50}$ of 46.9 µM) of L-type $Ca^{2+}$ channels suggesting that the inhibitory effect of cisapride on calcium channels might also contribute to its cardiotoxicity under pathophysiological conditions. Cisapride is metabolized by both cytochrome P450 3A4 and cytochrome P450 2D6; however the primary metabolic route is believed to be through cytochrome P450 3A4. When higher than normal dosages of cisapride are used or with concomitant ingestion of imidazole antifungals or macrolide antibiotics, it is believed that cisapride is metabolized to cardiotoxic metabolites through aromatic hydroxylation primarily by cytochrome P450 2D6.

Astemizole (Hismanal®) and terfenadine (Seldane®) are H₁ histamine antagonists that have also been removed from the market by the FDA because of QTc interval prolongation and ventricular arrhythmias such as torsade de pointes which produced sudden cardiac death.

Astemizole (Hismanal®), shown below, was commonly used to treat the symptoms associated with seasonal allergic rhinitis and chronic idiopathic urticaria.

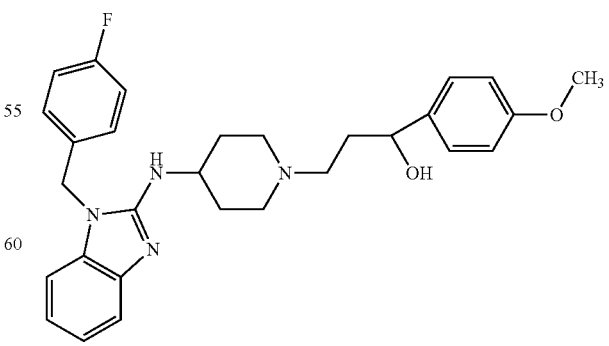

Terfenadine (Seldane®), shown below, was commonly used to symptoms associated with seasonal allergic rhinitis such as sneezing, rhinorrhea, pruritus, and lacrimation.

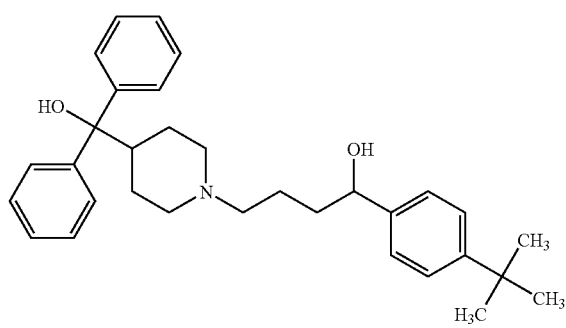

Astemizole (Hismanal®) and terfenadine (Seldane®) are metabolized by both cytochrome P450 3A4 and cytochrome P450 2D6, and at least astemizole is believed to be metabolized to cardiotoxic metabolites through aromatic hydroxylation. Terfenadine is believed to be metabolized to cardiotoxic metabolites primarily through aliphatic oxidation. Terfenadine and astemizole suppress the HERG current with $IC_{50}$ of 0.213 μM and 0.001 μM, respectively. Clinical use of astemizole and terfenadine has been associated with hypotension, QTc interval prolongation, development of early after-depolarization, torsade de pointes, cardiac arrest and sudden death. It is believed that torsade de pointes occurs when higher than normal dosages of astemizole are used or with concomitant ingestion of imidazole antifungals or macrolide antibiotics. Concomitant administration of astemizole with ketoconazole, itraconazole, erythromycin, clarithromycin or quinine was contraindicated. It is believed that these cardiovascular effects resulting in electrocardiographic conductance defects are associated with elevation of astemizole or its metabolites in plasma. Norastemizole is 13- to 16-fold more potent as an H1 antagonist than astemizole and 20- to 40-fold more potent in inhibiting histamine-induced bronchoconstriction.

Sertindole, shown below, was an atypical antipsychotic agent commonly used for the treatment of schizophrenia outside of the United States:

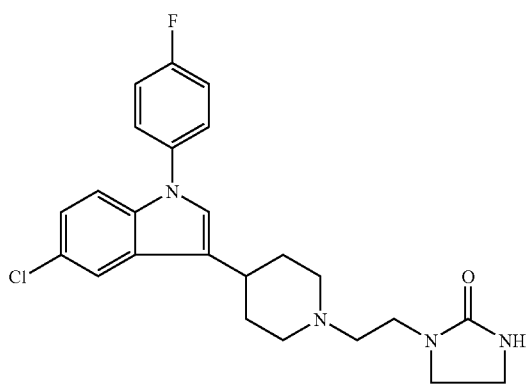

In 1996, sertindole (Serlect®) was rejected by the Food and Drug Administration because it prolonged the QTc interval and was associated with a significant number of unexplained deaths in clinical trials. Sertindole had been approved in 19 European countries, but more evidence of associated arrhythmias led to its withdrawal in Europe.

In trials involving more than 2,000 patients up to June 27, 1996 patients died while receiving sertindole, including 13 sudden deaths. Although there was no proof that the drug actually caused these deaths, sertindole was known to induce QT interval prolongation in some patients. Other antipsychotics have been associated with QT interval prolongation, and sudden death has been associated with schizophrenia.

Secondary and tertiary amines and other drug substrates for the P450 2D6 isozymes are lipophilic compounds that posses a planar component and are strong organic bases that are protonated at physiological pH. It is believed that a charged nitrogen atom on these amines is required to orient the drug correctly within the P450 2D6 active site where metabolic oxidation occurs. At this site, it is believed that the secondary or tertiary amine molecule adopts a conformation in which the positively-charged nitrogen ($N^+$) atom is oriented towards an anionic location ($COO^-$) on the P450 2D6 protein while the aromatic ring is aligned with a relatively planar, hydrophobic region of the protein. It is believed that when this conformation is adopted the nitrogen atom and the metabolic oxidation are in close proximity and metabolism of the drug occurs. Although cytochrome P450 3A4 is located both in the liver and the intestine, P450 2D6 is located in the liver and not the intestine.

Metabolic oxidation of drugs and other xenobiotic substances is a first step in a biotransformation that the body relies on to distribute active drug metabolites to tissues and also to eliminate them from the body. In some cases, this metabolic oxidation involves the formation of a pharmacologically active metabolite, and in other cases it involves the formation of hydroxylated metabolites through oxidation of an aromatic ring. Although metabolic oxidation to pharmacologically active metabolites is essential, metabolism of secondary and tertiary amine-containing drugs to hydroxymetabolites by cytochrome P450 2D6 and cytochrome P450 3A4 has serious cardiotoxicity implications to patients, particularly at high oral doses. We have found that the hydroxymetabolites are primarily responsible for the cardiotoxicity and not the parent secondary and tertiary amine-containing drugs. Published studies in humans (Dencker H et al. Clinical Pharmacology and Therapeutics 19: 584-586 (1976)) have also shown that the concentration of the tertiary-amine drugs is highest after leaving the liver and immediately prior to reaching the heart (8-10 times the concentration in the systemic circulation). Consequently, a patient is at highest risk during the first-pass metabolism of the secondary and tertiary amine drugs when the concentration of the cardiotoxic hydroxymetabolites is highest.

Published studies in humans (Gram L F and Christiansen J Clinical Pharmacology and Therapeutics 17: 555-563 (1975) have further shown that the concentration of the hydroxymetabolites of imipramine in plasma reaches significantly higher levels that the parent compounds or their active metabolites.

Likewise, published studies (Segura M et al. Rapid Communications in Mass Spectrometry 17: 1455-1461 (2003)) report that the concentration of the hydroxymetabolites of paroxetine in human plasma reaches significantly higher levels that the parent compounds or their active metabolites.

| Adapted from Segura et al. 2003 | | | |
|---|---|---|---|
| | Paroxetine | Hydroxylated Metabolite | Ratio of Metabolite to Paroxetine |
| Cmax (ug/L) | 8.60 | 92.40 | 10.7 |
| Tmax (hours) | 5 (3-5) | 3 (3-5) | — |
| AUC(0-24) (ug/L/h) | 96.50 | 988.10 | 10.2 |

Consequently, a patient is at greatest risk during the first-pass metabolism of the secondary and tertiary amine drugs when the concentration of the cardiotoxic hydroxymetabolites is highest. We believe that reventing metabolism of secondary and tertiary amine-containing drugs to hydroxymetabolites by cytochrome P450 2D6 and cytochrome P450 3A4 important to reducing their cardiotoxicity.

Inhibition studies on a series of imipramine analogs were conducted and the analogs tested for CYP2D6 activity, the enzyme that is responsible for the formation of the cardiotoxic hydroxylated metabolites (Halliday R C et al. European Journal of Drug Metabolism and Pharmacokinetics 22: 291-294 (1997)). The analogs of imipramine that were tested were designed to have the positively charged nitrogen atom removed from the active site of CYP2D6. The three approaches were adjustment of alkyl chain length, alkyl bond rigidity (restricted bond rotation) and removing the positive charge on the tertiary nitrogen atom using the prodrug imipramine-N-oxide. Halliday et al. reported that removal of the positively charged nitrogen atom of imipramine from the active site of CYP2D6 either by lengthening the alkyl chain length or altering the pKa of imipramine with using imipramine-N-oxide abolished the metabolism of imipramine by CYP2D6 to the hydroxymetabolite.

A considerable amount of preclinical and clinical data is available that demonstrates that imipramine-N-oxide is not subject to first-pass metabolism or aromatic hydroxylation to the cardiotoxic hydroxymetabolites by cytochrome P450 2D6 and cytochrome P450 3A4. This prodrug is rapidly converted in the systemic circulation to imipramine which is then metabolized under much lower systemic plasma concentrations to the active form (desipramine) and hydroxylated metabolites that are not as likely to produce severe cardiotoxicity. In published preclinical and clinical studies imipramine-N-oxide has been shown not produce the cardiotoxicity of the tertiary amine drug imipramine. Nevertheless, formulation difficulties and the complexities of imipramine-N-oxide metabolism in plasma limits its use.

It is believed, in accordance with the present invention that the piperidine chemical group with its tertiary amine in cisapride, astemizole, sertindole, trazadone, nefazadone, buspirone and terfenadine contributes to cardiac conduction disturbances and orientation of the drugs within the binding sites of the cytochrome enzymes responsible for the responsible metabolism of these drugs by aromatic or cycloalkyl hydroxylation.

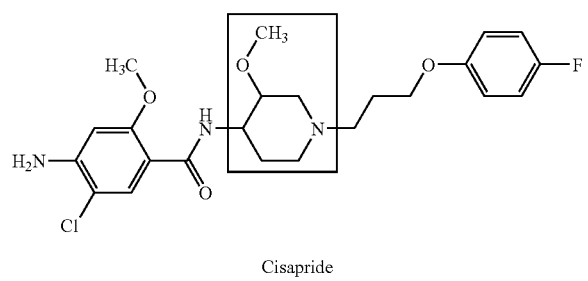

Cisapride

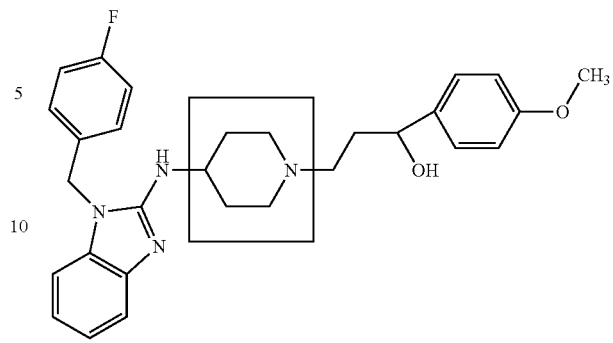

Astemizole

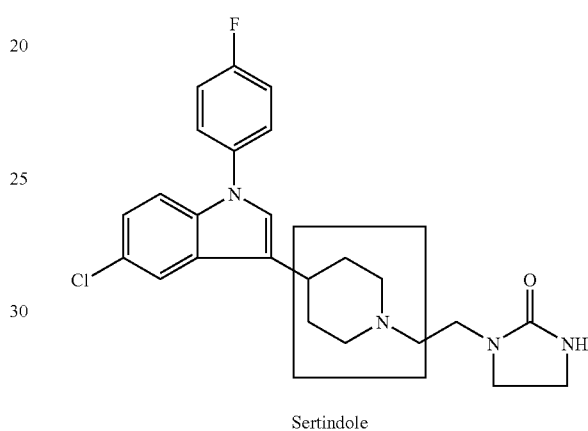

Sertindole

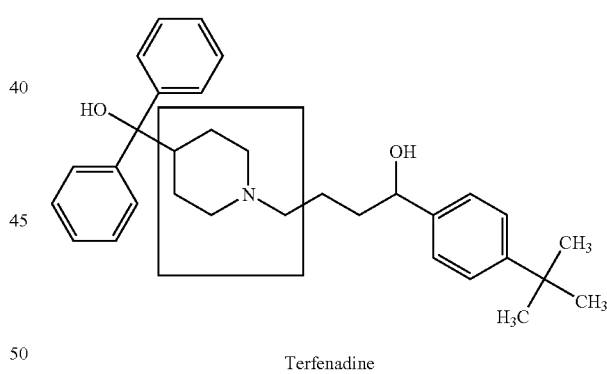

Terfenadine

It is further believed that the chemically related piperazine chemical group with its tertiary amine contributes to cardiac conduction disturbances and orientation of the drugs within the binding sites of the cytochrome enzymes responsible for the responsible metabolism of these drugs by for aromatic or cycloalkyl hydroxylation. Pharmacologic agents containing a piperazine group known to cause cardiac conduction disturbances include buclizine, buspirone, cyclizine, doxazosin, fluphenazine, gepirone, hydroxyzine, itraconazole, ketoconazole, loxapine, meclizine, olanzapine, perphenazine, quetiapine, trazadone, nefazadone and ziprasidone. By way of example, the chemical structures of a series of pharmacological compounds containing a piperazine moiety and having antihistamine activity are shown below:

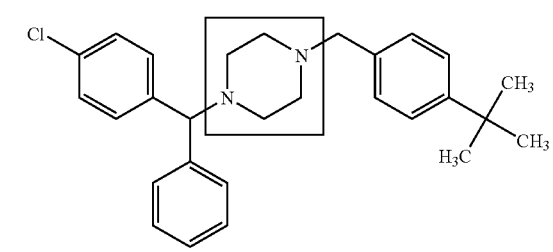

Buclizine

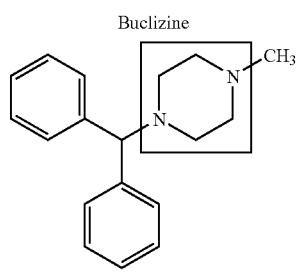

Cyclizine

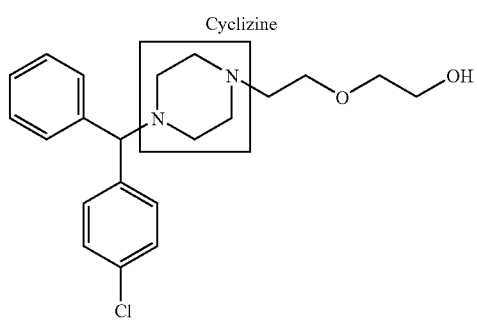

Hydroxyzine

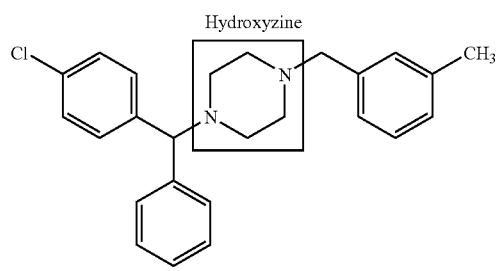

Meclizine

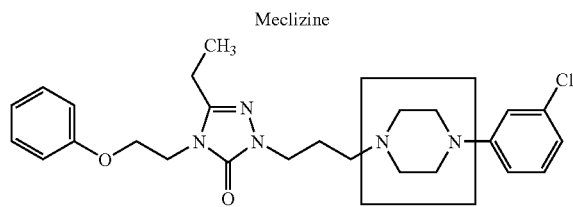

Nefazodone

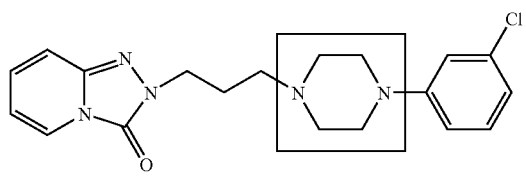

Trazadone

Fluoroquinolone antibiotics are pharmacologic agents containing a piperazine group known to cause serious cardiac conduction disturbances and torsade de pointes. Fluoroquinolone antibiotics approved for marketing and having a secondary amine on the piperazine ring include norfloxacin, lomefloxacin, ciprofloxacin, enoxacin, gatifloxacin, sparfloxacin, temafloxacin, grepafloxacin and moxifloxacin. Several of these fluoroquinolone agents have already been removed from the market because of life-threatening cardiac conduction disturbance or torsade de pointes. By way of example, the chemical structures of a series of fluoroquinolone compounds containing a secondary amine on the piperazine moiety are shown below:

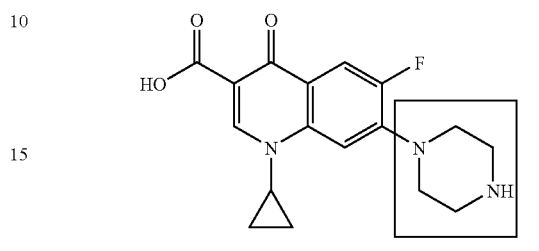

Ciprofloxacin

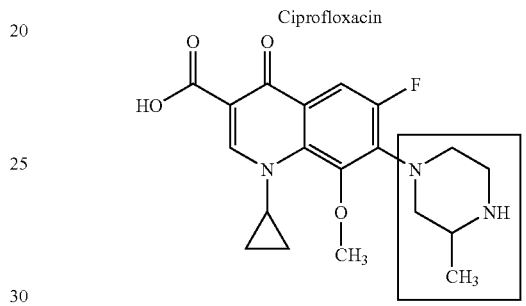

Gatifloxacin

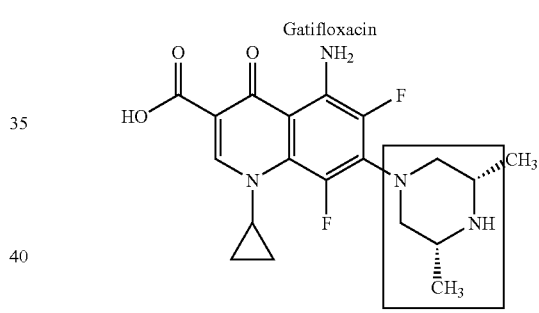

Sparfloxacin

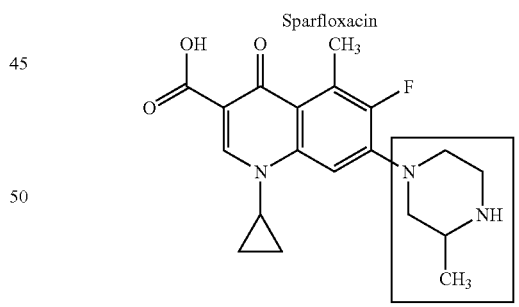

Grepafloxacin

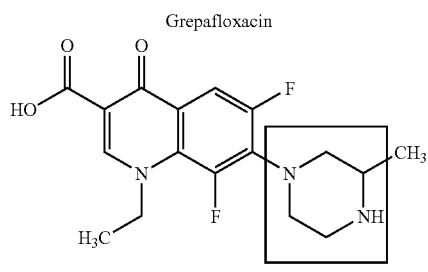

Lomefloxacin

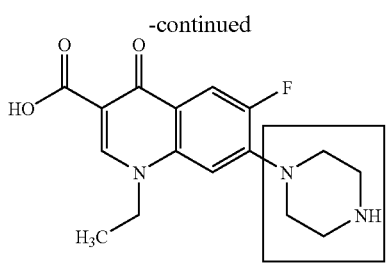

Norfloxacin

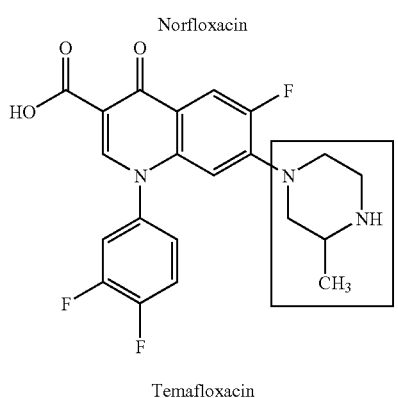

Temafloxacin

Fluoroquinolone antibiotics approved for marketing and having a secondary amine on the piperidine ring include moxifloxacin as shown below:

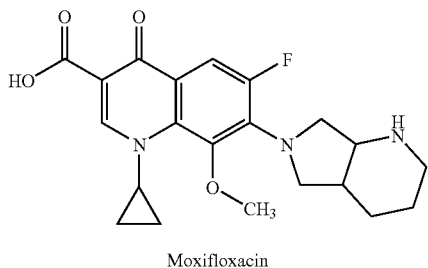

Moxifloxacin

It is therefore an object of the present invention to provide non-cardiotoxic pharmacologically active compounds having modulated cytochrome P 450 metabolism.

It is a further object of the invention to provide non-cardiotoxic pharmacologically active compounds having reduced metabolism by cytochrome P450 2D6.

It is a further object of the invention is to provide non-cardiotoxic prodrugs of pharmacologically active compounds having modulated cytochrome P 450 metabolism.

It is a further object of the invention to provide non-cardiotoxic pharmacologically active compounds having reduced metabolism by cytochrome P450 2D6 and cytochrome P450 3A4.

A further object of the invention is to provide non-cardiotoxic prodrugs that will modify the physicochemical properties of tertiary amine-containing drugs such that these drugs will exhibit reduced binding to the CYP2D6 metabolizing enzymes during first-pass absorption.

A further object of the invention is to provide non-cardiotoxic prodrugs that can be hydrolyzed in the plasma after absorption and be converted directly to the therapeutically active form of the parent compounds.

A further object of the invention is to provide non-cardiotoxic prodrugs that lower the pKa of the tertiary amine group to a level such that the majority of the tertiary amine is uncharged at physiological pH (pH 7.4). For example, imipramine has pKa of 9.5 and is completely ionized as it is transported through the gastrointestinal tract. After oral ingestion, imipramine is rapidly and completely absorbed from the small intestine, with peak plasma concentration within two to five hours. Imipramine is subject to extensive first-pass metabolism in the liver, and is eliminated by demethylation to the active metabolite, desipramine and to a lesser extent by aromatic hydroxylation to 2-hydroxyipramine. Desipramine, in turn, is metabolized by aromatic hydroxylation to 2-hydroxydesipramine. The systemic availability of imipramine in healthy subjects ranges from 27% to 80% and the corresponding first-pass metabolism ranges from 20% to 73%. Imipramine-N-oxide, a nitrogen-atom prodrug of imipramine which has a pKa of about 4.7, has a systemic availability of about 100% after oral administration suggesting that there is no first pass effect. Both preclinical and clinical studies have shown that the cardiotoxicity of imipramine-N-oxide is significantly reduced over that of imipramine.

BRIEF SUMMARY OF THE INVENTION

In accordance with the present invention, disclosed are enzyme-labile compounds having the formula

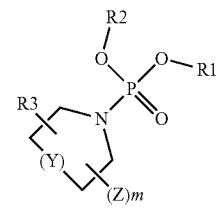

where $R_1$ and $R_2$ are independently hydrogen, alkyl having from 1 to about 7 carbon atoms, aryl, aralkyl, and cycloalkyl having from about 3 to about 6 carbon atoms, Y is $(CH_2)_n$ where n is from 0 to 2, Z is alkyl, alkoxy, alkoxy, aryloxy, or alkylaryloxy where m is from 0 to about 4, and $R_3$ is selected from the group consisting of substituted or unsubstituted aryl, substituted or unsubstituted heteroaryl, substituted or unsubstituted alkylaryl, substituted or unsubstituted heteroaryl, substituted or unsubstituted alkylaryloxy, substituted or unsubstituted indole, substituted or unsubstituted phenothiazine, substituted or unsubstituted dibenzoxazepine, substituted or unsubstituted dibenzathiazepine, substituted or unsubstituted oxopthalazine, substituted or unsubstituted quinoline, substituted or unsubstituted dihydroquinoline, substituted or unsubstituted dibenzodiazepine, substituted or unsubstituted benzocycloheptapyridine, substituted or unsubstituted carbazol, substituted or unsubstituted tetrahydrocarbazols, substituted or unsubstituted dibenzocycloheptenes, substituted or unsubstituted benzoimidazoles, substituted or unsubstituted piperazines, substituted or unsubstituted benzamides, substituted or unsubstituted benzhydrol, and substituted or unsubstituted diazabenzoazulene, substituted or unsubstituted oxobenzimidazole, 3,4 pyrrolo-dihydroquinoline, carbamoyl-2,3,4,9-tetrahydro-cabazol, and pharmaceutically acceptable salts thereof.

These enzyme-labile compounds, having lower pKa values than their corresponding secondary and tertiary amines, have significantly reduced cardiotoxicity than those secondary and tertiary amines from which they are derived. The compounds of the present invention are useful as gastrointestinal, antiinfective, antidepressant, antihistaminic, antipsychotic, antineoplastic and cardiovascular therapeutic agents.

DETAILED DESCRIPTION OF THE INVENTION

Figure 1:
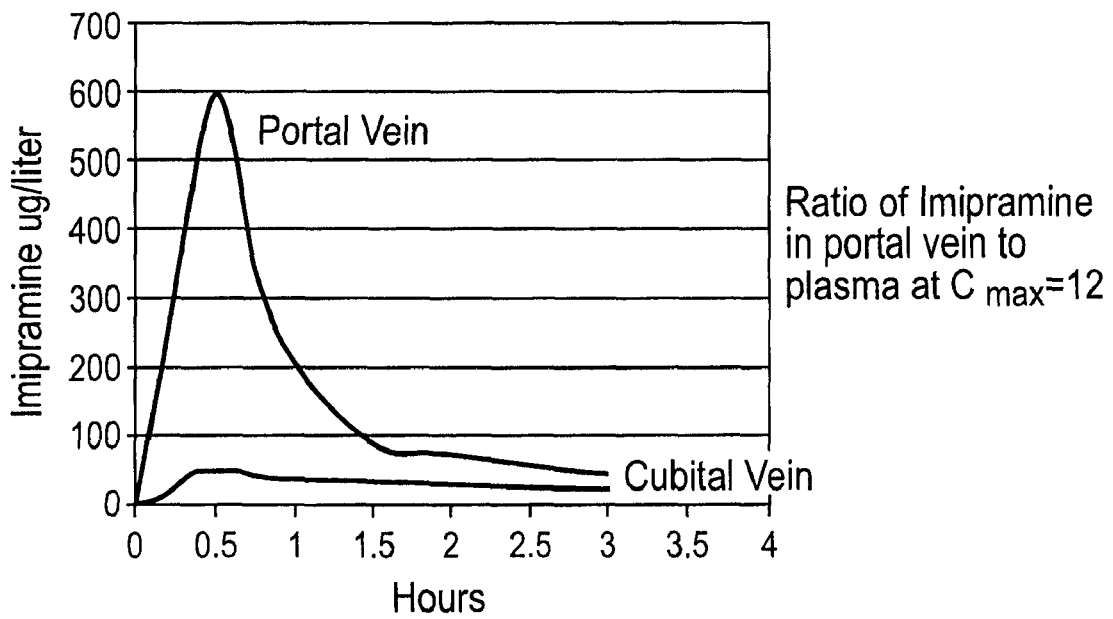
FIG. 1 shows intestinal absorption and metabolism of imipramine in human subjects, adapted from Dencker et al., 1976.
Figure 2:
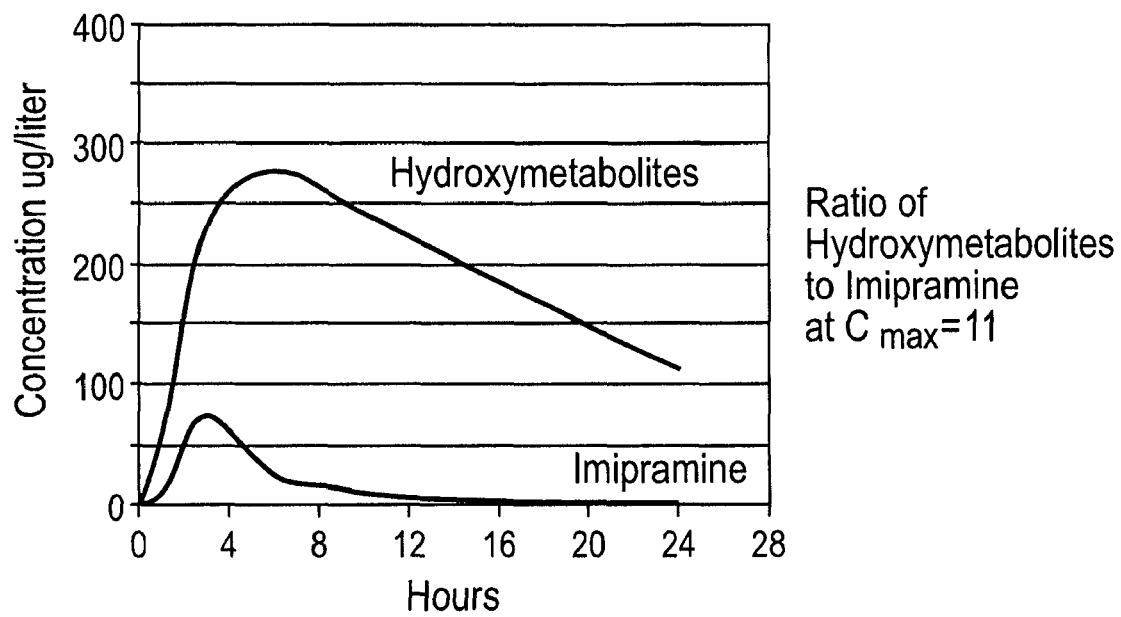
FIG. 2 shows plasma concentration for imipramine and its metabolites in human subjects, adapted from Gram et al., 1975.
Figure 3:
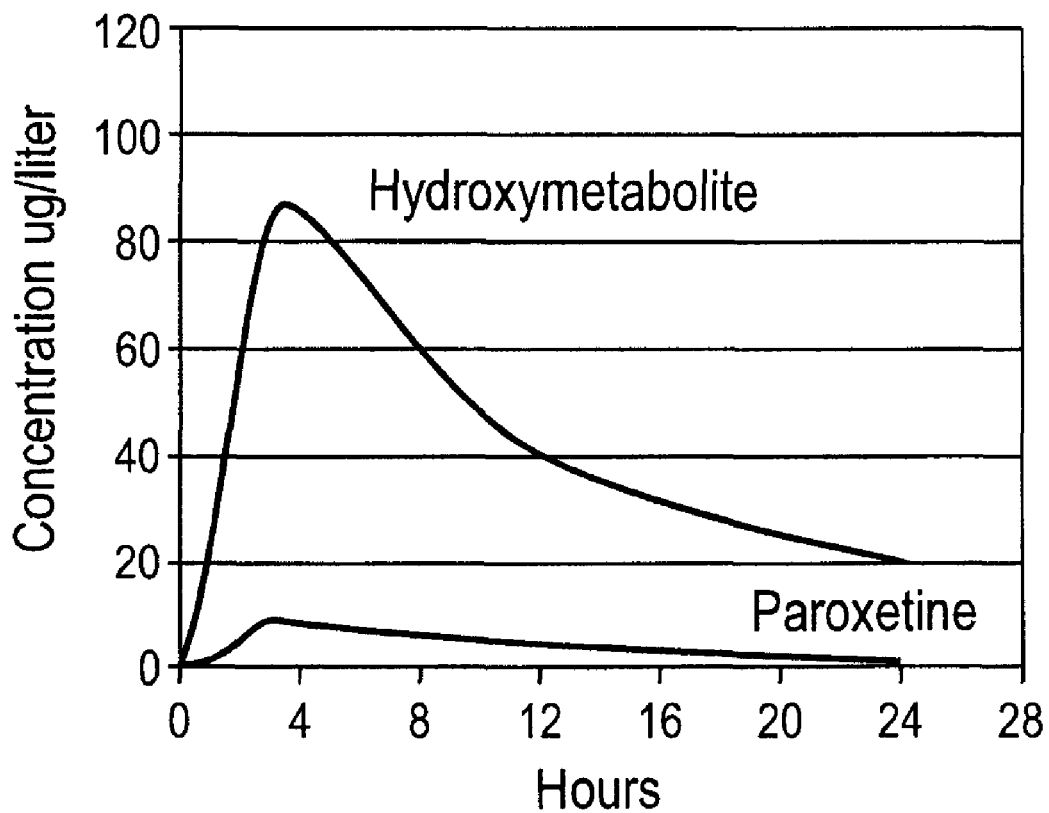
FIG. 3 shows plasma concentrations for parxetine and its metabolite, adapted from Segura et al., 2003.

In accordance with the present invention, disclosed are enzyme-labile prodrugs having a modified ionization potential (pKa) of the nitrogen atoms such that they are significantly less basic than on the highly basic nitrogen atoms of the parent drugs. In accordance with the present invention we describe chemical modifications of the highly basic that amines include formation of phosphoramidates which are stable toward hydrolysis in the intestine and plasma. Phosphoramidates are non-toxic organophosphorous compounds containing phosphorous-nitrogen bonds.

An unexpected advantage of these organophosphorous compounds over the N-oxides is that they are enzyme-labile and are selectively hydrolyzed after passage through the intestine to the pharmacologically active drug moiety. Unlike other prodrug technologies employing esters, phosphonates and peptide bonds, which are hydrolyzed by esterases, phosphatases and peptidases in the intestine, enterocytes, hepatic cells and plasma, the organophosphorous compounds of the present invention are stable in the intestine and the enterocytes and plasma.

In agreement with a limited number of published studies, we have shown that the hydroxymetabolites of several secondary and tertiary amine-containing drugs are primarily responsible for the cardiotoxicity and not the parent compound. In Langendorff isolated perfused rabbit heart studies we have demonstrated that the hydroxymetabolites demonstrated dose-dependent significant increases in cardiac conductance, notably in PR interval prolongation, QRS interval prolongation and QT interval prolongation at clinically relevant doses. None of these changes were accompanied by observed conductance changes associated with $K^+$ channel blockade. In receptor binding studies, no differences were noted in the affinity of the hydroxymetabolites and the parent drugs toward the voltage operated L-type calcium channel receptors or the Herg receptors of the $K^+$ channel.

In accordance with the present invention, we describe enzyme-labile prodrugs of the secondary and tertiary amine moiety that mask the enzyme(s) primarily responsible for the production of these hydroxymetabolites in the liver. We describe enzyme-labile prodrugs of secondary and tertiary amine-containing drugs that are not substrates of cytochrome P450 CYP2D6. We describe enzyme-labile prodrugs of secondary and tertiary amine-containing drugs having minimal capacity for aromatic hydroxylation or first-pass metabolism to the cardiotoxic hydroxymetabolites. These enzyme-label prodrugs are expected to be rapidly converted in the systemic circulation to the pharmacologically active form of the secondary and tertiary amine-containing drugs which are then metabolized under much lower systemic plasma concentrations that are not as likely to produce severe cardiotoxicity.

These enzyme-labile prodrugs modulate the physicochemical properties of secondary and tertiary amine-containing drugs such that these drugs do not bind to the cytochrome P450 2D6 metabolizing enzymes during first-pass absorption at physiological pH. The nitrogen atoms on these enzyme-labile prodrugs are significantly less basic (pKa<5.4) than on the highly basic nitrogen atoms of the parent drugs (pKa~9.5). Because these prodrugs are enzyme-labile, they can be hydrolyzed in the body after absorption directly to the non-cardiotoxic therapeutically active compounds. It is anticipated that specific therapeutic areas covered by this technology include, among others, all types of antidepressants, antihistamines, antipsychotics, gastrointestinal and several classes of antiinfective drugs. In a preferred embodiment of the present invention, chemical modification of the highly basic amines of known cardiotoxic drugs includes formation of phosphoramidates whose hydrolysis is primarily restricted to the liver and are stable in the intestine and plasma. Phosphoramidates are organophosphorous compounds containing phosphorous-nitrogen bonds.

A partial list of therapeutic compounds having a highly basic nitrogen atom that have reported cases of QT interval prolongation, torsade de pointes or both and their corresponding pKa values include the following: dextromethorphan (9.20), methadone (8.25), propoxyphene (8.91), tramadol (9.41), amoxapine (7.60), citalopram (9.50), clomipramine (9.50), desipramine (10.40), doxepin (8.00), duloxetine (10.00), escitalopram (9.60), femoxetine (9.00), fluoxetine (8.70), maprotiline (10.20), mianserin (8.26), mirtazapine (8.10), nefazodone (7.90), nortriptyline (10.10), paroxetine (9.90), selegiline (7.53), sertraline (9.50), venlafaxine (9.40), zimeldine (8.00), astemizole (9.90), azelastine (9.06), chlorpheniramine (9.20), chlorphenoxamine (8.21), clemastine (10.23), desloratadine (9.40), diphenhydramine (9.00), doxylamine (9.30), fexofenadine (9.53), promethazine (9.10), terfenadine (9.60), ciprofloxacin (7.68), halofantrine (9.60), levofloxacin(7.09), moxifloxacin (10.01), ofloxacin (7.09), rimantadine (11.70), tamoxifen (8.85), chlorpromazine (9.30), clozapine (8.20), loxapine (7.64), norsertindole (10.61), olanzapine (6.37), risperidone (8.24), sertindole (9.06), thioridazine (9.50), trifluoperazine (7.98), ziprasidone (8.24), amphetamine (9.90), atomoxetine (10.12), carbamazepine (7.00), cyclobenzaprine (9.21), fenfluramine (9.92), methamphetamine (10.28), methylphenidate (8.90), oxybutynin (6.96), phenytoin (8.31), sibutramine (9.36), tolterodine (9.87), cimetidine (6.80), cisapride (7.04), cyclizine (8.35), meclizine (7.32), norcisapride (8.46), ranitidine (8.20), almotriptan (9.58), eletriptan (10.13), frovatriptan (10.63), naratriptan (9.74), rizatriptan (9.49), rumatriptan (9.50), and Zolmitriptan (9.52).

In accordance with a preferred embodiment of the present invention, the pharmaceutical formulations comprise phosphoramidate-based prodrugs having pKa of less than about 5.4. In accordance with a more preferred embodiment of the present invention, the pharmaceutical formulations comprise phosphoramidate-based prodrugs having pKa values in the range from about 1 to about 5. In yet an even more preferred embodiment of the present invention, the phosphoramidate-based prodrugs have a pKa less than 4. It will be appreciated by those skilled in the art that this reduction in pKa represents a considerable difference in the proportion of positively charged amines present at physiological pH compared to the highly basic amine parent drugs.

Pharmaceutical compounds in accordance with the present invention have considerable similarity because of the similar pharmacologic requirements for therapeutic activity. Accordingly, the chemical structures of the enzyme-labile prodrugs can be characterized by a few general structure types. The first type include those containing cyclic aliphatic groups such as piperidine and piperazine containing a secondary or tertiary nitrogen atom such as found in amoxapine, and another type includes those having and alkylamine group such as found in imipramine.

In accordance with one embodiment of the present invention, compounds have the formula

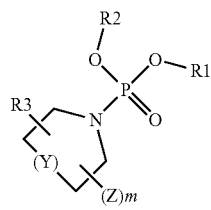

where $R_1$ and $R_2$ are independently hydrogen, alkyl having from 1 to about 7 carbon atoms, aryl, aralkyl, and cycloalkyl having from about 3 to about 6 carbon atoms, Y is $(CH_2)_n$ where n is from 0 to 2, Z is alkyl, alkoxy, alkoxy, aryloxy, or alkylaryloxy where m is from 0 to about 4, and $R_3$ is selected from the group consisting of substituted or unsubstituted aryl, substituted or unsubstituted heteroaryl, substituted or unsubstituted alkylaryl, substituted or unsubstituted heteroaryl, substituted or unsubstituted alkylaryloxy, substituted or unsubstituted indole, substituted or unsubstituted phenothiazine, substituted or unsubstituted dibenzoxazepine, substituted or unsubstituted dibenzathiazepine, substituted or unsubstituted oxopthalazine, substituted or unsubstituted quinoline, substituted or unsubstituted dihydroquinoline, substituted or unsubstituted dibenzodiazepine, substituted or unsubstituted benzocycloheptapyridine, substituted or unsubstituted carbazol, substituted or unsubstituted tetrahydrocarbazols, substituted or unsubstituted dibenzocycloheptenes, substituted or unsubstituted benzoimidazoles, substituted or unsubstituted piperazines, substituted or unsubstituted benzamides, substituted or unsubstituted benzhydrol, and substituted or unsubstituted diazabenzoazulene, substituted or unsubstituted oxobenzimidazole, 3,4 pyrrolodihydroquinoline, carbamoyl-2,3,4,9-tetrahydro-cabazol, and pharmaceutically acceptable salts thereof. In accordance with a preferred embodiment of the present invention, n is 2. In a more preferred embodiment of the present invention, n is 2 and m is from 0 to 3.

In accordance with another embodiment of the present invention, compounds have the formula

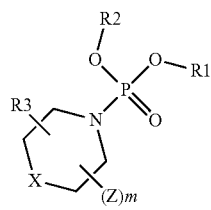

where $R_1$ and $R_2$ are independently hydrogen, alkyl having from 1 to about 7 carbon atoms, aryl, aralkyl, and cycloalkyl having from about 3 to about 6 carbon, X is oxygen, nitrogen or carbon, and m is from 0 to about 3.

Another type of compound in accordance with the present invention has the formula

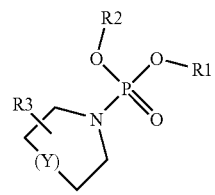

where $R_3$ is a group having the formula

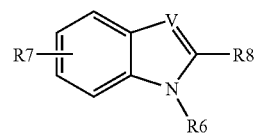

where V is carbon or nitrogen, $R_6$ is hydrogen, alkyl, aryl or aralkyl, $R_7$ is hydrogen, alkyl, aralkyl, cycloalkyl, alkylcycloalkyl, alkylsulfonylcycloalkyl, alkylsulfonylaryl, alkylsulfonylaminoalkyl or alkylsulfonylalkyl and $R_8$ is hydrogen, carbonyl or a direct bond.

Preferred compounds in accordance with this embodiment of the present invention include those where $R_3$ has the formula

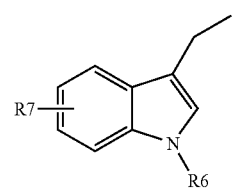

In accordance with the present invention, $R_7$ is preferably selected form the group consisting of:

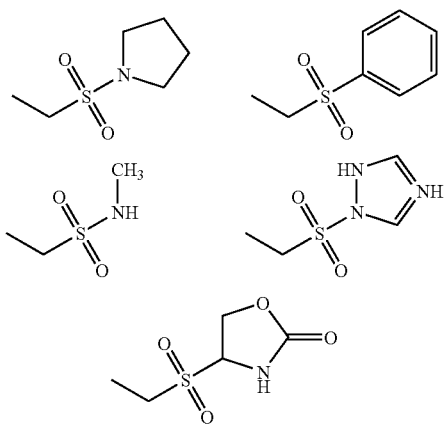

In yet another embodiment of the present invention, the compounds have the formula

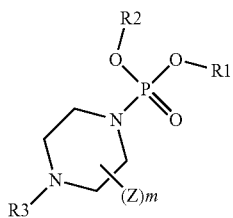

where R₃ is a group having the formula

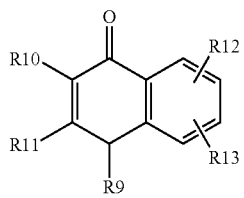

where $R_9$ and $R_{11}$ are hydrogen, alkyl, aryl, alkylaryl, cycloalkyl or together form a cyoalkyl or cycloheteroalkyl group, and $R_{10}$ is hydrogen, alkyl or a carboxylic acid group, and $R_{12}$ and $R_{13}$ are independently hydrogen, halogen, alkyl, alkoxy or amino.

In a preferred embodiment of the present invention the compounds have the formula

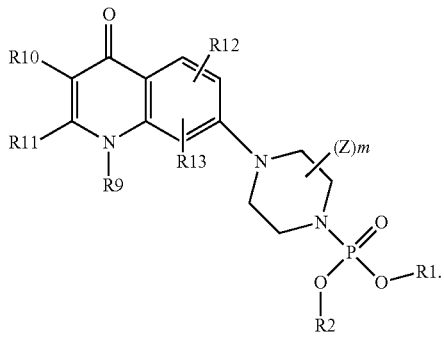

In another embodiment of the present invention the compounds have the formula

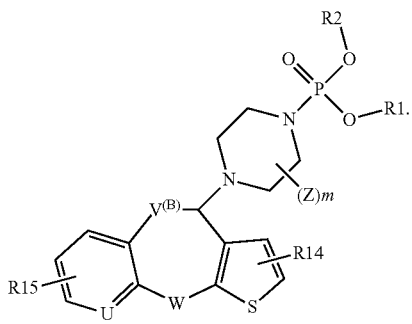

where V is carbon or nitrogen, W is carbon, nitrogen or oxygen, U is carbon or nitrogen, B is a single or double bond, and $R_{14}$ and $R_{15}$ are independently hydrogen, halogen, or alkyl.

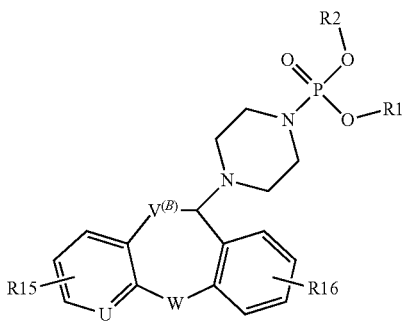

where V is carbon or nitrogen, W is carbon, nitrogen or oxygen, U is carbon or nitrogen, B is a single or double bond, and $R_{15}$ and $R_{16}$ are independently hydrogen, halogen or alkyl.

In still another embodiment of the present invention, the compounds have the formula

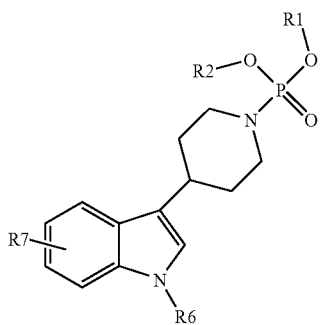

where $R_6$ is hydrogen, alkyl, alkylaryl or aralkyl, and $R_7$ is hydrogen, alkyl, aralkyl, cycloalkyl, alkylcycloalkyl, alkylsulfonylcycloalkyl, alkylsulfonylaryl, alkylsulfonylaminoalkyl or alkylsulfonylalkyl.

Another type includes those containing short linear aliphatic chains depending from a nitrogen atom such as those found with imipramine.

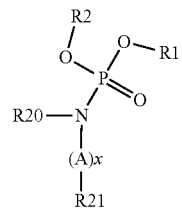

In accordance with this aspect of the present invention, $R_1$ and $R_2$ are independently hydrogen, alkyl having from 1 to about 7 carbon atoms including but not limited to methyl, ethyl, propyl, butyl, isobutyl, and pentyl, aryl including but not limited to phenyl and pyridinyl, aralkyl such as benzyl, and cycloalkyl having from about 3 to about 6 carbon atoms including but not limited to cyclopropyl, cyclobutyl, cyclopentyl, and cyclohexyl, A is a lower alkyl, lower heteroalkyl, carbonyl or cycloalkyl, X is 0 or 1, $R_1$ and $R_2$ are independently hydrogen, alkyl having from 1 to about 7 carbon atoms, aryl, aralkyl, and cycloalkyl having from about 3 to about 6 carbon atoms, $R_{20}$ is hydrogen, phenyl or lower alkyl, and $R_{21}$ is selected from the group consisting of substituted or unsubstituted aryl, substituted or unsubstituted heteroaryl, substituted or unsubstituted alkylaryl, substituted or unsubstituted heteroaryl, substituted or unsubstituted alkylaryoxy, substituted or unsubstituted indole, substituted or unsubstituted phenothiazine, substituted or unsubstituted dibenzoxazepine, substituted or unsubstituted dibenzathiazepine, substituted or unsubstituted oxopthalazine, substituted or unsubstituted quinoline, substituted or unsubstituted dihydroquinoline, substituted or unsubstituted dibenzodiazepine, substituted or unsubstituted benzocycloheptapyridine, substituted or unsubstituted carbazol, substituted or unsubstituted tetrahydrocarbazols, substituted or unsubstituted dibenzocycloheptenes, substituted or unsubstituted benzoimidazoles, substituted or unsubstituted piperazines, substituted or unsubstituted benzamides, substituted or unsubstituted benzhydrol, and substituted or unsubstituted diazabenzoazulene, substituted or unsubstituted oxobenzimidazole, 3,4 pyrrolo-dihydroquinoline, carbamoyl-2,3,4,9-tetrahydro-cabazol, and pharmaceutically acceptable salts thereof.

In accordance with another embodiment of the present invention, the compounds have the formula

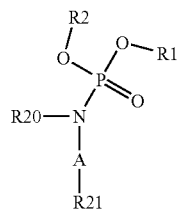

where A is a lower alkyl, lower heteroalkyl or cycloalkyl, $R_{20}$ is hydrogen, phenyl or lower alkyl and $R_{21}$ is a group having the formula

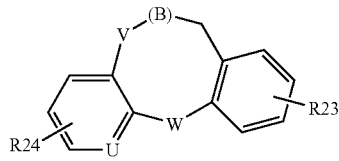

where V is carbon or nitrogen, W is carbon, nitrogen or oxygen, U is carbon or nitrogen, $R_{23}$ and $R_{24}$ are independently hydrogen, halogen, alkyl or alkoxy, and B is a single or double bond.

In accordance with another aspect of the present invention, the compounds have the formula

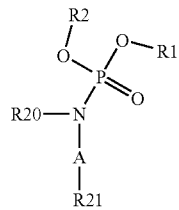

where A is a lower alkyl, lower heteroalkyl or cycloalkyl, $R_{20}$ is hydrogen, phenyl or lower alkyl and $R_{21}$ is a group having the formula

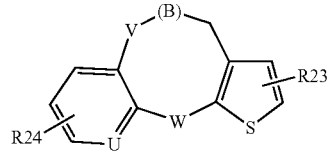

where V is carbon or nitrogen, W is carbon, nitrogen or oxygen, U is carbon or nitrogen, $R_{23}$ and $R_{24}$ are independently hydrogen, halogen, alkyl or alkoxy, and B is a single or double bond.

In accordance with another embodiment of the present invention, the compounds have the formula

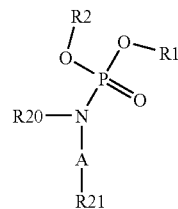

where A is a lower alkyl, lower heteroalkyl or cycloalkyl, $R_{20}$ is hydrogen, phenyl or lower alkyl and $R_{21}$ is a group having the formula

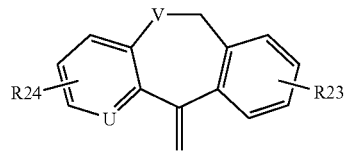

where V is carbon or nitrogen, U is carbon or nitrogen, $R_{23}$ and $R_{24}$ are independently hydrogen, halogen, alkyl or alkoxy, and B is a single or double bond.

In accordance with another embodiment of the present invention, the compounds have the formula

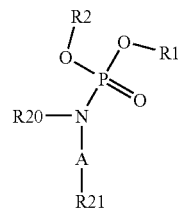

where A is a lower alkyl, lower heteroalkyl or cycloalkyl, $R_{20}$ is hydrogen, phenyl or lower alkyl and $R_{21}$ is a group having the formula

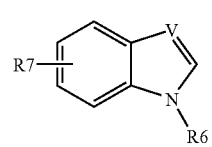

where V is carbon or nitrogen, $R_6$ is hydrogen, alkyl, aryl or aralkyl, and $R_7$ is hydrogen, halogen, aralkyl, cycloalkyl, alkylcycloalkyl, alkylsulfonylcycloalkyl, alkylsulfonylaryl, alkylsulfonylaminoalkyl or alkylsulfonylalkyl.

In accordance with another embodiment of the present invention, the compounds have the formula

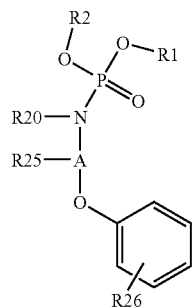

where A is a lower alkyl, lower heteroalkyl or cycloalkyl, $R_{20}$ is hydrogen, phenyl or lower alkyl, $R_{26}$ is hydrogen, alkyl, alkoxy, alkylaryl, alkenylaryl, halogen, halogen-substituted alkyl, alkylaryloxy, alkanoyl, arylalkanoyl, or a group having the formula

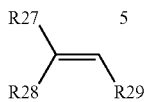

where $R_{27}$, $R_{28}$ and $R_{29}$ are independently substituted or unsubstituted alkyl, substituted or unsubstituted aryl, substituted or unsubstituted aralkyl, substituted or unsubstituted alkylaryl, substituted or unsubstituted cycloalkyl or substituted or unsubstituted heterocycloalkyl, and $R_{25}$ is hydrogen, hydroxy, alkyl, alkylaryl, aryl, cycloalkyl or heteroaryl.

In accordance with another embodiment of the present invention, the compounds have the formula

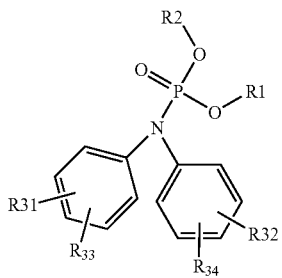

where $R_{31}$, $R_{32}$, $R_{33}$, $R_{34}$ are independently hydrogen, halogen, alkyl, alkoxy or a group having the formula $(CH2)_n$COOH where n=1 to about 5.

Unless otherwise specifically identified or claimed for preferred embodiments, the following general definitions are used in accordance with the present invention.

"Alkyl" refers to a branched or straight chain acyclic alkyl group comprising one to about ten carbon atoms, a haloalkyl group, an alkenyl group, an alkynyl group, a bridged cycloalkyl group, a cycloalkyl group or a heterocyclic ring.

"Lower alkyl" refers to a branched or straight chain acyclic alkyl group comprising one to about six carbon atoms. In accordance with the present invention, lower alkyl groups include methyl, ethyl, n-propyl, isopropyl, n-butyl, isobutyl, sec-butyl, t-butyl, pentyl, neopentyl, iso-amyl, hexyl, and the like.

"Haloalkyl" refers to a lower alkyl group, an alkenyl group, an alkynyl group, a bridged cycloalkyl group, a cycloalkyl group or a heterocyclic ring, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon which can comprise one or more carbon-carbon double bonds. In accordance with the present invention, alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$-$C_{10}$ hydrocarbon which can comprise one or more carbon-carbon triple bonds. In accordance with the present invention, alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. In accordance with the present invention, cycloalkyl groups include cyclopropyl, cyclobutyl, cyclopentyl, cyclohexyl, cyclohexenyl, cycloheptyl and the like.

"Heterocyclic ring or group" refers to a saturated, unsaturated, cyclic or aromatic or polycyclic hydrocarbon group having about 3 to about 7 carbon atoms where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. In accordance with the present invention, heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicydo[3,3,0]octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like. "Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. In accordance with the present invention, aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. In accordance with the present invention, substituted aryl groups include tetrafluoro-phenyl, pentafluorophenyl, sulfonamide, alkylsulfonyl, arylsulfonyl, and the like.

"Alkylaryl" refers to an alkyl group to which is appended an aryl group. In accordance with the present invention, alkylaryl groups include benzyl, phenylethyl, hydroxybenzyl, fluorobenzyl, fluorophenylethyl, and the like.

"Arylalkyl" refers to an aryl radical, attached to an alkyl radical in accordance with the present invention, "Cycloalkylalkyl" refers to a cycloalkyl radical attached to an alkyl radical in accordance with the present invention, "Alkoxy" refers to RO-, wherein R is an alkyl group in accordance with the present invention. In accordance with the present invention, alkoxy groups include methoxy, ethoxy, t-butoxy, cyclopentyloxy, and the like.

"Arylalkoxy or alkoxyaryl" refers to an alkoxy group, as defined herein, to which is appended an aryl group in accordance with the present invention, In accordance with the present invention, arylalkoxy groups indude benzyloxy, phenylethoxy, chlorophenylethoxy, and the like.

"Alkoxyaryl" refers to an alkoxy group, in accordance with the present invention, appended to an alkyl group. In accordance with the present invention, alkoxyaryl groups include methoxymethyl, methoxyethyl, isopropoxymethyl, and the like.

In accordance with the present invention, $R_1$ is hydrogen, an alkyl having from 1 to about 5 carbon atoms including but not limited to methyl, ethyl, propyl, butyl, isopropyl, isobutyl, and pentyl, an aryl including but not limited to phenyl, aralkyl such as benzyl, or cycloalkyl having from about 3 to about 6 carbon atoms including but not limited to cyclopropyl, cyclobutyl, cyclopentyl, and cyclohexyl.

In accordance with a preferred embodiment of the present invention $R_2$ is hydrogen, lower alkyl including but not limited to methoxy and ethoxy. In accordance with a more preferred embodiment of the present invention, $R_2$ is hydrogen or $OCH_3$.

In accordance with a preferred embodiment of the present invention $R_1$ and $R_2$ are independently hydrogen, methyl, ethyl, propyl or phenyl. In accordance with a more preferred embodiment of the present invention, $R_1$ is methyl, ethyl or phenyl and $R_2$ is hydrogen. In accordance with a most preferred embodiment of the present invention, $R_1$ and $R_2$ are both ethyl.

Illustrative compounds in accordance with a most preferred embodiment of the present invention include the following:

Methyl-{2-[6-(pyrrolidine-1-sulfonylmethyl)-1H-indol-3-yl]-ethyl}-phosphoramidic acid diethyl ester

[4-(2-Chloro-dibenzo[b,f][1,4]oxazepin-11-yl)-piperazin-1-yl]-phosphonic acid diethyl ester (1-Methyl-2-phenyl-ethyl)-phosphoramidic acid diethyl ester Methyl-(3-phenyl-3-o-tolyloxy-propyl)-phosphoramidic acid diethyl ester {4-[4-(3-Chloro-benzyl)-1-oxo-1H-phthalazin-2-yl]-azepan-1-yl}-phosphonic acid diethyl ester (Dibenzo[b,f]azepine-5-carbonyl)-phosphoramidic acid diethyl ester

[3-(4-Chloro-phenyl)-3-pyridin-2-yl-propyl]-methyl-phosphoramidic acid diethyl ester {2-[1-(4-Chloro-phenyl)-1-phenyl-ethoxy]-ethyl}-methyl-phosphoramidic acid diethyl ester

[3-(2-Chloro-phenothiazin-10-yl)-propyl]-methyl-phosphoramidic acid diethyl ester 1-Cyclopropyl-7-[4-(diethoxy-phosphoryl)-piperazin-1-yl]-6-fluoro-4-oxo-1,4-dihydro-quinoline-3-carboxylic acid {3-[5-Cyano-1-(4-fluoro-phenyl)-1,3-dihydro-isobenzofuran-1-yl]-propyl}-methyl-phosphoramidic acid diethyl ester

[4-(8-Chloro-5H-dibenzo[b,e][1,4]diazepin-11-yl)-piperazin-1-yl]-phosphonic acid diethyl ester (3-Dibenzo[a,d]cyclohepten-5-ylidene-propyl)-methyl-phosphoramidic acid diethyl ester

[3-(10,11-Dihydro-dibenzo[b,f]azepin-5-yl)-propyl]-methyl-phosphoramidic acid diethyl ester

[4-(8-Chloro-5,6-dihydro-benzo[5,6]cyclohepta[1,2-b]pyridin-11-ylidene)-piperidin-1-yl]-phosphonic acid diethyl ester (6-Ethyl-8-methoxy-11-propyl-1,2,5,6-tetrahydro-4H-2,6-methano-benzo[d]azocin-3-yl)-phosphonic acid diethyl ester {2-[(2,6-Dichloro-phenyl)-(diethoxy-phosphoryl)-amino]-phenyl}-acetic acid

[3-(6H-Dibenzo[b,e]oxepin-11-ylidene)-propyl]-methyl-phosphoramidic acid diethyl ester Methyl-[2-(1-phenyl-1-pyridin-2-yl-ethoxy)-ethyl]-phosphoramidic acid diethyl ester Methyl-[2-(naphthalen-1-yloxy)-2-thiophen-2-yl-ethyl]-phosphoramidic acid diethyl ester {2-[5-(2-Benzenesulfonyl-ethyl)-1H-indol-3-ylmethyl]-pyrrolidin-1-yl}-phosphonic acid diethyl ester (2-Hydroxy-1-methyl-2-phenyl-ethyl)-methyl-phosphoramidic acid diethyl ester {3-[5-Cyano-1-(4-fluoro-phenyl)-1,3-dihydro-isobenzofuran-11(S)-yl]-propyl}-methyl-phosphoramidic acid diethyl ester

[3-(4-Methoxy-phenoxymethyl)-4-phenyl-piperidin-1-yl]-phosphonic acid diethyl ester Ethyl-[1-methyl-2-(3-trifluoromethyl-phenyl)-ethyl]-phosphoramidic acid diethyl ester Ethyl-[2-phenyl-2-(4-trifluoromethyl-phenoxy)-ethyl]-phosphoramidic acid diethyl ester
(6-Carbamoyl-2,3,4,9-tetrahydro-1H-carbazol-3-yl)-methyl-phosphoramidic acid diethyl ester
6H-benzofuro[3a,3,2-ef][2]benzazepin-6-ol,4a,5,9,10,11,12-hexahydro-3-methoxy-11-methyl-, (4aS,6-R,8aS)-phosphoramidic acid diethyl ester
1-Cyclopropyl-7-[4-(diethoxy-phosphoryl)-3-methyl-piperazin-1-yl]-6-fluoro-8-methoxy-4-oxo-1,4-dihydro-quinoline-3-carboxylic acid
1-Cyclopropyl-7-[4-(diethoxy-phosphoryl)-3-methyl-piperazin-1-yl]6-fluoro-5-methyl-4-oxo-1,4-dihydro-quinoline-3-carboxylic acid
Butyl-[3-(6,8-dichloro-3-trifluoromethyl-phenanthren-9-yl)-3-hydroxy-propyl]-phosphoramidic acid diethyl ester
9-[4-(Diethoxy-phosphoryl)-piperazin-1-yl]-8-fluoro-6-oxo-2,3-dihydro-6H-1-oxa-3a-aza-phenalene-5-carboxylic acid
7-[4-(Diethoxy-phosphoryl)-3-methyl-piperazin-1-yl]-1-ethyl-6,8-difluoro-4-oxo-1,4-dihydro-quinoline-3-carboxylic acid
[4-(8-Chloro-dibenzo[b,f][1,4]oxazepin-11-yl)-piperazin-1-yl]-phosphonic acid diethyl ester
[9,10-ethanoanthracene-9(10H)-propylamine]-methyl phosphoramidic acid diethyl ester
(2-Benzo[1,3]dioxol-5-yl-1-methyl-ethyl)-methyl-phosphoramidic acid diethyl ester
[4-(3-Chloro-phenyl)-piperazin-1-yl]-phosphonic acid diethyl ester
Methyl-(1-methyl-4-oxo-3,3-diphenyl-hexyl)-phosphoramidic acid diethyl ester
Methyl-(1-methyl-2-phenyl-ethyl)-phosphoramidic acid diethyl ester
[1-(Diethoxy-phosphoryl)-piperidin-2-yl]-phenyl-acetic acid methyl ester
[2-(2-Methoxy-phenyl)-1-methyl-ethyl]-phosphoramidic acid diethyl ester
(3,4,9,13b-Tetrahydro-1H-2,4a-diaza-tribenzo[a,c,e]cyclohepten-2-yl)-phosphonic acid diethyl ester
(3,4,9,13b-Tetrahydro-1H-2,4a,5-triaza-tribenzo[a,c,e]cyclohepten-2-yl)-phosphonic acid diethyl ester
1-Cyclopropyl-7-[1-(diethoxy-phosphoryl)-octahydro-pyrrolo[3,4-b]pyridin-6-yl]-6-fluoro-8-methoxy-4-oxo-1,4-dihydro-quinoline-3-carboxylic acid
[4-(6-Methylsulfamoylmethyl-1H-indol-3-yl)-piperidin-1-yl]-phosphonic acid diethyl ester
{4-[1-(4-Fluoro-benzyl)-1H-benzoimidazol-2-ylamino]-piperidin-1-yl}-phosphonic acid diethyl ester
(4-Pyrimidin-2-yl-piperazin-1-yl)-phosphonic acid diethyl ester
[4-(4-Amino-5-chloro-2-methoxy-benzoylamino)-3-methoxy-piperidin-1-yl]-phosphonic acid diethyl ester
(4-Benzhydryl-piperazin-1-yl)-phosphonic acid diethyl ester
7-[4-(Diethoxy-phosphoryl)-piperazin-1-yl]-1-ethyl-6-fluoro-4-oxo-1,4-dihydro-quinoline-3-carboxylic acid
[4-(2-Oxo-2,3-dihydro-benzoimidazol-1-yl)-piperidin-1-yl]-phosphonic acid diethyl ester
[3-(10,11-Dihydro-dibenzo[ad]cyclohepten-5-ylidene)-propyl]-methyl-phosphoramidic acid diethyl ester
{4-[5-Chloro-1-(4-fluoro-phenyl)-1H-indol-3-yl]-piperidin-1-yl}-phosphonic acid diethyl ester
[4-(2-Methyl-4H-3-thia-4,9-diaza-benzo[f]azulen-10-yl)-piperazin-1-yl]-phosphonic acid diethyl ester
Cyclohexyl-hydroxy-phenyl-acetic acid 3-[(diethoxy-phosphoryl)-ethyl-amino]-prop-1-ynyl ester
[3-(Benzo[1,3]dioxol-5-yloxymethyl)-4-(4-fluoro-phenyl)-piperidin-1-yl]-phosphonic acid diethyl ester
(Amino-carbamimidoylimino-methyl)-phenethyl-phosphoramidic acid diethyl ester
(2,5-Dioxo-4,4-diphenyl-imidazolidin-1-yl)-phosphonic acid diethyl ester
{2-Hydroxy-3-[2-(3-phenyl-propionyl)-phenoxy]-propyl}-propyl-phosphoramidic acid diethyl ester
{2-[(2-Ethoxy-phenoxy)-phenyl-methyl]-morpholin-4-yl}-phosphonic acid diethyl ester
(1-Adamantan-1-yl-ethyl)-phosphoramidic acid diethyl ester
Methyl-[2-(5-[1,2,4]triazol-1-ylmethyl-1H-indol-3-yl)-ethyl]-phosphoramidic acid dimethyl ester(1-Methyl-2-phenyl-ethyl)-prop-2-ynyl-phosphoramidic acid diethyl ester
[4-(3,4-Dichloro-phenyl)-1,2,3,4-tetrahydro-naphthalen-1-yl]-methyl-phosphoramidic acid diethyl ester
{1-[1-(4-Chloro-phenyl)-cyclobutyl]-3-methyl-butyl}-methyl-phosphoramidic acid diethyl ester
{1-[1-(4-Chloro-phenyl)-cyclobutyl]-3-methyl-butyl}-phosphoramidic acid diethyl ester
5-Amino-1-cyclopropyl-7-[4-(diethoxy-phosphoryl)-3,5-dimethyl-piperazin-1-yl]-6,8-difluoro-4-oxo-1,4-dihydro-quinoline-3-carboxylic acid
Methyl-[2-(5-methylsulfamoylmethyl-1H-indol-3-yl)-ethyl]-phosphoramidic acid diethyl ester
{2-[4-(1,2-Diphenyl-but-1-enyl)-phenoxy]-ethyl}-methyl-phosphoramidic acid diethyl ester
1-(3,4-Difluoro-phenyl)-7-[4-(diethoxy-phosphoryl)-3-methyl-piperazin-1-yl]-6-fluoro-4-oxo-1,4-dihydro-quinoline-3-carboxylic acid
{2-[2-(2-Methylsulfanyl-phenothiazin-10-yl)-ethyl]-piperidin-1-yl}-phosphonic acid diethyl ester
[2-Hydroxy-2-(3-methoxy-phenyl)-cyclohexylmethyl]-methyl-phosphoramidic acid diethyl ester
[3-Hydroxy-2-(4-methoxy-phenyl)-3-propyl-hexyl]-methyl-phosphoramidic acid diethyl ester
[3-(4-Bromo-phenyl)-3-pyridin-3-yl-allyl]-methyl-phosphoramidic acid diethyl ester
Methyl-{2-[5-(2-oxo-oxazolidin-4-ylmethyl)-1H-indol-3-yl]-ethyl}-phosphoramidic acid diethyl ester The compounds of the present invention can be administered alone but will generally be administered in admixture with a suitable pharmaceutical excipient, diluent or carrier selected with regard to the intended route of administration and standard pharmaceutical practice. For example, the compounds of the present invention can be administered orally, in the form of tablets, capsules, multi-particulates, elixirs, solutions or suspensions, which may contain flavoring or coloring agents, either for immediate-, delayed-, modified-, sustained-, pulsed- or controlled-release applications. Suitable formulations of the compounds of the present invention may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, may be included.

Almotriptan (Axert ®)

Chemical Structure 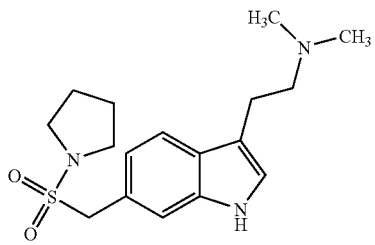 Hydroxylated Metabolite 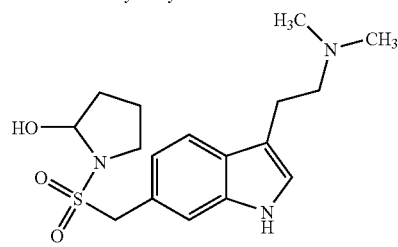

| Compound | R1 | R2 | Chemical Name | Estimated LogP | pKa |
|---|---|---|---|---|---|
| E1229 | hydrogen | hydrogen | Methyl-{2-[6-(pyrrolidine-1-sulfonylmethyl)-1H-indol-3-yl]-ethyl}-phosphoramidic acid | 1.86 | 2.87 |
| E1230 | hydrogen | methyl | Methyl-{2-[6-(pyrrolidine-1-sulfonylmethyl)-1H-indol-3-yl]-ethyl}-phosphoramidic acid monomethyl ester | 1.92 | 4.79 |
| E1231 | methyl | methyl | Methyl-{2-[6-(pyrrolidine-1-sulfonylmethyl)-1H-indol-3-yl]-ethyl}-phosphoramidic acid dimethyl ester | 1.97 | 4.21 |
| E1232 | phenyl | hydrogen | Methyl-{2-[6-(pyrrolidine-1-sulfonylmethyl)-1H-indol-3-yl]-ethyl}-phosphoramidic acid monophenyl ester | 3.69 | 4.35 |
| E1233 | phenyl | methyl | Methyl-{2-[6-(pyrrolidine-1-sulfonylmethyl)-1H-indol-3-yl]-ethyl}-phosphoramidic acid methyl ester phenyl ester | 3.74 | 3.77 |

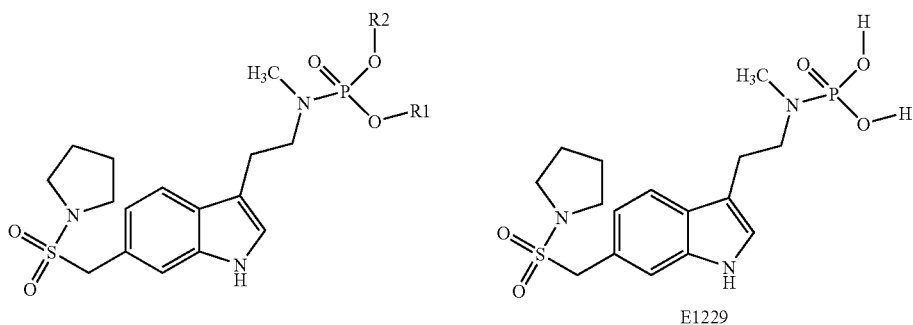

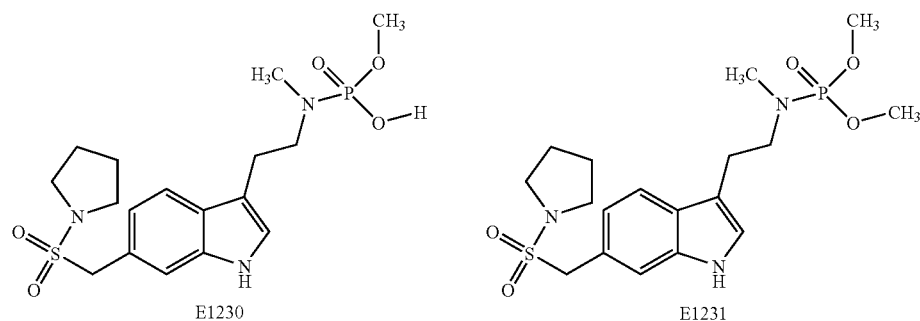

-continued

Almotriptan (Axert ®)

Chemical Structure 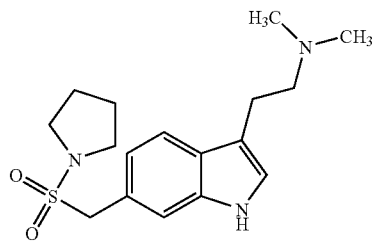

Hydroxylated Metabolite 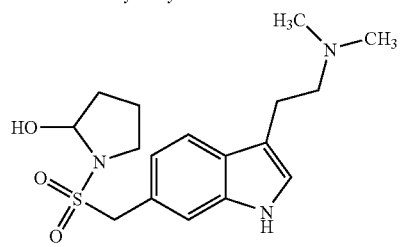

| Compound | R1 | R2 | Chemical Name | Estimated LogP | pKa |
|---|---|---|---|---|---|

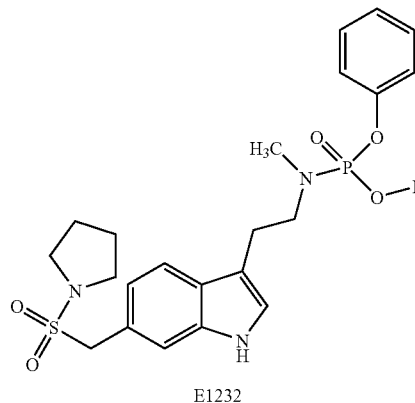

E1232

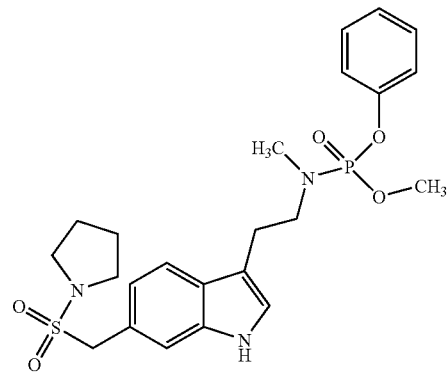

E1233

Amoxapine (Ascendin ®)

Chemical Structure 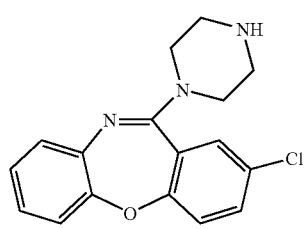

Hydroxylated Metabolite 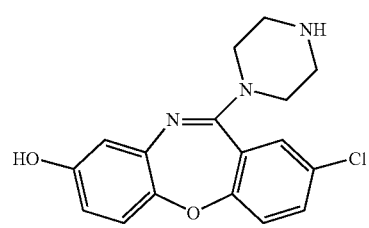

| Compound | R1 | R2 | Chemical Name | Estimated LogP | pKa |
|---|---|---|---|---|---|
| E1121 | hydrogen | hydrogen | [4-(2-Chloro-dibenzo[b,f][1,4]oxazepin-11-yl)-piperazin-1-yl]-phosphonic acid | 2.97 | 4.83 |
| E1122 | hydrogen | methyl | [4-(2-Chloro-dibenzo[b,f][1,4]oxazepin-11-yl)-piperazin-1-yl]-phosphonic acid monomethyl ester | 3.03 | 2.59 |
| E1123 | methyl | methyl | [4-(2-Chloro-dibenzo[b,f][1,4]oxazepin-11-yl)-piperazin-1-yl]-phosphonic acid dimethyl ester | 3.93 | 5.90 |
| E1124 | phenyl | hydrogen | [4-(2-Chloro-dibenzo[b,f][1,4]oxazepin-11-yl)-piperazin-1-yl]-phosphonic acid monophenyl ester | 5.64 | 2.35 |

-continued
Amoxapine (Ascendin ®)
Chemical Structure
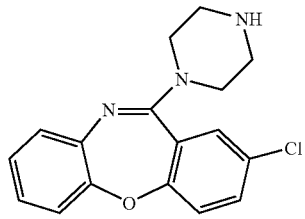
Hydroxylated Metabolite
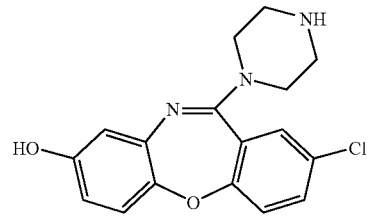
| Compound | R1 | R2 | Chemical Name | Estimated LogP | pKa |
|---|---|---|---|---|---|
| E1125 | phenyl | methyl | [4-(2-Chloro-dibenzo[b,f][1,4]oxazepin-11-yl)-piperazin-1-yl]-phosphonic acid methyl ester phenyl ester | 5.70 | 6.04 |
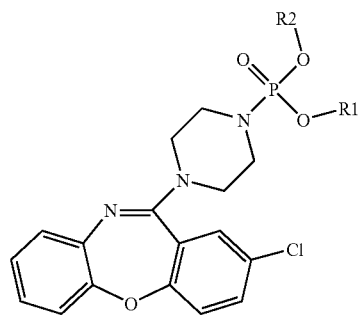
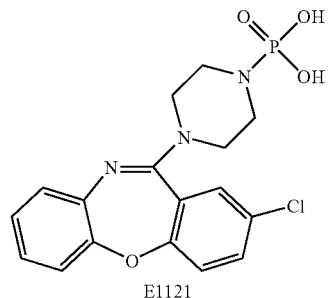
E1121
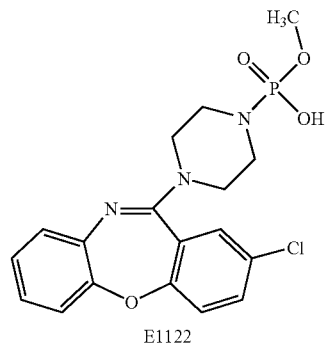
E1122
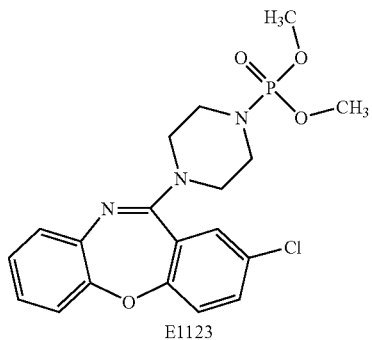
E1123
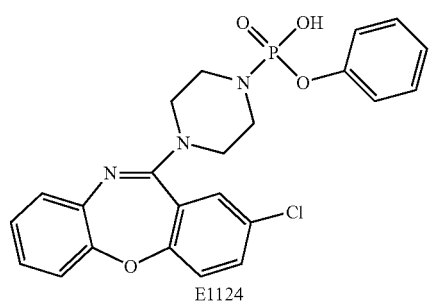
E1124
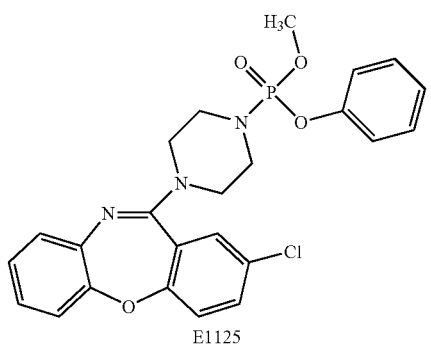
E1125

| Amphetamine (Adderall ®) | | | | | |
|---|---|---|---|---|---|
| Chemical Structure | | | Hydroxylated Metabolite | | |
| 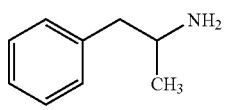 | | | 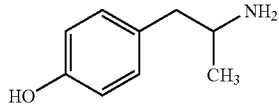 | | |
| Compound | R1 | R2 | Chemical Name | Estimated LogP | pKa |
| E1222 | hydrogen | hydrogen | (1-Methyl-2-phenyl-ethyl)-phosphoramidic acid | 1.48 | 1.90 |
| E1223 | hydrogen | methyl | (1-Methyl-2-phenyl-ethyl)-phosphoramidic acid monomethyl ester | 1.54 | 6.07 |
| E1224 | methyl | methyl | (1-Methyl-2-phenyl-ethyl)-phosphoramidic acid dimethyl ester | | |
| E1225 | phenyl | hydrogen | (1-Methyl-2-phenyl-ethyl)-phosphoramidic acid monophenyl ester | 3.31 | 5.61 |
| E1226 | phenyl | methyl | (1-Methyl-2-phenyl-ethyl)-phosphoramidic acid cyclohexa-1,5-dienyl ester | 3.36 | 3.36 |

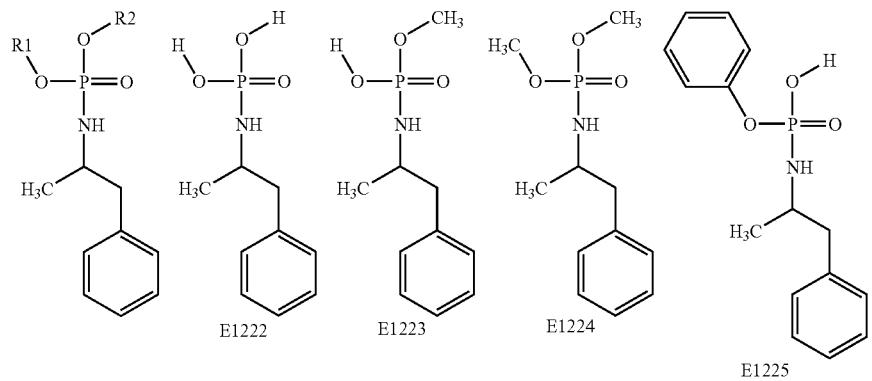

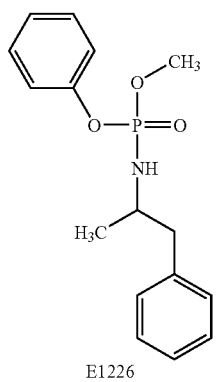

| Atomoxetine (Strattera ®) | |
|---|---|
| Chemical Structure | Hydroxylated Metabolite |
| 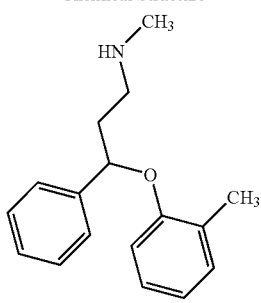 | 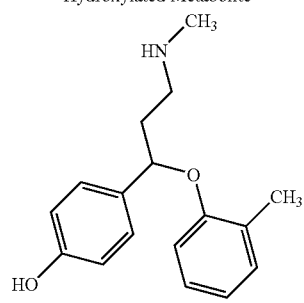 |

| Compound | R1 | R2 | Chemical Name | Estimated LogP | pKa |
|---|---|---|---|---|---|
| E1021 | hydrogen | hydrogen | Methyl-(3-phenyl-3-o-tolyloxy-propyl)-phosphoramidic acid | 3.82 | 3.48 |
| E1022 | hydrogen | methyl | Methyl-(3-phenyl-3-o-tolyloxy-propyl)-phosphoramidic acid monomethyl ester | 3.87 | 4.18 |
| E1023 | methyl | methyl | Methyl-(3-phenyl-3-o-tolyloxy-propyl)-phosphoramidic acid dimethyl ester | 3.93 | 3.47 |
| E1024 | phenyl | hydrogen | Methyl-(3-phenyl-3-o-tolyloxy-propyl)-phosphoramidic acid monophenyl ester | 5.64 | 3.75 |
| E1025 | phenyl | methyl | Methyl-(3-phenyl-3-o-tolyloxy-propyl)-phosphoramidic acid methyl ester phenyl ester | 5.70 | 4.02 |

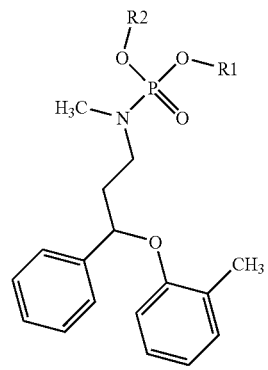

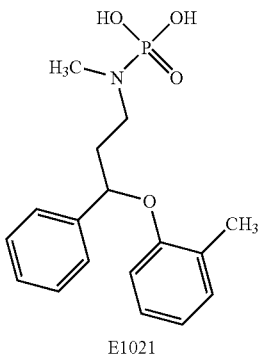

E1021

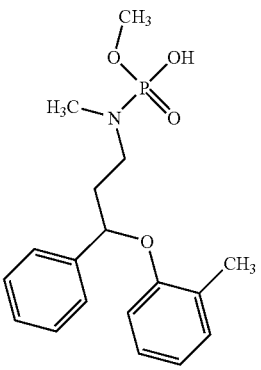

E1022

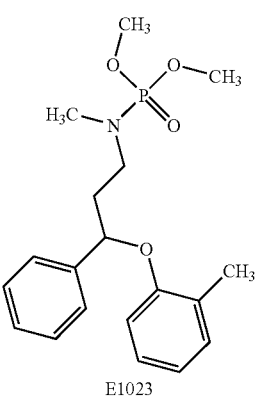

E1023

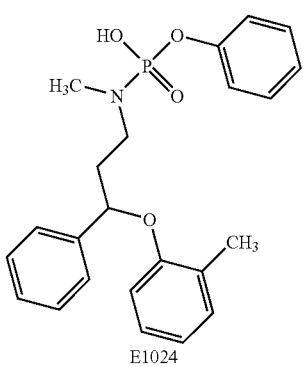

E1024

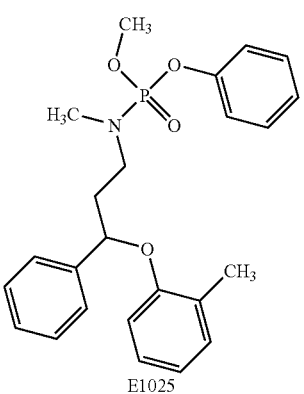

E1025

| Azelastine (Azelastin ®) | | | | | |
|---|---|---|---|---|---|
| Chemical Structure | | | Active Metabolite Structure | | |

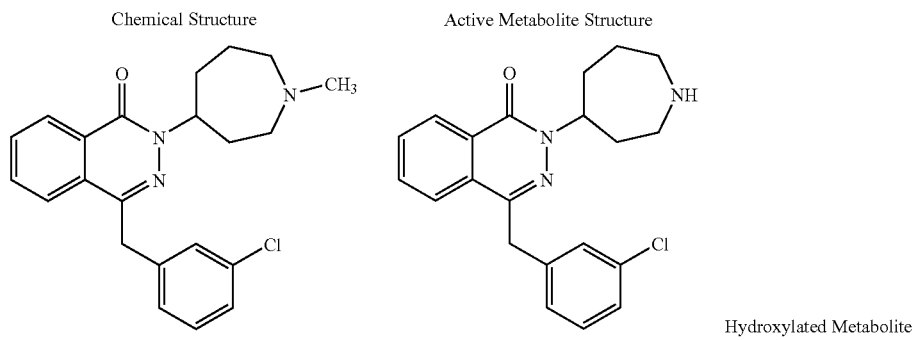

Hydroxylated Metabolite

| Compound | R1 | R2 | Chemical Name | Estimated LogP | pKa |
|---|---|---|---|---|---|
| E1234 | hydrogen | hydrogen | {4-[4-(3-Chloro-benzyl)-1-oxo-1H-phthalazin-2-yl]-aze-pan-1-yl}-phosphonic acid | 5.10 | 3.41 |
| E1235 | hydrogen | methyl | {4-[4-(3-Chloro-benzyl)-1-oxo-1H-phthalazin-2-yl]-aze-pan-1-yl}-phosphonic acid monomethyl ester | 5.15 | 4.25 |
| E1236 | methyl | methyl | {4-[4-(3-Chloro-benzyl)-1-oxo-1H-phthalazin-2-yl]-aze-pan-1-yl}-phosphonic acid dimethyl ester | 5.21 | 4.48 |
| E1237 | phenyl | hydrogen | {4-[4-(3-Chloro-benzyl)-1-oxo-1H-phthalazin-2-yl]-aze-pan-1-yl}-phosphonic acid monophenyl ester | 6.92 | 3.78 |
| E1238 | phenyl | methyl | {4-[4-(3-Chloro-benzyl)-1-oxo-1H-phthalazin-2-yl]-aze-pan-1-yl}-phosphonic acid methyl ester phenyl ester | 6.98 | 4.65 |

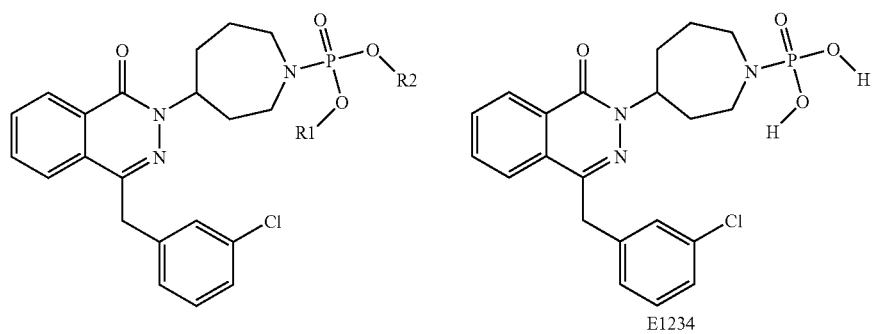

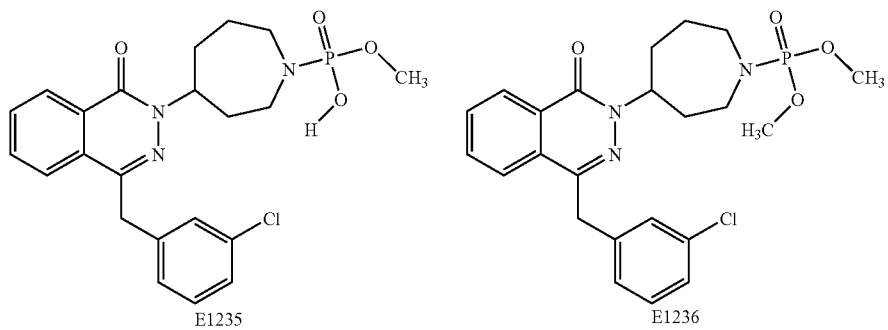

Azelastine (Azelastin ®)

Chemical Structure | Active Metabolite Structure

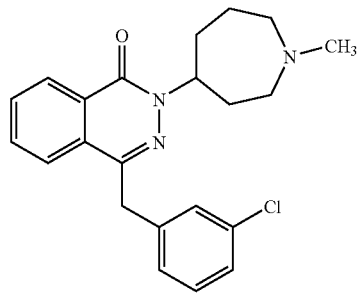 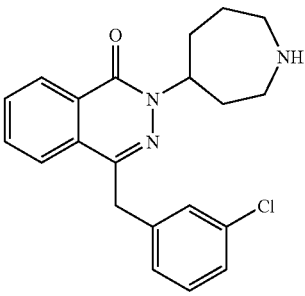

Hydroxylated Metabolite

| Compound | R1 | R2 | Chemical Name | Estimated LogP | pKa |
|---|---|---|---|---|---|

E1237

E1238

Carbamazepine (Tegetrol ®)

Chemical Structure | Hydroxylated Metabolite

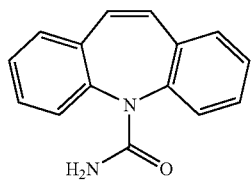 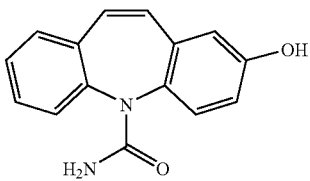

| Compound | R1 | R2 | Chemical Name |
|---|---|---|---|
| E1179 | hydrogen | hydrogen | (Dibenzo[b,f]azepine-5-carbonyl)-phosphoramidic acid |
| E1180 | hydrogen | methyl | (Dibenzo[b,f]azepine-5-carbonyl)-phosphoramidic acid monomethyl ester |
| E1181 | methyl | methyl | (Dibenzo[b,f]azepine-5-carbonyl)-phosphoramidic acid dimethyl ester |
| E1182 | phenyl | hydrogen | (Dibenzo[b,f]azepine-5-carbonyl)-phosphoramidic acid monophenyl ester |

-continued
Carbamazepine (Tegetrol ®)
Chemical Structure 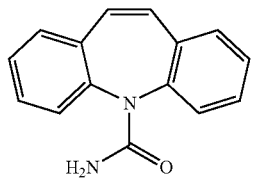
Hydroxylated Metabolite 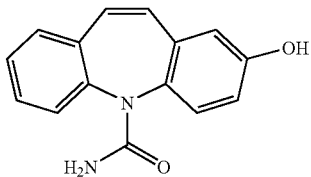
| Compound | R1 | R2 | Chemical Name |
|---|---|---|---|
| E1183 | phenyl | methyl | (Dibenzo[b,f]azepine-5-carbonyl)-phosphoramidic acid methyl ester phenyl ester |
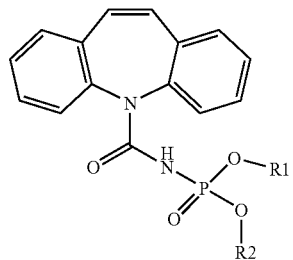
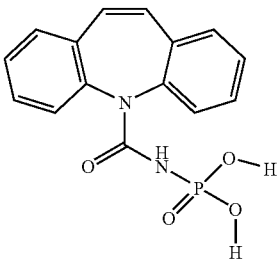
E1179
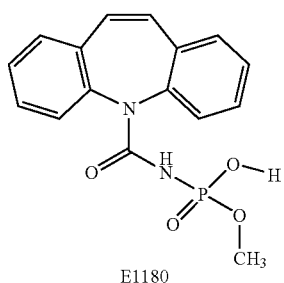
E1180
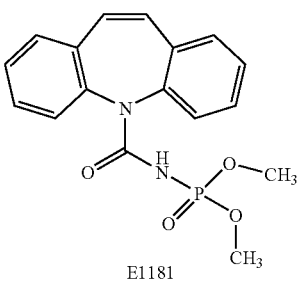
E1181
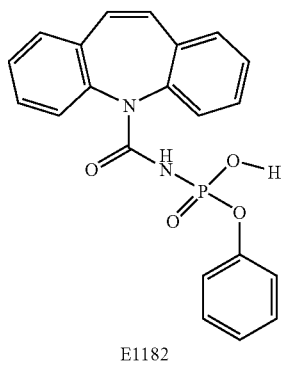
E1182
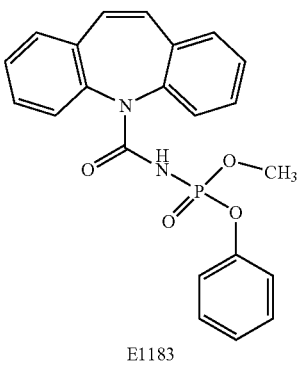
E1183

| Chlorpheniramine (Chlor-Trimetron ®) | |
|---|---|
| Chemical Structure | Hydroxylated Metabolite |

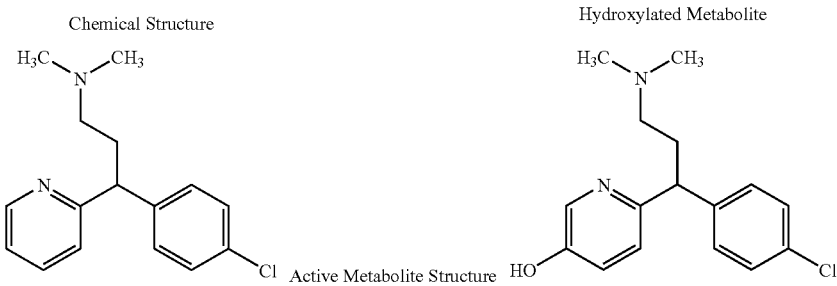

Active Metabolite Structure

| Compound | R1 | R2 | Chemical Name |
|---|---|---|---|
| E1349 | hydrogen | hydrogen | [3-(4-Chloro-phenyl)-3-pyridin-2-yl-propyl]-methyl-phosphoramidic acid |
| E1350 | hydrogen | methyl | [3-(4-Chloro-phenyl)-3-pyridin-2-yl-propyl]-methyl-phosphoramidic acid monomethyl ester |
| E1351 | methyl | methyl | [3-(4-Chloro-phenyl)-3-pyridin-2-yl-propyl]-methyl-phosphoramidic acid dimethyl ester |
| E1352 | hydrogen | phenyl | [3-(4-Chloro-phenyl)-3-pyriidn-2-yl-propyl]-methyl-phosphoramidic acid monophenyl ester |
| E1353 | methyl | phenyl | [3-(4-Chloro-phenyl)-3-pyridin-2-yl-propyl]-methyl-phosphoramidic acid methyl ester phenyl ester |

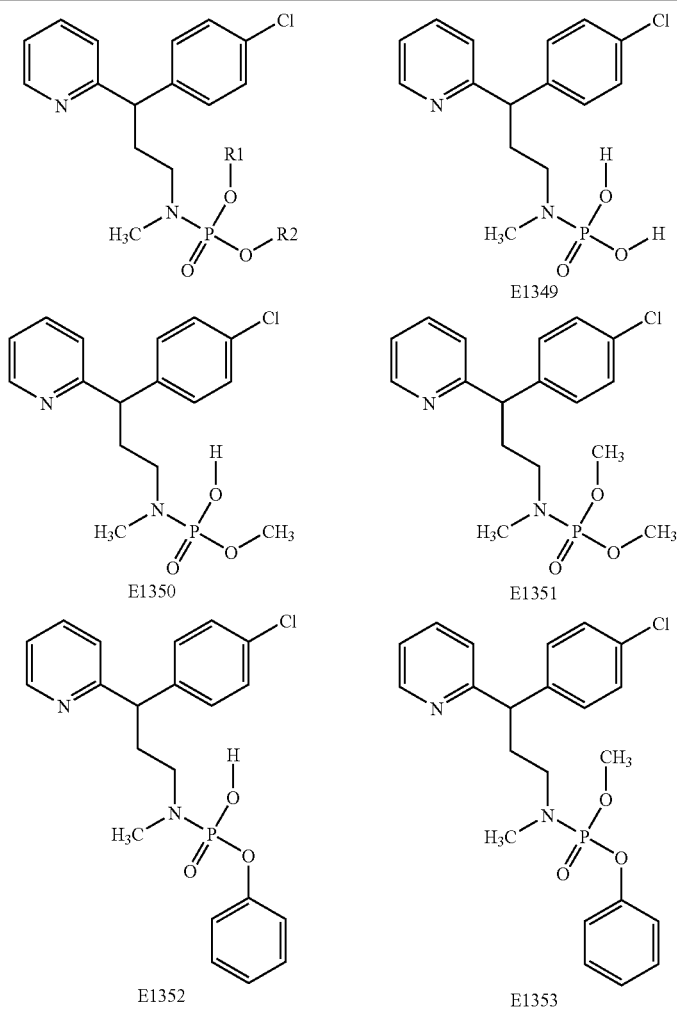

| Chlorphenoxamine (Phenoxene ®) | |
|---|---|
| Chemical Structure | Hydroxylated Metabolite |

Active Metabolite Structure

| Compound | R1 | R2 | Chemical Name |
|---|---|---|---|
| E1354 | hydrogen | hydrogen | {2-[1-(4-Chloro-phenyl)-1-phenyl-ethoxy]-ethyl}-methyl-phosphoramidic acid |
| E1355 | hydrogen | methyl | {2-[1-(4-Chloro-phenyl)-1-phenyl-ethoxy]-ethyl}-methyl-phosphoramidic acid monomethyl ester |
| E1356 | methyl | methyl | {2-[1-(4-Chloro-phenyl)-1-phenyl-ethoxy]-ethyl}-methyl-phosphoramidic acid dimethyl ester |
| E1357 | phenyl | hydrogen | {2-[1-(4-Chloro-phenyl)-1-phenyl-ethoxy]-ethyl}-methyl-phosphoramidic acid monophenyl ester |
| E1358 | phenyl | methyl | {2-[1-(4-Chloro-phenyl)-1-phenyl-ethoxy]-ethyl}-methyl-phosphoramidic acid methyl ester phenyl ester |

| Chlorpromazine (Thorazine ®) | | | | | |
|---|---|---|---|---|---|
| Chemical Structure | | Active Metabolite Structure | | Hydroxylated Metabolite | |
| 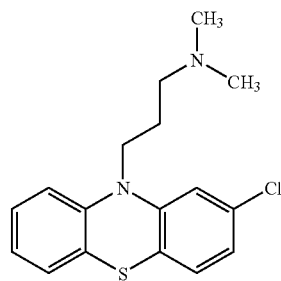 | | 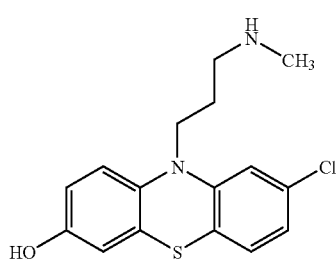 | | 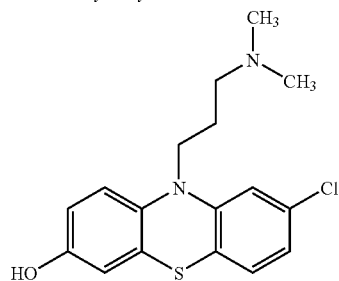 | |
| Compound | R1 | R2 | Chemical Name | Estimated LogP | Estimated Pka |
| E1154 | hydrogen | hydrogen | [3-(2-Chloro-phenothiazin-10-yl)-propyl]-methyl-phosphoramidic acid | 4.58 | 3.29 |
| E1155 | hydrogen | methyl | [3-(2-Chloro-phenothiazin-10-yl)-propyl]-methyl-phosphoramidic acid monomethyl ester | 4.64 | 4.36 |
| E1156 | methyl | methyl | [3-(2-Chloro-phenothiazin-10-yl)-propyl]-methyl-phosphoramidic acid dimethyl ester | 4.69 | 3.55 |
| E1157 | phenyl | hydrogen | [3-(2-Chloro-phenothiazin-10-yl)-propyl]-methyl-phosphoramidic acid monophenyl ester | 6.40 | 3.93 |
| E1158 | phenyl | methyl | [3-(2-Chloro-phenothiazin-10-yl)-propyl]-methyl-phosphoramidic acid methyl ester phenyl ester | 6.46 | 4.11 |

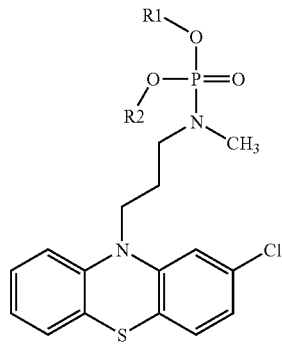

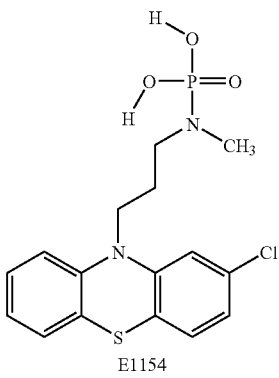

E1154

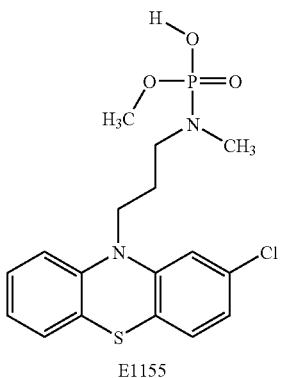

E1155

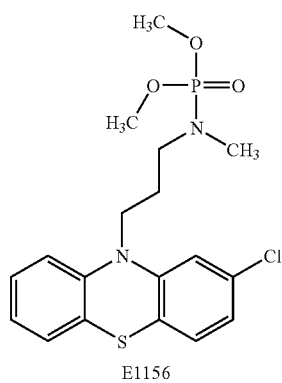

E1156

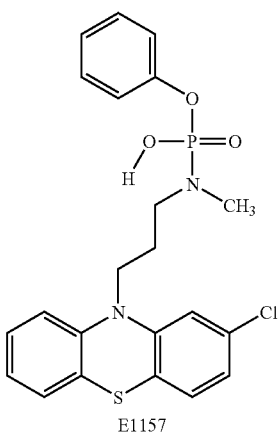

E1157

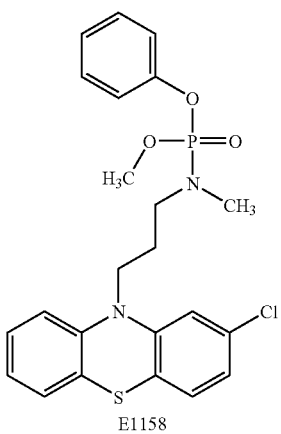

E1158

| Ciprofloxacin (Cipro ®) | | | | | |
|---|---|---|---|---|---|
| Chemical Structure | | | | | |
| 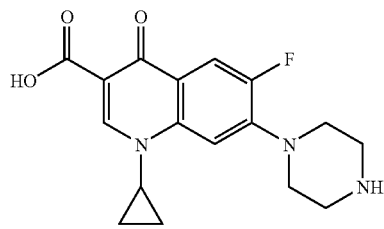 | | | | | |
| | | | | Hydroxylated Metabolite | |
| Compound | R1 | R2 | Chemical Name | Estimated LogP | pKa |
| E1239 | hydrogen | hydrogen | 1-Cyclopropyl-6-fluoro-4-oxo-7-(4-phosphono-piperain-1-yl)-1,4-dihydro-quinoline-3-carboxylic acid | 1.28 | 5.63 |
| E1240 | hydrogen | methyl | 1-Cyclopropyl-6-fluoro-7-[4-(hydroxy-methoxy-phosphoryl)-piperazin-1-yl]-4-oxo-1,4-dihydro-quinoline-3-carboxylic acid | 1.34 | 2.03 |
| E1241 | methyl | methyl | 1-Cyclopropyl-7-[4-(dimethyoxy-phosphoryl)-piperazin-1-yl]-6-fluoro-4-oxo-1,4-dihydro-quinoline-3-carboxylic acid | 1.40 | 6.70 |
| E1242 | phenyl | hydrogen | 1-Cyclopropyl-6-fluoro-7-[4-(hydroxy-phenoxy-phosphoryl)-piperazin-1-yl]-4-oxo-1,4-dihydro-quinoline-3-carboxylic acid | 3.11 | 1.56 |
| E1243 | phenyl | methyl | 1-Cyclopropyl-6-fluoro-7-[4-(methoxy-phenoxy-phosphoryl)-piperazin-1-yl]-4-oxo-1,4-dihydro-quinoline-3-carboxylic acid | 3.16 | 6.83 |

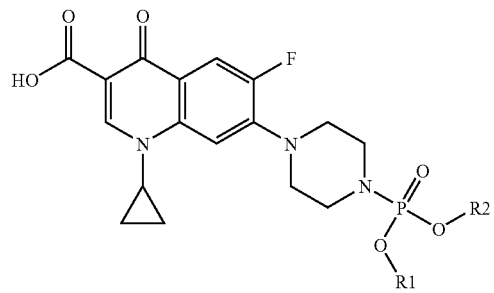

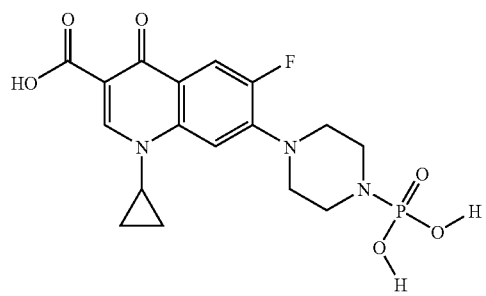

E1239

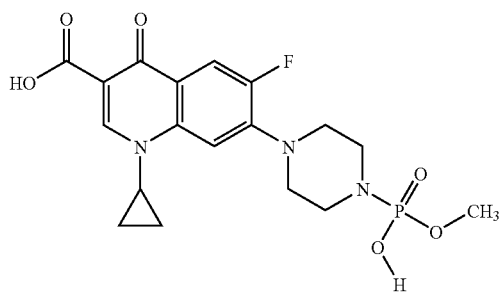

E1240

Ciprofloxacin (Cipro ®)
Chemical Structure
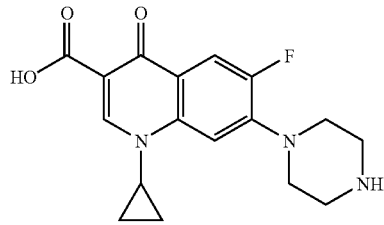
Hydroxylated Metabolite
| Compound | R1 | R2 | Chemical Name | Estimated LogP | pKa |
|---|---|---|---|---|---|
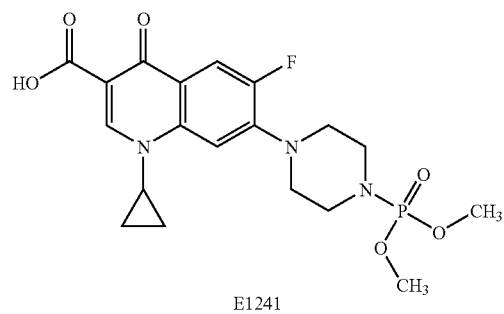
E1241
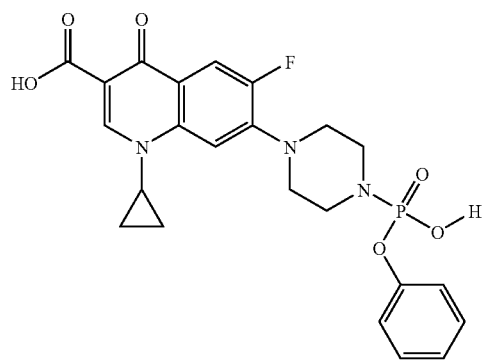
E1242
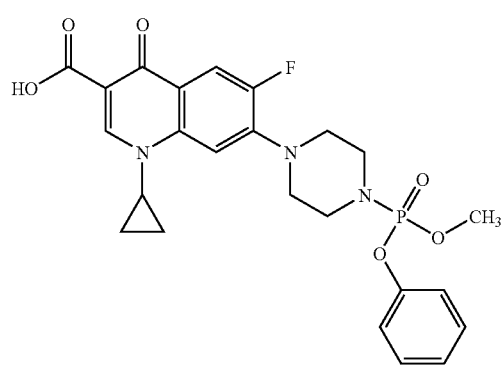
E1243

| Citalopram (Celexa ®) | |
|---|---|
| Chemical Structure | Active Metabolite Structure |
| 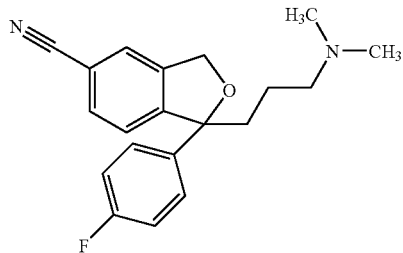 | 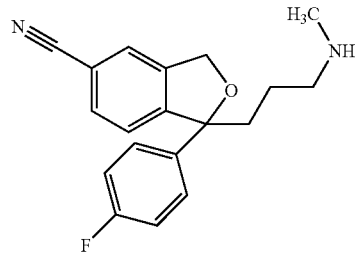 |

| Compound | R1 | R2 | Chemical Name | Estimated LogP | Estimated pKa |
|---|---|---|---|---|---|
| E1031 | hydrogen | hydrogen | {3-[5-Cyano-1-(4-fluoro-phenyl)-1,3-dihydro-iso-benzofuran-1-yl]-propyl}-methyl-phosphoramidic acid | 3.12 | 3.35 |
| E1032 | hydrogen | methyl | {3-[5-Cyano-1-(4-fluoro-phenyl)-1,3{3-[5-Cyano-1-(4-fluoro-phenyl)-1,3-dihydro-isobenzofuran-1-yl]-propyl}-methyl-phosphoramidic acid monomethyl ester | 3.17 | 4.31 |
| E1033 | methyl | methyl | {3-[5-Cyano-1-(4-fluoro-phenyl)-1,3-dihydro-iso-benzofuran-1-yl]-propyl}-methyl-phosphoramidic acid dimethyl ester | 3.23 | 4.43 |
| E1034 | phenyl | hydrogen | {3-[5-Cyano-1-(4-fluoro-phenyl)-1,3-dihydro-iso-benzofuran-1-yl]-propyl}-methyl-phosphoramidic acid monophenyl ester | 4.94 | 3.86 |
| E1035 | phenyl | methyl | {3-[5-Cyano-1-(4-fluoro-phenyl)-1,3-dihydro-iso-benzofuran-1-yl]-propyl}-methyl-phosphoramidic acid methyl ester phenyl ester | 5.00 | 4.99 |

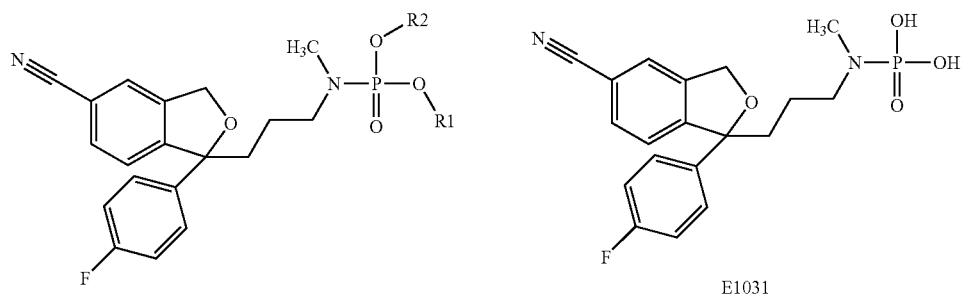

E1031

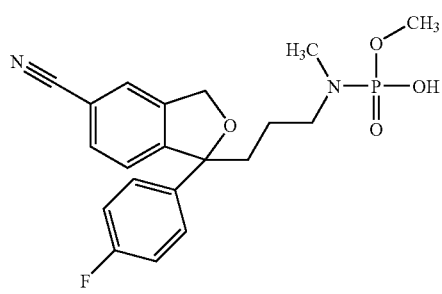

E1032

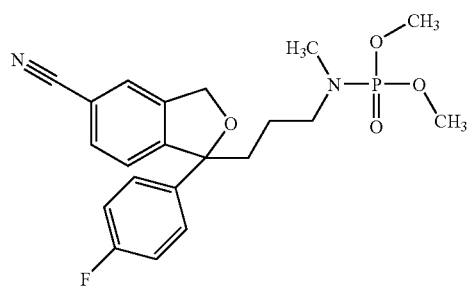

E1033

| Citalopram (Celexa ®) | |
|---|---|
| Chemical Structure | Active Metabolite Structure |
| 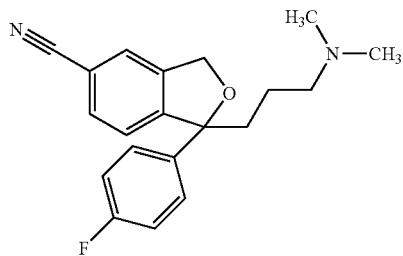 | 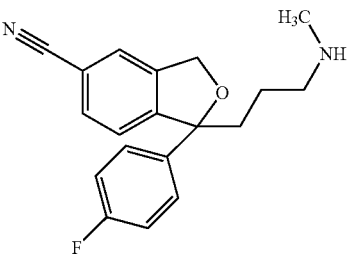 |

| Compound | R1 | R2 | Chemical Name | Estimated LogP | Estimated pKa |
|---|---|---|---|---|---|

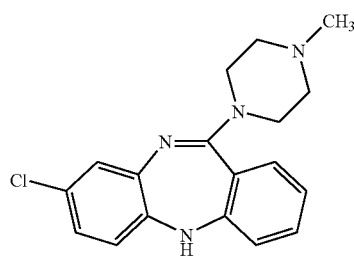 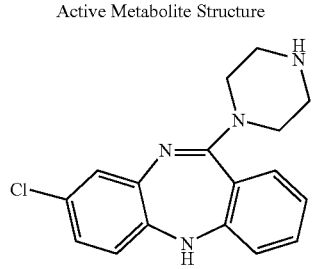

E1034          E1035

| Clozapine (Clozaril ®) | | |
|---|---|---|
| Chemical Structure | Active Metabolite Structure | Hydroxylated Metabolite |

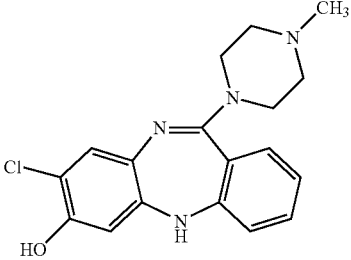

| Compound | R1 | R2 | Chemical Name | Estimated LogP | Estimated pKa |
|---|---|---|---|---|---|
| E1041 | hydrogen | hydrogen | [4-(8-Chloro-5H-dibenzo[b,e][1,4]diazepin-11-yl)-piperazin-1-yl]-phosphonic acid | 2.21 | 4.67 |
| E1042 | hydrogen | methyl | [4-(8-Chloro-5H-dibenzo[b,e][1,4]diazepin-11-yl)-piperazin-1-yl]-phosphonic acid monomethyl ester | 2.27 | 2.99 |
| E1043 | methyl | methyl | [4-(8-Chloro-5H-dibenzo[b,e][1,4]diazepin-11-yl)-piperazin-1-yl]-phosphonic acid dimethyl ester | 2.32 | 5.74 |
| E1044 | phenyl | hydrogen | 4-(8-Chloro-5H-dibenzo[b,e][1,4]diazepin-11-yl)-piperazin-1-yl]-phosphonic acid monophenyl ester | 4.04 | 5.89 |

Clozapine (Clozaril ®)
Chemical Structure 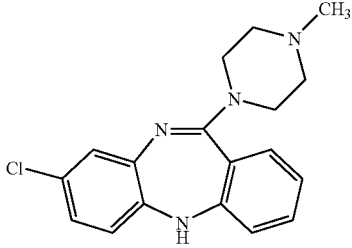
Active Metabolite Structure 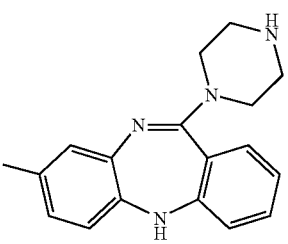
Hydroxylated Metabolite 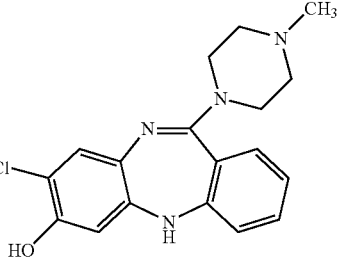
| Compound | R1 | R2 | Chemical Name | Estimated LogP | Estimated pKa |
|---|---|---|---|---|---|
| E1045 | phenyl | methyl | [4-(8-Chloro-5H-dibenzo[b,e][1,4]diazepin-11-yl)-piperazin-1-yl]-phosphonic acid methyl ester phenyl ester | 4.09 | 2.52 |
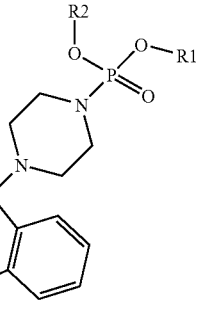
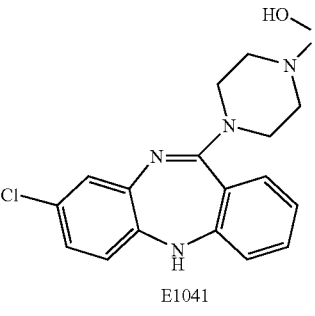
E1041
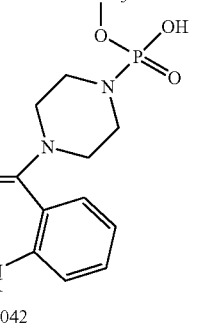
E1042
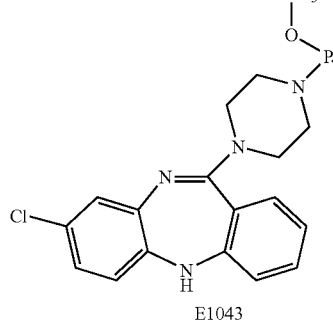
E1043
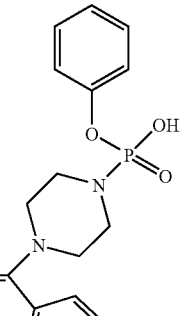
E1044
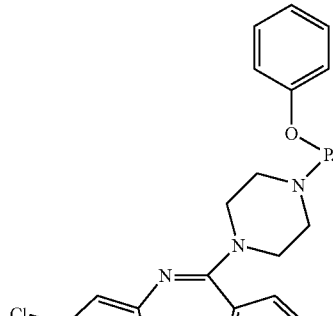
E1045

| Cyclobenzaprine (Flexeril ®) |

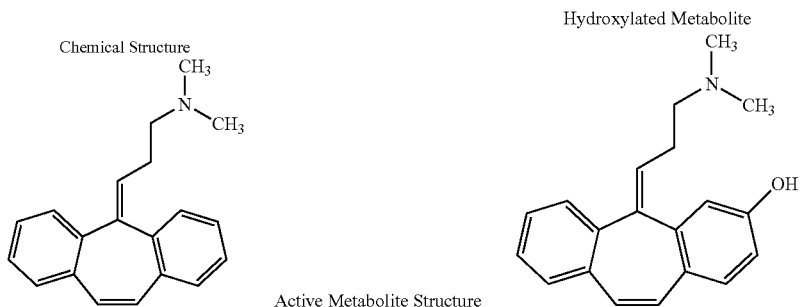

| Compound | R1 | R2 | Chemical Name |
|---|---|---|---|
| E1359 | hydrogen | hydrogen | (3-Dibenzo[a,d]cyclohepten-5-ylidene-propyl)-methyl-phosphoramidic acid |
| E1360 | hydrogen | methyl | (3-Dibenzo[a,d]cyclohepten-5-ylidene-propyl)-methyl-phosphoramidic acid monomethyl ester |
| E1361 | methyl | methyl | (3-Dibenzo[a,d]cyclohepten-5-ylidene-propyl)-methyl-phosphoramidic acid dimethyl ester |
| E1362 | phenyl | hydrogen | (3-Dibenzo[a,d]cyclohepten-5-ylidene-propyl)-methyl-phosphoramidic acid monophenyl ester |
| E1363 | phenyl | methyl | (3-Dibenzo[a,d]cyclohepten-5-ylidene-propyl)-methyl-phosphoramidic acid methyl ester phenyl ester |

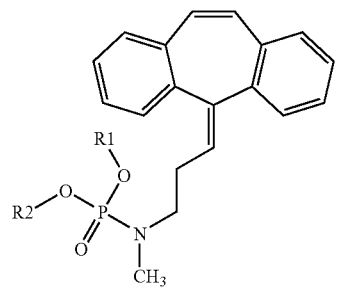

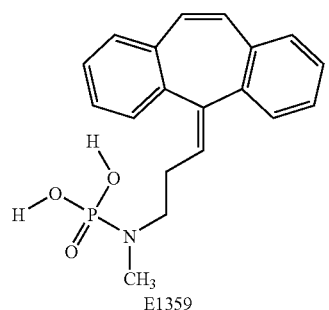

E1359

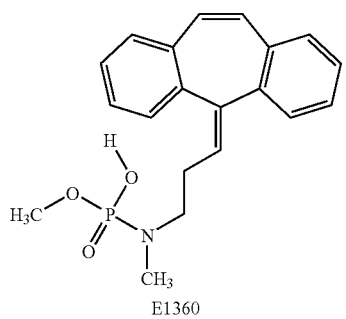

E1360

| Cyclobenzaprine (Flexeril ®) |
|---|
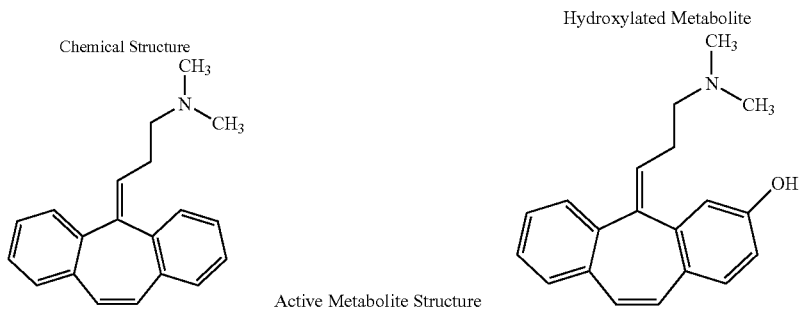
| Compound | R1 | R2 | Chemical Name |
|---|---|---|---|
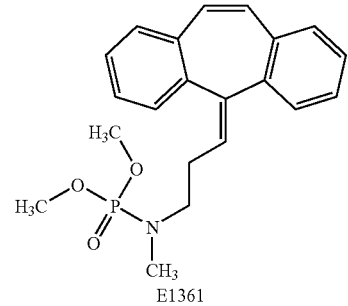
E1361
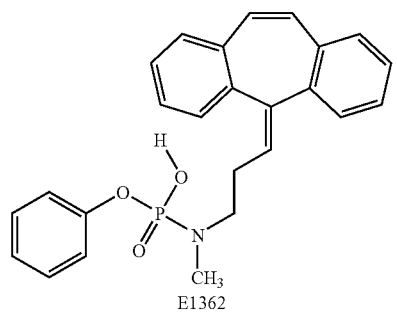
E1362
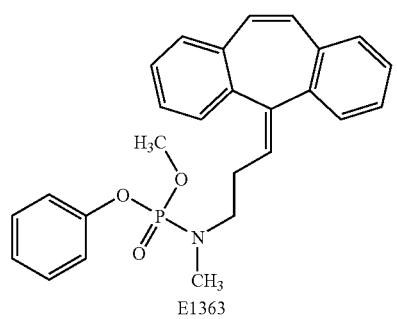
E1363

| Desipramine (Norpramin ®) | |
|---|---|
| Chemical Structure 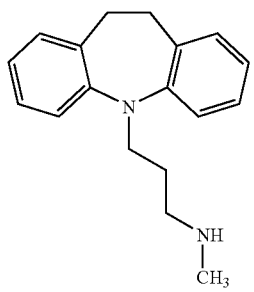 | Hydroxylated Metabolite 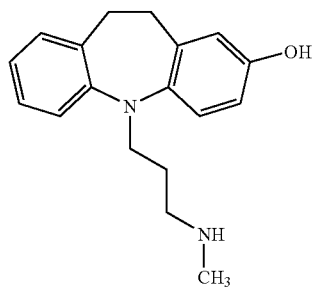 |

| Compound | R1 | R2 | Chemical Name | Estimated LogP | pKa |
|---|---|---|---|---|---|
| E1056 | hydrogen | hydrogen | [3-(10,11-Dihydro-dibenzo[b,f]azepin-5-yl)-propyl]-methyl-phosphoramidic acid | 4.38 | 3.01 |
| E1057 | hydrogen | methyl | [3-(10,11-Dihydro-dibenzo[b,f]azepin-5-yl)-propyl]-methyl-phosphoramidic acid monomethyl ester | 4.44 | 4.64 |
| E1058 | methyl | methyl | [3-(10,11-Dihydro-dibenzo[b,f]azepin-5-yl)-propyl]-methyl-phosphoramidic acid dimethyl ester | 4.50 | 3.27 |
| E1059 | phenyl | hydrogen | [3-(10,11-Dihydro-dibenzo[b,f]azepin-5-yl)-propyl]-methyl-phosphoramidic acid monophenyl ester | 6.21 | 4.20 |
| E1060 | phenyl | methyl | [3-(10,11-Dihydro-dibenzo[b,f]azepin-5-yl)-propyl]-methyl-phosphoramidic acid methyl ester phenyl ester | 6.26 | 3.83 |

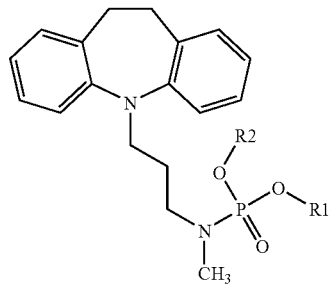

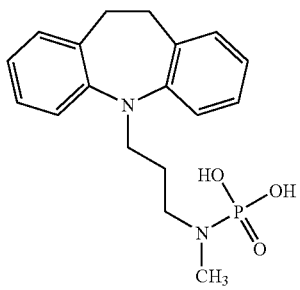
E1056

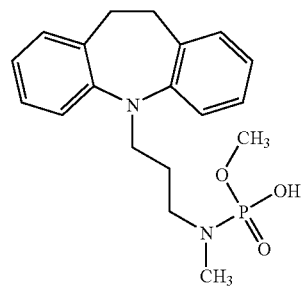
E1057

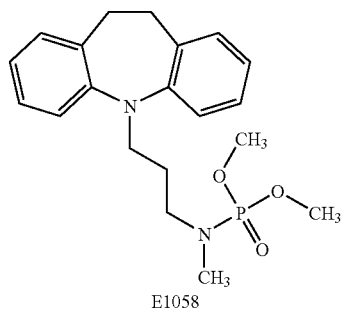
E1058

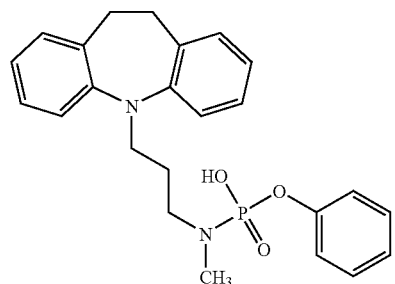
E1059

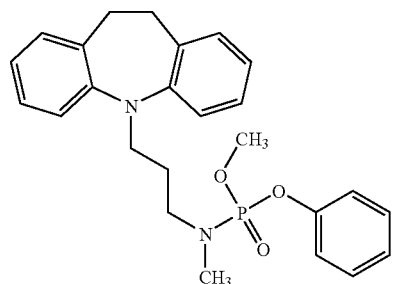
E1060

| Desloratadine (Clarinex ®) |
|---|

Chemical Structure

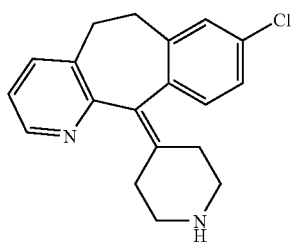

Hydroxylated Metabolite

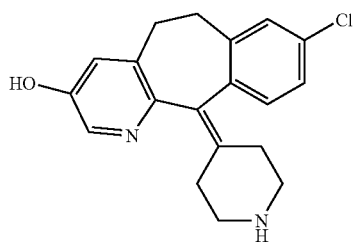

| Compound | R1 | R2 | Chemical Name | Estimated LogP | pKa |
|---|---|---|---|---|---|
| E1111 | hydrogen | hydrogen | [4-(8-Chloro-5,6-dihydro-benzo[5,6]cyclohepta[1,2-b]py-ridin-11-ylidene)-piperidin-1-yl]-phosphonic acid | 4.21 | 3.86 |
| E1112 | hydrogen | methyl | [4-(8-Chloro-5,6-dihydro-benzo[5,6]cyclohepta[1,2-b]py-ridin-11-ylidene)-piperidin-1-yl]-phosphonic acid monom | 4.27 | 3.80 |
| E1113 | methyl | methyl | [4-(8-Chloro-5,6-dihydro-benzo[5,6]cyclohepta[1,2-b]py-ridin-11-ylidene)-piperidin-1-yl]-phosphonic acid dimethyl ester | 4.33 | 4.93 |
| E1114 | phenyl | hydrogen | [4-(8-Chloro-5,6-dihydro-benzo[5,6]cyclohepta[1,2-b]py-ridin-11-ylidene)-piperidin-1-yl]-phosphonic acid monophenyl ester | 6.04 | 3.32 |
| E1115 | phenyl | methyl | [4-(8-Chloro-5,6-dihydro-benzo[5,6]cyclohepta[1,2-b]py-ridin-11-ylidene)-piperidin-1-yl]-phosphonic acid methyl ester phenyl ester | 6.09 | 5.07 |

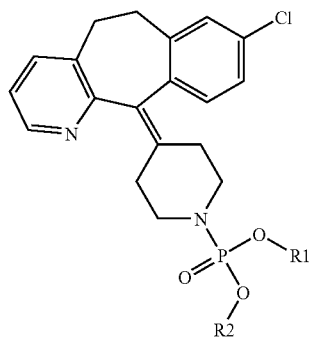

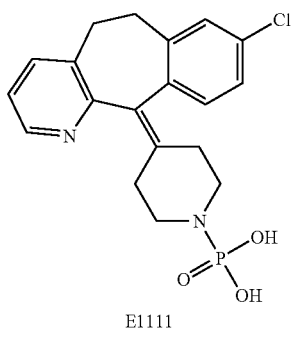

E1111

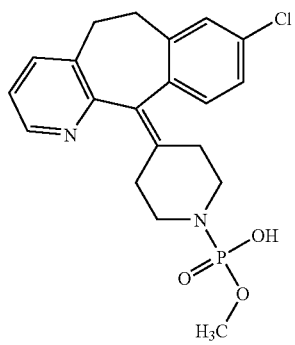

E1112

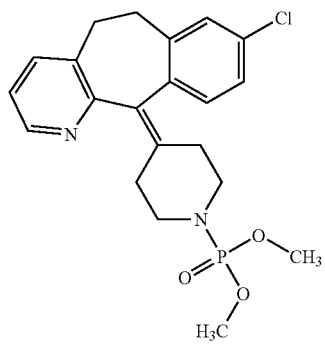

E1113

-continued

| Desloratadine (Clarinex ®) |
|---|

Chemical Structure

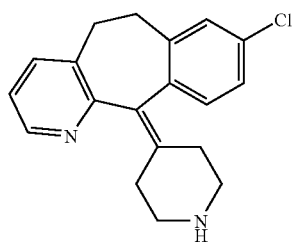

Hydroxylated Metabolite

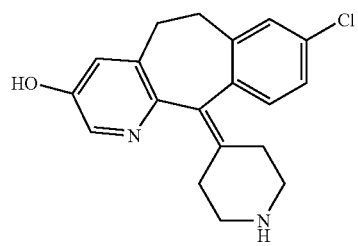

| Compound | R1 | R2 | Chemical Name | Estimated LogP | pKa |
|---|---|---|---|---|---|

E1114

E1115

| Dextromethorphan (Dextrophan ®) |
|---|

Chemical Structure

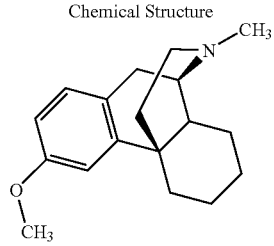

Active Metabolite Structure

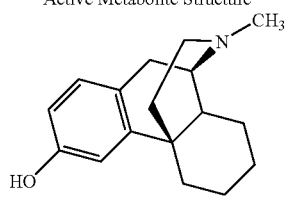

Hydroxylated Metabolite

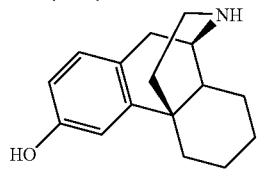

| Compound | R1 | R2 | Chemical Name | Estimated LogP | pKa |
|---|---|---|---|---|---|
| E1244 | hydrogen | hydrogen | (6-Ethyl-8-methoxy-11-propyl-1,2,5,6-tetrahydro-4H-2,6-meth-ano-benzo[d]azocin-3-yl)-phosphonic acid | 3.57 | 3.13 |
| E1245 | hydrogen | methyl | (6-Ethyl-8-methoxy-11-propyl-1,2,5,6-tetrahydro-4H-2,6-meth-ano-benzo[d]azocin-3-yl)-phosphonic acid monomethyl ester | 3.62 | 4.54 |
| E1246 | methyl | methyl | (6-Ethyl-8-methoxy-11-propyl-1,2,5,6-tetrahydro-4H-2,6-meth-ano-benzo[d]azocin-3-yl)-phosphonic acid dimethyl ester | 3.68 | 4.19 |
| E1247 | phenyl | hydrogen | (6-Ethyl-8-methoxy-11-propyl-1,2,5,6-tetrahydro-4H-2,6-meth-ano-benzo[d]azocin-3-yl)-phosphonic acid monophenyl ester | 5.39 | 4.08 |

-continued
Dextromethorphan (Dextrophan ®)
Chemical Structure
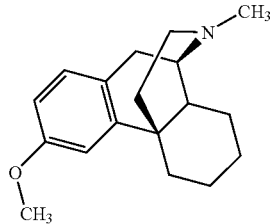
Active Metabolite Structure
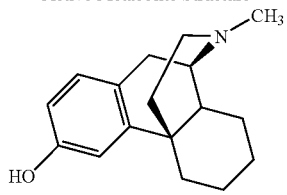
Hydroxylated Metabolite
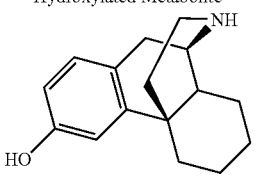
| Compound | R1 | R2 | Chemical Name | Estimated LogP | pKa |
|---|---|---|---|---|---|
| E1248 | phenyl | methyl | (6-Ethyl-8-methoxy-11-propyl-1,2,5,6-tetrahydro-4H-2,6-methano-benzo[d]azocin-3-yl)-phosphonic acid methyl ester phenyl ester | 5.44 | 4.33 |
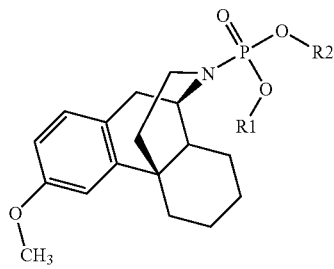
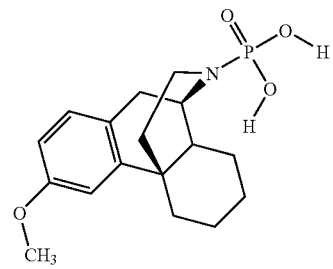
E1244
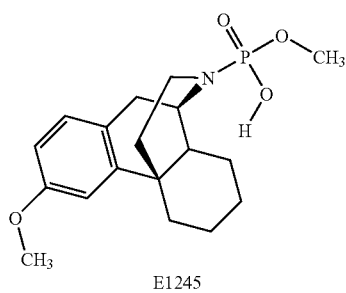
E1245
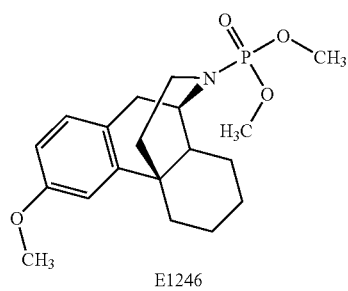
E1246
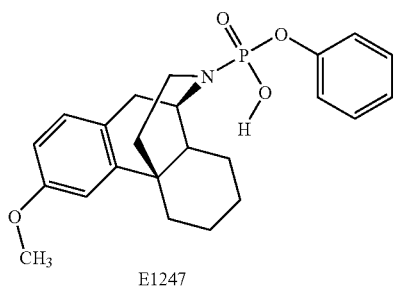
E1247
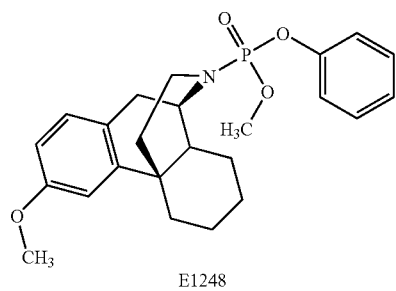
E1248

| Diclofenac (Voltaren ®) | |
|---|---|
| Chemical Structure 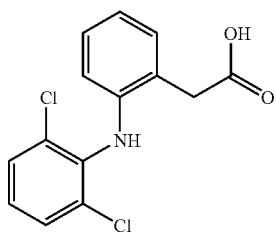 | Hydroxylated Metabolite 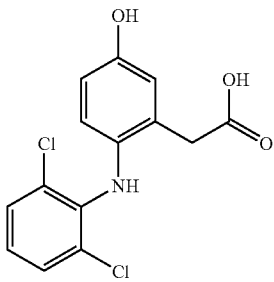 |

| Compound | R1 | R2 | Chemical Name |
|---|---|---|---|
| E1249 | hydrogen | hydrogen | {2-[(2,6-Dichloro-phenyl)-phosphono-amino]-phenyl}-acetic acid |
| E1250 | hydrogen | methyl | {2-[(2,6-Dichloro-phenyl)-(hydroxy-methoxy-phosphoryl)-amino]-phenyl}-acetic acid |
| E1251 | methyl | methyl | {2-[(2,6-Dichloro-phenyl)-(dimethoxy-phosphoryl)-amino]-phenyl}-acetic acid |
| E1252 | phenyl | hydrogen | {2-[(2,6-Dichloro-phenyl)-(hydroxy-phenoxy-phosphoryl)-amino]-phenyl}-acetic acid |
| E1253 | phenyl | methyl | {2-[(2,6-Dichloro-phenyl)-(methoxy-phenoxy-phosphoryl)-amino]-phenyl}-acetic acid |

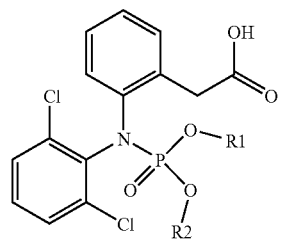
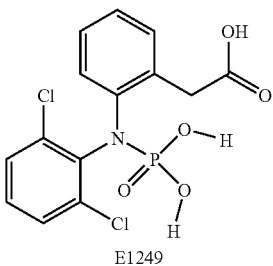
E1249
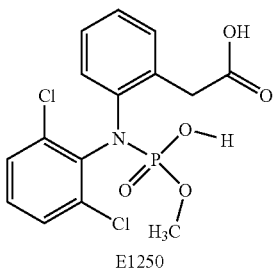
E1250

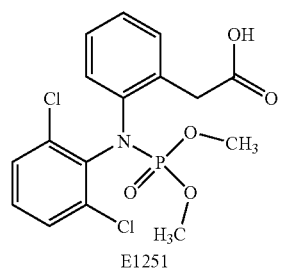
E1251
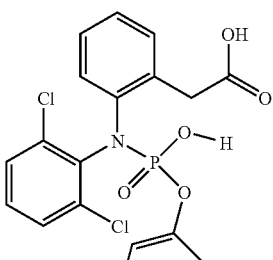
E1252
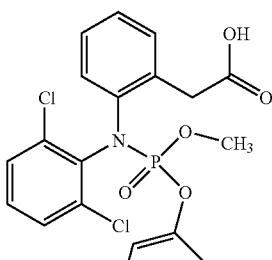
E1253

| Doxepin (Adapin ®, Sinequan ®) | | |
|---|---|---|
| Chemical Structure 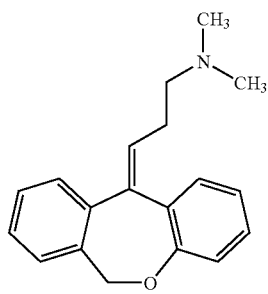 | Active Metabolite Structure 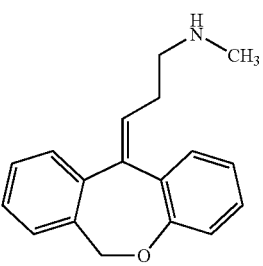 | Hydroxylated Metabolite 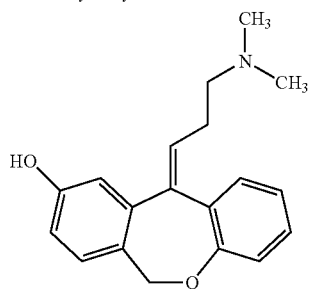 |

| Compound | R1 | R2 | Chemical Name | Estimated LogP | pKa |
|---|---|---|---|---|---|
| E1254 | hydrogen | hydrogen | [3-(6H-Dibenzo[b,e]oxepin-11-ylidene)-propyl]-methyl-phosphoramidic acid | 3.37 | 2.91 |
| E1255 | hydrogen | methyl | [3-(6H-Dibenzo[b,e]oxepin-11-ylidene)-propyl]-methyl-phosphoramidic acid monomethyl ester | 3.42 | 4.75 |
| E1256 | methyl | methyl | [3-(6H-Dibenzo[b,e]oxepin-11-ylidene)-propyl]-methyl-phosphoramidic acid dimethyl ester | 3.48 | 3.99 |
| E1257 | phenyl | hydrogen | [3-(6H-Dibenzo[b,e]oxepin-11-ylidene)-propyl]-methyl-phosphoramidic acid monophenyl ester | 5.19 | 4.31 |
| E1258 | phenyl | methyl | [3-(6H-Dibenzo[b,e]oxepin-11-ylidene)-propyl]-methyl-phosphoramidic acid methyl ester phenyl ester | 5.25 | 4.54 |

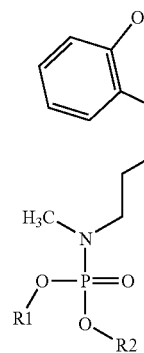

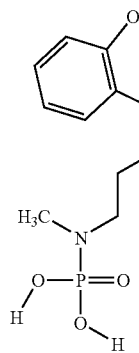
E1254

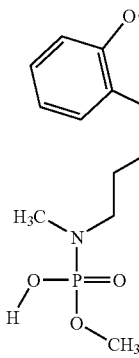
E1255

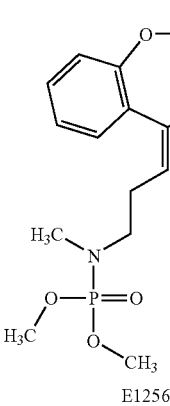
E1256

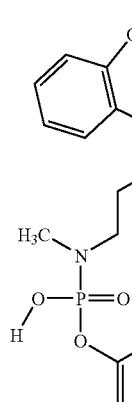
E1257

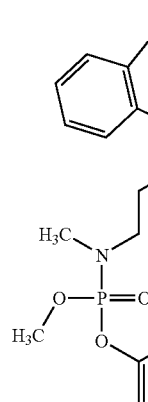
E1258

| Doxylamine (Mereprin ®) | |
|---|---|
| Chemical Structure 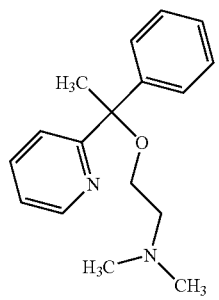 | Hydroxylated Metabolite 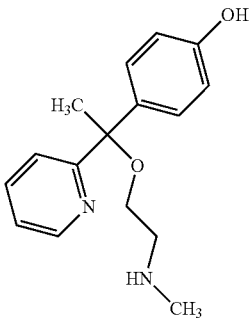 |
| | Active Metabolite Structure |

| Compound | R1 | R2 | Chemical Name |
|---|---|---|---|
| E1369 | hydrogen | hydrogen | Methyl-[2-(1-phenyl-1-pyridin-2-yl-ethoxy)-ethyl]-phosphoramidic acid |
| E1370 | hydrogen | methyl | Methyl-[2-(1-phenyl-1-pyridin-2-yl-ethoxy)-ethyl]-phosphoramidic acid monomethyl ester |
| E1371 | methyl | methyl | Methyl-[2-(1-phenyl-1-pyridin-2-yl-ethoxy)-ethyl]-phosphoramidic acid dimethyl ester |
| E1372 | phenyl | hydrogen | Methyl-[2-(1-phenyl-1-pyridin-2-yl-ethoxy)-ethyl]-phosphoramidic acid monophenyl ester |
| E1373 | phenyl | methyl | Methyl-[2-(1-phenyl-1-pyridin-2-yl-ethoxy)-ethyl]-phosphoramidic acid methyl ester phenyl ester |

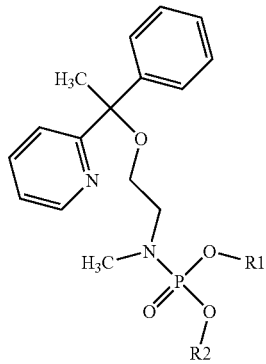

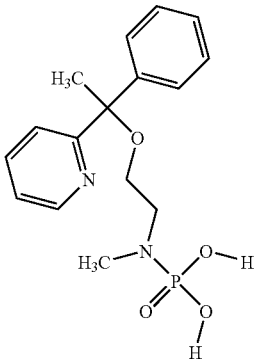
E1369

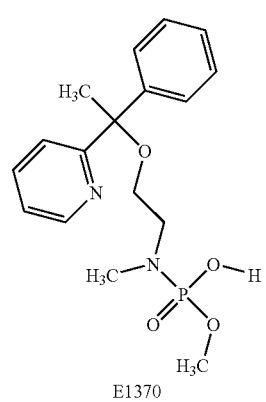
E1370

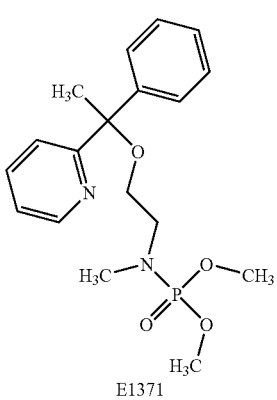
E1371

Doxylamine (Mereprin ®)

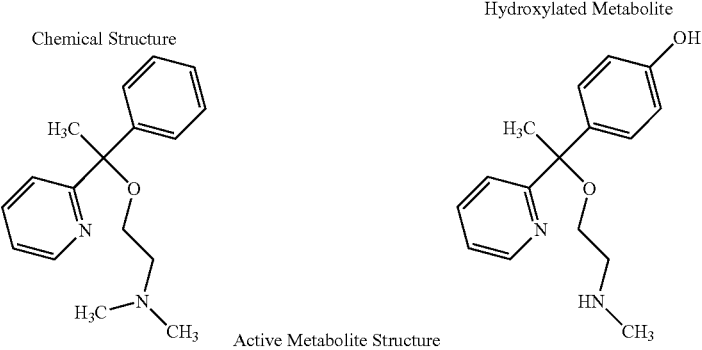

Chemical Structure

Hydroxylated Metabolite

Active Metabolite Structure

| Compound | R1 | R2 | Chemical Name |
|---|---|---|---|

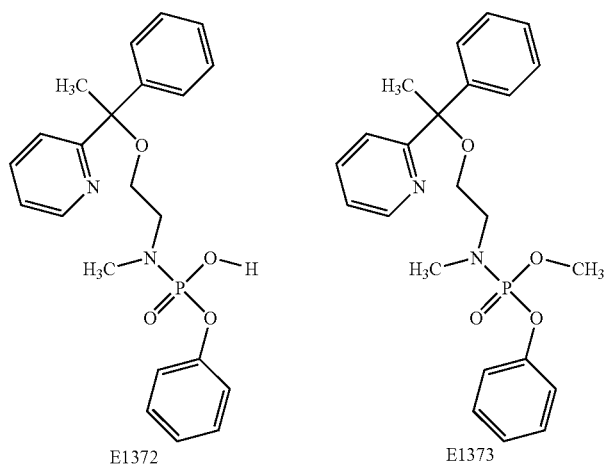

E1372

E1373

Duloxetine (Cymbalta ®)

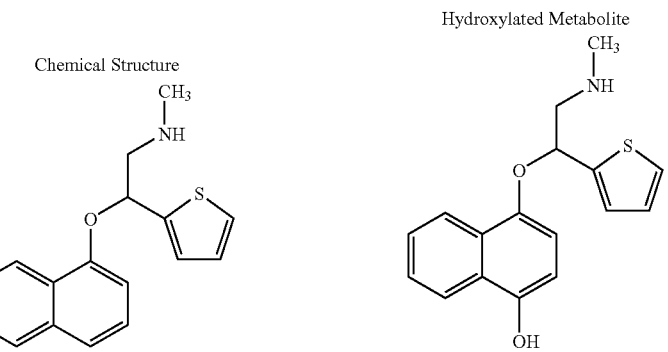

Chemical Structure

Hydroxylated Metabolite

| Compound | R1 | R2 | Chemical Name | Estimated LogP | Estimated pKa |
|---|---|---|---|---|---|
| E1106 | hydrogen | hydrogen | Methyl-[2-(naphthalen-1-yloxy)-2-thiophen-2-yl-ethyl]-phosphoramidic acid | 3.78 | 4.48 |
| E1107 | hydrogen | methyl | Methyl-[2-(naphthalen-1-yloxy)-2-thiophen-2-yl-ethyl]-phosphoramidic acid monomethyl ester | 3.83 | 3.18 |

-continued

Duloxetine (Cymbalta ®)

Chemical Structure

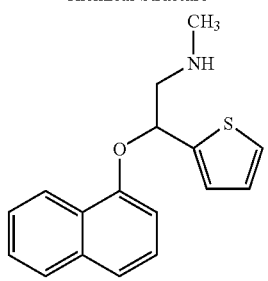

Hydroxylated Metabolite

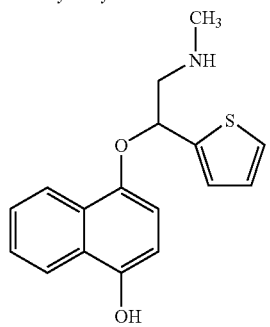

| Compound | R1 | R2 | Chemical Name | Estimated LogP | Estimated pKa |
|---|---|---|---|---|---|
| E1108 | methyl | methyl | Methyl-[2-(naphthalen-1-yloxy)-2-thiophen-2-yl-ethyl]-phosphoramidic acid dimethyl ester | 3.89 | 4.32 |
| E1109 | phenyl | hydrogen | Methyl-[2-(naphthalen-1-yloxy)-2-thiophen-2-yl-ethyl]-phosphoramidic acid monophenyl ester | 5.60 | 2.76 |
| E1110 | phenyl | methyl | Methyl-[2-(naphthalen-1-yloxy)-2-thiophen-2-yl-ethyl]-phosphoramidic acid methyl ester phenyl ester | 5.66 | 4.86 |

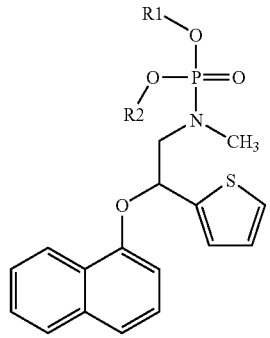

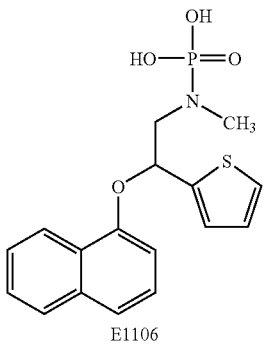
E1106

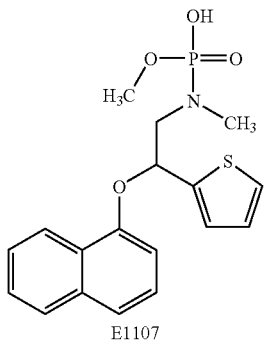
E1107

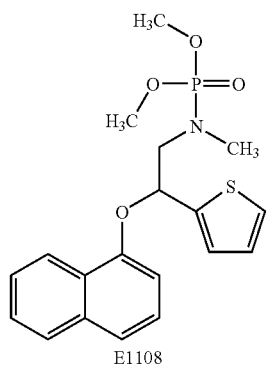
E1108

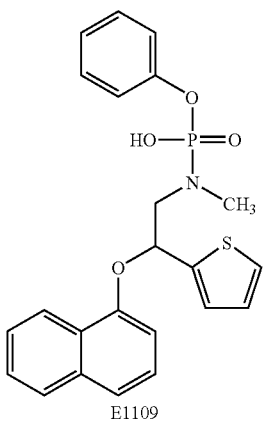
E1109

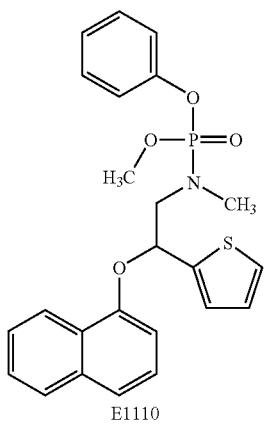
E1110

Eletriptan (Relbox ®)

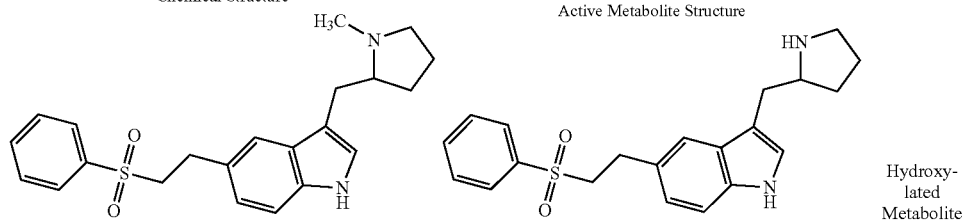

Chemical Structure     Active Metabolite Structure

Hydroxylated Metabolite

| Compound | R1 | R2 | Chemical Name | Estimated LogP | pKa |
|---|---|---|---|---|---|
| E1169 | hydrogen | hydrogen | {2-[5-(2-Benzenesulfonyl-ethyl)-1H-indol-3-ylmethyl]-pyrrolidin-1-yl}-phosphonic acid | 3.24 | 2.30 |
| E1170 | hydrogen | methyl | {2-[5-(2-Benzenesulfonyl-ethyl)-1H-indol-3-ylmethyl]-pyrrolidin-1-yl}-phosphonic acid monomethyl ester | 3.29 | 5.36 |
| E1171 | methyl | methyl | {2-[5-(2-Benzenesulfonyl-ethyl)-1H-indol-3-ylmethyl]-pyrrolidin-1-yl}-phosphonic acid dimethyl ester | 3.35 | 4.45 |
| E1172 | phenyl | hydrogen | {2-[5-(2-Benzenesulfonyl-ethyl)-1H-indol-3-ylmethyl]-pyrrolidin-1-yl}-phosphonic acid monophenyl ester | 5.06 | 4.88 |
| E1173 | phenyl | methyl | {2-[5-(2-Benzenesulfonyl-ethyl)-1H-indol-3-ylmethyl]-pyrrolidin-1-yl}-phosphonic acid methyl ester phenyl ester | 5.12 | 4.52 |

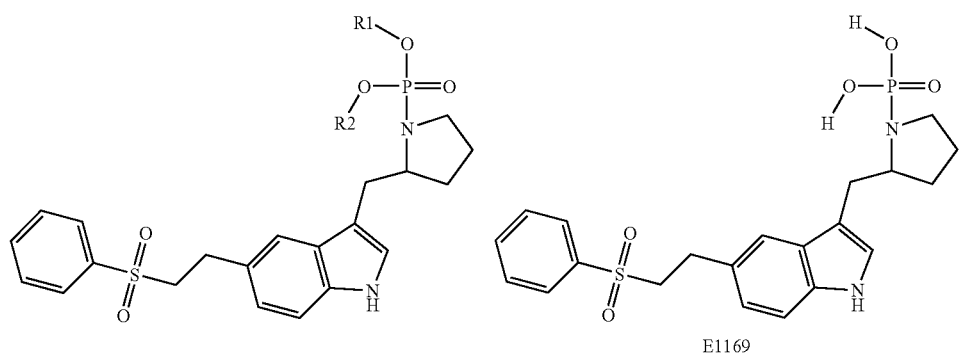

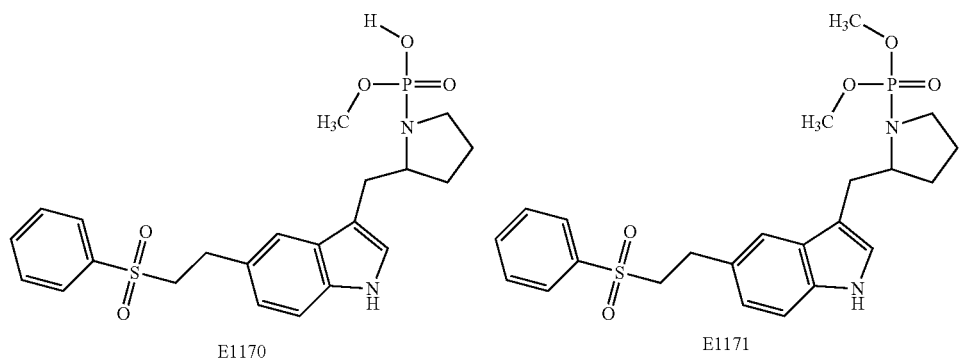

Eletriptan (Relbox ®)

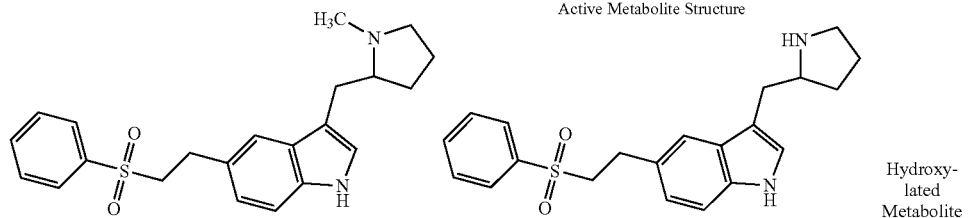

Chemical Structure | Active Metabolite Structure | Hydroxylated Metabolite

| Compound | R1 | R2 | Chemical Name | Estimated LogP | pKa |
|---|---|---|---|---|---|

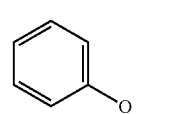

E1172 | E1173

Ephedrine (Broncholate ®)

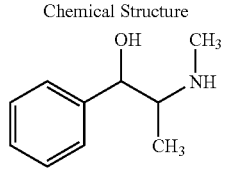 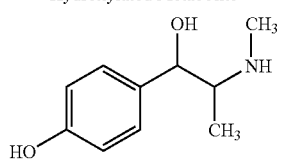

Chemical Structure | Hydroxylated Metabolite

| Compound | R1 | R2 | Chemical Name | Estimated LogP | pKa |
|---|---|---|---|---|---|
| E1334 | hydrogen | hydrogen | (2-Hydroxy-1-methyl-2-phenyl-ethyl)-methyl-phosphoramidic acid | 0.49 | 3.47 |
| E1335 | hydrogen | methyl | (2-Hydroxy-1-methyl-2-phenyl-ethyl)-methyl-phosphoramidic acid monomethyl ester | 0.55 | 4.18 |
| E1336 | methyl | methyl | (2-Hydroxy-1-methyl-2-phenyl-ethyl)-methyl-phosphoramidic acid dimethyl ester | 0.60 | 3.58 |
| E1337 | phenyl | hydrogen | (2-Hydroxy-1-methyl-2-phenyl-ethyl)-methyl-phosphoramidic acid monophenyl ester | 2.31 | 3.80 |

Ephedrine (Broncholate ®)

Chemical Structure

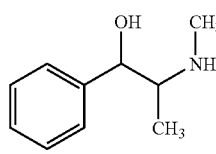

Hydroxylated Metabolite

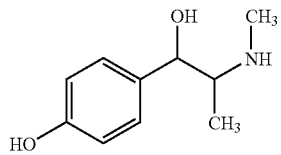

| Compound | R1 | R2 | Chemical Name | Estimated LogP | pKa |
|---|---|---|---|---|---|
| E1338 | phenyl | methyl | (2-Hydroxy-1-methyl-2-phenyl-ethyl)-methyl-phosphoramidic acid methyl ester phenyl ester | 2.37 | 3.80 |

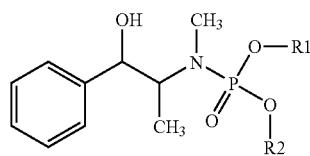

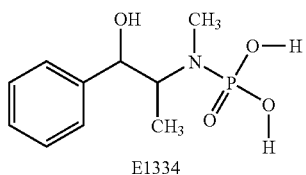

E1334

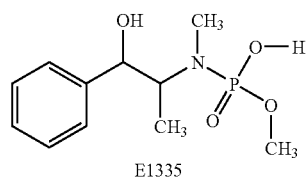

E1335

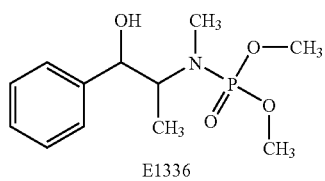

E1336

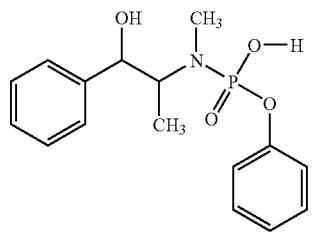

E1337

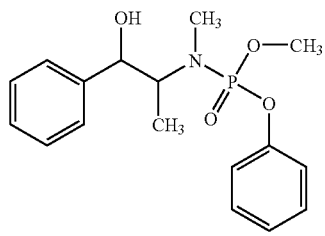

E1338

Escitalopram (Lexapro ®)

Chemical Structure

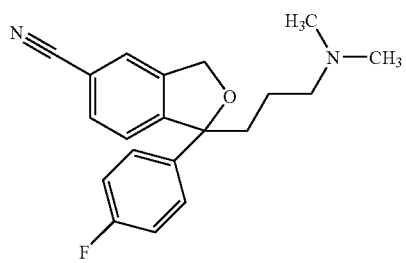

Active Metabolite Structure

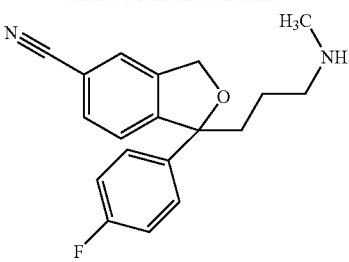

| Compound | R1 | R2 | Chemical Name | Estimated LogP | pKa |
|---|---|---|---|---|---|
| E1031 | hydrogen | hydrogen | {3-[5-Cyano-1-(4-fluoro-phenyl)-1,3-dihydro-iso-benzofuran-1(S)-yl]-propyl}-methyl-phosphoramidic acid | 3.12 | |

-continued

Escitalopram (Lexapro ®)

Chemical Structure 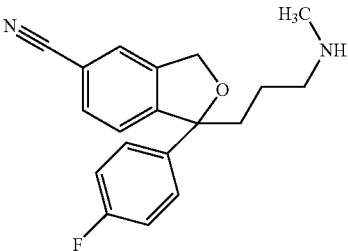 Active Metabolite Structure

| Compound | R1 | R2 | Chemical Name | Estimated LogP | pKa |
|---|---|---|---|---|---|
| E1032 | hydrogen | methyl | {3-[5-Cyano-1-(4-fluoro-phenyl)-1,3{3-[5-Cyano-1-(4-fluoro-phenyl)-1,3-dihydro-isobenzofuran-1(S)-yl]-propyl}-methyl-phosphoramidic acid monomethyl ester | 3.17 | |
| E1033 | methyl | methyl | {3-[5-Cyano-1-(4-fluoro-phenyl)-1,3-dihydro-iso-benzofuran-11(S)-yl]-propyl}-methyl-phosphoramidic acid dimethyl ester | 3.23 | |
| E1034 | phenyl | hydrogen | {3-[5-Cyano-1-(4-fluoro-phenyl)-1,3-dihydro-iso-benzofuran-11(S)-yl]-propyl}-methyl-phosphoramidic acid monophenyl ester | 4.94 | |
| E1035 | phenyl | methyl | {3-[5-Cyano-1-(4-fluoro-phenyl)-1,3-dihydro-iso-benzofuran-11(S)-yl]-propyl}-methyl-phosphoramidic acid methyl ester phenyl ester | 5.00 | |

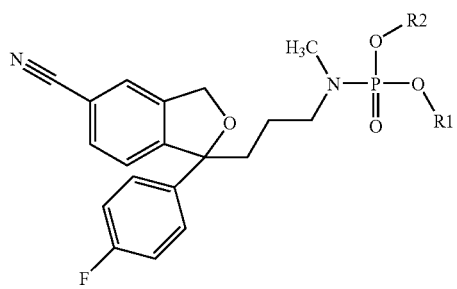

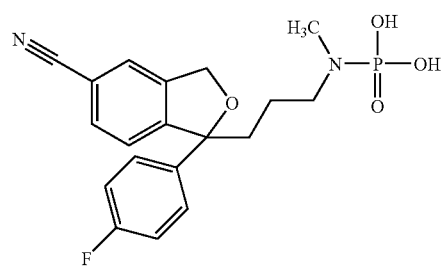

E1031

Escitalopram (Lexapro ®)
Chemical Structure
Active Metabolite Structure
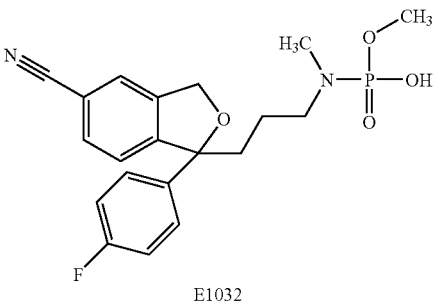
| Compound | R1 | R2 | Chemical Name | Estimated LogP | pKa |
|---|---|---|---|---|---|
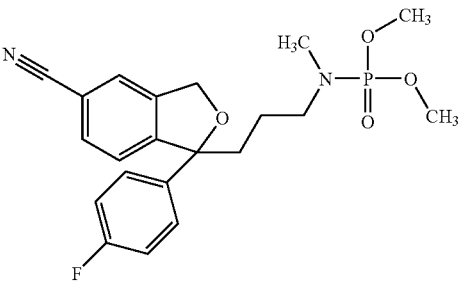
E1032
E1033
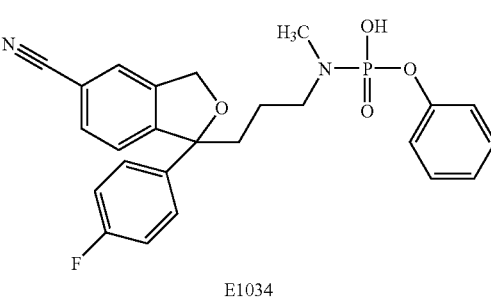
E1034
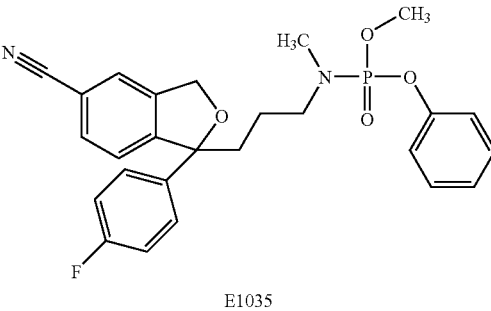
E1035

| Femoxetine (Malexil ®) |
|---|

Chemical Structure

Active Metabolite Structure

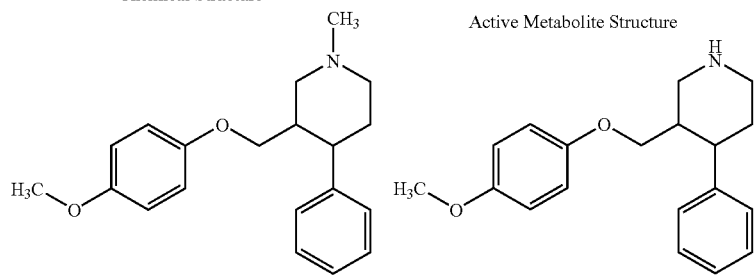

Hydroxylated Metabolite

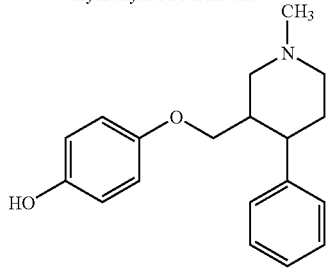

| Compound | R1 | R2 | Chemical Name |
|---|---|---|---|
| E1374 | hydrogen | hydrogen | [3-(4-Methoxy-phenoxymethyl)-4-phenyl-piperidin-1-yl]-phosphonic acid |
| E1375 | hydrogen | methyl | [3-(4-Methoxy-phenoxymethyl)-4-phenyl-piperidin-1-yl]-phosphonic acid monomethyl ester |
| E1376 | methyl | methyl | [3-(4-Methoxy-phenoxymethyl)-4-phenyl-piperidin-1-yl]-phosphonic acid dimethyl ester |
| E1377 | phenyl | hydrogen | [3-(4-Methoxy-phenoxymethyl)-4-phenyl-piperidin-1-yl]-phosphonic acid monophenyl ester |
| E1378 | phenyl | methyl | [3-(4-Methoxy-phenoxymethyl)-4-phenyl-piperidin-1-yl]-phosphonic acid methyl ester phenyl ester |

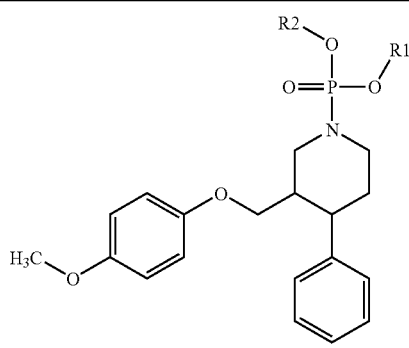

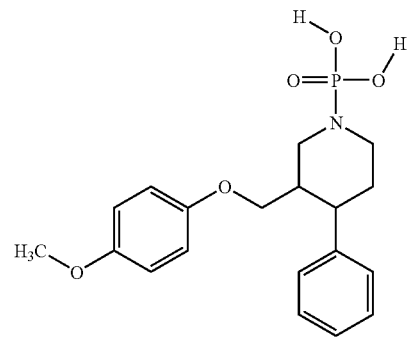

E1374

Femoxetine (Malexil ®)
Chemical Structure
Active Metabolite Structure
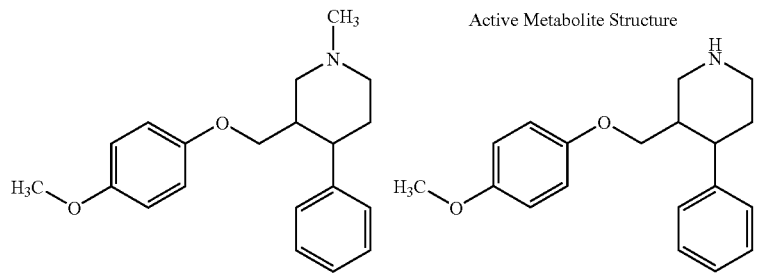
Hydroxylated Metabolite
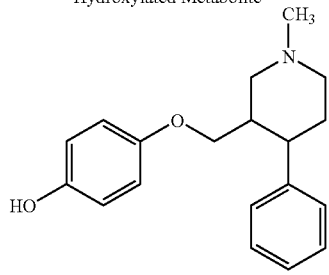
| Compound | R1 | R2 | Chemical Name |
|---|---|---|---|
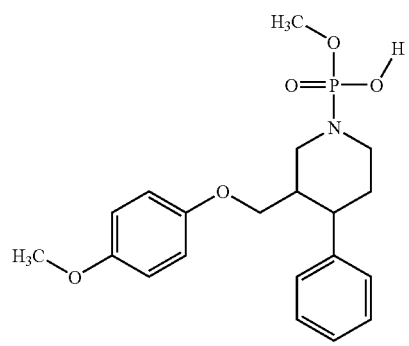
E1375
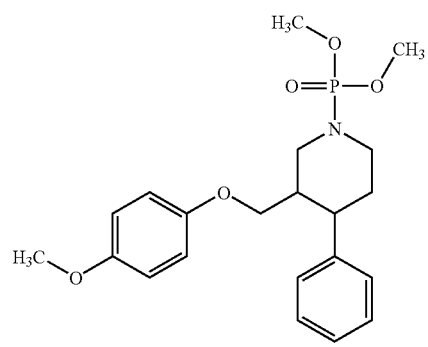
E1376

Femoxetine (Malexil ®)
Chemical Structure
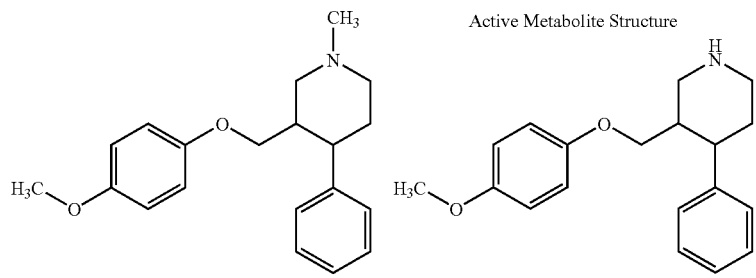
Active Metabolite Structure
Hydroxylated Metabolite
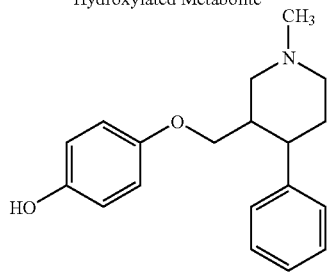
| Compound | R1 | R2 | Chemical Name |
|---|---|---|---|
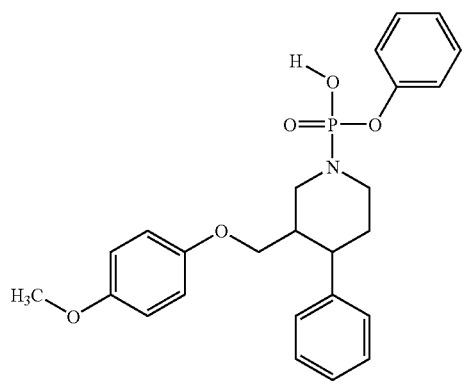
E1377
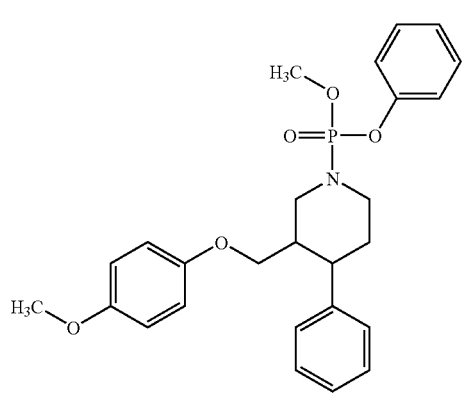
E1378

| Fenfluramine (Pondimin ®) |
|---|

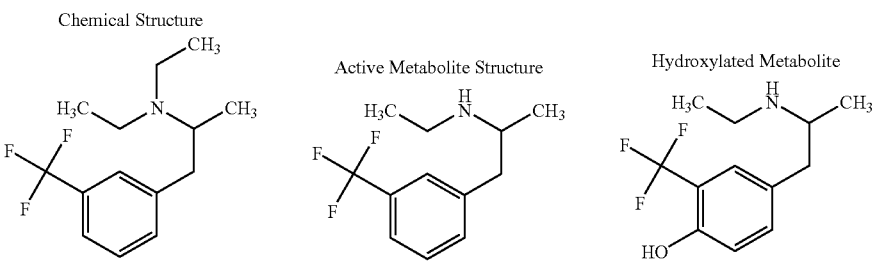

| Compound | R1 | R2 | Chemical Name | Estimated LogP | pKa |
|---|---|---|---|---|---|
| E1314 | hydrogen | hydrogen | Ethyl-[1-methyl-2-(3-trifluoromethyl-phenyl)-ethyl]-phosphoramidic acid | 3.48 | 3.29 |
| E1315 | hydrogen | methyl | Ethyl-[1-methyl-2-(3-trifluoromethyl-phenyl)-ethyl]-phosphoramidic acid monomethyl ester | 3.54 | 4.36 |
| E1316 | methyl | methyl | Ethyl-[1-methyl-2-(3-trifluoromethyl-phenyl)-ethyl]-phosphoramidic acid dimethyl ester | 3.60 | 3.60 |
| E1317 | phenyl | hydrogen | Ethyl-[1-methyl-2-(3-trifluoromethyl-phenyl)-ethyl]-phosphoramidic acid monophenyl ester | 5.31 | 4.00 |
| E1318 | phenyl | methyl | Ethyl-[1-methyl-2-(3-trifluoromethyl-phenyl)-ethyl]-phosphoramidic acid methyl ester phenyl ester | 5.36 | 4.11 |

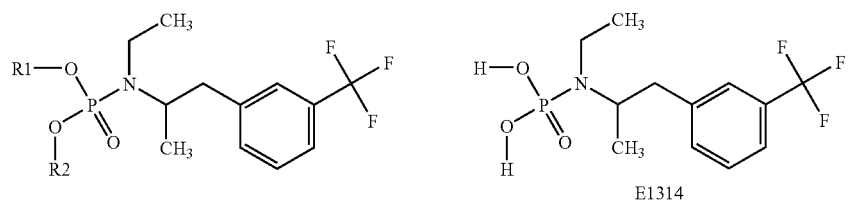

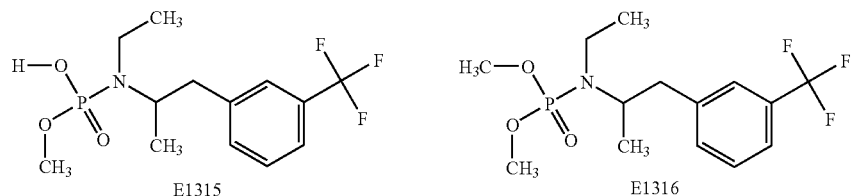

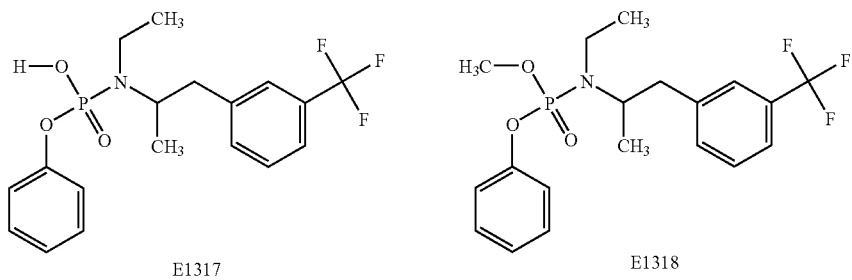

| | Floxetine (Prozac ®) | |
|---|---|---|
| Chemical Structure | Active Metabolite Structure | Hydroxylated Metabolite |

| Compound | R1 | R2 | Chemical Name | Estimated LogP | Estimated pKa |
|---|---|---|---|---|---|
| E1046 | hydrogen | hydrogen | Ethyl-[2-phenyl-2-(4-trifluoromethyl-phenoxy)-ethyl]-phosphoramidic acid | 4.23 | 4.64 |
| E1047 | hydrogen | methyl | Ethyl-[2-phenyl-2-(4-trifluoromethyl-phenoxy)-ethyl]-phosphoramidic acid monomethyl ester | 4.29 | 3.02 |
| E1048 | methyl | methyl | Ethyl-[2-phenyl-2-(4-trifluoromethyl-phenoxy)-ethyl]-phosphoramidic acid dimethyl ester | 4.35 | 3.96 |
| E1049 | phenyl | hydrogen | Ethyl-[2-phenyl-2-(4-trifluoromethyl-phenoxy)-ethyl]-phosphoramidic acid monophenyl ester | 6.06 | 2.64 |
| E1050 | phenyl | methyl | Ethyl-[2-phenyl-2-(4-trifluoromethyl-phenoxy)-ethyl]-phosphoramidic acid methyl ester phenyl ester | 6.11 | 4.49 |

Frovatriptan (Frova ®)

Chemical Structure

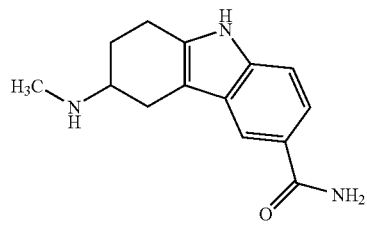

Hydroxylated Metabolite

| Compound | R1 | R2 | Chemical Name | Estimated LogP | pKa |
|---|---|---|---|---|---|
| E1319 | hydrogen | hydrogen | (6-Carbamoyl-2,3,4,9-tetrahydro-1H-carbazol-3-yl)-methyl-phosphoramidic acid | 1.27 | 2.52 |
| E1320 | hydrogen | methyl | (6-Carbamoyl-2,3,4,9-tetrahydro-1H-carbazol-3-yl)-methyl-phosphoramidic acid monomethyl ester | 1.33 | 5.13 |
| E1321 | methyl | methyl | (6-Carbamoyl-2,3,4,9-tetrahydro-1H-carbazol-3-yl)-methyl-phosphoramidic acid dimethyl ester | 1.38 | 3.65 |
| E1322 | phenyl | hydrogen | (6-Carbamoyl-2,3,4,9-tetrahydro-1H-carbazol-3-yl)-methyl-phosphoramidic acid monophenyl ester | 3.09 | 4.70 |
| E1323 | phenyl | methyl | (6-Carbamoyl-2,3,4,9-tetrahydro-1H-carbazol-3-yl)-methyl-phosphoramidic acid methyl ester phenyl ester | 3.15 | 3.13 |

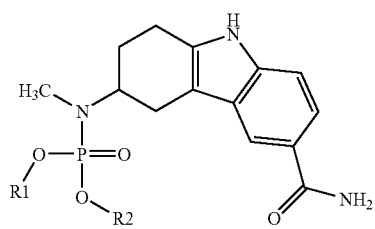

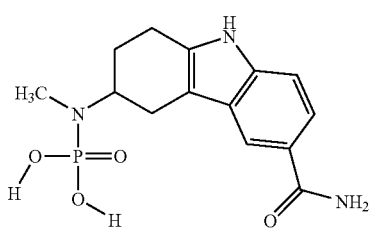

E1319

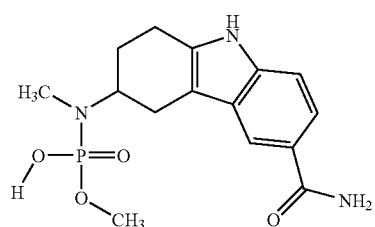

E1320

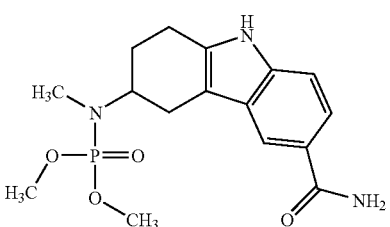

E1321

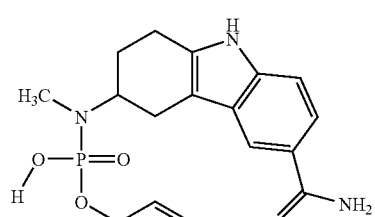

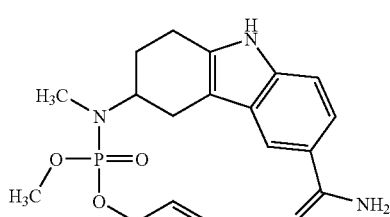

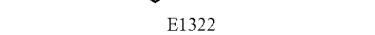

E1322

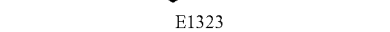

E1323

| Galantamine (Reminyl ®) | |
|---|---|
| Chemical Structure 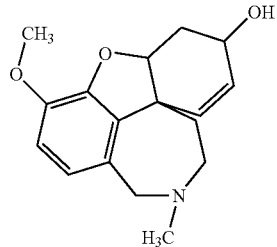 | Hydroxylated Metabolite 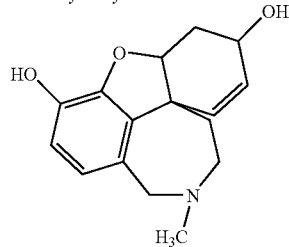 |

Active Metabolite Structure

| Compound | R1 | R2 | Chemical Name |
|---|---|---|---|
| E1259 | hydrogen | hydrogen | 6H-benzofuro[3a,3,2-ef][2]benzazepin-6-ol,4a,5,9,10,11,12-hexa-hydro-3-methoxy-11-meth-yl-, (4aS,6-R,8aS)-phosphoramidic acid |
| E1260 | hydrogen | methyl | 6H-benzofuro[3a,3,2-ef][2]benzazepin-6-ol,4a,5,9,10,11,12-hexa-hydro-3-methoxy-11-meth-yl-, (4aS,6-R,8aS)-phosphoramidic acid monomethyl ester |
| E1261 | methyl | methyl | 6H-benzofuro[3a,3,2-ef][2]benzazepin-6-ol,4a,5,9,10,11,12-hexa-hydro-3-methoxy-11-meth-yl-, (4aS,6-R,8aS)-phosphoramidic acid dimethyl ester |
| E1262 | phenyl | hydrogen | 6H-benzofuro[3a,3,2-ef][2]benzazepin-6-ol,4a,5,9,10,11,12-hexa-hydro-3-methoxy-11-meth-yl-, (4aS,6-R,8aS)-phosphoramidic acid monophenyl ester |
| E1263 | phenyl | methyl | 6H-benzofuro[3a,3,2-ef][2]benzazepin-6-ol,4a,5,9,10,11,12-hexa-hydro-3-methoxy-11-meth-yl-, (4aS,6-R,8aS)-phosphoramidic acid methyl ester phenyl ester |

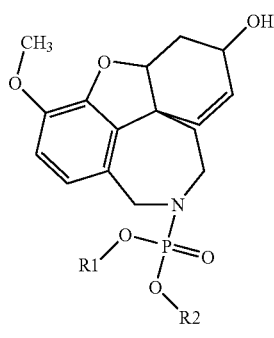

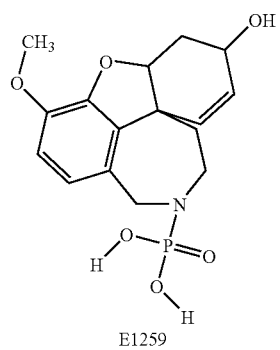
E1259

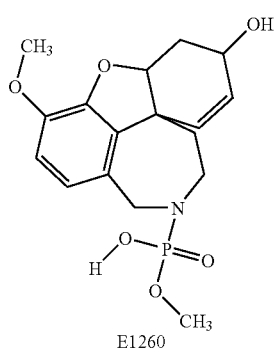
E1260

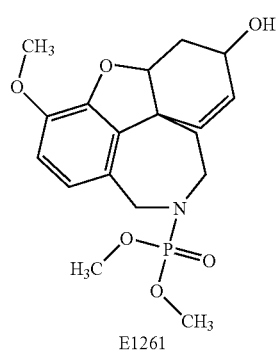
E1261

Galantamine (Reminyl ®)

Chemical Structure

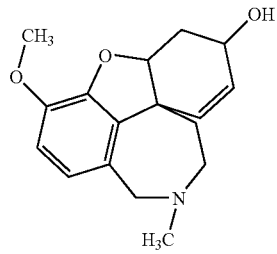

Hydroxylated Metabolite

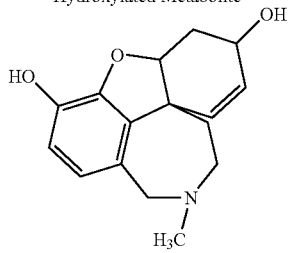

Active Metabolite Structure

| Compound | R1 | R2 | Chemical Name |
|---|---|---|---|

E1262

E1263

Gatifloxacin (Tequine ®)

Chemical Structure

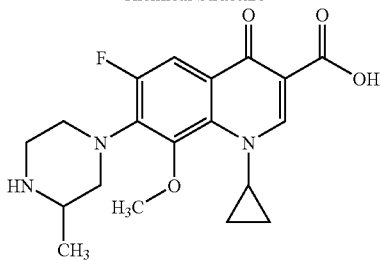

Hydroxylated Metabolite

| Compound | R1 | R2 | Chemical Name | Estimated LogP | pKa |
|---|---|---|---|---|---|
| E1289 | hydrogen | hydrogen | 1-Cyclopropyl-6-fluoro-8-methoxy-7-(3-methyl-4-phosphono-piperazin-1-yl)-4-oxo-1,4-dihydro-quinoline-3-carboxylic acid | 1.78 | 5.15 |
| E1290 | hydrogen | methyl | 1-Cyclopropyl-6-fluoro-7-[4-(hydroxy-methoxy-phosphoryl)-3-methyl-piperazin-1-yl]-8-methoxy-4-oxo-1,4-dihydro-quinoline-3-carboxylic acid | 1.84 | 2.51 |
| E1291 | methyl | methyl | 1-Cyclopropyl-7-[4-(dimethoxy-phosphoryl))-3-methyl-piperazin-1-yl]-6-fluoro-8-methoxy-4-oxo-1,4-dihydro-quinoline-3-carboxylic acid | 1.90 | 6.22 |
| E1292 | phenyl | hydrogen | 1-Cyclopropyl-6-fluoro-7-[4-(hydroxy-phenoxy-phosphoryl)-3-methyl-piperazin-1-yl]-8-methoxy-4-oxo-1,4-dihydro-quinoline-3-carboxylic acid | 3.61 | 2.04 |

-continued
Gatifloxacin (Tequine ®)
Chemical Structure
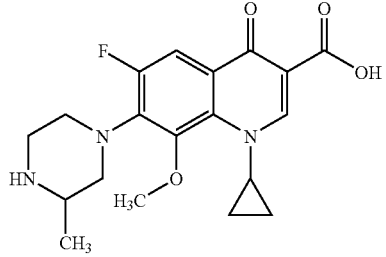
Hydroxylated Metabolite
| Compound | R1 | R2 | Chemical Name | Estimated LogP | pKa |
|---|---|---|---|---|---|
| E1293 | phenyl | methyl | 1-Cyclopropyl-6-fluoro-8-methoxy-7-[4-(methoxy-phenoxy-phosphoryl)-3-methyl-piperazin-1-yl]-4-oxo-1,4-di-hydro-quinoline-3-carboxylic acid | 3.66 | 6.36 |
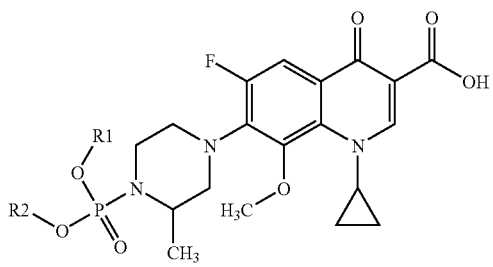
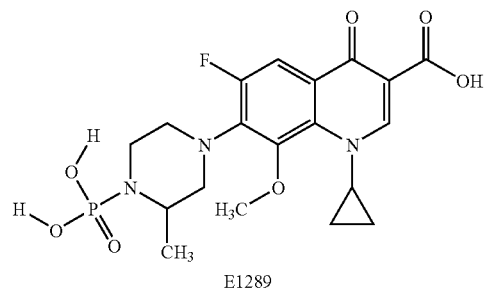
E1289
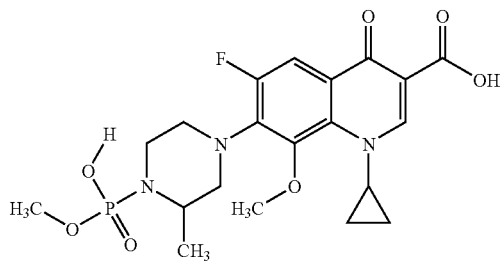
E1290
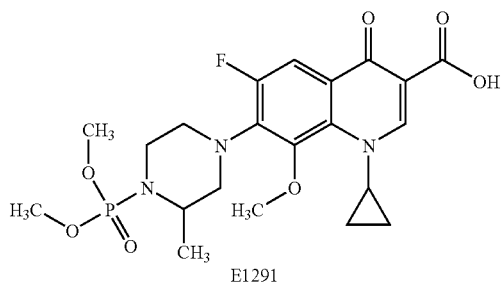
E1291

Gatifloxacin (Tequine ®)

Chemical Structure

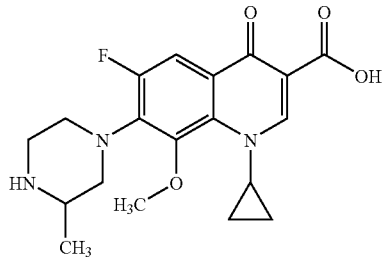

Hydroxylated Metabolite

| Compound | R1 | R2 | Chemical Name | Estimated LogP | pKa |
|---|---|---|---|---|---|

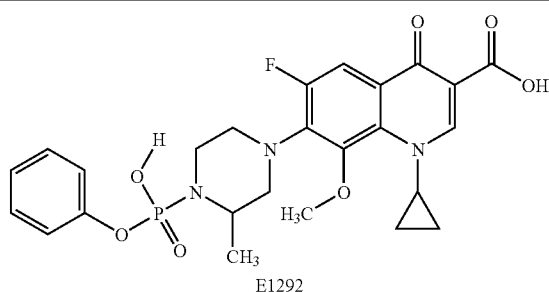

E1292

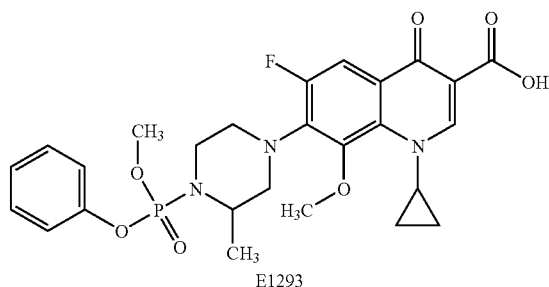

E1293

Grepafloxacin (Raxar ®)

Chemical Structure

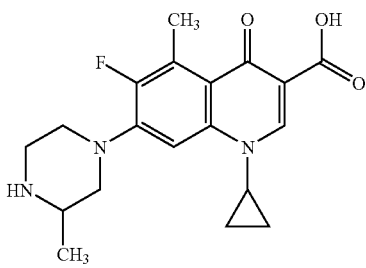

Hydroxylated Metabolite

| Compound | R1 | R2 | Chemical Name | Estimated LogP | pKa |
|---|---|---|---|---|---|
| E1294 | hydrogen | hydrogen | 1-Cyclopropyl-6-fluoro-5-methyl-7-(3-methyl-4-phosphono-piperazin-1-yl)-4-oxo-1,4-dihydro-quinoline-3-carboxylic acid | | |
| E1295 | hydrogen | methyl | 1-Cyclopropyl-6-fluoro-7-[4-(hydroxy-methoxy-phosphoryl)-3-methyl-piperazin-1-yl]-5-methyl-4-oxo-1,4-dihydro-quinoline-3-carboxylic acid | | |
| E1296 | methyl | methyl | 1-Cyclopropyl-7-[4-(dimethoxy-phosphoryl)-3-methyl-piperazin-1-yl]-6-fluoro-5-methyl-4-oxo-1,4-dihydro-quinoline-3-carboxylic acid | 2.36 | 6.49 |

Grepafloxacin (Raxar ®)

Chemical Structure

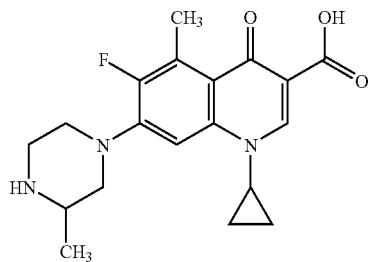

Hydroxylated Metabolite

| Compound | R1 | R2 | Chemical Name | Estimated LogP | pKa |
|---|---|---|---|---|---|
| E1297 | phenyl | hydrogen | 1-Cyclopropyl-6-fluoro-7-[4-(hydroxy-phenoxy-phosphoryl)-3-methyl-piperazin-1-yl]-5-methyl-4-oxo-1,4-di-hydro-quinoline-3-carboxylic acid | 4.07 | 1.76 |
| E1298 | phenyl | methyl | 1-Cyclopropyl-6-fluoro-7-[4-(methoxy-phenoxy-phosphoryl)-3-methyl-piperazin-1-yl]-5-methyl-4-oxo-1,4-di-hydro-quinoline-3-carboxylic acid | 4.13 | 6.63 |

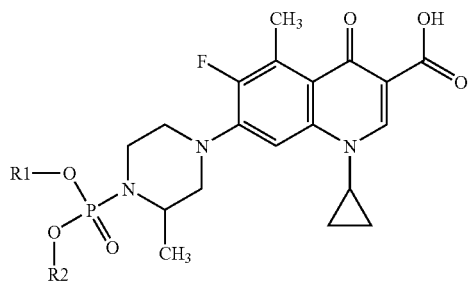

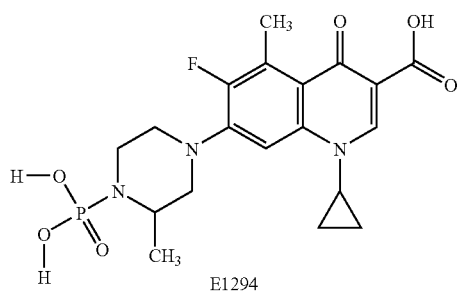

E1294

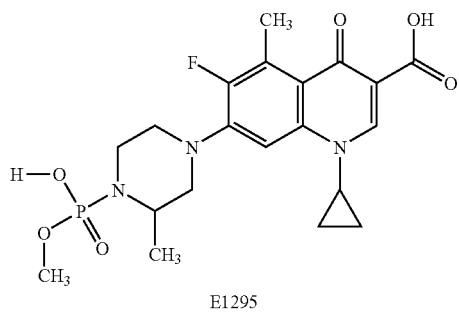

E1295

| Grepafloxacin (Raxar ®) |
|---|
| Chemical Structure |
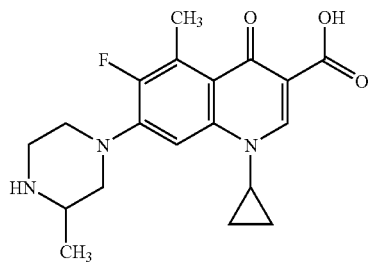
Hydroxylated Metabolite
| Compound | R1 | R2 | Chemical Name | Estimated LogP | pKa |
|---|---|---|---|---|---|
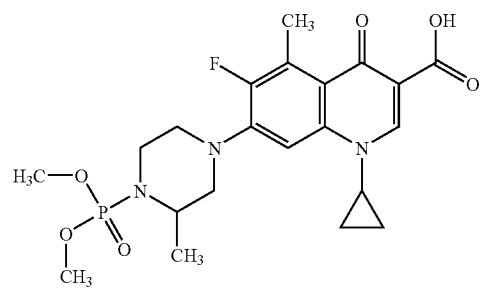
E1296
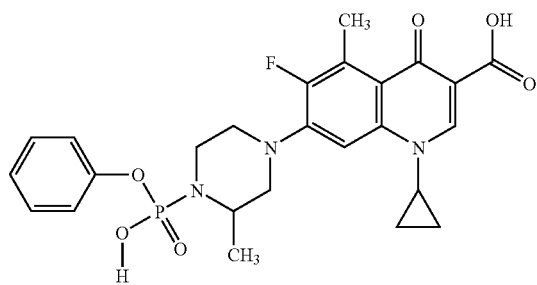
E1297
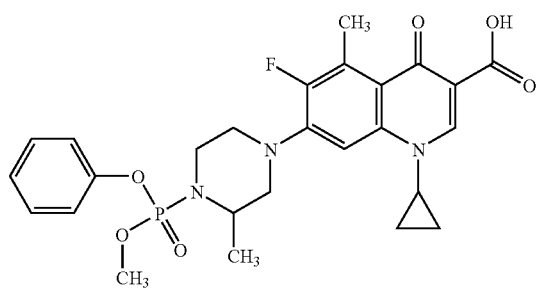
E1298

| Halofantrine (Halfan ®) | |
|---|---|
| Chemical Structure 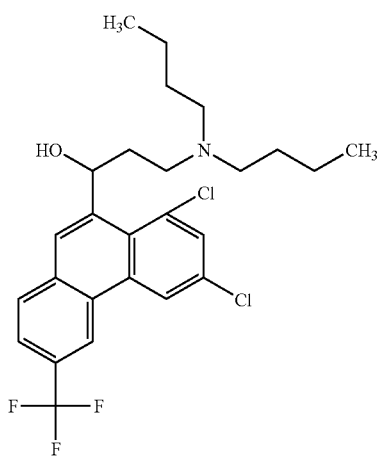 | Active Metabolite Structure 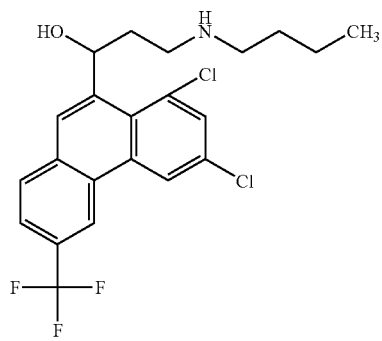 |

| Compound | R1 | R2 | Chemical Name | Estimated LogP | Estimated pKa |
|---|---|---|---|---|---|
| E1066 | hydrogen | hydrogen | Butyl-[3-(6,8-dichloro-3-trifluoromethyl-phenanthren-9-yl)-3-hydroxy-propyl]-phosphoramidic acid | 6.64 | 3.57 |
| E1067 | hydrogen | methyl | Butyl-[3-(6,8-dichloro-3-trifluoromethyl-phenanthren-9-yl)-3-hydroxy-propyl]-phosphoramidic acid monomethyl ester | 6.70 | 4.09 |
| E1068 | methyl | methyl | Butyl-[3-(6,8-dichloro-3-trifluoromethyl-phenanthren-9-yl)-3-hydroxy-propyl]-phosphoramidic acid dimethyl ester | 6.75 | 3.77 |
| E1069 | phenyl | hydrogen | Butyl-[3-(6,8-dichloro-3-trifluoromethyl-phenanthren-9-yl)-3-hydroxy-propyl]-phosphoramidic acid monophenyl ester | 8.47 | 3.70 |
| E1070 | phenyl | methyl | Butyl-[3-(6,8-dichloro-3-trifluoromethyl-phenanthren-9-yl)-3-hydroxy-propyl]-phosphoramidic acid methyl ester phenyl ester | 8.52 | 4.29 |

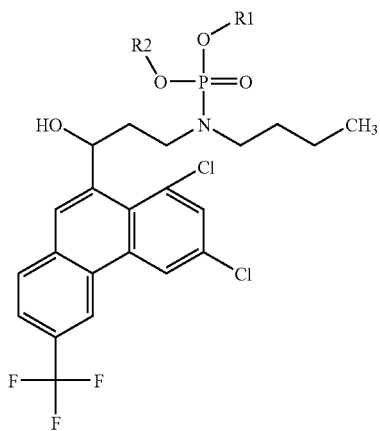

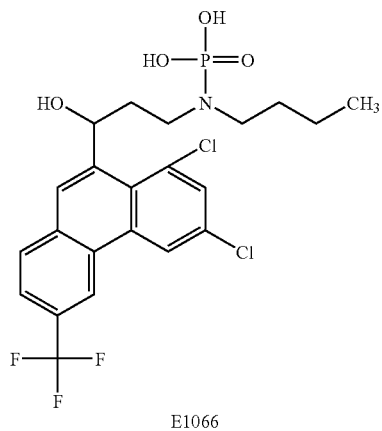

E1066

Halofantrine (Halfan ®)
Chemical Structure
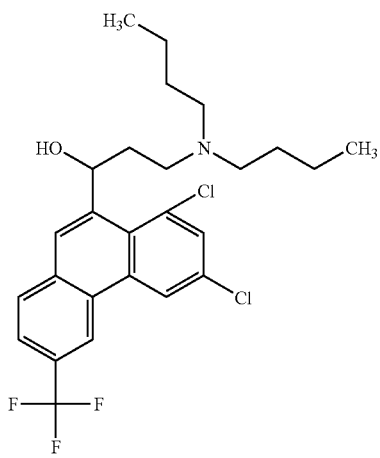
Active Metabolite Structure
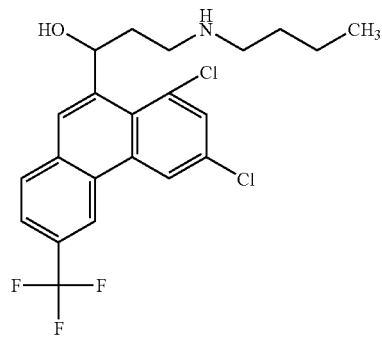
| Compound | R1 | R2 | Chemical Name | Estimated LogP | Estimated pKa |
|---|---|---|---|---|---|
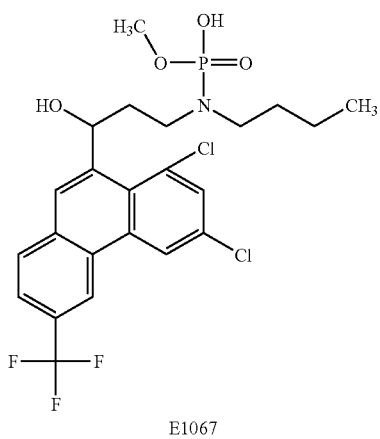
E1067
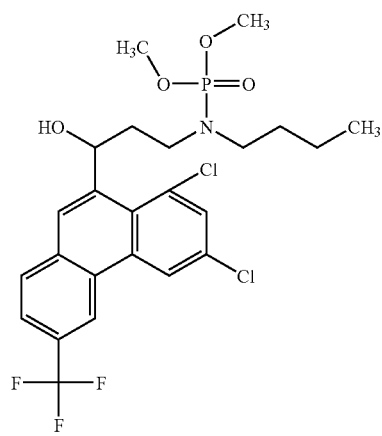
E1068
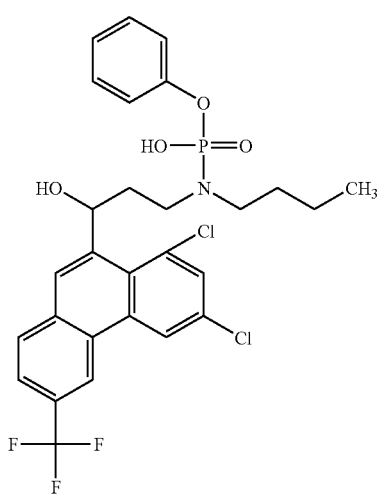
E1069
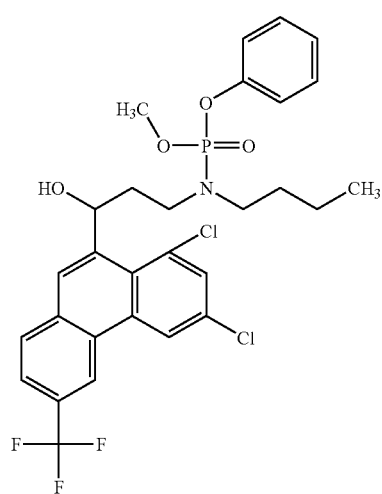
E1070

Levofloxacin (Levaquin ®)

Chemical Structure

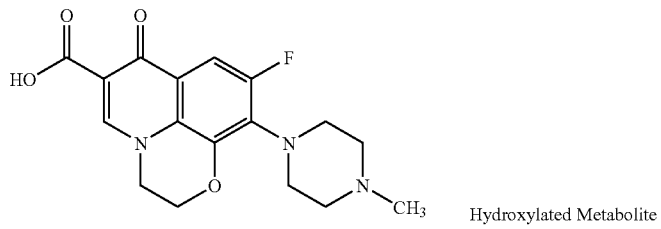

Hydroxylated Metabolite

| Compound | R1 | R2 | Chemical Name |
|---|---|---|---|
| E1383 | hydrogen | hydrogen | 8-Fluoro-6-oxo-9-(4-phosphono-piperazin-1-yl)-2,3-di-hydro-6H-1-oxa-3a-aza-phenalene-5-carboxylic acid |
| E1384 | hydrogen | methyl | 8-Fluoro-9-[4-(hydroxy-methoxy-phosphoryl)-piperazin-1-yl]-6-oxo-2,3-dihydro-6H-1-oxa-3a-aza-phenalene-5-carboxylic acid |
| E1385 | methyl | methyl | 9-[4-(Dimethoxy-phosphoryl)-piperazin-1-yl]-8-fluoro-6-oxo-2,3-dihydro-6H-1-oxa-3a-aza-phenalene-5-carboxylic acid |
| E1386 | phenyl | hydrogen | 8-Fluoro-9-[4-(hydroxy-phenoxy-phosphoryl)-piperazin-1-yl]-6-oxo-2,3-dihydro-6H-1-oxa-3a-aza-phenalene-5-carboxylic acid |
| E1387 | phenyl | methyl | 8-Fluoro-9-[4-(methoxy-phenoxy-phosphoryl)-piperazin-1-yl]-6-oxo-2,3-dihydro-6H-1-oxa-3a-aza-phenalene-5-carboxylic acid |

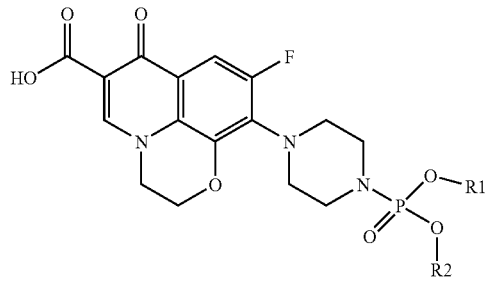

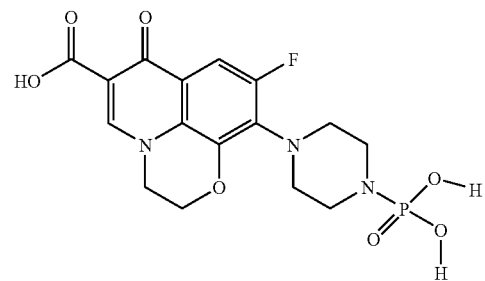

E1383

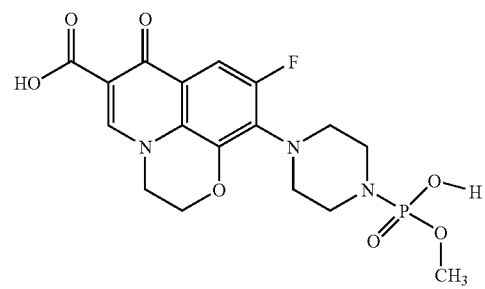

E1384

-continued
| Levofloxacin (Levaquin ®) |
|---|
Chemical Structure
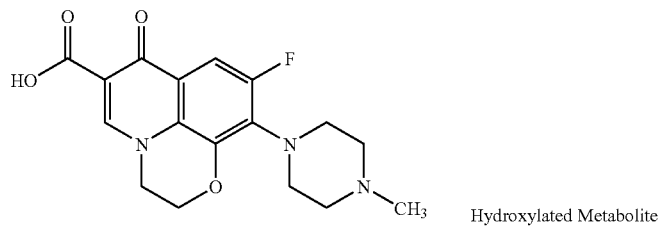
Hydroxylated Metabolite
| Compound | R1 | R2 | Chemical Name |
|---|---|---|---|
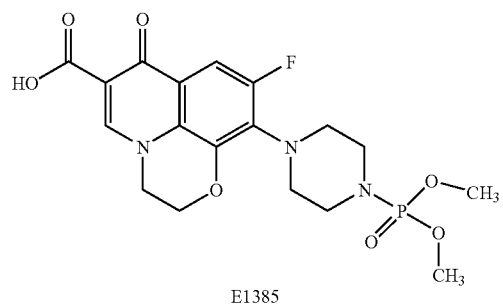
E1385
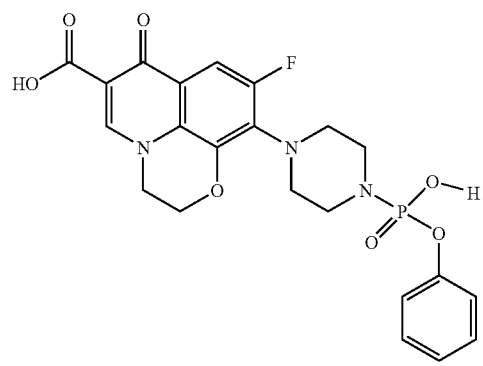
E1386
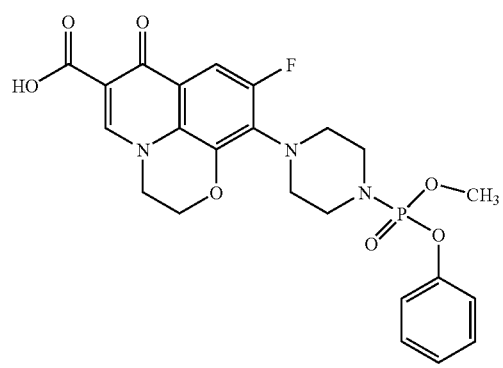
E1387

| Lomefloxacin (Maxaquin ®) | | | | | |
|---|---|---|---|---|---|
| Chemical Structure | | | | | |
| 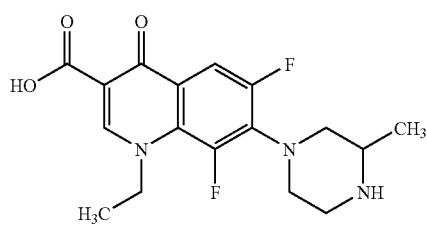 | | | | | |
| | | | | Hydroxylated Metabolite | |
| Compound | R1 | R2 | Chemical Name | Estimated LogP | Estimated pKa |
| E1439 | hydrogen | hydrogen | 1-Ethyl-6,8-difluoro-7-(3-methyl-4-phos-phono-piperazin-1-yl)-4-oxo-1,4-di-hydro-quinoline-3-carboxylic acid | | |
| E1440 | hydrogen | methyl | 1-Ethyl-6,8-difluoro-7-[4-(hydroxy-methoxy-phosphoryl)-3-methyl-piperazin-1-yl]-4-oxo-1,4-di-hydro-quinoline-3-carboxylic acid | | |
| E1441 | methyl | methyl | 7-[4-(Dimethoxy-phosphoryl)-3-methyl-piperazin-1-yl]-1-ethyl-6,8-difluoro-4-oxo-1,4-di-hydro-quinoline-3-carboxylic acid | | |
| E1442 | phenyl | hydrogen | 1-Ethyl-6,8-difluoro-7-[4-(hydroxy-phenoxy-phosphoryl)-3-methyl-piperazin-1-yl]-4-oxo-1,4-di-hydro-quinoline-3-carboxylic acid | | |
| E1443 | phenyl | methyl | 1-Ethyl-6,8-difluoro-7-[4-(methoxy-phenoxy-phosphoryl)-3-methyl-piperazin-1-yl]-4-ox-o-1,4-dihydro-quinoline-3-carboxylic acid; compound with benzene | | |

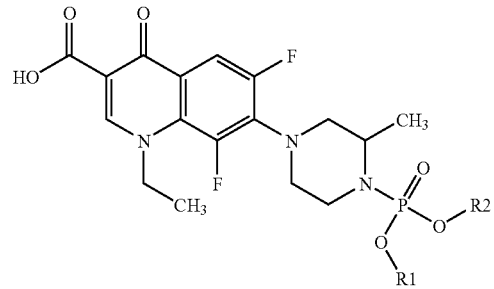

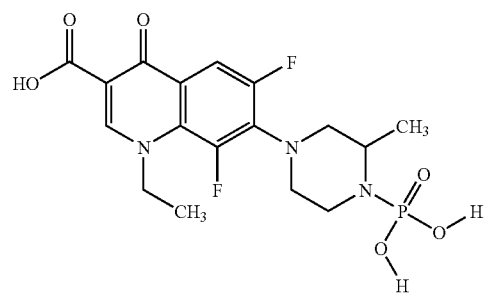

E1439

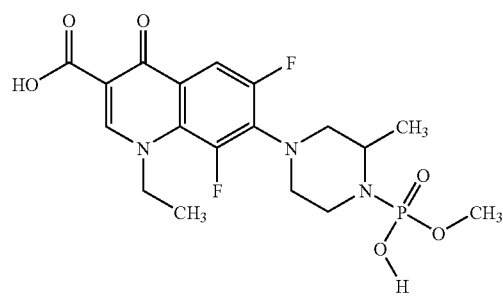

E1440

-continued
Lomefloxacin (Maxaquin ®)
Chemical Structure
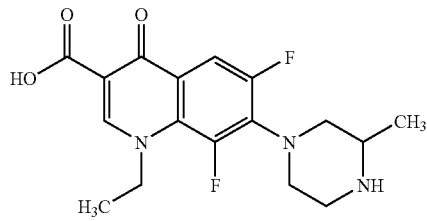
Hydroxylated Metabolite
| Compound | R1 | R2 | Chemical Name | Estimated LogP | Estimated pKa |
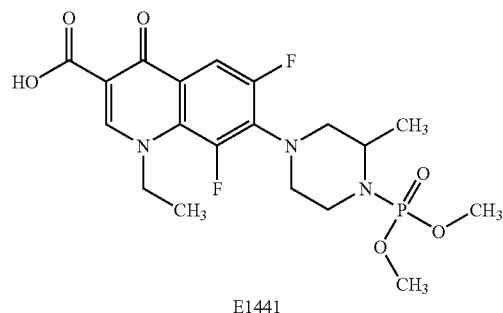
E1441
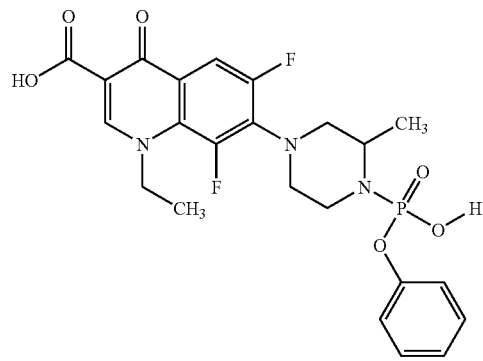
E1442
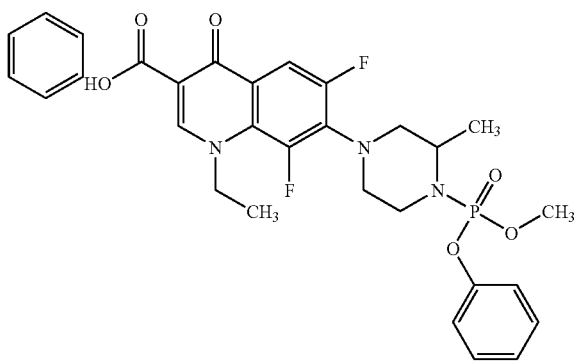
E1443

| Loxapine (Loxitane ®) | |
|---|---|
| Chemical Structure 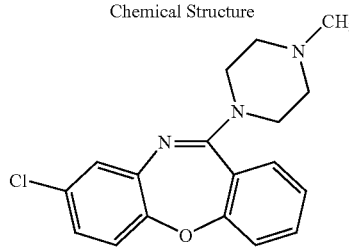 | Active Metabolite Structure 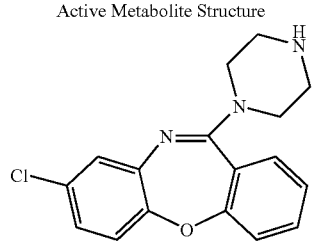 |

Hydroxylated Metabolite

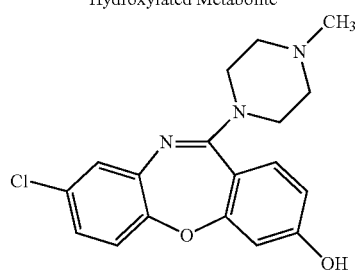

| Compound | R1 | R2 | Chemical Name | Estimated LogP | pKa |
|---|---|---|---|---|---|
| E1264 | hydrogen | hydrogen | [4-(8-Chloro-dibenzo[b,f][1,4]oxazepin-11-yl)-pipe-razin-1-yl]-phosphonic acid | 2.47 | 4.81 |
| E1265 | hydrogen | methyl | [4-(8-Chloro-dibenzo[b,f][1,4]oxazepin-11-yl)-pipe-razin-1-yl]-phosphonic acid monomethyl ester | 3.03 | 2.85 |
| E1266 | methyl | methyl | [4-(8-Chloro-dibenzo[b,f][1,4]oxazepin-11-yl)-pipe-razin-1-yl]-phosphonic acid dimethyl ester | 3.08 | 5.88 |
| E1267 | phenyl | hydrogen | [4-(8-Chloro-dibenzo[b,f][1,4]oxazepin-11-yl)-pipe-razin-1-yl]-phosphonic acid monophenyl ester | 4.79 | 2.38 |
| E1268 | phenyl | methyl | [4-(8-Chloro-dibenzo[b,f][1,4]oxazepin-11-yl)-pipe-razin-1-yl]-phosphonic acid methyl ester phenyl ester | 4.85 | 6.02 |

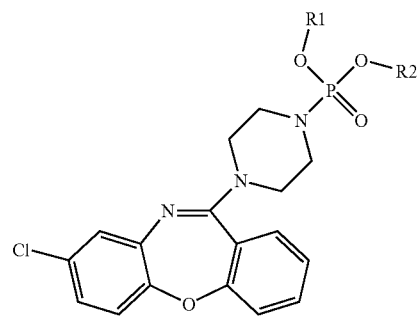

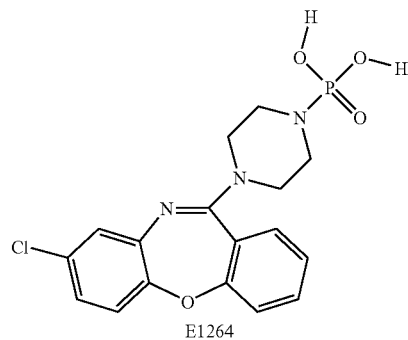

E1264

| Loxapine (Loxitane ®) |
|---|
Chemical Structure
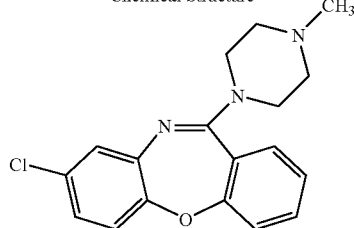
Active Metabolite Structure
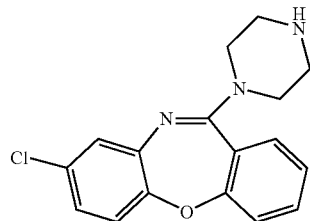
Hydroxylated Metabolite
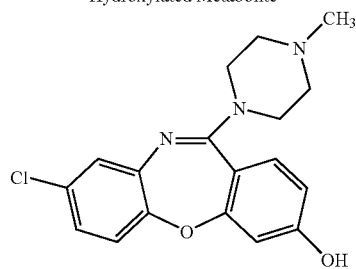
| Compound | R1 | R2 | Chemical Name | Estimated LogP | pKa |
|---|---|---|---|---|---|
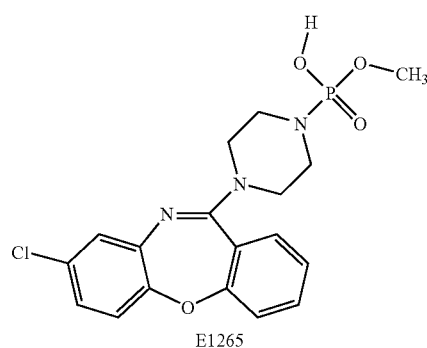
E1265
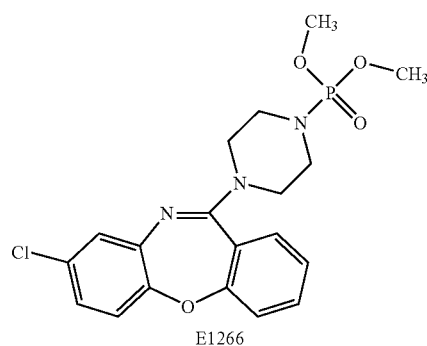
E1266

-continued
Loxapine (Loxitane ®)
Chemical Structure
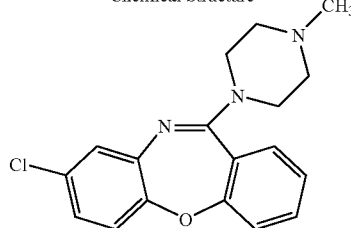
Active Metabolite Structure
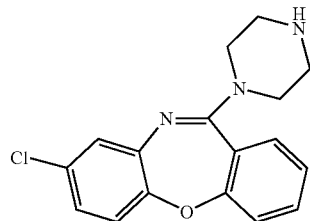
Hydroxylated Metabolite
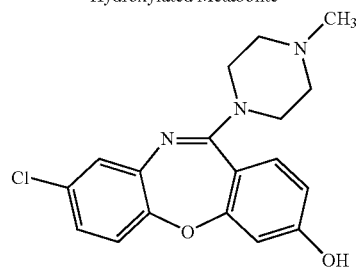
| Compound | R1 | R2 | Chemical Name | Estimated LogP | pKa |
|---|---|---|---|---|---|
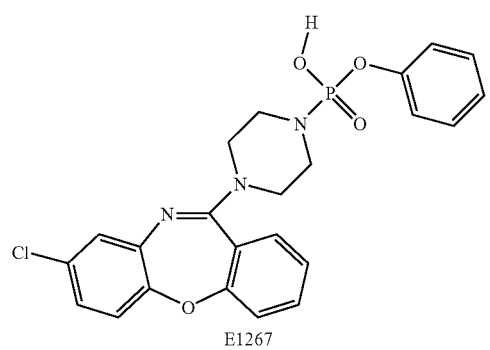
E1267
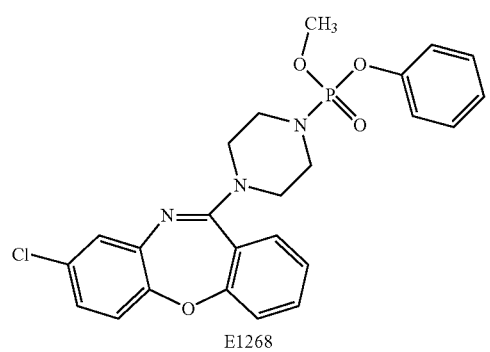
E1268

Maprotiline (Ludiomil ®)

Chemical Structure / Hydroxylated Metabolite

| Compound | R1 | R2 | Chemical Name | Estimated LogP | pKa |
|---|---|---|---|---|---|
| E1344 | hydrogen | hydrogen | [9,10-ethanoanthracene-9(10H)-propylamine]-methyl phosphoramidic acid | 3.56 | 1.73 |
| E1345 | hydrogen | methyl | [9,10-ethanoanthracene-9(10H)-propylamine]-methyl phosphoramidic acid monomethyl ester | 3.61 | 6.24 |
| E1346 | methyl | methyl | [9,10-ethanoanthracene-9(10H)-propylamine]-methyl phosphoramidic acid dimethyl ester | 3.67 | 2.28 |
| E1347 | phenyl | hydrogen | [9,10-ethanoanthracene-9(10H)-propylamine]-methyl phosphoramidic acid monophenyl ester | 5.38 | 5.57 |
| E1348 | phenyl | methyl | [9,10-ethanoanthracene-9(10H)-propylamine]-methyl phosphoramidic acid methyl ester phenyl ester | 5.44 | 2.89 |

E1344   E1345   E1346   E1347   E1348

MDMA (Ecstasy ®)

Chemical Structure / Active Metabolite Structure / Hydroxylated Metabolite

| Compound | R1 | R2 | Chemical Name | Estimated LogP | pKa |
|---|---|---|---|---|---|
| E1269 | hydrogen | hydrogen | (2-Benzo[1,3]dioxol-5-yl-1-methyl-ethyl)-methyl-phosphoramidic acid | 0.71 | 2.83 |
| E1270 | hydrogen | methyl | (2-Benzo[1,3]dioxol-5-yl-1-methyl-ethyl)-methyl-phosphoramidic acid monomethyl ester | 0.76 | 4.83 |
| E1271 | methyl | methyl | (2-Benzo[1,3]dioxol-5-yl-1-methyl-ethyl)-methyl-phosphoramidic acid dimethyl ester | 0.82 | 3.46 |
| E1272 | phenyl | hydrogen | (2-Benzo[1,3]dioxol-5-yl-1-methyl-ethyl)-methyl-phosphoramidic acid monophenyl ester | 2.53 | 4.42 |

MDMA (Ecstasy ®)

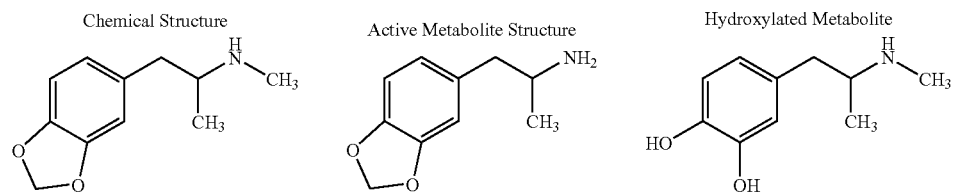

| Compound | R1 | R2 | Chemical Name | Estimated LogP | pKa |
|---|---|---|---|---|---|
| E1273 | phenyl | methyl | (2-Benzo[1,3]dioxol-5-yl-1-methyl-ethyl)-methyl-phosphoramidic acid methyl ester phenyl ester | 2.59 | 3.99 |

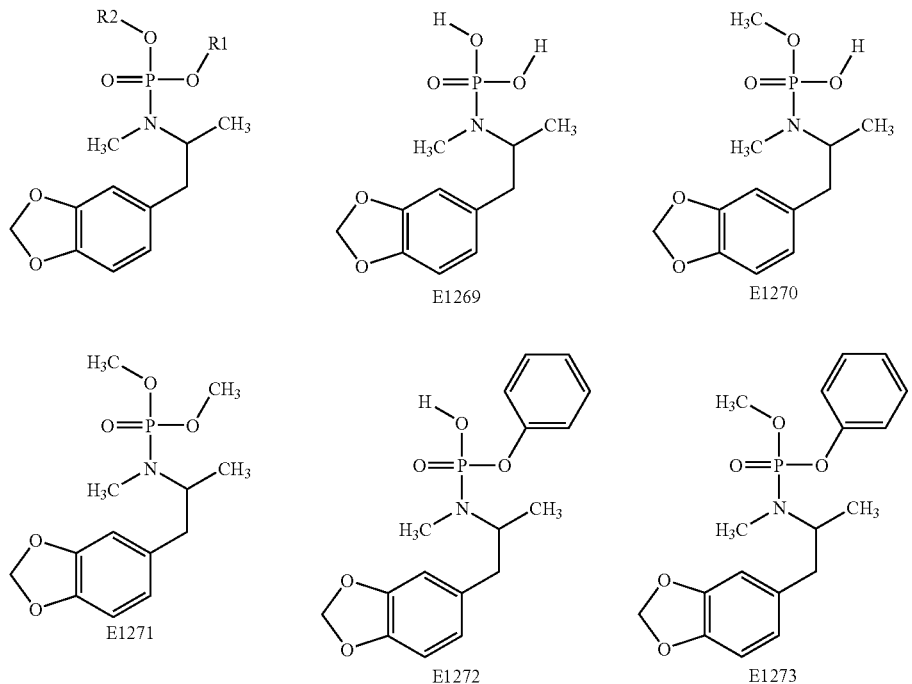

Metachlorophenylpiperazine

Chemical Structure

Hydroxylated Metabolite

| Compound | R1 | R2 | Chemical Name | Estimated LogP | pKa |
|---|---|---|---|---|---|
| E1195 | hydrogen | hydrogen | [4-(3-Chloro-phenyl)-piperazin-1-yl]-phosphonic acid | 1.77 | 4.99 |
| E1196 | hydrogen | methyl | [4-(3-Chloro-phenyl)-piperazin-1-yl]-phosphonic acid monomethyl ester | 1.83 | 2.67 |

-continued

Metachlorophenylpiperazine

Chemical Structure

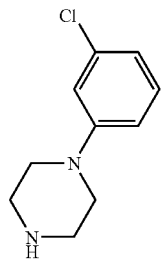

Hydroxylated Metabolite

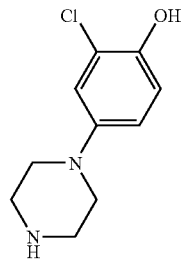

| Compound | R1 | R2 | Chemical Name | Estimated LogP | pKa |
|---|---|---|---|---|---|
| E1197 | methyl | methyl | [4-(3-Chloro-phenyl)-piperazin-1-yl]-phosphonic acid dimethyl ester | 1.89 | 6.06 |
| E1198 | phenyl | hydrogen | [4-(3-Chloro-phenyl)-piperazin-1-yl]-phosphonic acid monophenyl ester | 3.60 | 2.20 |
| E1199 | phenyl | methyl | [4-(3-Chloro-phenyl)-piperazin-1-yl]-phosphonic acid methyl ester phenyl ester | 3.65 | 6.20 |

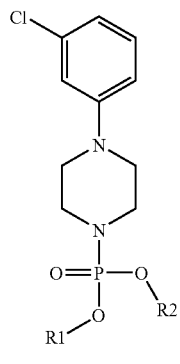

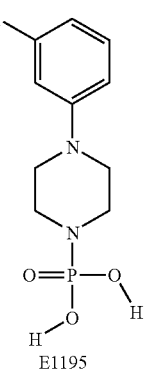
E1195

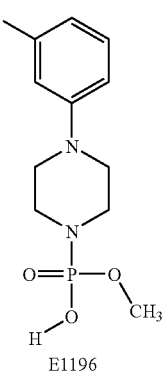
E1196

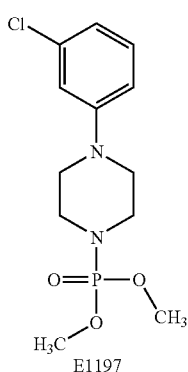
E1197

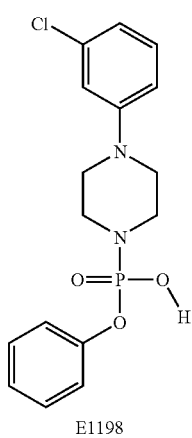
E1198

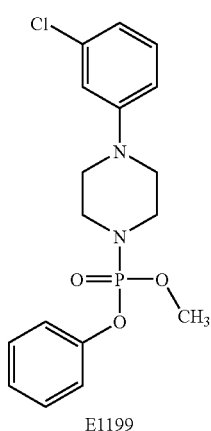
E1199

| Methadone (Dolophine ®) | |
|---|---|
| Chemical Structure 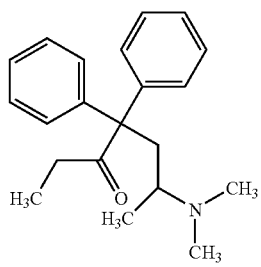 | Hydroxylated Metabolite 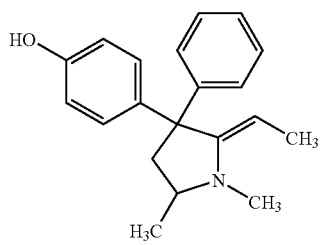 |
| | Active Metabolite Structure |

| Compound | R1 | R2 | Chemical Name | Estimated LogP | pKa |
|---|---|---|---|---|---|
| E1299 | hydrogen | hydrogen | Methyl-(1-methyl-4-oxo-3,3-diphenyl-hexyl)-phosphoramidic acid | 3.54 | 3.26 |
| E1300 | hydrogen | methyl | Methyl-(1-methyl-4-oxo-3,3-diphenyl-hexyl)-phosphoramidic acid monomethyl ester | 3.60 | 4.40 |
| E1301 | methyl | methyl | Methyl-(1-methyl-4-oxo-3,3-diphenyl-hexyl)-phosphoramidic acid dimethyl ester | 3.65 | 3.36 |
| E1302 | phenyl | hydrogen | Methyl-(1-methyl-4-oxo-3,3-diphenyl-hexyl)-phosphoramidic acid monophenyl ester | 5.36 | 4.01 |
| E1303 | phenyl | methyl | Methyl-(1-methyl-4-oxo-3,3-diphenyl-hexyl)-phosphoramidic acid methyl ester phenyl ester | 5.42 | 4.01 |

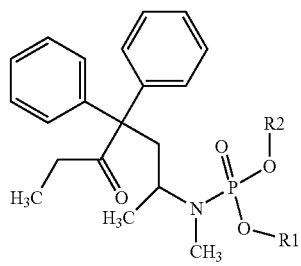

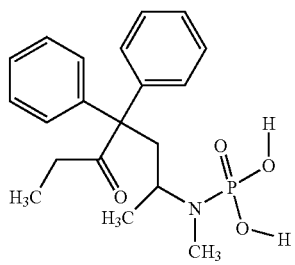

E1299

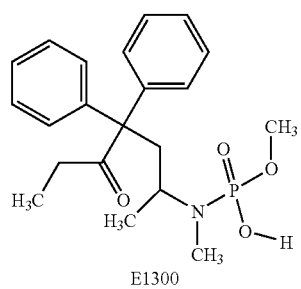

E1300

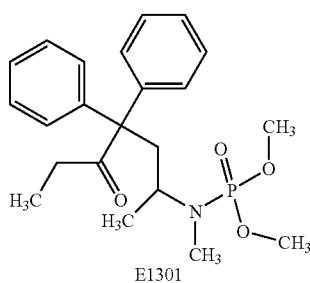

E1301

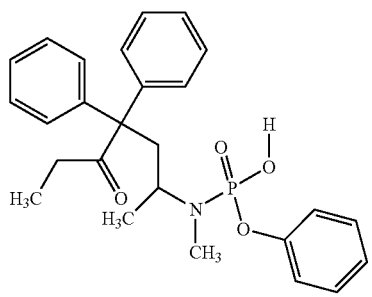

E1302

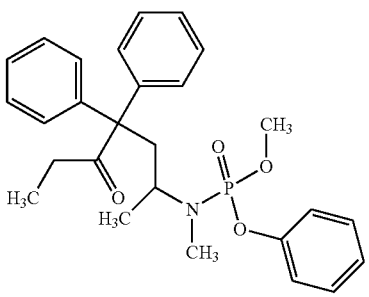

E1303

| Methamphetamine (Desoxyn ®) | |
|---|---|
| Chemical Structure | Hydroxylated Metabolite |
| 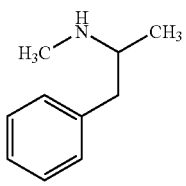 | 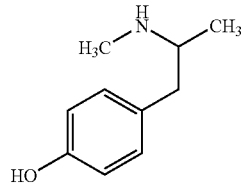 |

| Compound | R1 | R2 | Chemical Name | Estimated LogP | pKa |
|---|---|---|---|---|---|
| E1217 | hydrogen | hydrogen | Methyl-(1-methyl-2-phenyl-ethyl)-phosphoramidic acid | 2.03 | 2.77 |
| E1218 | hydrogen | methyl | Methyl-(1-methyl-2-phenyl-ethyl)-phosphoramidic acid monomethyl ester | 2.09 | 2.89 |
| E1219 | methyl | methyl | Methyl-(1-methyl-2-phenyl-ethyl)-phosphoramidic acid dimethyl ester | 2.14 | 3.39 |
| E1220 | phenyl | hydrogen | Methyl-(1-methyl-2-phenyl-ethyl)-phosphoramidic acid monophenyl ester | 3.85 | 4.49 |
| E1221 | phenyl | methyl | Methyl-(1-methyl-2-phenyl-ethyl)-phosphoramidic acid methyl ester phenyl ester | 3.91 | 3.92 |

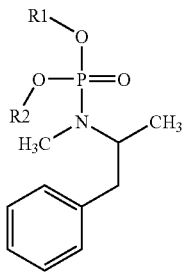

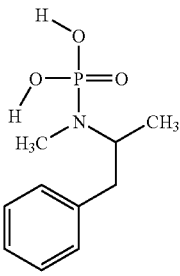
E1217

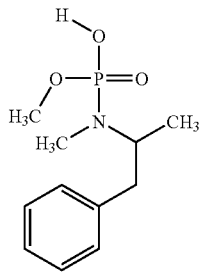
E1218

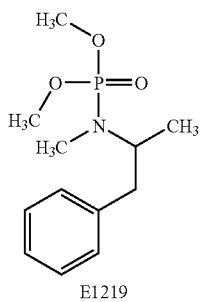
E1219

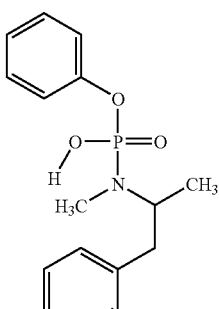
E1220

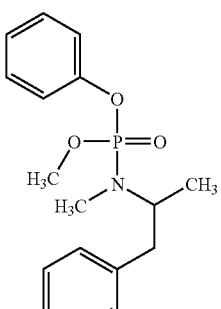
E1221

| Methylphenidate (Ritalin ®) | |
|---|---|
| Chemical Structure | Hydroxylated Metabolite |
| 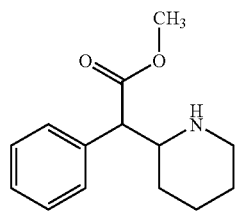 | 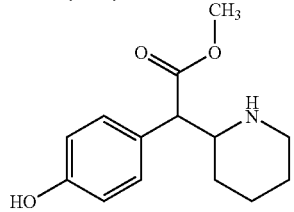 |
| Active Metabolite Structure | |

| Compound | R1 | R2 | Chemical Name | Estimated LogP | pKa |
|---|---|---|---|---|---|
| E1086 | hydrogen | hydrogen | Phenyl-(1-phosphono-piperidin-2-yl)-acetic acid methyl ester | 2.37 | 3.57 |

Methylphenidate (Ritalin ®)

Chemical Structure

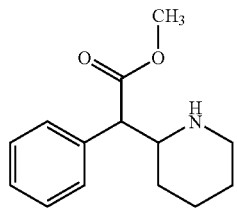

Hydroxylated Metabolite

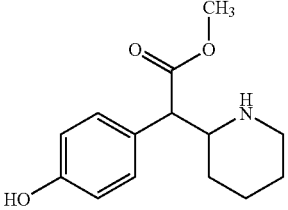

Active Metabolite Structure

| Compound | R1 | R2 | Chemical Name | Estimated LogP | pKa |
|---|---|---|---|---|---|
| E1087 | hydrogen | methyl | [1-(Hydroxy-methoxy-phosphoryl)-piperidin-2-yl]-phenyl-acetic acid ethyl ester | 2.42 | 4.09 |
| E1088 | methyl | methyl | [1-(Dimethoxy-phosphoryl)-piperidin-2-yl]-phenyl-acetic acid methyl ester | 2.48 | 4.63 |
| E1089 | phenyl | hydrogen | [1-(Dimethoxy-phosphoryl)-piperidin-2-yl]-phenyl-acetic acid methyl ester | 4.19 | 3.62 |
| E1090 | phenyl | phenyl | [1-(Methoxy-phenoxy-phosphoryl)-piperidin-2-yl]-phenyl-acetic acid methyl ester | 4.25 | 4.78 |

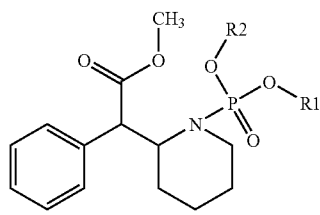

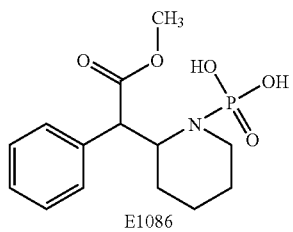

E1086

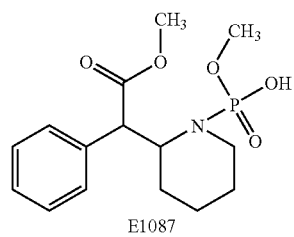

E1087

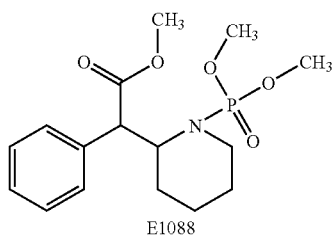

E1088

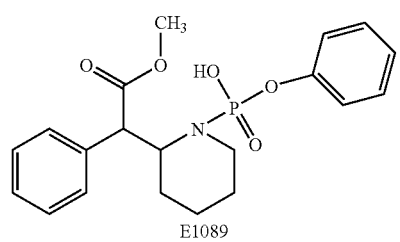

E1089

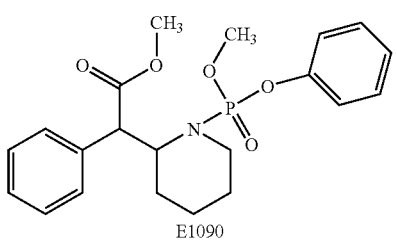

E1090

| Methoxyphenamine (Orthoxinine ®) | | | | | |
|---|---|---|---|---|---|
| Chemical Structure | | | Hydroxylated Metabolite | | |
| 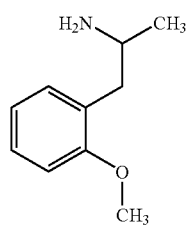 | | | 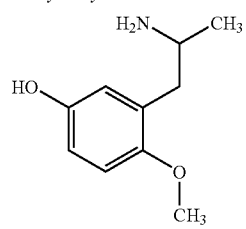 | | |
| Compound | R1 | R2 | Chemical Name | Estimated LogP | pKa |
| E1304 | hydrogen | hydrogen | [2-(2-Methoxy-phenyl)-1-methyl-ethyl]-phosphoramidic acid | 1.56 | 2.29 |
| E1305 | hydrogen | methyl | [2-(2-Methoxy-phenyl)-1-methyl-ethyl]-phosphoramidic acid monomethyl ester | 1.62 | 5.68 |
| E1306 | methyl | methyl | [2-(2-Methoxy-phenyl)-1-methyl-ethyl]-phosphoramidic acid dimethyl ester | 1.68 | 3.03 |
| E1307 | phenyl | hydrogen | [2-(2-Methoxy-phenyl)-1-methyl-ethyl]-phosphoramidic acid monophenyl ester | 3.39 | 5.23 |
| E1308 | phenyl | methyl | [2-(2-Methoxy-phenyl)-1-methyl-ethyl]-phosphoramidic acid methyl ester phenyl ester | 3.44 | 3.61 |

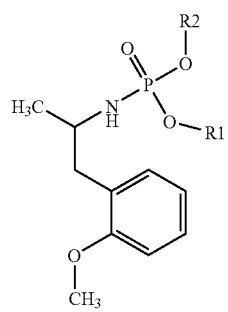

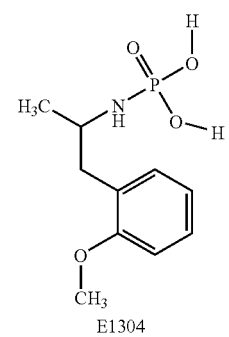
E1304

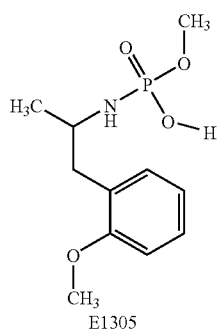
E1305

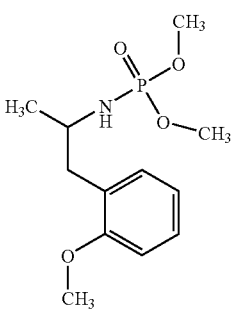
E1306

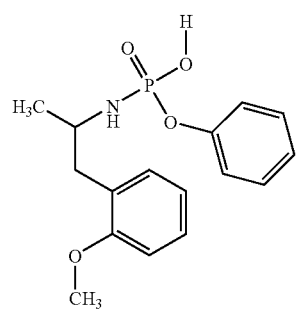
E1307

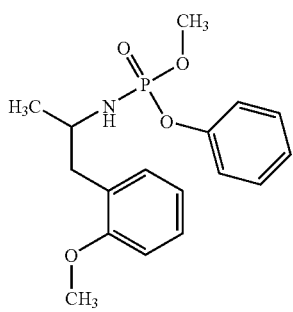
E1308

Mianserin (Tolvon ®)

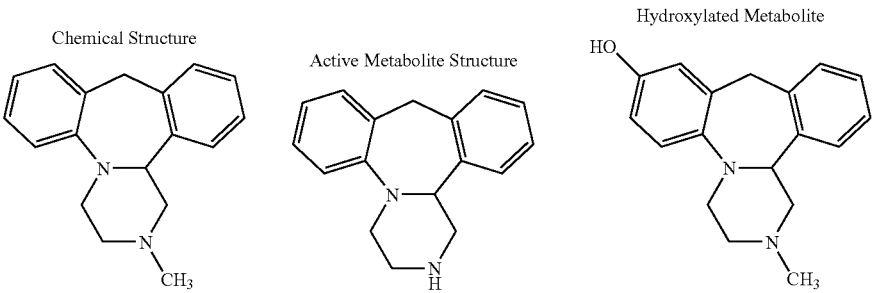

| Compound | R1 | R2 | Chemical Name | Estimated LogP | pKa |
|---|---|---|---|---|---|
| E1164 | hydrogen | hydrogen | (3,4,9,13b-Tetrahydro-1H-2,4a-diaza-tribenzo[a,c,e]cyclo-hepten-2-yl)-phosphonic acid | 2.72 | 4.72 |
| E1165 | hydrogen | methyl | (3,4,9,13b-Tetrahydro-1H-2,4a-diaza-tribenzo[a,c,e]cyclo-hepten-2-yl)-phosphonic acid monomethyl ester | 2.78 | 2.94 |
| E1166 | methyl | methyl | (3,4,9,13b-Tetrahydro-1H-2,4a-diaza-tribenzo[a,c,e]cyclo-hepten-2-yl)-phosphonic acid dimethyl ester | 2.83 | 5.79 |
| E1167 | phenyl | hydrogen | (3,4,9,13b-Tetrahydro-1H-2,4a-diaza-tribenzo[a,c,e]cyclo-hepten-2-yl)-phosphonic acid monophenyl ester | 4.55 | 2.46 |
| E1168 | phenyl | methyl | (3,4,9,13b-Tetrahydro-1H-2,4a-diaza-tribenzo[a,c,e]cyclo-hepten-2-yl)-phosphonic acid methyl ester phenyl ester | 4.60 | 5.93 |

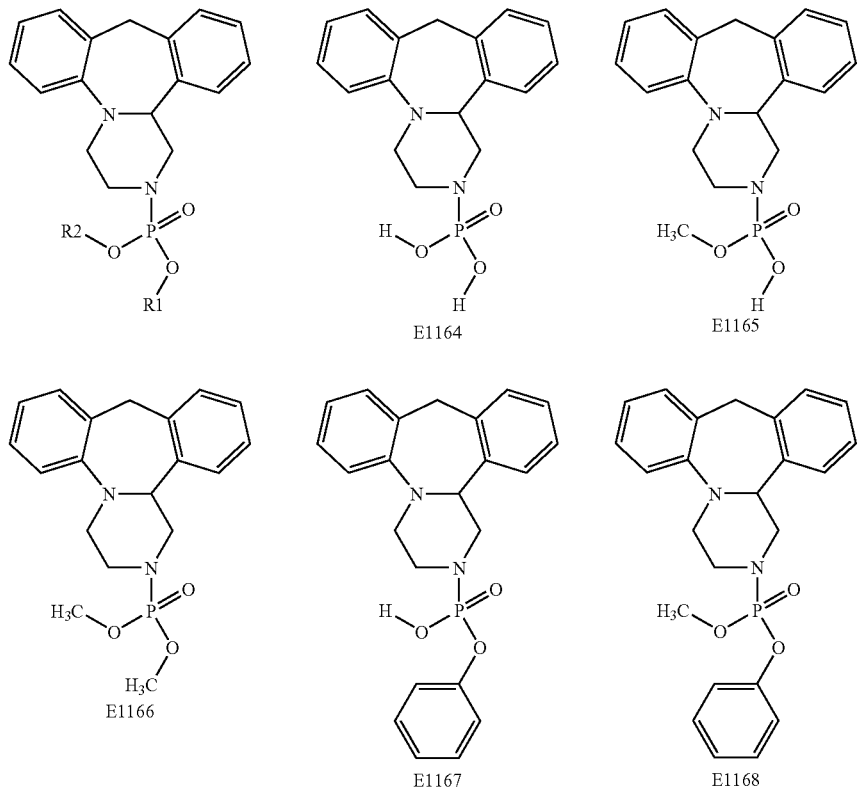

| Mirtazapine (Remeron ®) | | |
|---|---|---|
| Chemical Structure 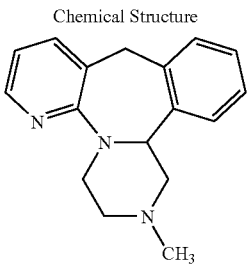 | Active Metabolite Structure 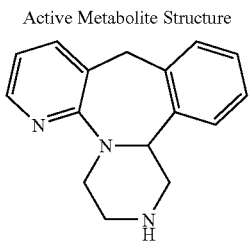 | Hydroxylated Metabolite 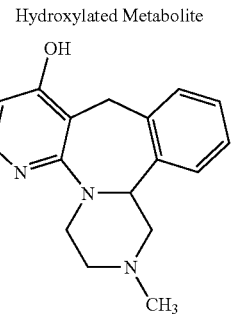 |

| Compound | R1 | R2 | Chemical Name | Estimated LogP | Estimated pKa |
|---|---|---|---|---|---|
| E1061 | hydrogen | hydrogen | (3,4,9,13b-Tetrahydro-1H-2,4a,5-triaza-tribenzo[a,c,e]cyclo-hepten-2-yl)-phosphonic acid | 2.41 | 4.91 |
| E1062 | hydrogen | methyl | (3,4,9,13b-Tetrahydro-1H-2,4a,5-triaza-tribenzo[a,c,e]cyclo-hepten-2-yl)-phosphonic acid monomethyl ester | 2.46 | 2.74 |
| E1063 | methyl | methyl | (3,4,9,13b-Tetrahydro-1H-2,4a,5-triaza-tribenzo[a,c,e]cyclo-hepten-2-yl)-phosphonic acid dimethyl ester | 2.52 | 6.11 |
| E1064 | phenyl | hydrogen | (3,4,9,13b-Tetrahydro-1H-2,4a,5-triaza-tribenzo[a,c,e]cyclo-hepten-2-yl)-phosphonic acid monophenyl ester | 4.23 | 2.14 |
| E1065 | phenyl | methyl | (3,4,9,13b-Tetrahydro-1H-2,4a,5-triaza-tribenzo[a,c,e]cyclo-hepten-2-yl)-phosphonic acid methyl ester phenyl ester | 4.29 | 6.25 |

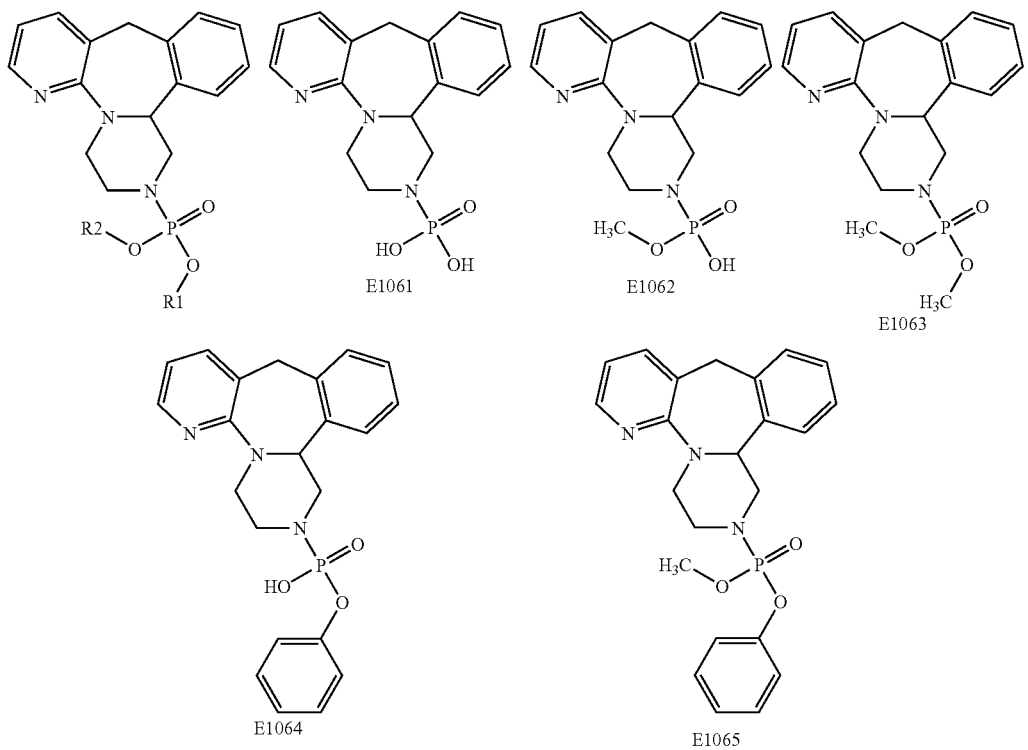

| Moxifloxacin (Avalox ®) | | | |
|---|---|---|---|
| Chemical Structure | | | |
| 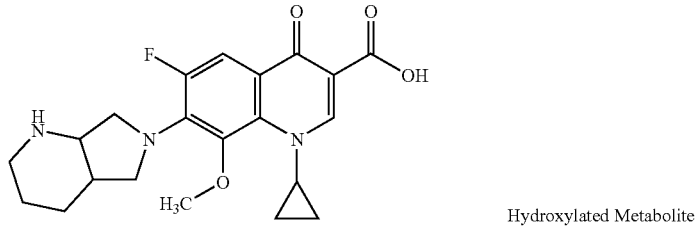 | | | |
| Hydroxylated Metabolite | | | |
| Compound | R1 | R2 | Chemical Name |
| E1434 | hydrogen | hydrogen | 1-Cyclopropyl-6-fluoro-8-methoxy-4-oxo-7-(1-phosphono-octahydro-pyrrolo[3,4-b]pyridin-6-yl)-1,4-dihydro-quinoline-3-carboxylic acid |
| E1435 | hydrogen | methyl | 1-Cyclopropyl-6-fluoro-7-[1-(hydroxy-methoxy-phosphoryl)-octahydro-pyrrolo[3,4-b]pyridin-6-yl]-8-methoxy-4-oxo-1,4-dihydro-quinoline-3-carboxylic acid |
| E1436 | methyl | methyl | 1-Cyclopropyl-7-[1-(dimethoxy-phosphoryl)-octahydro-pyrrolo[3,4-b]pyridin-6-yl]-6-fluoro-8-methoxy-4-oxo-1,4-dihydro-quinoline-3-carboxylic acid |
| E1437 | phenyl | hydrogen | 1-Cyclopropyl-6-fluoro-7-[1-(hydroxy-phenoxy-phosphoryl)-octahydro-pyrrolo[3,4-b]pyridin-6-yl]-8-methoxy-4-oxo-1,4-dihydro-quinoline-3-carboxylic acid |
| E1438 | phenyl | methyl | 1-Cyclopropyl-6-fluoro-8-methoxy-7-[1-(methoxy-phenoxy-phosphoryl)-octahydro-pyrrolo[3,4-b]pyridin-6-yl]-4-oxo-1,4-dihydro-quinoline-3-carboxylic acid |

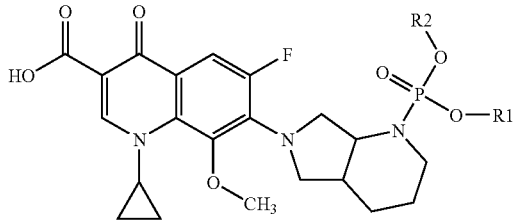

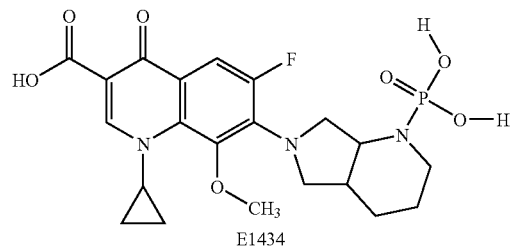

E1434

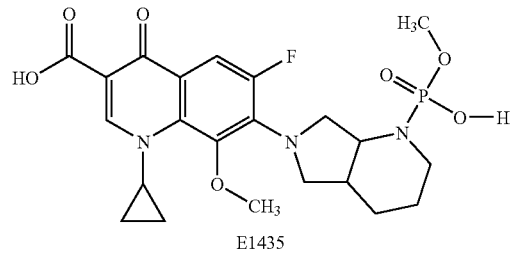

E1435

Moxifloxacin (Avalox ®)
Chemical Structure
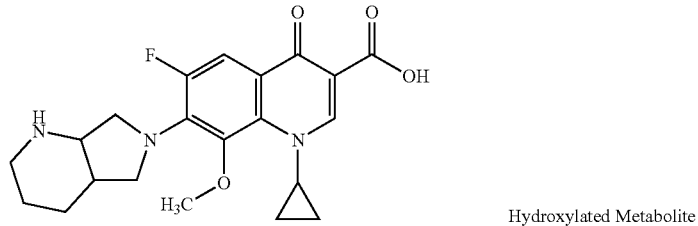
Hydroxylated Metabolite
| Compound | R1 | R2 | Chemical Name |
|---|---|---|---|
E1436
E1437
E1438
Naratriptan (Amerge ®)
Chemical Structure 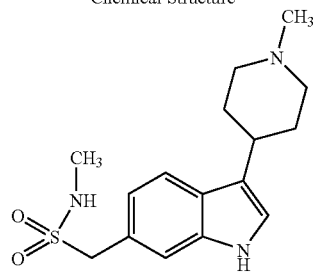   Active Metabolite Structure 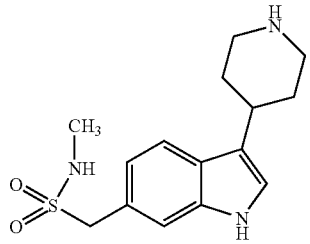
| Compound | R1 | R2 | Chemical Name | Estimated LogP | Estimated pKa |
|---|---|---|---|---|---|
| E1091 | hydrogen | hydrogen | 4-(6-Methylsulfamoylmethyl-1H-indol-3-yl)-piperidin-1-yl]-phosphonic acid | 1.58 | 2.70 |

-continued

| Naratriptan (Amerge ®) | |
|---|---|
| Chemical Structure 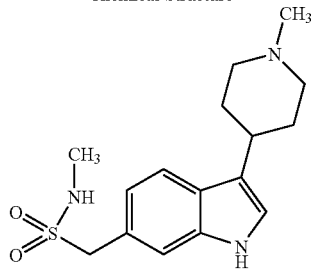 | Active Metabolite Structure 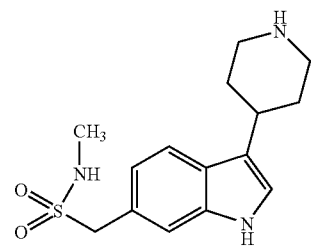 |

| Compound | R1 | R2 | Chemical Name | Estimated LogP | Estimated pKa |
|---|---|---|---|---|---|
| E1092 | hydrogen | methyl | [4-(6-Methylsulfamoylmethyl-1H-indol-3-yl)-piperidin-1-yl]-phosphonic acid monomethyl ester | 1.63 | 4.95 |
| E1093 | methyl | methyl | [4-(6-Methylsulfamoylmethyl-1H-indol-3-yl)-piperidin-1-yl]-phosphonic acid dimethy lester | 1.69 | 3.77 |
| E1094 | phenyl | hydrogen | [4-(6-Methylsulfamoylmethyl-1H-indol-3-yl)-piperidin-1-yl]-phosphonic acid monophenyl ester | 3.40 | 4.48 |
| E1095 | phenyl | methyl | [4-(6-Methylsulfamoylmethyl-1H-indol-3-yl)-piperidin-1-yl]-phosphonic acid methyl ester phenyl ester | 3.46 | 3.92 |

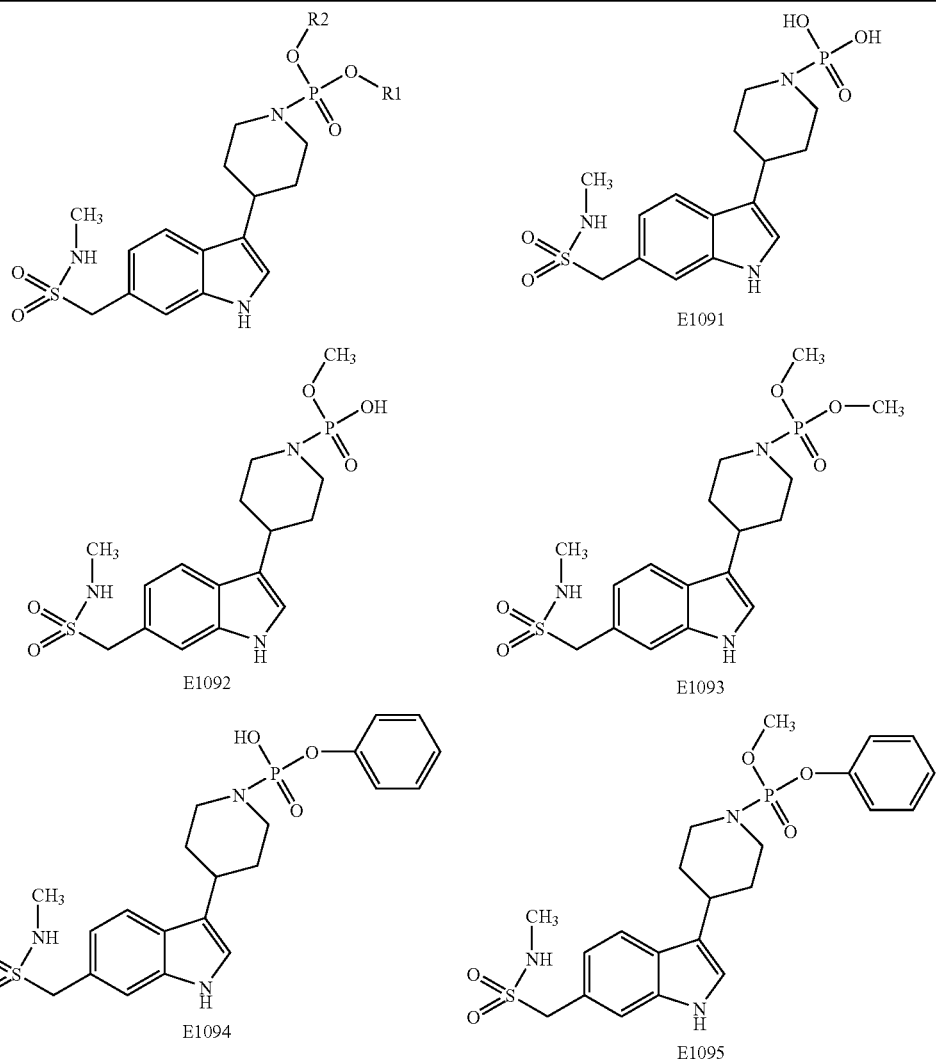

Norastemizole

Chemical Structure

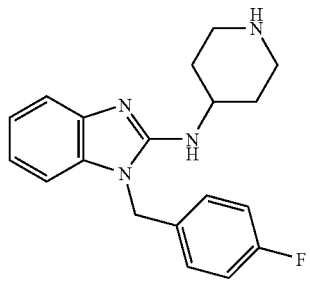

| Compound | R1 | R2 | Chemical Name | Estimated LogP | Estimated pKa |
|---|---|---|---|---|---|
| E1101 | hydrogen | hydrogen | {4-[1-(4-Fluoro-benzyl)-1H-benzoimidazol-2-yl-amino]-piperidin-1-yl}-phosphonic acid | 3.75 | 3.92 |
| E1102 | hydrogen | methyl | {4-[1-(4-Fluoro-benzyl)-1H-benzoimidazol-2-yl-amino]-piperidin-1-yl}-phosphonic acid monomethyl ester | 3.80 | 3.74 |
| E1103 | methyl | methyl | {4-[1-(4-Fluoro-benzyl)-1H-benzoimidazol-2-yl-amino]-piperidin-1-yl}-phosphonic acid dimethyl ester | 3.86 | 4.99 |
| E1104 | phenyl | hydrogen | {4-[1-(4-Fluoro-benzyl)-1H-benzoimidazol-2-yl-amino]-piperidin-1-yl}-phosphonic acid monophenyl ester | 5.57 | 3.26 |
| E1105 | phenyl | methyl | {4-[1-(4-Fluoro-benzyl)-1H-benzoimidazol-2-yl-amino]-piperidin-1-yl}-phosphonic acid methyl ester phenyl ester | 5.63 | 5.13 |

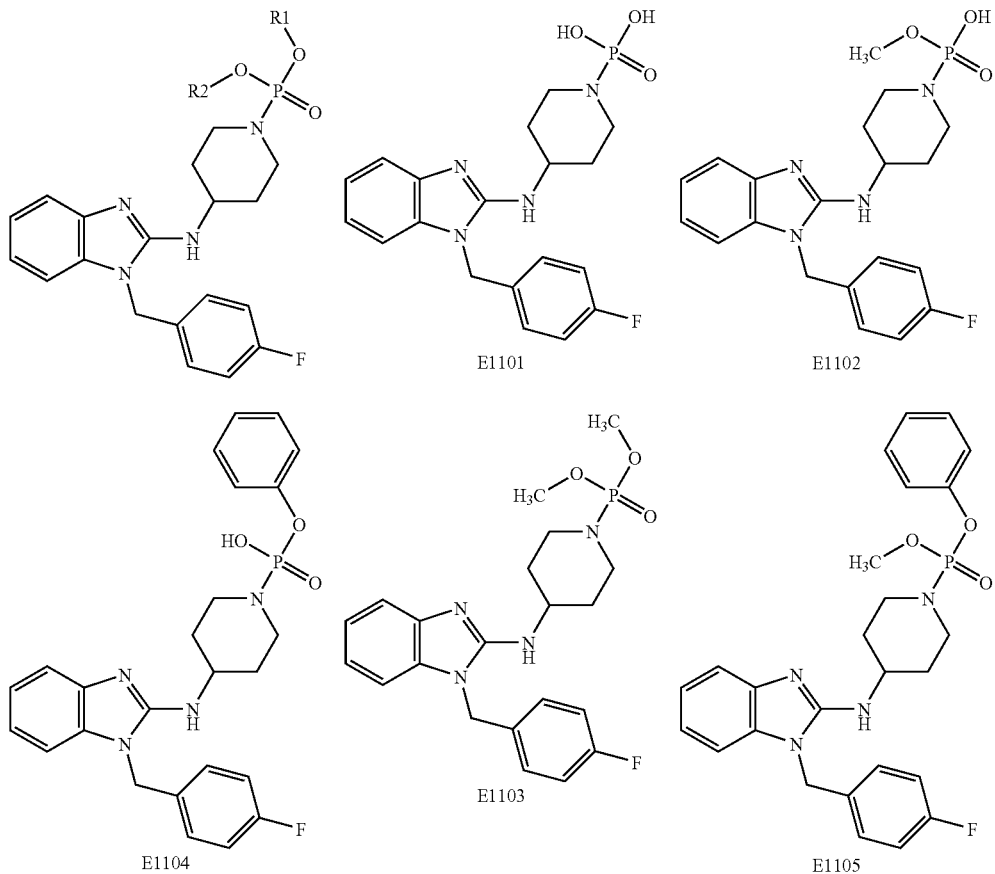

| Norbuspirone | | | | | |
|---|---|---|---|---|---|
| Chemical Structure 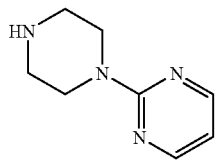 | | | Hydroxylated Metabolite 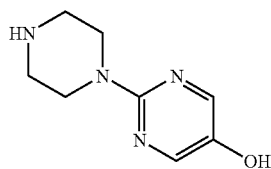 | | |
| Compound | R1 | R2 | Chemical Name | Estimated LogP | pKa |
| E1200 | hydrogen | hydrogen | (4-Pyrimidin-2-yl-piperazin-1-yl)-phosphonic acid | −0.07 | 6.04 |
| E1201 | hydrogen | methyl | (4-Pyrimidin-2-yl-piperazin-1-yl)-phosphonic acid monomethyl ester | −0.01 | 1.62 |
| E1202 | methyl | methyl | (4-Pyrimidin-2-yl-piperazin-1-yl)-phosphonic acid dimethyl ester | 0.05 | 7.10 |
| E1203 | phenyl | hydrogen | (4-Pyrimidin-2-yl-piperazin-1-yl)-phosphonic acid monophenyl ester | 1.76 | 1.14 |
| E1204 | phenyl | methyl | (4-Pyrimidin-2-yl-piperazin-1-yl)-phosphonic acid methyl ester phenyl ester | 1.81 | 7.25 |

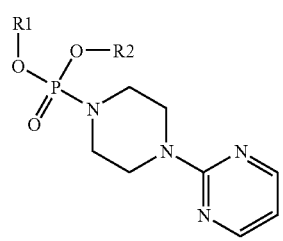

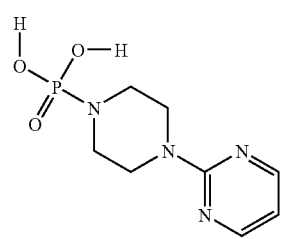
E1200

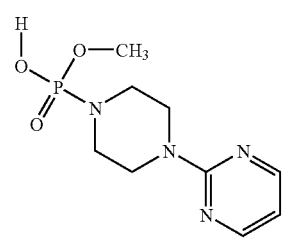
E1201

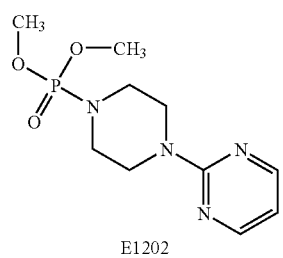
E1202

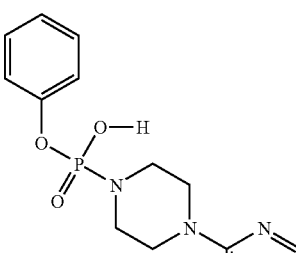
E1203

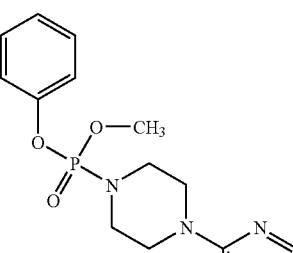
E1204

| Norcisapride | |
|---|---|
| Chemical Structure | Hydroxylated Metabolite |

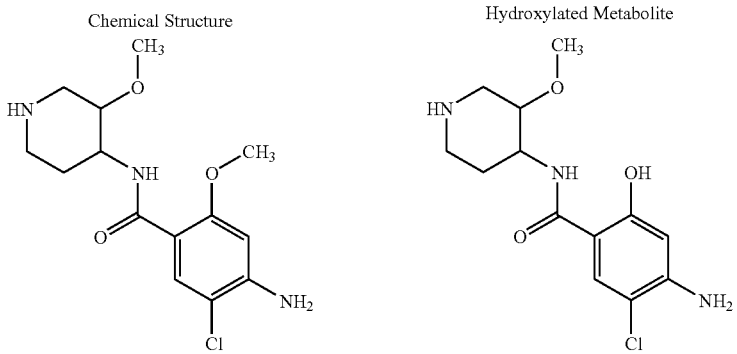

| Compound | R1 | R2 | Chemical Name | Estimated LogP | pKa |
|---|---|---|---|---|---|
| E1144 | hydrogen | hydrogen | [4-(4-Amino-5-chloro-2-methoxy-benzoylamino)-3-methoxy-piperidin-1-yl]-phosphonic acid | 0.04 | 4.78 |
| E1145 | hydrogen | methyl | [4-(4-Amino-5-chloro-2-methoxy-benzoylamino)-3-methoxy-piperidin-1-yl]-phosphonic acid monomethyl ester | 0.10 | 2.89 |
| E1146 | methyl | methyl | [4-(4-Amino-5-chloro-2-methoxy-benzoylamino)-3-methoxy-piperidin-1-yl]-phosphonic acid dimethyl ester | 0.15 | 5.85 |
| E1147 | phenyl | hydrogen | [4-(4-Amino-5-chloro-2-methoxy-benzoylamino)-3-methoxy-piperidin-1-yl]-phosphonic acid monophenyl ester | 1.86 | 2.41 |
| E1148 | phenyl | methyl | [4-(4-Amino-5-chloro-2-methoxy-benzoylamino)-3-methoxy-piperidin-1-yl]-phosphonic acid methyl ester phenyl ester | 1.92 | 5.99 |

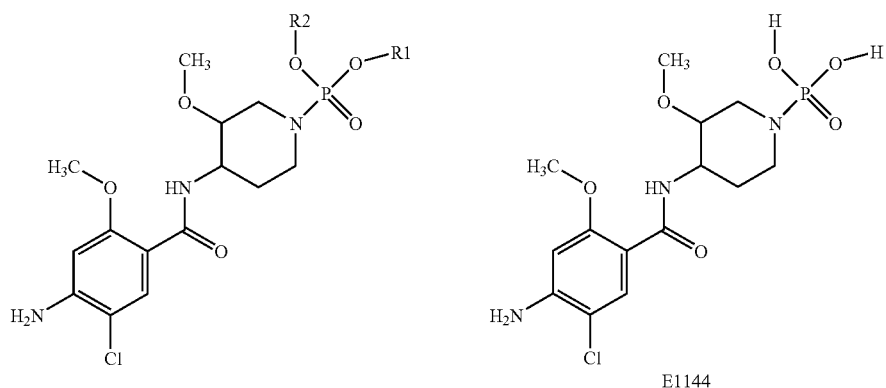

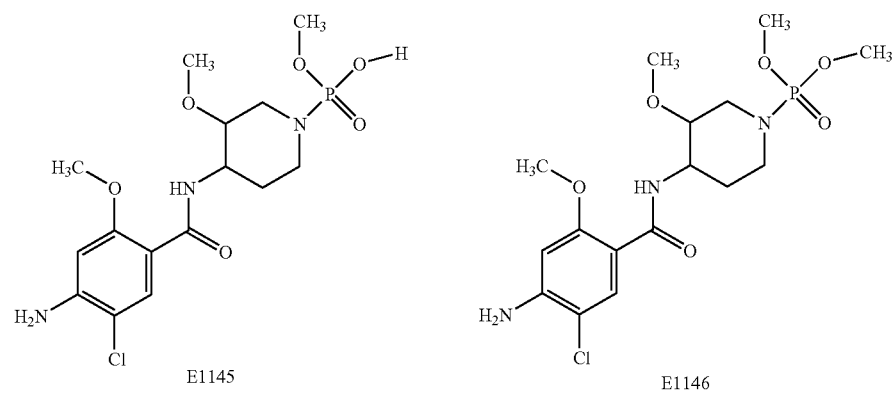

-continued

Norcisapride

| Chemical Structure | Hydroxylated Metabolite |
|---|---|

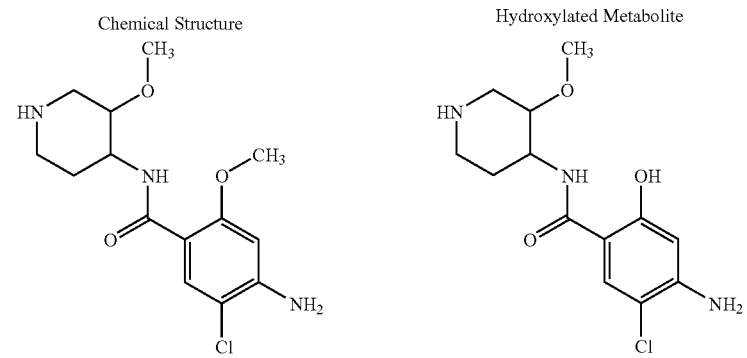

| Compound | R1 | R2 | Chemical Name | Estimated LogP | pKa |
|---|---|---|---|---|---|

E1147                                                                   E1148

Norcyclizine

| Chemical Structure | Hydroxylated Metabolite |
|---|---|

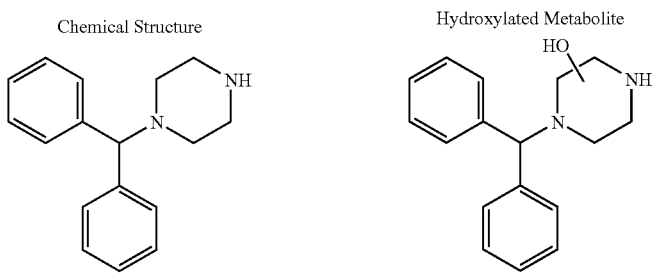

| Compound | R1 | R2 | Chemical Name | Estimated LogP | pKa |
|---|---|---|---|---|---|
| E1309 | hydrogen | hydrogen | (4-Benzhydryl-piperazin-1-yl)-phosphonic acid | 2.34 | 4.10 |
| E1310 | hydrogen | methyl | (4-Benzhydryl-piperazin-1-yl)-phosphonic acid monomethyl ester | 2.40 | 3.56 |
| E1311 | methyl | methyl | (4-Benzhydryl-piperazin-1-yl)-phosphonic acid dimethyl ester | 2.45 | 5.16 |
| E1312 | phenyl | hydrogen | (4-Benzhydryl-piperazin-1-yl)-phosphonic acid monophenyl ester | 4.16 | 3.09 |
| E1313 | phenyl | methyl | (4-Benzhydryl-piperazin-1-yl)-phosphonic acid methyl ester phenyl ester | 4.22 | 5.31 |

-continued
Norcyclizine
| Chemical Structure | Hydroxylated Metabolite |
|---|---|
| 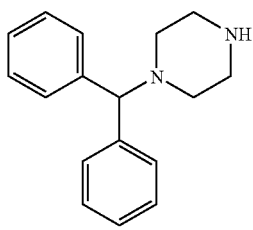 | 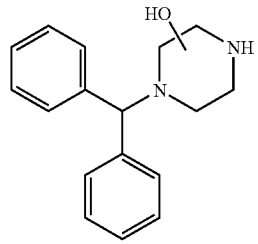 |
| Compound | R1 | R2 | Chemical Name | Estimated LogP | pKa |
|---|---|---|---|---|---|
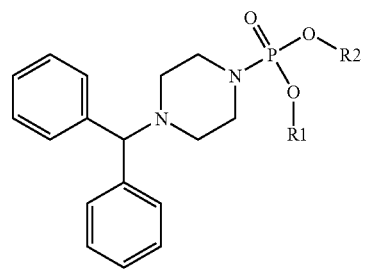
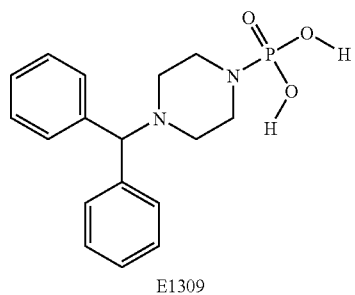
E1309
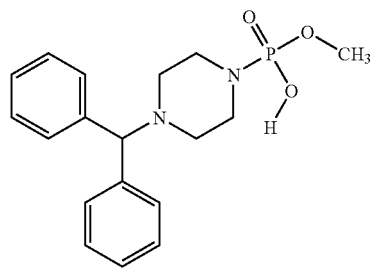
E1310
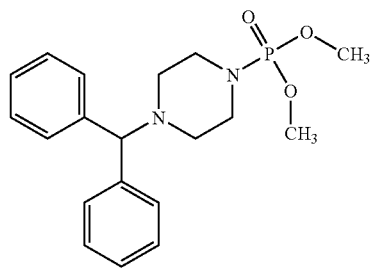
E1311
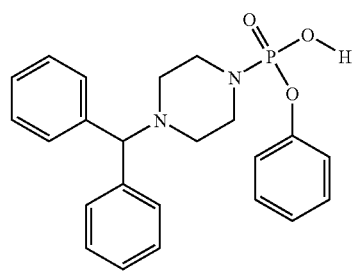
E1312
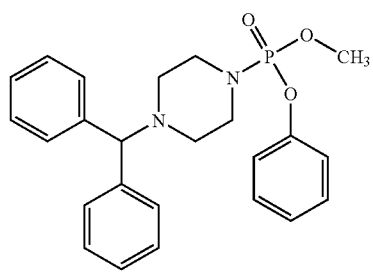
E1313

| | Norfloxacin (Noroxin ®) | | |
|---|---|---|---|
| | Chemical Structure | | |
| 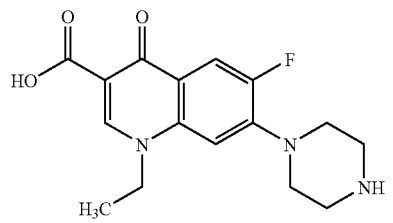 | | | |
| | | | Hydroxylated Metabolite |
| Compound | R1 | R2 | Chemical Name |
| E1429 | hydrogen | hydrogen | 1-Ethyl-6-fluoro-4-oxo-7-(4-phosphono-piperazin-1-yl)-1,4-di-hydro-quinoline-3-carboxylic acid |
| E1430 | hydrogen | methyl | 1-Ethyl-6-fluoro-7-[4-(hydroxy-methoxy-phosphoryl)-pipe-razin-1-yl]-4-oxo-1,4-dihydro-quinoline-3-carboxylic acid |
| E1431 | methyl | methyl | 7-[4-(Dimethoxy-phosphoryl)-piperazin-1-yl]-1-ethyl-6-fluor-o-4-oxo-1,4-dihydro-quinoline-3-carboxylic acid |
| E1432 | phenyl | hydrogen | 1-Ethyl-6-fluoro-7-[4-(hydroxy-phenoxy-phosphoryl)-pipe-razin-1-yl]-4-oxo-1,4-dihydro-quinoline-3-carboxylic acid |
| E1433 | phenyl | methyl | 1-Ethyl-6-fluoro-7-[4-(methoxy-phenoxy-phosphoryl)-pipe-razin-1-yl]-4-oxo-1,4-dihydro-quinoline-3-carboxylic acid |

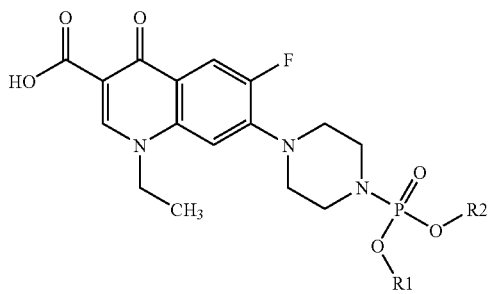

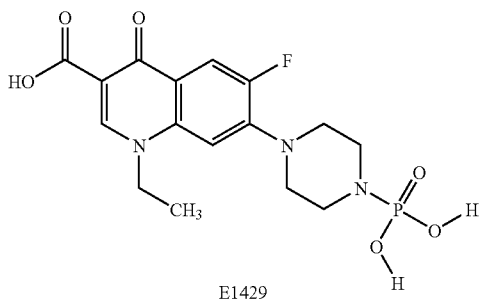

E1429

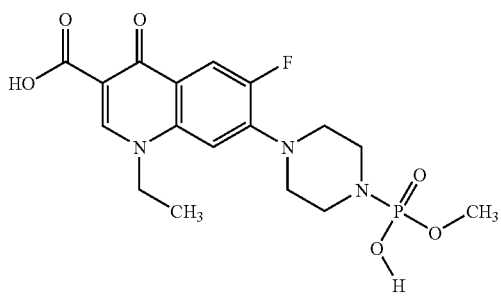

E1430

-continued
Norfloxacin (Noroxin®)
Chemical Structure
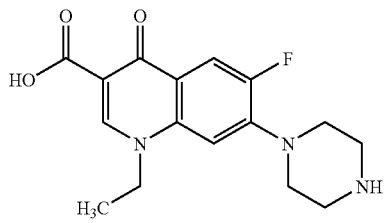
Hydroxylated Metabolite
| Compound | R1 | R2 | Chemical Name |
|---|---|---|---|
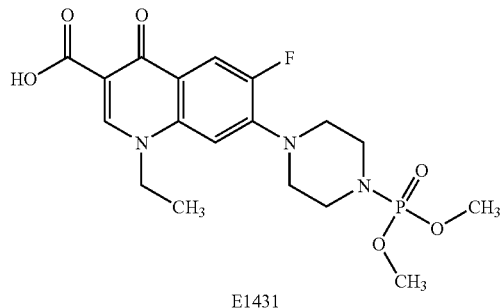
E1431
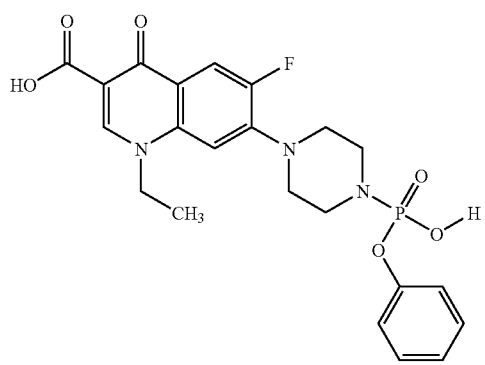
E1432
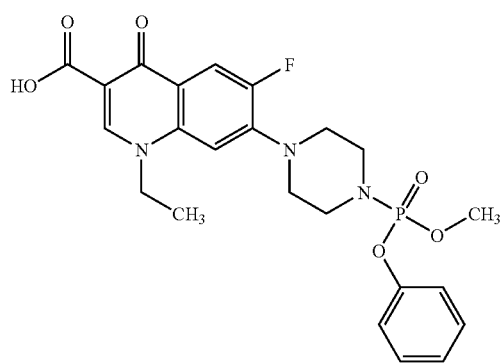
E1433

| | Norpimozide | |
|---|---|---|
| | Chemical Structure | |

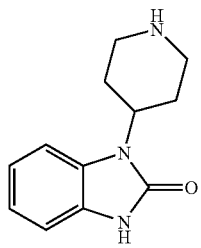

Hydroxylated Metabolite

| Compound | R1 | R2 | Chemical Name | Estimated LogP | pKa |
|---|---|---|---|---|---|
| E1279 | hydrogen | hydrogen | [4-(2-Oxo-2,3-dihydro-benzoimidazol-1-yl)-piperidin-1-yl]-phosphonic acid | 0.90 | 2.92 |
| E1280 | hydrogen | methyl | [4-(2-Oxo-2,3-dihydro-benzoimidazol-1-yl)-piperidin-1-yl]-phosphonic acid monomethyl ester | 0.96 | 4.74 |
| E1281 | methyl | methyl | [4-(2-Oxo-2,3-dihydro-benzoimidazol-1-yl)-piperidin-1-yl]-phosphonic acid dimethyl ester | 1.01 | 3.99 |
| E1282 | phenyl | hydrogen | [4-(2-Oxo-2,3-dihydro-benzoimidazol-1-yl)-piperidin-1-yl]-phosphonic acid monophenyl ester | 2.72 | 4.26 |
| E1283 | phenyl | methyl | [4-(2-Oxo-2,3-dihydro-benzoimidazol-1-yl)-piperidin-1-yl]-phosphonic acid methyl ester phenyl ester | 2.78 | 4.13 |

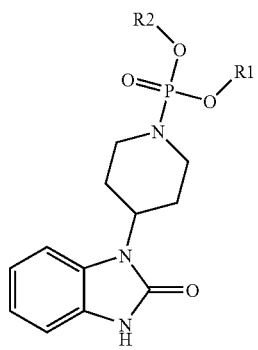

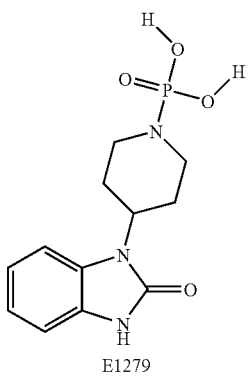
E1279

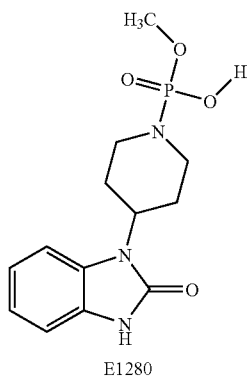
E1280

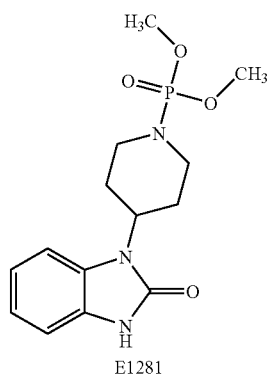
E1281

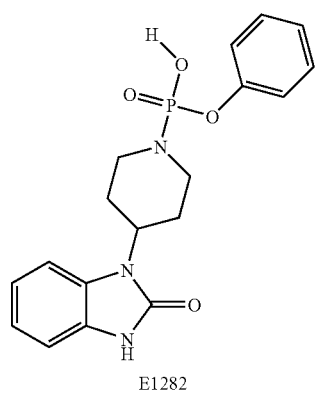
E1282

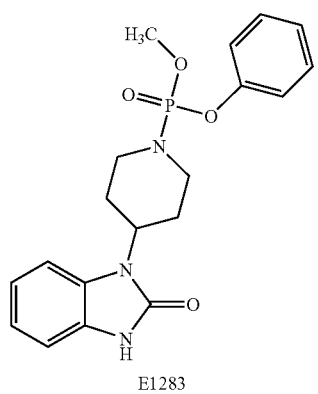
E1283

| Nortriptyline (Aventyl ®) | |
|---|---|
| Chemical Structure 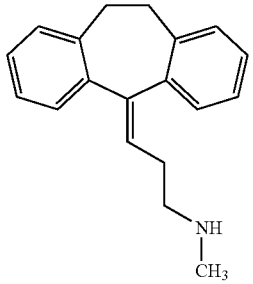 | Hydroxylated Metabolite 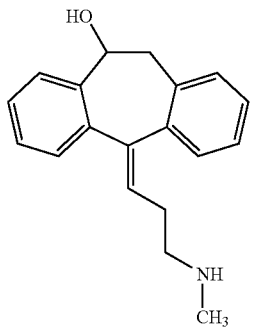 |

| Compound | R1 | R2 | Chemical Name | Estimated LogP | Estimated pKa |
|---|---|---|---|---|---|
| E1051 | hydrogen | hydrogen | 3-(10,11-Dihydro-dibenzo[a,d]cyclohepten-5-yl-idene)-propyl]-methyl-phosphoramidic acid | 4.32 | 2.90 |
| E1052 | hydrogen | methyl | 3-(10,11-Dihydro-dibenzo[a,d]cyclohepten-5-yl-idene)-propyl]-methyl-phosphoramidic acid monomethyl ester | 4.38 | 4.76 |
| E1053 | methyl | methyl | [3-(10,11-Dihydro-dibenzo[a,d]cyclohepten-5-yl-idene)-propyl]-methyl-phosphoramidic acid dimethyl ester | 4.44 | 3.99 |
| E1054 | phenyl | hydrogen | [3-(10,11-Dihydro-dibenzo[a,d]cyclohepten-5-yl-idene)-propyl]-methyl-phosphoramidic acid monophenyl ester | 6.15 | 4.32 |
| E1055 | phenyl | methyl | 3-(10,11-Dihydro-dibenzo[a,d]cyclohepten-5-yl-idene)-propyl]-methyl-phosphoramidic acid methyl ester phenyl ester | 6.20 | 4.54 |

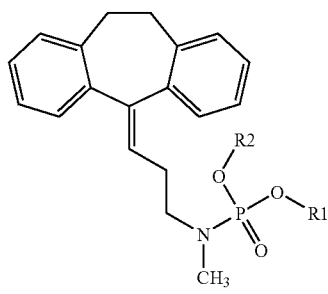

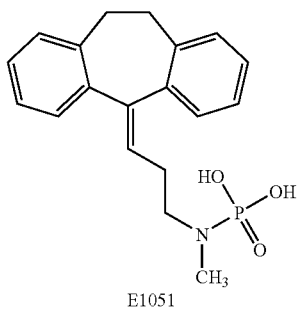
E1051

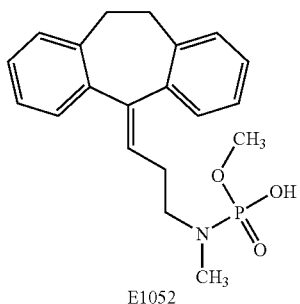
E1052

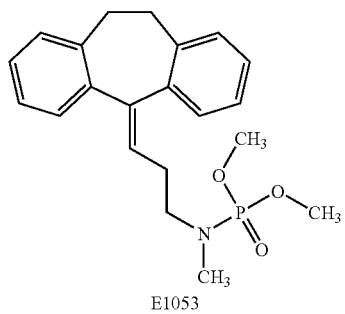
E1053

| Nortriptyline (Aventyl ®) | |
|---|---|
| Chemical Structure | Hydroxylated Metabolite |
| 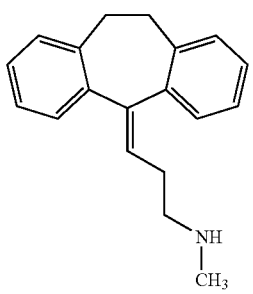 | 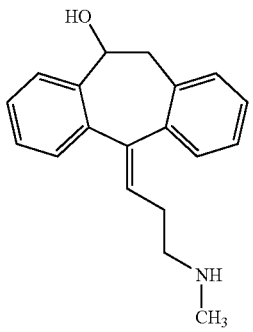 |

| Compound | R1 | R2 | Chemical Name | Estimated LogP | Estimated pKa |
|---|---|---|---|---|---|
| 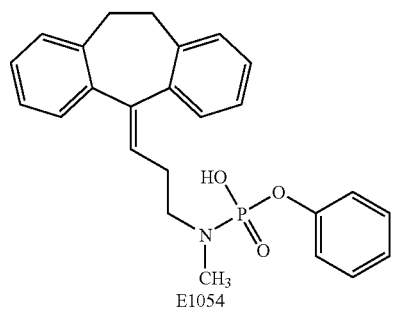<br>E1054 | | | | | |
| 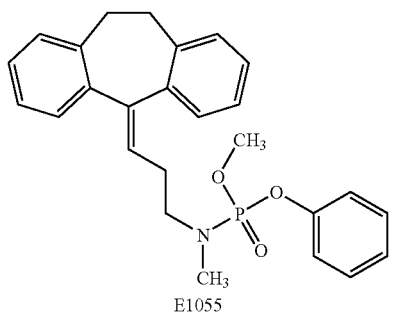<br>E1055 | | | | | |

| Norsertindole | |
|---|---|
| Chemical Structure | |
| 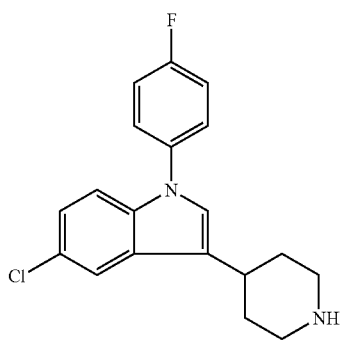 | |
| | Hydroxylated Metabolite |

| Compound | R1 | R2 | Chemical Name | Estimated LogP | pKa |
|---|---|---|---|---|---|
| E1149 | hydrogen | hydrogen | {4-[5-Chloro-1-(4-fluoro-phenyl)-1H-indol-3-yl]-piperidin-1-yl}-phosphonic acid | 5.08 | 2.77 |
| E1150 | hydrogen | methyl | {4-[5-Chloro-1-(4-fluoro-phenyl)-1H-indol-3-yl]-piperidin-1-yl}-phosphonic acid monomethyl ester | 5.14 | 4.89 |
| E1151 | methyl | methyl | {4-[5-Chloro-1-(4-fluoro-phenyl)-1H-indol-3-yl]-piperidin-1-yl}-phosphonic acid dimethyl ester | 5.19 | 3.84 |

| | Norsertindole | | | | | |
|---|---|---|---|---|---|---|
| | Chemical Structure | | | | | |
| | 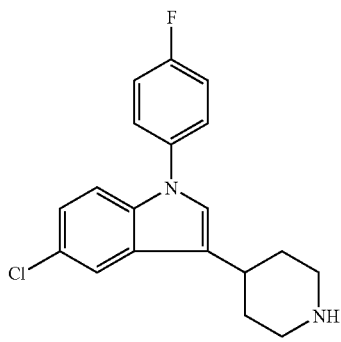 | | | | | |
| | | | | Hydroxylated Metabolite | | |
| Compound | R1 | R2 | Chemical Name | | Estimated LogP | pKa |
| E1152 | phenyl | hydrogen | {4-[5-Chloro-1-(4-fluoro-phenyl)-1H-indol-3-yl]-piperidin-1-yl}-phosphonic acid monophenyl ester | | 6.90 | 4.41 |
| E1153 | phenyl | methyl | {4-[5-Chloro-1-(4-fluoro-phenyl)-1H-indol-3-yl]-piperidin-1-yl}-phosphonic acid methyl ester phenyl ester | | 6.96 | 3.98 |
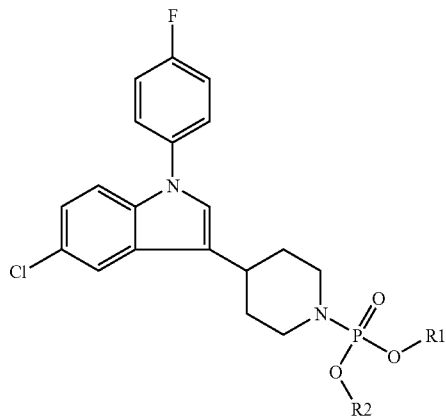
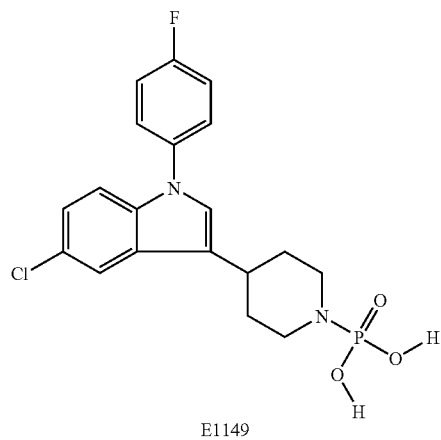
E1149
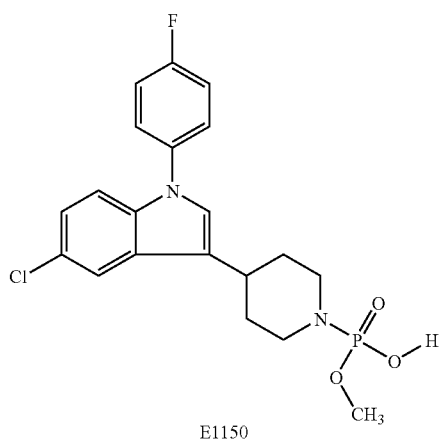
E1150
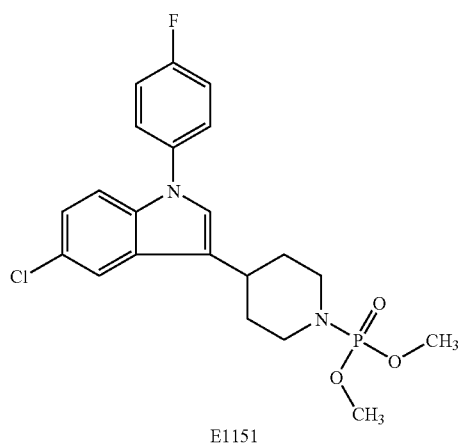
E1151

| Norsertindole |
|---|
| Chemical Structure |

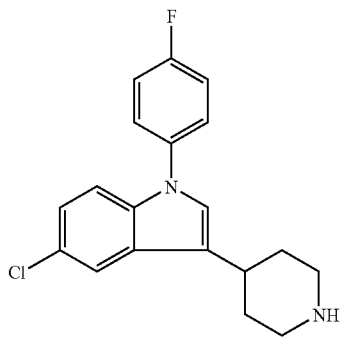

Hydroxylated Metabolite

| Compound | R1 | R2 | Chemical Name | Estimated LogP | pKa |
|---|---|---|---|---|---|

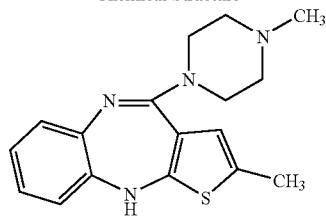

E1152

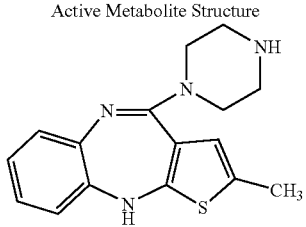

E1153

| Olanzapine (Zyprexa ®) |
|---|
| Chemical Structure    Active Metabolite Structure    Hydroxylated Metabolite |

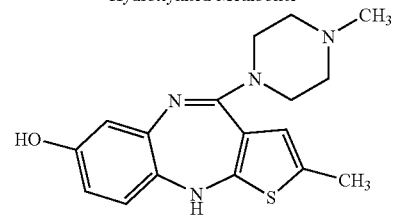

| Compound | R1 | R2 | Chemical Name | Estimated LogP | Estimated pKa |
|---|---|---|---|---|---|
| E1006 | hydrogen | hydrogen | [4-(2-Methyl-4H-3-thia-4,9-diaza-benzo[f]azulen-10-yl)-piperazin-1-yl]-phosphonic acid | 1.94 | 4.96 |
| E1007 | hydrogen | methyl | [4-(2-Methyl-4H-3-thia-4,9-diaza-benzo[f]azulen-10-yl)-piperazin-1-yl]-phosphonic acid monomethyl ester | 1.99 | 2.70 |
| E1008 | methyl | methyl | [4-(2-Methyl-4H-3-thia-4,9-diaza-benzo[f]azulen-10-yl)-piperazin-1-yl]-phosphonic acid dimethyl ester | 2.05 | 6.02 |
| E1009 | phenyl | hydrogen | [4-(2-Methyl-4H-3-thia-4,9-diaza-benzo[f]azulen-10-yl)-piperazin-1-yl]-phosphonic acid monophenyl ester | 3.76 | 2.22 |

-continued
Olanzapine (Zyprexa ®)
| Chemical Structure | Active Metabolite Structure | Hydroxylated Metabolite |
|---|---|---|
| 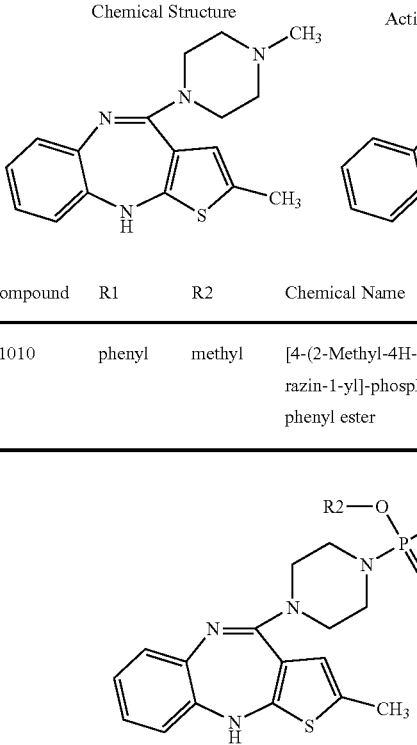 | 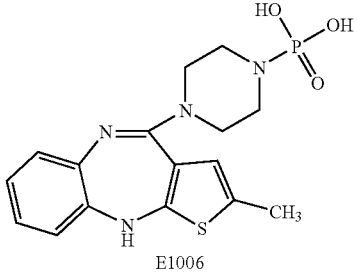 | 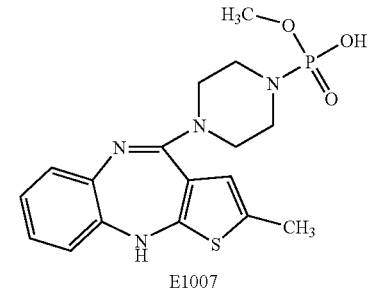 |
| Compound | R1 | R2 | Chemical Name | Estimated LogP | Estimated pKa |
|---|---|---|---|---|---|
| E1010 | phenyl | methyl | [4-(2-Methyl-4H-3-thia-4,9-diaza-benzo[f]azulen-10-yl)-piperazin-1-yl]-phosphonic acid methyl ester phenyl ester | 3.82 | 6.17 |
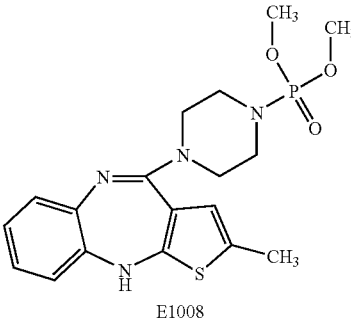
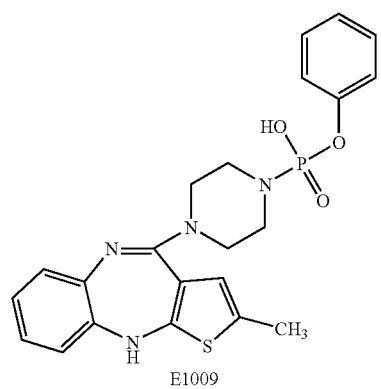
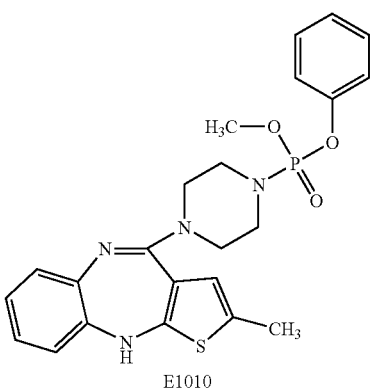

| Oxybutynin (Ditropan ®) |
|---|

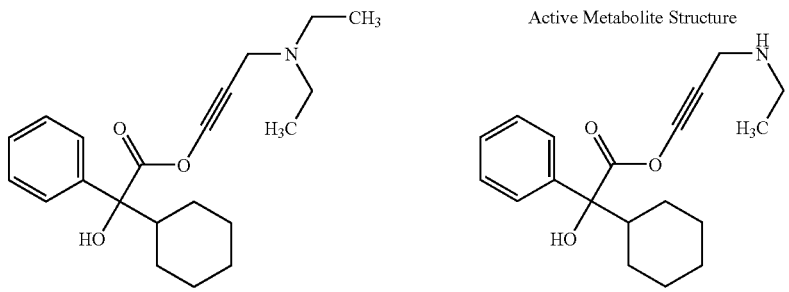

| Compound | R1 | R2 | Chemical Name | Estimated LogP | pKa |
|---|---|---|---|---|---|
| E1116 | hydrogen | hydrogen | Cyclohexyl-hydroxy-phenyl-acetic acid 3-(ethyl-phosphono-amino)-prop-1-ynyl ester | 2.35 | 3.67 |
| E1117 | hydrogen | methyl | Cyclohexyl-hydroxy-phenyl-acetic acid 3-(ethyl-(hydroxy-methoxy-phosphoryl)-amino]-prop-1-ynyl ester | 2.41 | 3.99 |
| E1118 | methyl | methyl | Cyclohexyl-hydroxy-phenyl-acetic acid 3-[(dimethoxy-phosphoryl)-ethyl-amino]-prop-1-ynyl ester | 2.47 | 4.44 |
| E1119 | phenyl | hydrogen | Cyclohexyl-hydroxy-phenyl-acetic acid 3-[ethyl-(hydroxy-phenoxy-phosphoryl)-amino]-prop-1-ynyl | 4.18 | 3.58 |
| E1120 | phenyl | methyl | Cyclohexyl-hydroxy-phenyl-acetic acid 3-[ethyl-(methoxy-phenoxy-phosphoryl)-amino]-prop-1-ynyl | 4.23 | 4.49 |

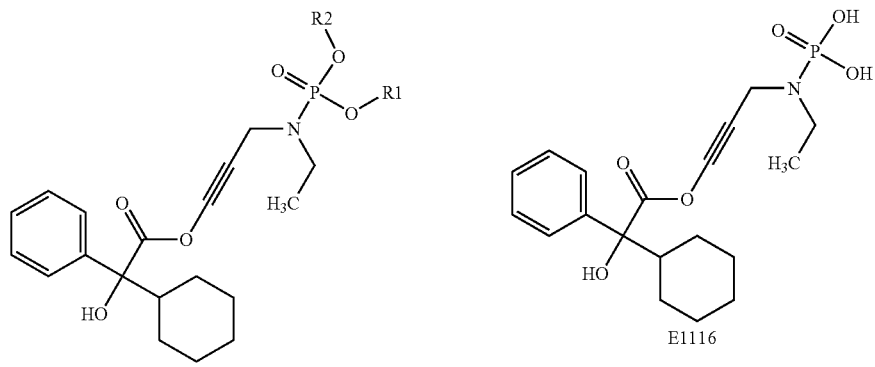

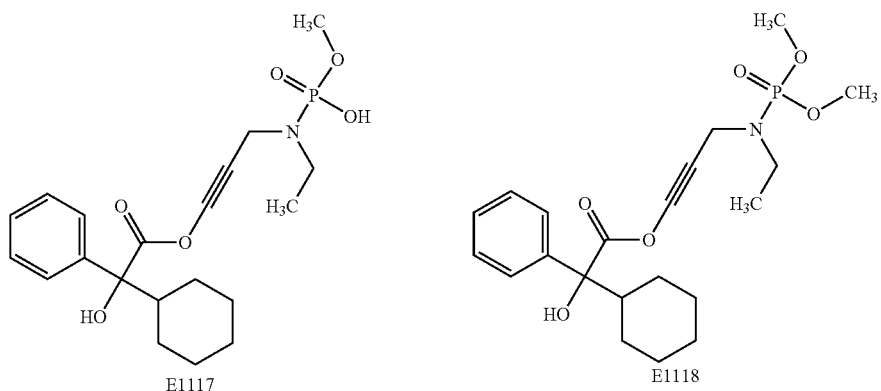

-continued

Oxybutynin (Ditropan ®)

Chemical Structure

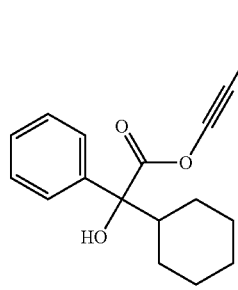

Active Metabolite Structure

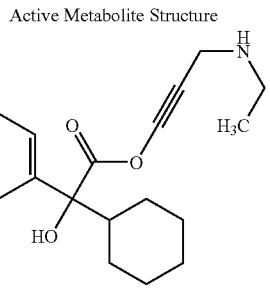

| Compound | R1 | R2 | Chemical Name | Estimated LogP | pKa |
|---|---|---|---|---|---|

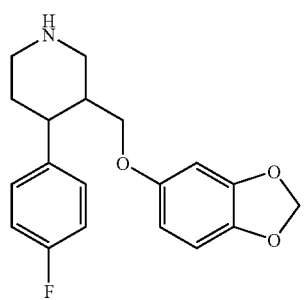

E1119

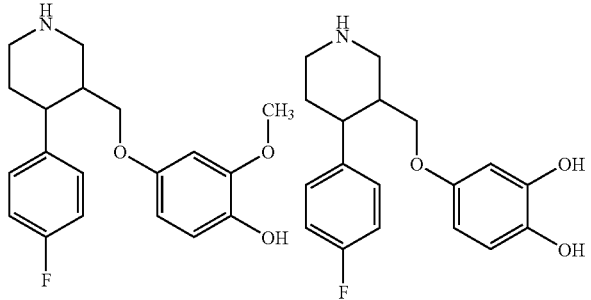

E1120

Paroxetine (Paxil ®)

Chemical Structure

Active Metabolite Structure

| Compound | R1 | R2 | Chemical Name | Estimated LogP | Estimated pKa |
|---|---|---|---|---|---|
| E1001 | hydrogen | hydrogen | [3-(Benzo[1,3]dioxol-5-yloxymethyl)-4-(4-fluoro-phenyl)-piperidin-1-yl]-phosphonic acid | 4.33 | 3.80 |
| E1002 | hydrogen | methyl | [3-(Benzo[1,3]dioxol-5-yloxymethyl)-4-(4-fluoro-phenyl)-piperidin-1-yl]-phosphonic acid monomethyl ester | 4.39 | 3.86 |
| E1003 | methyl | methyl | [3-(Benzo[1,3]dioxol-5-yloxymethyl)-4-(4-fluoro-phenyl)-piperidin-1-yl]-phosphonic acid dimethyl ester | 4.44 | 4.86 |

-continued

Paroxetine (Paxil ®)

Chemical Structure

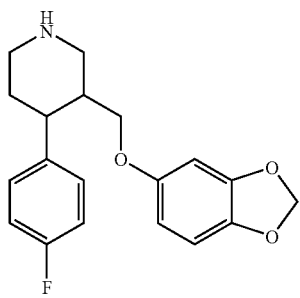

Active Metabolite Structure

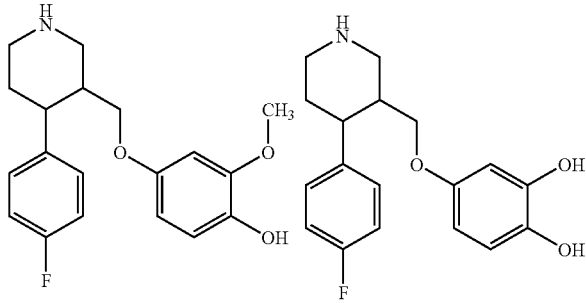

| Compound | R1 | R2 | Chemical Name | Estimated LogP | Estimated pKa |
|---|---|---|---|---|---|
| E1004 | phenyl | hydrogen | [3-(Benzo[1,3]dioxol-5-yloxymethyl)-4-(4-fluoro-phenyl)-piperidin-1-yl]-phosphonic acid monophenyl ester | 6.15 | 4.86 |
| E1005 | phenyl | methyl | [3-(Benzo[1,3]dioxol-5-yloxymethyl)-4-(4-fluoro-phenyl)-piperidin-1-yl]-phosphonic acid methyl ester phenyl ester | 6.21 | 5.00 |

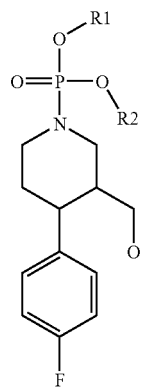

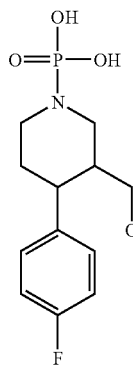

E1001

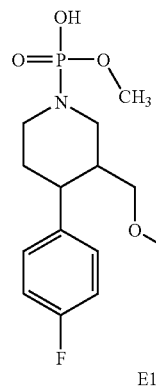

E1002

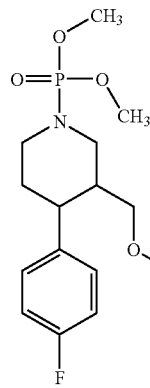

E1003

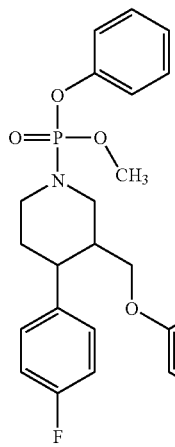

E1005

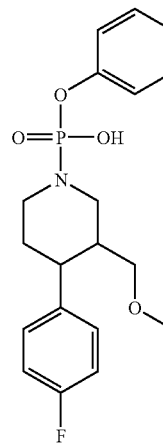

E1004

Phenformin (Dibotin ®)

Chemical Structure

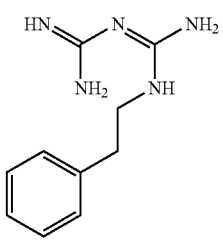

Hydroxylated Metabolite

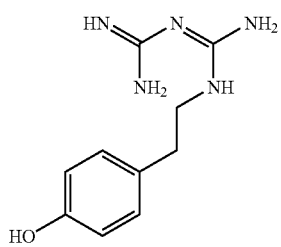

| Compound | R1 | R2 | Chemical Name |
|---|---|---|---|
| E1324 | hydrogen | hydrogen | (Amino-carbamimidoylimino-methyl)-phenethyl-phosphoramidic acid |
| E1325 | hydrogen | methyl | (Amino-carbamimidoylimino-methyl)-phenethyl-phosphoramidic acid monomethyl ester |
| E1326 | methyl | methyl | (Amino-carbamimidoylimino-methyl)-phenethyl-phosphoramidic acid dimethyl ester |
| E1327 | phenyl | hydrogen | (Amino-carbamimidoylimino-methyl)-phenethyl-phosphoramidic acid monophenyl ester |
| E1328 | phenyl | methyl | (Amino-carbamimidoylimino-methyl)-phenethyl-phosphoramidic acid methyl ester phenyl ester |

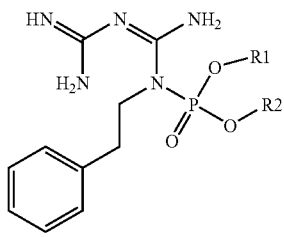

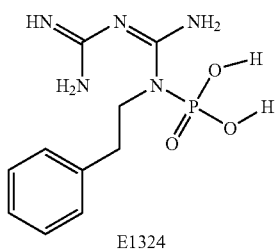

E1324

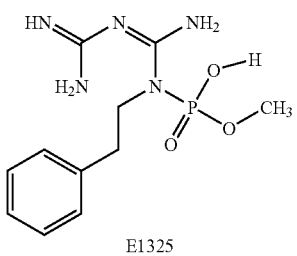

E1325

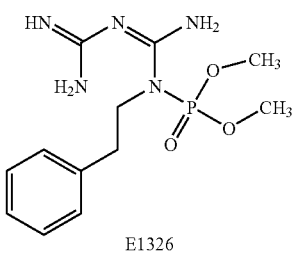

E1326

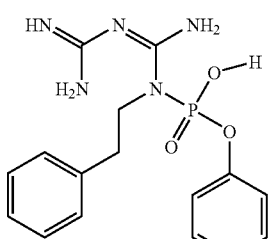

E1327

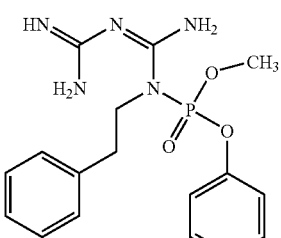

E1328

| | Phenytoin (Dilantin ®) | |
|---|---|---|
| | 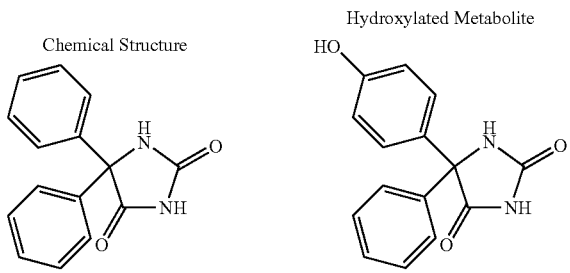 | |
| | Chemical Structure | Hydroxylated Metabolite |

| Compound | R1 | R2 | Chemical Name |
|---|---|---|---|
| E1126 | hydrogen | hydrogen | (2,5-Dioxo-4,4-diphenyl-imidazolidin-1-yl)-phosphonic acid |
| E1127 | hydrogen | methyl | (2,5-Dioxo-4,4-diphenyl-imidazolidin-1-yl)-phosphonic acid monomethyl ester |
| E1128 | methyl | methyl | (2,5-Dioxo-4,4-diphenyl-imidazolidin-1-yl)-phosphonic acid dimethyl ester |
| E1129 | phenyl | hydrogen | (2,5-Dioxo-4,4-diphenyl-imidazolidin-1-yl)-phosphonic acid monophenyl ester |
| E1130 | phenyl | methyl | (2,5-Dioxo-4,4-diphenyl-imidazolidin-1-yl)-phosphonic acid methyl ester phenyl ester |

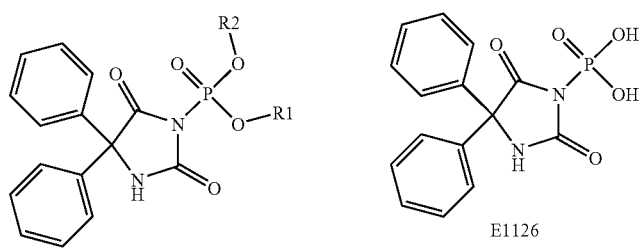

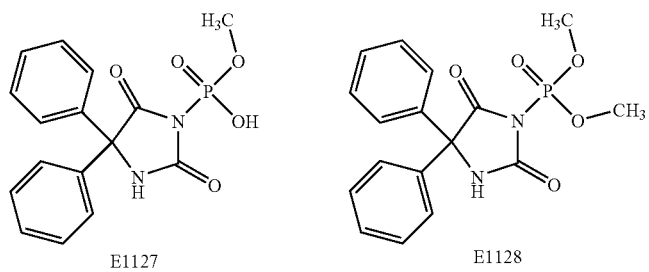

E1127

E1128

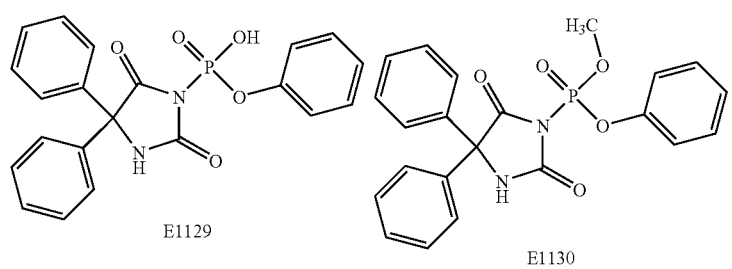

E1129

E1130

| Propafenone (Rhythmol ®) | |
|---|---|
| Chemical Structure | Hydroxylated Metabolite |
| 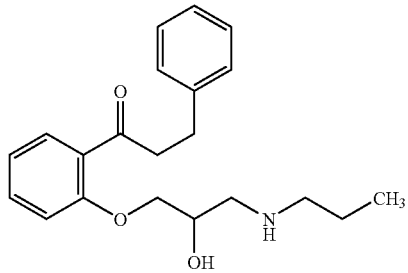 | 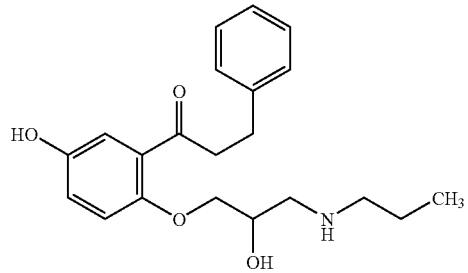 |

| Compound | R1 | R2 | Chemical Name | Estimated LogP | pKa |
|---|---|---|---|---|---|
| E1081 | hydrogen | hydrogen | {2-Hydroxy-3-[2-(3-phenyl-propionyl)-phenoxy]-propyl)-propyl-phosphoramidic acid | 2.96 | 4.07 |
| E1082 | hydrogen | methyl | {2-Hydroxy-3-[2-(3-phenyl-propionyl)-phenoxy]-propyl)-propyl-phosphoramidic acid monomethyl ester | 3.02 | 3.59 |
| E1083 | methyl | methyl | {2-Hydroxy-3-[2-(3-phenyl-propionyl)-phenoxy]-propyl}-propyl-phosphoramidic acid dimethyl ester | 3.07 | 4.36 |
| E1084 | phenyl | hydrogen | {2-Hydroxy-3-[2-(3-phenyl-propionyl)-phenoxy]-propyl}-propyl-phosphoramidic acid monophenyl ester | 4.78 | 3.21 |
| E1085 | phenyl | methyl | {2-Hydroxy-3-[2-(3-phenyl-propionyl)-phenoxy]-propyl}-propyl-phosphoramidic acid methyl ester phenyl ester | 4.84 | 4.89 |

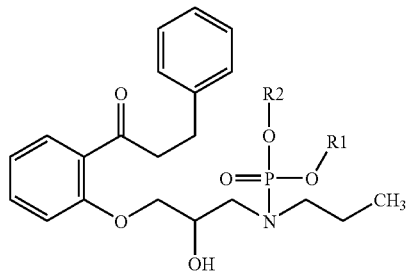

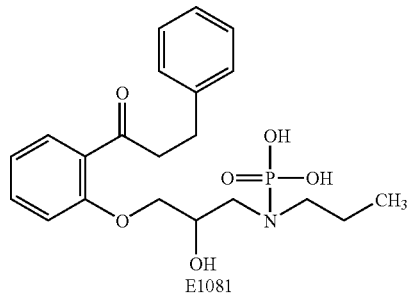
E1081

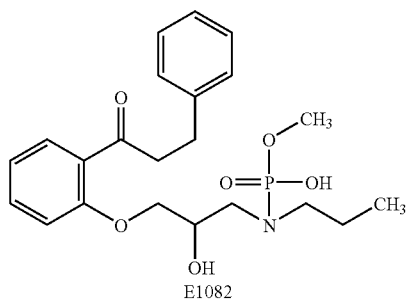
E1082

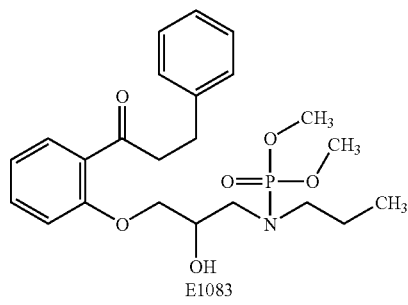
E1083

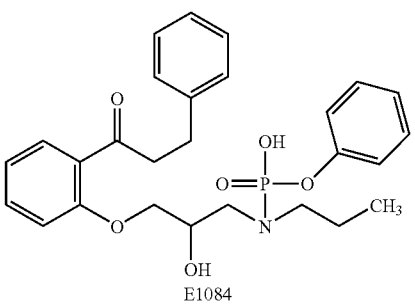
E1084

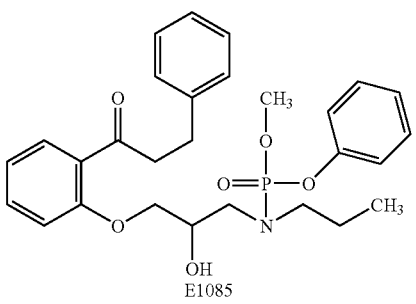
E1085

| Reboxetine (Vestra ®) | |
|---|---|
| Chemical Structure | Hydroxylated Metabolite |
| 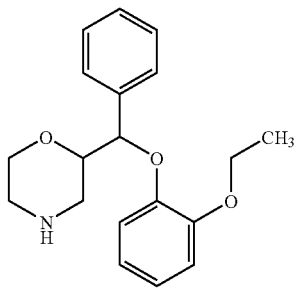 | 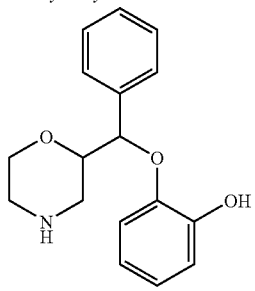 |

| Compound | R1 | R2 | Chemical Name | Estimated LogP | pKa |
|---|---|---|---|---|---|
| E1284 | hydrogen | hydrogen | {2-[(2-Ethoxy-phenoxy)-phenyl-methyl]-morpholin-4-yl}-phosphonic acid | 2.37 | 5.87 |
| E1285 | hydrogen | methyl | {2-[(2-Ethoxy-phenoxy)-phenyl-methyl]-morpholin-4-yl}-phosphonic acid monomethyl ester | 2.43 | 1.79 |
| E1286 | methyl | methyl | {2-[(2-Ethoxy-phenoxy)-phenyl-methyl]-morpholin-4-yl}-phosphonic acid dimethyl ester | 2.49 | 6.94 |
| E1287 | phenyl | hydrogen | {2-[(2-Ethoxy-phenoxy)-phenyl-methyl]-morpholin-4-yl}-phosphonic acid monophenyl ester | 4.20 | 1.31 |
| E1288 | phenyl | methyl | {2-[(2-Ethoxy-phenoxy)-phenyl-methyl]-morpholin-4-yl}-phosphonic acid methyl ester phenyl ester | 4.25 | 7.09 |

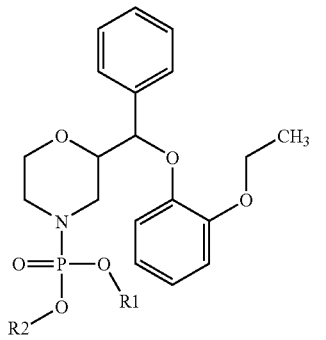

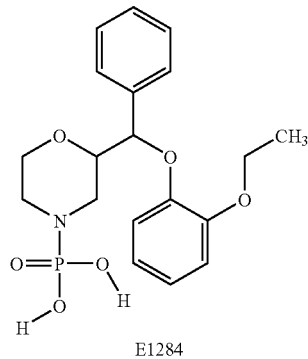
E1284

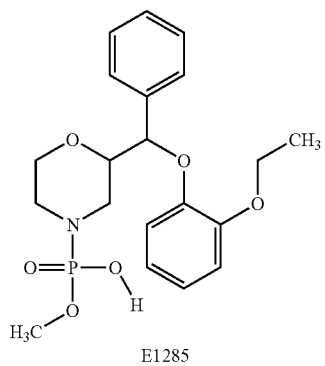
E1285

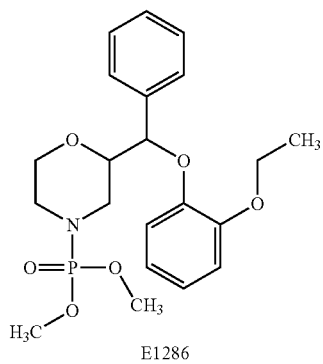
E1286

-continued

| Reboxetine (Vestra ®) |
|---|

Chemical Structure 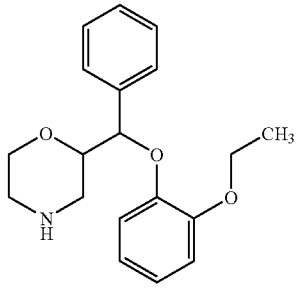     Hydroxylated Metabolite 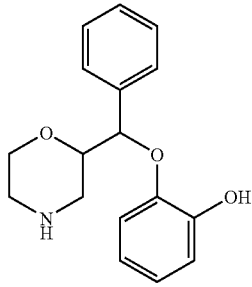

| Compound | R1 | R2 | Chemical Name | Estimated LogP | pKa |
|---|---|---|---|---|---|

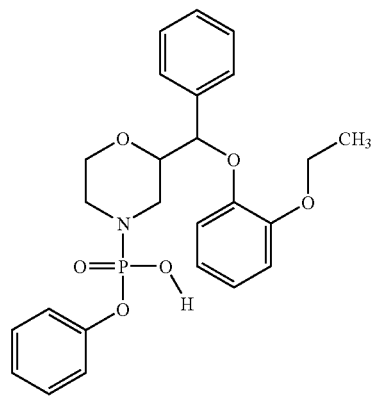
E1287

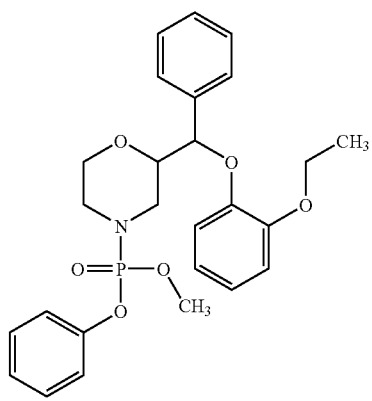
E1288

| Rimantadine (Flumadine ®) |
|---|

Chemical Structure 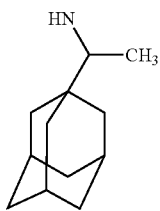    Active Metabolite Structure 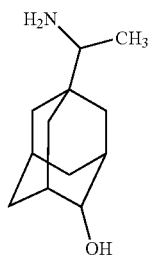    Hydroxylated Metabolite 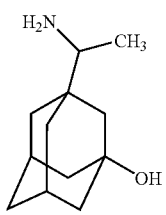

| Compound | R1 | R2 | Chemical Name |
|---|---|---|---|
| E1403 | hydrogen | hydrogen | (1-Adamantan-1-yl-ethyl)-phosphoramidic acid |
| E1404 | hydrogen | methyl | (1-Adamantan-1-yl-ethyl)-phosphoramidic acid monomethyl ester |

| Rimantadine (Flumadine ®) |
|---|
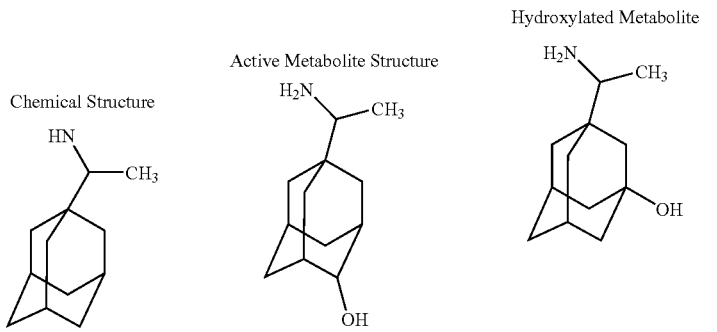
| Compound | R1 | R2 | Chemical Name |
|---|---|---|---|
| E1405 | methyl | methyl | (1-Adamantan-1-yl-ethyl)-phosphoramidic acid dimethyl ester |
| E1406 | phenyl | hydrogen | (1-Adamantan-1-yl-ethyl)-phosphoramidic acid monophenyl ester |
| E1407 | phenyl | methyl | (1-Adamantan-1-yl-ethyl)-phosphoramidic acid methyl ester phenyl ester |
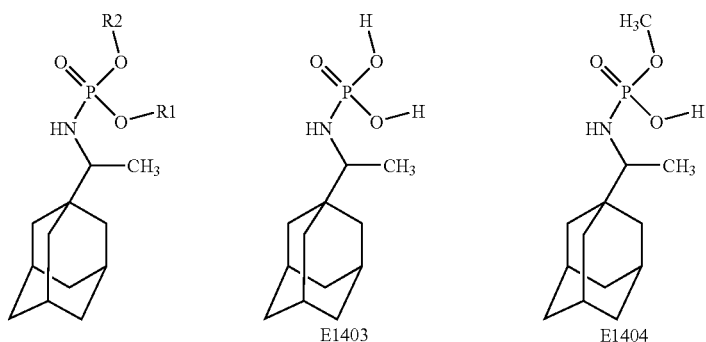
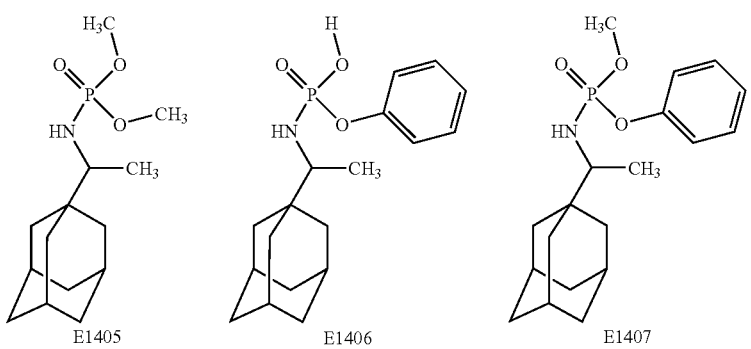

| Rizatriptan (Maxalt ®) | |
|---|---|
| Chemical Structure 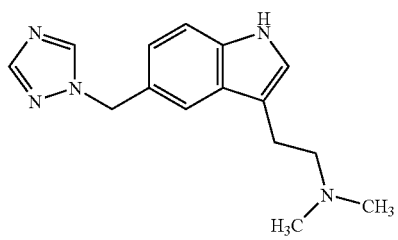 | Active Metabolite Structure 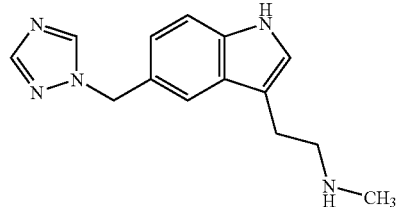 |

Hydroxylated Metabolite

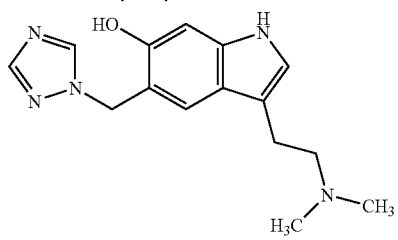

| Compound | R1 | R2 | Chemical Name | Estimated LogP | pKa |
|---|---|---|---|---|---|
| E1174 | hydrogen | hydrogen | Methyl-[2-(5-[1,2,4]triazol-1-ylmethyl-1H-indol-3-yl)-ethyl]-phosphoramidic acid | 1.17 | 2.64 |
| E1175 | hydrogen | methyl | Methyl-[2-(5-[1,2,4]triazol-1-ylmethyl-1H-indole-3yl)-ethyl]-phosphoramidic acid monomethyl ester | 1.23 | 5.02 |
| E1176 | methyl | methyl | Methyl-[2-(5-[1,2,4]triazol-1-ylmethyl-1H-indol-3-yl)-ethyl]-phosphoramidic acid dimethyl ester | 1.29 | 3.99 |
| E1177 | phenyl | hydrogen | Methyl-[2-(5-[1,2,4]triazol-1-ylmethyl-1H-indol-3-yl)-ethyl]-phosphoramidic acid monophenyl ester | 3.00 | 4.57 |
| E1178 | phenyl | methyl | Methyl-[2-(5-[1,2,4]triazol-1-ylmethyl-1H-indol-3-yl)-ethyl]-phosphoramidic acid methyl ester phenyl ester | 3.05 | 3.55 |

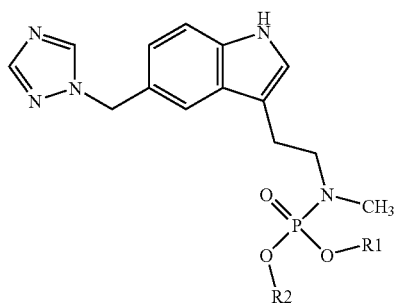

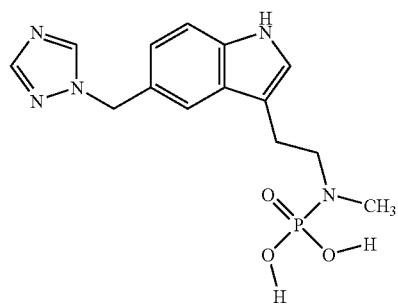

E1174

Rizatriptan (Maxalt ®)
Chemical Structure
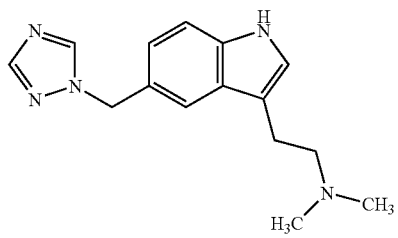
Active Metabolite Structure
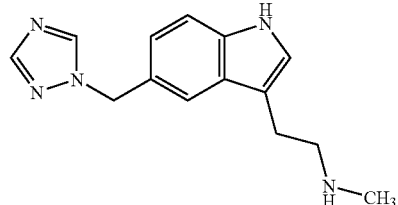
Hydroxylated Metabolite
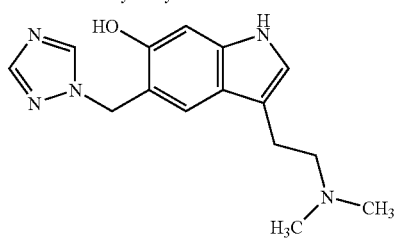
| Compound | R1 | R2 | Chemical Name | Estimated LogP | pKa |
|---|---|---|---|---|---|
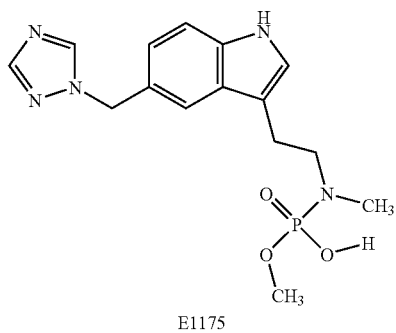
E1175
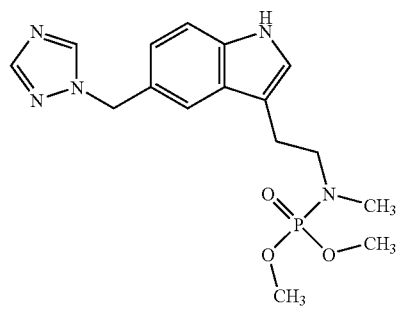
E1176
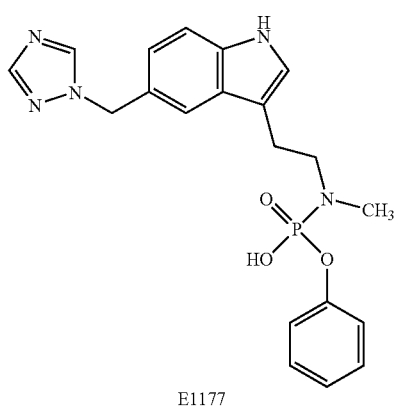
E1177
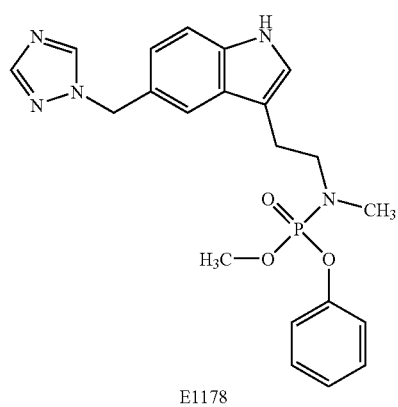
E1178

Selegiline (Eldepryl ®)

Chemical Structure / Active Metabolite Structure / Hydroxylated Metabolite

| Compound | R1 | R2 | Chemical Name |
|---|---|---|---|
| E1444 | hydrogen | hydrogen | (1-Methyl-2-phenyl-ethyl)-prop-2-ynyl-phosphoramidic acid |
| E1445 | hydrogen | methyl | (1-Methyl-2-phenyl-ethyl)-prop-2-ynyl-phosphoramidic acid monomethyl ester |
| E1446 | methyl | methyl | (1-Methyl-2-phenyl-ethyl)-prop-2-ynyl-phosphoramidic acid dimethyl ester |
| E1447 | phenyl | hydrogen | (1-Methyl-2-phenyl-ethyl)-prop-2-ynyl-phosphoramidic acid monophenyl ester |
| E1448 | phenyl | methyl | (1-Methyl-2-phenyl-ethyl)-prop-2-ynyl-phosphoramidic acid methyl ester phenyl ester |

E1444

E1445   E1446

E1447   E1448

Sertraline (Zoloft ®)

Chemical Structure / Active Metabolite Structure / Hydroxylated Metabolite

| Compound | R1 | R2 | Chemical Name | Estimated LogP | Estimated pKa |
|---|---|---|---|---|---|
| E1016 | hydrogen | hydrogen | [4-(3,4-Dichloro-phenyl)-1,2,3,4-tetrahydro-naphthalen-1-yl]-methyl-phosphoramidic acid | 4.87 | 3.50 |

-continued

Sertraline (Zoloft ®)

| | Chemical Structure | Active Metabolite Structure | Hydroxylated Metabolite | | |
|---|---|---|---|---|---|
| Compound | R1 | R2 | Chemical Name | Estimated LogP | Estimated pKa |
| E1017 | hydrogen | methyl | [4-(3,4-Dichloro-phenyl)-1,2,3,4-tetrahydro-naphthalen-1-yl]-methyl-phosphoramidic acid monomethyl ester | 4.93 | 4.16 |
| E1018 | methyl | methyl | [4-(3,4-Dichloro-phenyl)-1,2,3,4-tetrahydro-naphthalen-1-yl]-methyl-phosphoramidic acid dimethyl ester | 4.98 | 3.84 |
| E1019 | phenyl | hydrogen | [4-(3,4-Dichloro-phenyl)-1,2,3,4-tetrahydro-naphthalen-1-yl]-methyl-phosphoramidic acid monophenyl ester | 6.70 | 3.73 |
| E1020 | phenyl | methyl | [4-(3,4-Dichloro-phenyl)-1,2,3,4-tetrahydro-naphthalen-1-yl]-methyl-phosphoramidic acid methyl ester phenyl ester | 6.75 | 4.39 |

E1016

E1017

E1018

E1019

E1020

Sibutramine (Meridia ®)

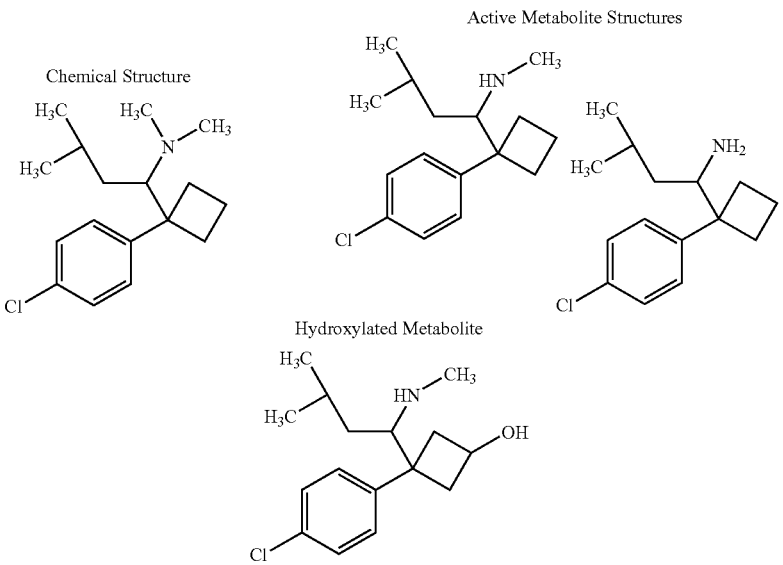

| Compound | R1 | R2 | Chemical Name | Estimated LogP | pKa |
|---|---|---|---|---|---|
| E1139 | hydrogen | hydrogen | {1-[1-(4-Chloro-phenyl)-cyclobutyl]-3-methyl-butyl}-methyl-phosphoramidic acid | 5.32 | 3.08 |
| E1140 | hydrogen | methyl | {1-[1-(4-Chloro-phenyl)-cyclobutyl]-3-methyl-butyl}-methyl-phosphoramidic acid monomethyl ester | 5.38 | 4.57 |
| E1141 | methyl | methyl | {1-[1-(4-Chloro-phenyl)-cyclobutyl]-3-methyl-butyl}-methyl-phosphoramidic acid dimethyl ester | 5.44 | 3.14 |
| E1142 | phenyl | hydrogen | {1-[1-(4-Chloro-phenyl)-cyclobutyl]-3-methyl-butyl}-methyl-phosphoramidic acid monophenyl ester | 7.15 | 4.19 |
| E1143 | phenyl | methyl | {1-[1-(4-Chloro-phenyl)-cyclobutyl]-3-methyl-butyl}-methyl-phosphoramidic acid methyl ester phenyl ester | 7.2 | 3.67 |
| E1227 | hydrogen | hydrogen | {1-[1-(4-Chloro-phenyl)-cyclobutyl]-3-methyl-butyl}-phosphoramidic acid | | |
| E1228 | hydrogen | methyl | {1-[1-(4-Chloro-phenyl)-cyclobutyl]-3-methyl-butyl}-phosphoramidic acid monomethyl ester | | |

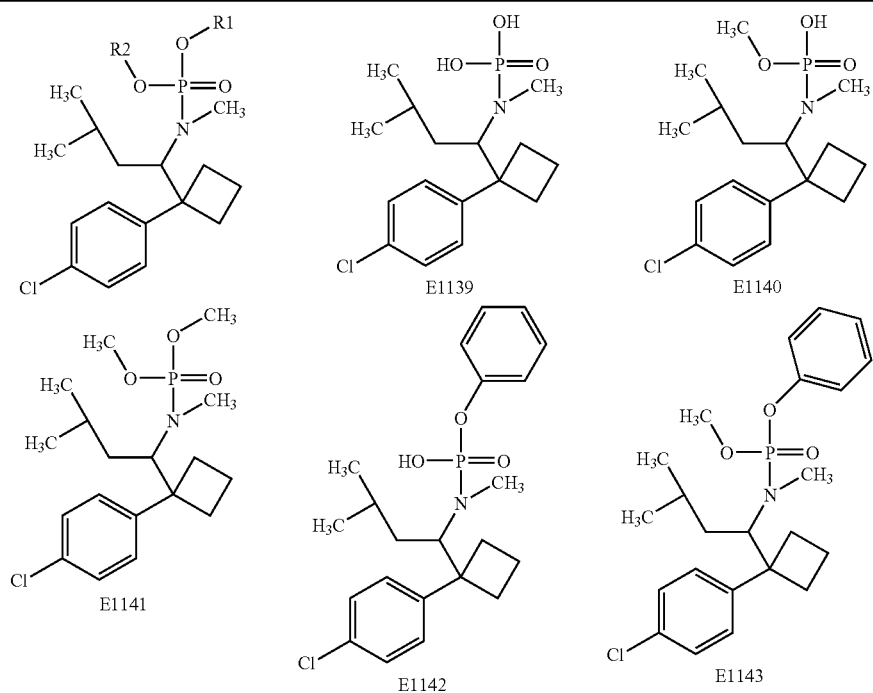

| Sibutramine (Meridia ®) |
|---|

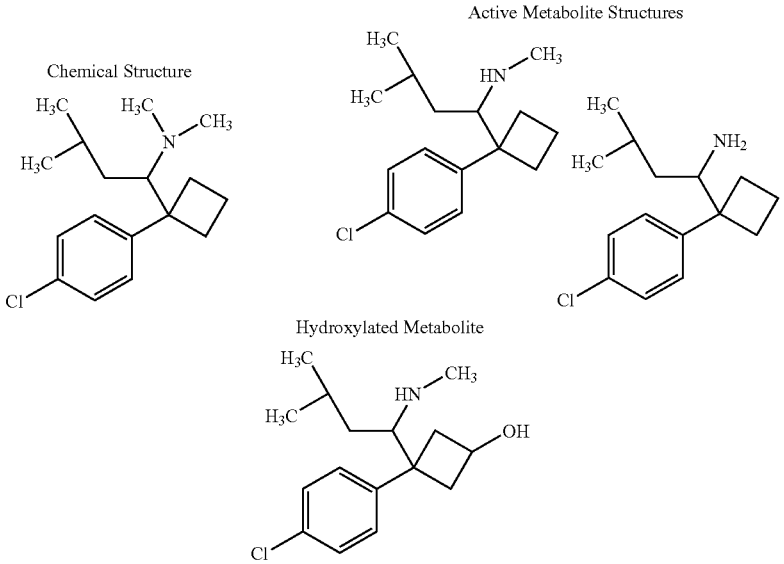

| Compound | R1 | R2 | Chemical Name | Estimated LogP | pKa |
|---|---|---|---|---|---|
| E1227 | | | | | |
| E1228 | | | | | |

| Sparfloxacin (Zagam ®) |
|---|

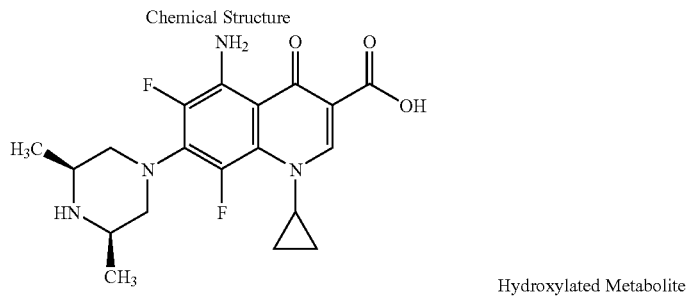

Hydroxylated Metabolite

| Compound | R1 | R2 | Chemical Name |
|---|---|---|---|
| E1424 | hydrogen | hydrogen | 5-Amino-1-cyclopropyl-7-(3,5-dimethyl-4-phosphono-piperazin-1-yl)-6,8-difluoro-4-oxo-1,4-dihydro-quinoline-3-carboxylic acid |
| E1425 | hydrogen | methyl | 5-Amino-1-cyclopropyl-6,8-difluoro-7-[4-(hydroxy-methoxy-phosphoryl)-3,5-dimethyl-piperazin-1-yl]-4-oxo-1,4-dihydro-quinoline-3-carboxylic acid |
| E1426 | methyl | methyl | 5-Amino-1-cyclopropyl-7-[4-(dimethoxy-phosphoryl)-3,5-di-methyl-piperazin-1-yl]-6,8-difluoro-4-oxo-1,4-dihydro-quinoline-3-carboxylic acid |

-continued

Sparfloxacin (Zagam ®)

Chemical Structure

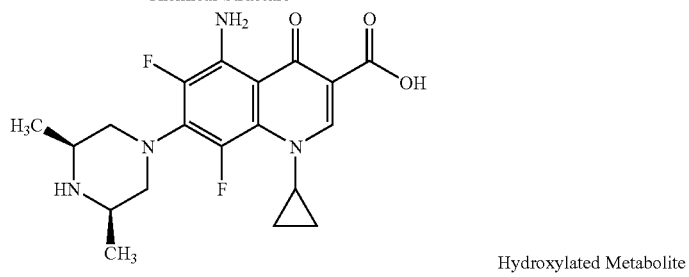

Hydroxylated Metabolite

| Compound | R1 | R2 | Chemical Name |
|---|---|---|---|
| E1427 | phenyl | hydrogen | 5-Amino-1-cyclopropyl-6,8-difluoro-7-[4-(hydroxy-phenoxy-phosphoryl)-3,5-dimethyl-piperazin-1-yl]-4-oxo-1,4-di-hydro-quinoline-3-carboxylic acid |
| E1428 | phenyl | methyl | 5-Amino-1-cyclopropyl-6,8-difluoro-7-[4-(methoxy-phenoxy-phosphoryl)-3,5-dimethyl-piperazin-1-yl]-4-oxo-1,4-di-hydro-quinoline-3-carboxylic acid |

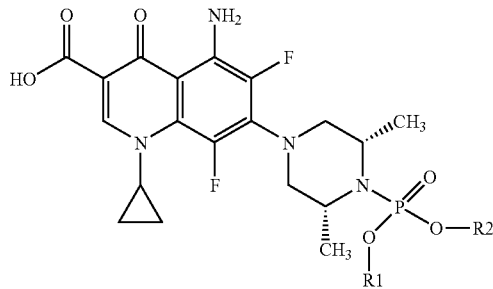

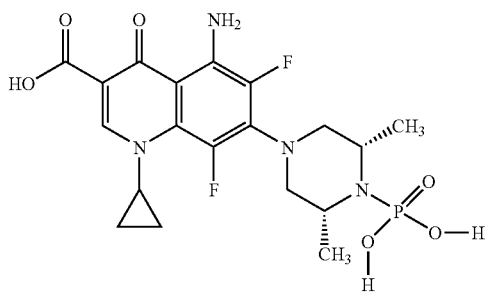

E1424

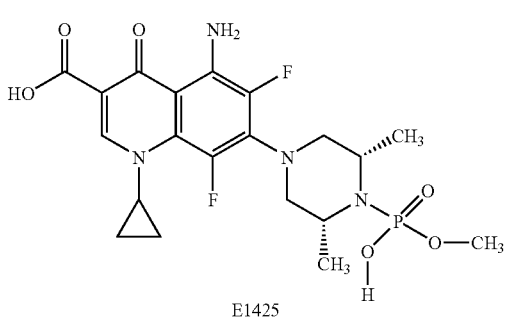

E1425

-continued
Sparfloxacin (Zagam ®)
Chemical Structure
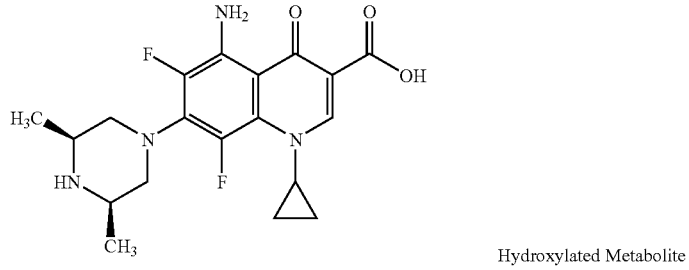
Hydroxylated Metabolite
| Compound | R1 | R2 | Chemical Name |
|---|---|---|---|
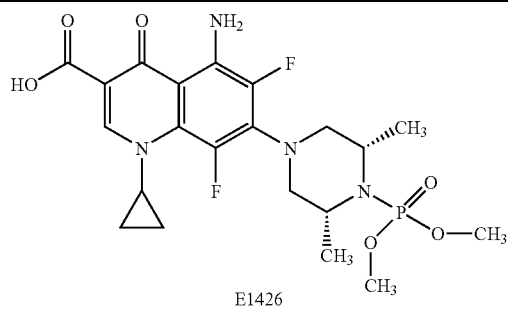
E1426
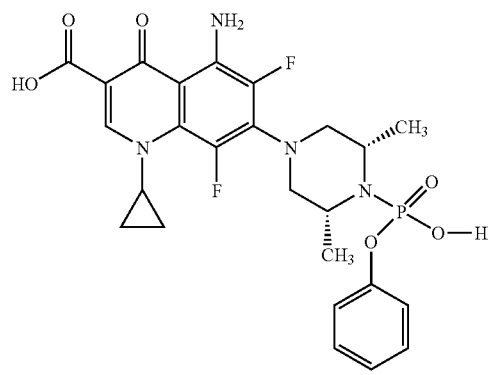
E1427
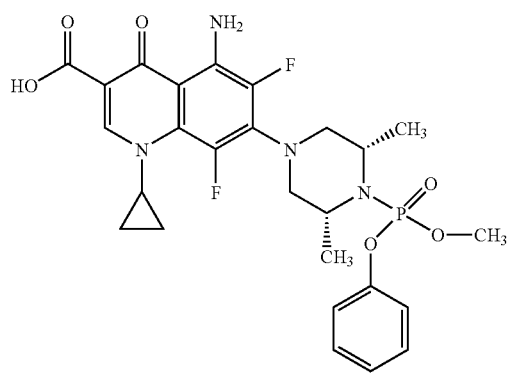
E1428

| Sumatriptan (Imitrex ®) | | | | | |
|---|---|---|---|---|---|
| Chemical Structure | | | Active Metabolite Structure | | |
| 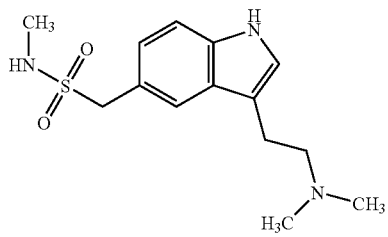 | | | 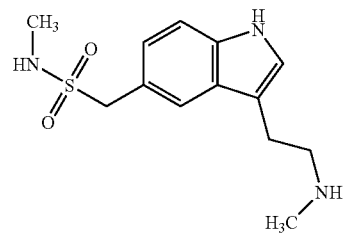 | | |
| Compound | R1 | R2 | Chemical Name | Estimate of LogP | pKa |
| E1026 | hydrogen | hydrogen | Methyl-[2-(5-methylsulfamoylmethyl-1H-indol-3-yl)-ethyl]-phosphoramidic acid | 0.78 | 2.78 |
| E1027 | hydrogen | methyl | Methyl-[2-(5-methylsulfamoylmethyl-1H-indol-3-yl)-ethyl]-phosphoramidic acid monomethyl ester | 0.84 | 4.88 |
| E1028 | methyl | methyl | Methyl-[2-(5-methylsulfamoylmethyl-1H-indol-3-yl)-ethyl]-phosphoramidic acid dimethyl ester | 0.89 | 4.13 |
| E1029 | phenyl | hydrogen | Methyl-[2-(5-methylsulfamoylmethyl-1H-indol-3-yl)-ethyl]-phosphoramidic acid monophenyl ester | 2.60 | 4.44 |
| E1030 | phenyl | methyl | Methyl-[2-(5-methylsulfamoylmethyl-1H-indol-3-yl)-ethyl]-phosphoramidic acid methyl ester phenyl ester | 2.66 | 3.69 |

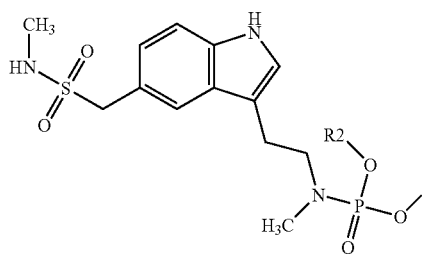

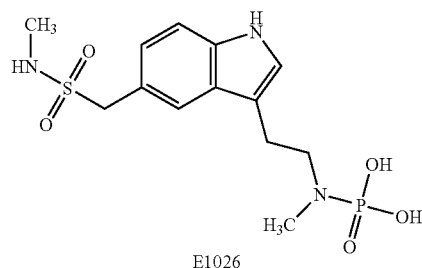

E1026

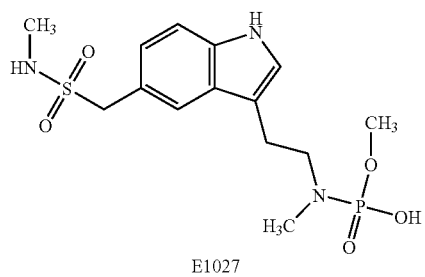

E1027

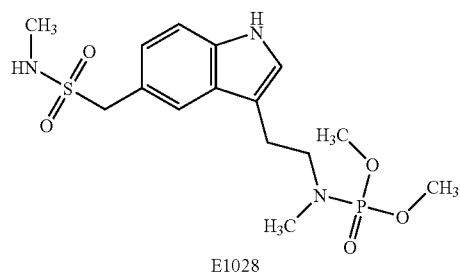

E1028

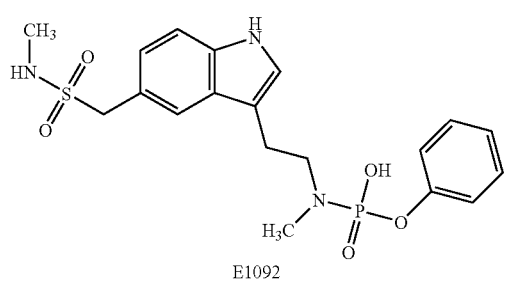

E1092

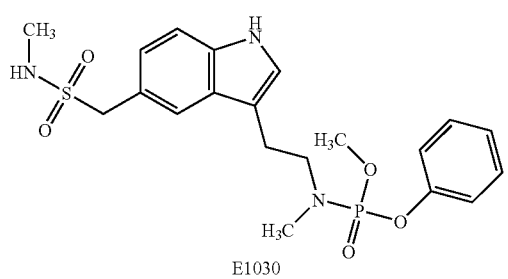

E1030

| Tamoxifen (Nolvadex ®) |

Chemical Structure 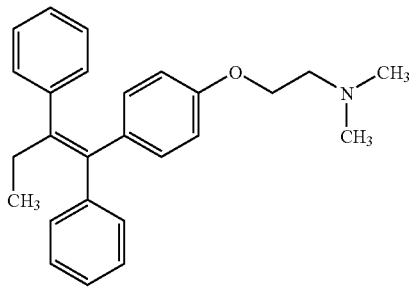 Active Metabolite Structure 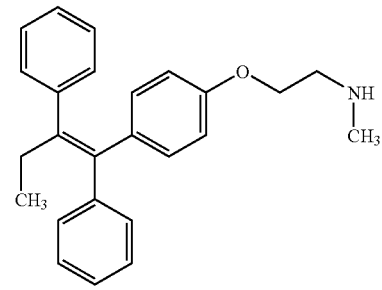

Hydroxylated Metabolite 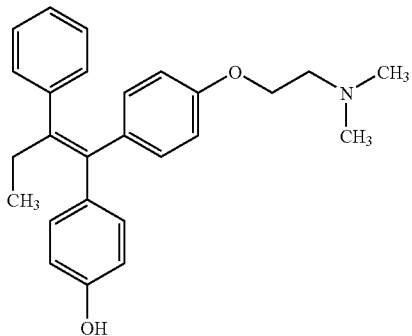

| Compound | R1 | R2 | Chemical Name | Estimated LogP | pKa |
|---|---|---|---|---|---|
| E1071 | hydrogen | hydrogen | {2-[4-(1,2-Diphenyl-but-1-enyl)-phenoxy]-ethyl}-methyl-phosphoramidic acid | 5.68 | 4.02 |
| E1072 | hydrogen | methyl | {2-[4-(1,2-Diphenyl-but-1-enyl)-phenoxy]-ethyl}-methyl-phosphoramidic acid monomethyl ester | 5.73 | 3.64 |
| E1073 | methyl | methyl | {2-[4-(1,2-Diphenyl-but-1-enyl)-phenoxy]-ethyl}-methyl-phosphoramidic acid dimethyl ester | 5.79 | 5.37 |
| E1074 | phenyl | hydrogen | {2-[4-(1,2-Diphenyl-but-1-enyl)-phenoxy]-ethyl}-methyl-phosphoramidic acid monophenyl ester | 7.50 | 3.20 |
| E1075 | phenyl | methyl | {2-[4-(1,2-Diphenyl-but-1-enyl)-phenoxy]-ethyl}-methyl-phosphoramidic acid methyl ester phenyl ester | 7.56 | 4.94 |

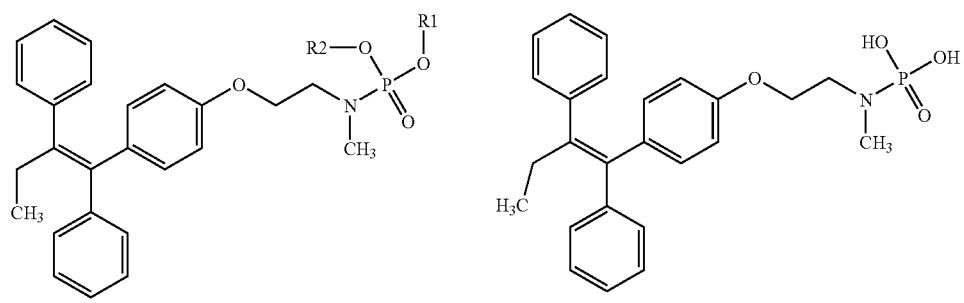

E1071

| Tamoxifen (Nolvadex ®) |
|---|
| Chemical Structure        Active Metabolite Structure 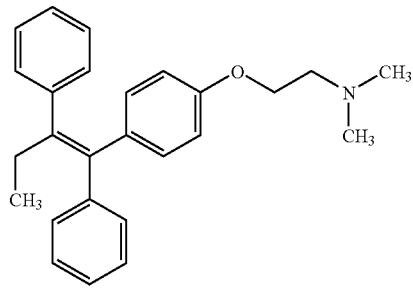 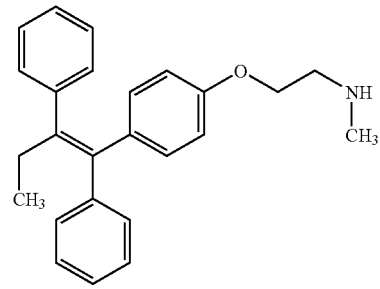 Hydroxylated Metabolite 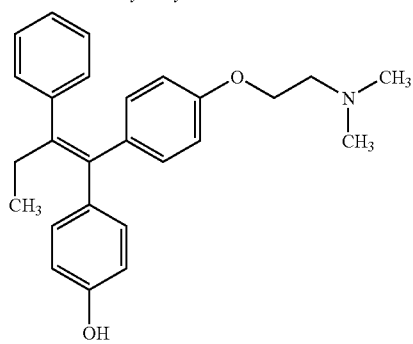 |
| Compound | R1 | R2 | Chemical Name | Estimated LogP | pKa |
|---|---|---|---|---|---|
E1072
E1073
E1074
E1075

| Temafloxacin (Omniflox ®) |
|---|
| Chemical Structure |

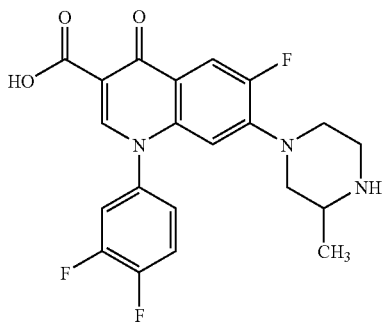

Hydroxylated Metabolite

| Compound | R1 | R2 | Chemical Name |
|---|---|---|---|
| E1419 | hydrogen | hydrogen | 1-(3,4-Difluoro-phenyl)-6-fluoro-7-(3-methyl-4-phosphono-piperazin-1-yl)-4-oxo-1,4-dihydro-quinoline-3-carboxylic acid |
| E1420 | hydrogen | methyl | 1-(3,4-Difluoro-phenyl)-6-fluoro-7-[4-(hydroxy-methoxy-phosphoryl)-3-methyl-piperazin-1-yl]-4-oxo-1,4-dihydro-quinoline-3-carboxylic acid |
| E1421 | methyl | methyl | 1-(3,4-Difluoro-phenyl)-7-[4-(dimethoxy-phosphoryl)-3-methyl-piperazin-1-yl]-6-fluoro-4-oxo-1,4-dihydro-quinoline-3-carboxylic acid |
| E1422 | phenyl | hydrogen | 1-(3,4-Difluoro-phenyl)-6-fluoro-7-[4-(hydroxy-phenoxy-phosphoryl)-3-methyl-piperazin-1-yl]-4-oxo-1,4-dihydro-quinoline-3-carboxylic acid |
| E1423 | phenyl | methyl | 1-(3,4-Difluoro-phenyl)-6-fluoro-7-[4-(methoxy-phenoxy-phosphoryl)-3-methyl-piperazin-1-yl]-4-oxo-1,4-dihydro-quinoline-3-carboxylic acid |

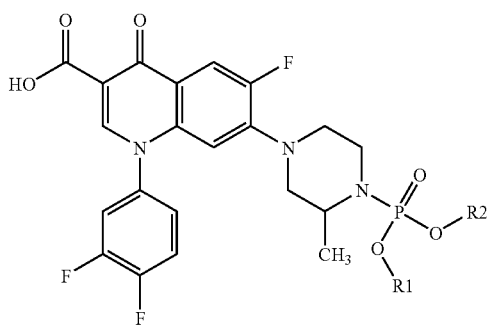

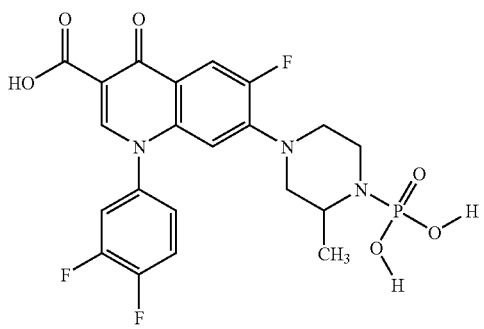

E1419

| | | | |
|---|---|---|---|
| Temafloxacin (Omniflox ®) | | | |
Chemical Structure
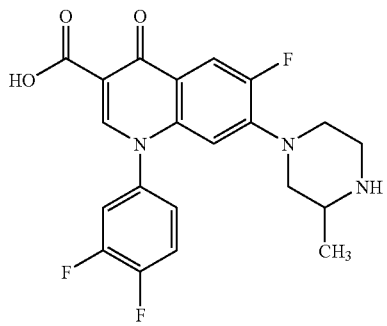
Hydroxylated Metabolite
| Compound | R1 | R2 | Chemical Name |
|---|---|---|---|
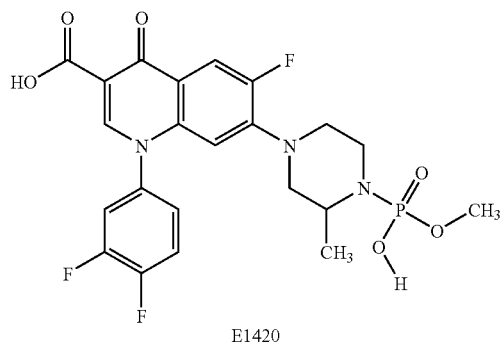
E1420
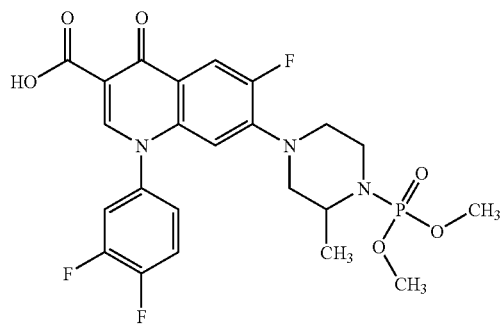
E1421
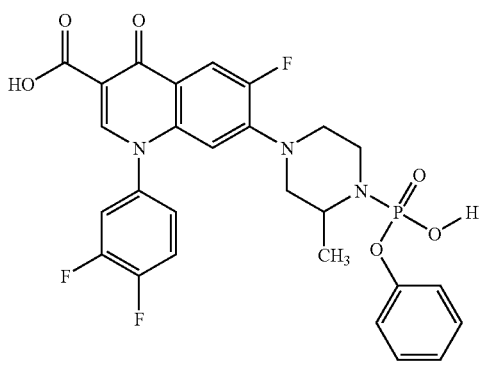
E1422

Temafloxacin (Omniflox ®)
Chemical Structure
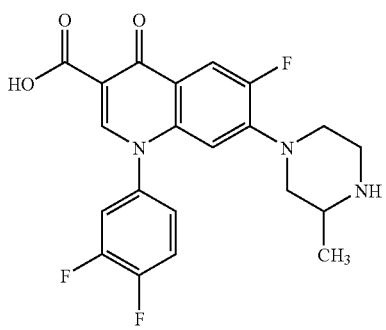
| Compound | R1 | R2 | Chemical Name |
|---|---|---|---|
Hydroxylated Metabolite
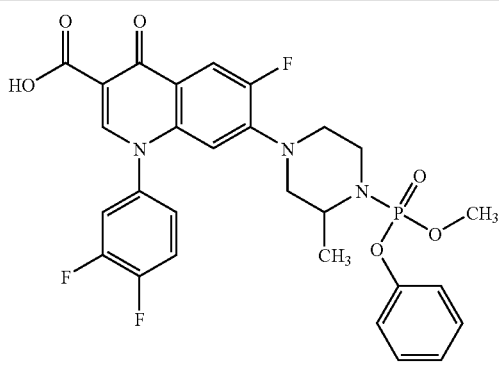
E1423
Thioridazine (Mellaril ®)
Chemical Structure 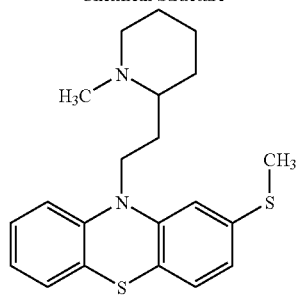  Active Metabolite Structure 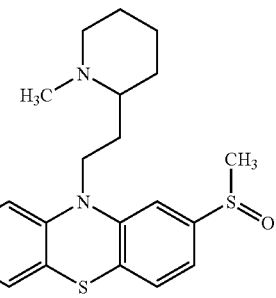
Hydroxylated Metabolite
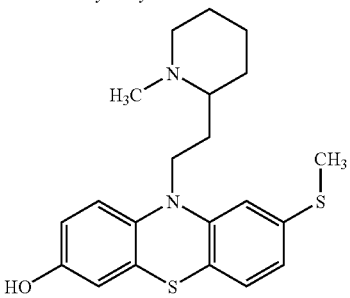
| Compound | R1 | R2 | Chemical Name | Estimated LogP | pKa |
|---|---|---|---|---|---|
| E1159 | hydrogen | hydrogen | {2-[2-(2-Methylsulfanyl-phenothiazin-10-yl)-ethyl]-piperidin-1-yl}-phosphonic acid | 5.82 | 2.81 |

Thioridazine (Mellaril ®)

Chemical Structure

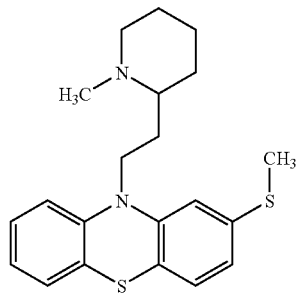

Active Metabolite Structure

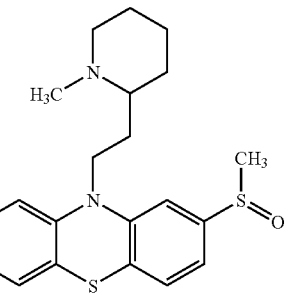

Hydroxylated Metabolite

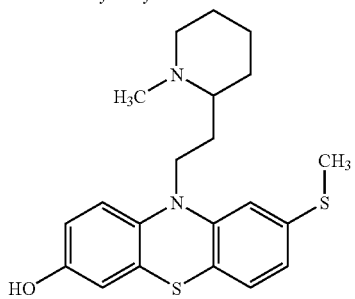

| Compound | R1 | R2 | Chemical Name | Estimated LogP | pKa |
|---|---|---|---|---|---|
| E1160 | hydrogen | methyl | {2-[2-(2-Methylsulfanyl-phenothiazin-10-yl)-ethyl]-piperidin-1-yl}-phosphonic acid monomethyl ester | 5.88 | 4.85 |
| E1161 | methyl | methyl | {2-[2-(2-Methylsulfanyl-phenothiazin-10-yl)-ethyl]-piperidin-1-yl}-phosphonic acid dimethyl ester | 5.94 | 3.87 |
| E1162 | phenyl | hydrogen | {2-[2-(2-Methylsulfanyl-phenothiazin-10-yl)-ethyl]-piperidin-1-yl}-phosphonic acid monophenyl ester | 7.65 | 4.38 |
| E1163 | phenyl | methyl | {2-[2-(2-Methylsulfanyl-phenothiazin-10-yl)-ethyl]-piperidin-1-yl}-phosphonic acid methyl ester phenyl ester | 7.70 | 4.02 |

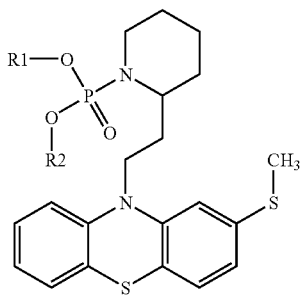

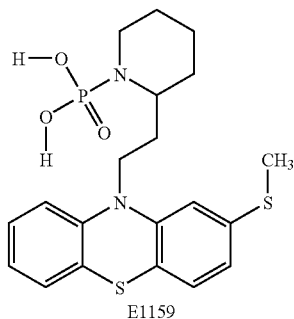

E1159

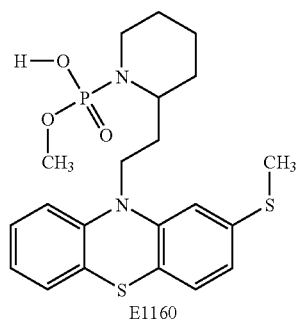

E1160

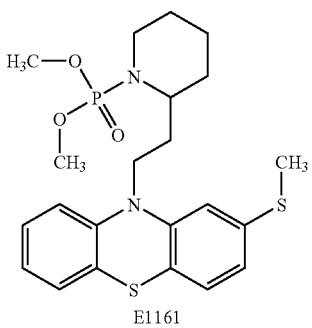

E1161

| | Thioridazine (Mellaril ®) | |
|---|---|---|
| Chemical Structure | Active Metabolite Structure | |
| 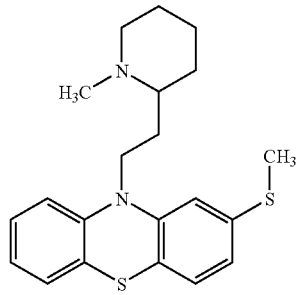 | 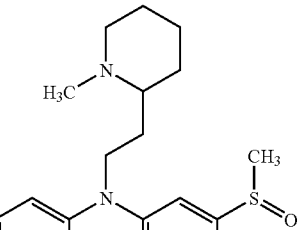 | |
| | Hydroxylated Metabolite | |
| | 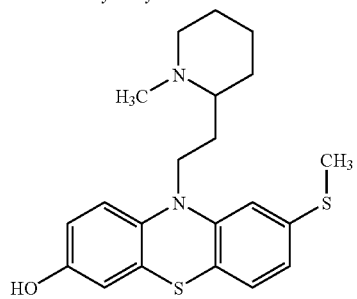 | |

| Compound | R1 | R2 | Chemical Name | Estimated LogP | pKa |
|---|---|---|---|---|---|
| 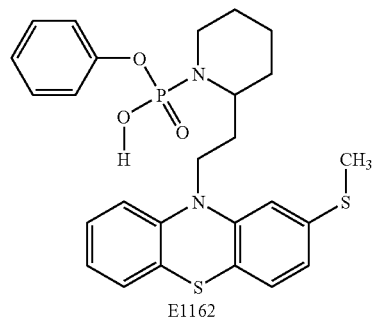 E1162 | | | | | |
| 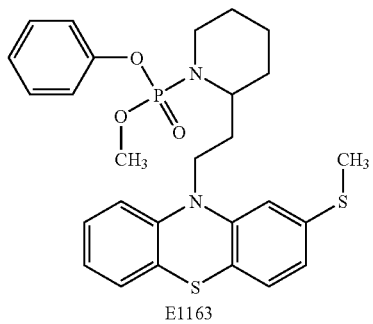 E1163 | | | | | |

| | Tramadol (Ultram ®) | |
|---|---|---|
| Chemical Structure | Active Metabolite Structure | Hydroxylated Metabolite |
| 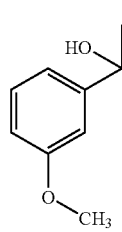 | 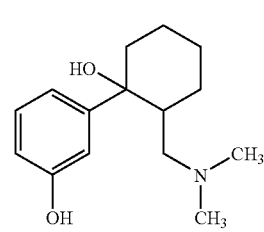 | 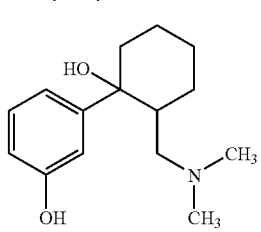 |

| Compound | R1 | R2 | Chemical Name |
|---|---|---|---|
| E1329 | hydrogen | hydrogen | [2-Hydroxy-2-(3-methoxy-phenyl)-cyclohexylmethyl]-methyl-phosphoramidic acid |

Tramadol (Ultram ®)

| Chemical Structure | Active Metabolite Structure | Hydroxylated Metabolite |
|---|---|---|
| 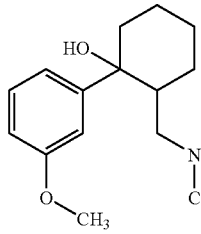 | 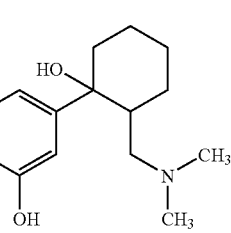 | 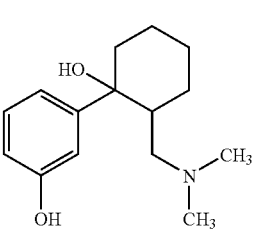 |

| Compound | R1 | R2 | Chemical Name |
|---|---|---|---|
| E1330 | hydrogen | methyl | [2-Hydroxy-2-(3-methoxy-phenyl)-cyclohexylmethyl]-methyl-phosphoramidic acid monomethyl ester |
| E1131 | methyl | methyl | [2-Hydroxy-2-(3-methoxy-phenyl)-cyclohexylmethyl]-methyl-phosphoramidic acid dimethyl ester |
| E1332 | phenyl | hydrogen | [2-Hydroxy-2-(3-methoxy-phenyl)-cyclohexylmethyl]-methyl-phosphoramidic acid monophenyl ester |
| E1333 | phenyl | methyl | [2-Hydroxy-2-(3-methoxy-phenyl)-cyclohexylmethyl]-methyl-phosphoramidic acid methyl ester phenyl ester |

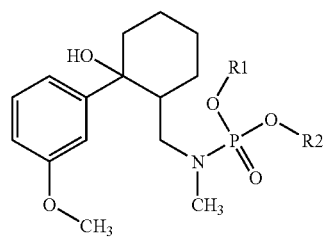

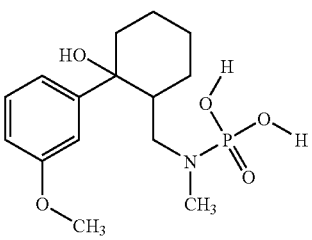
E1329

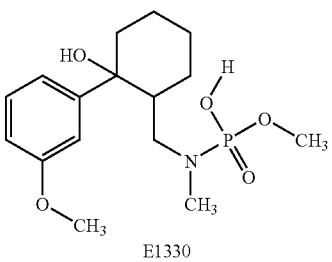
E1330

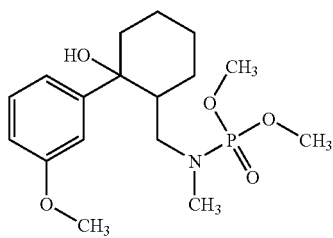
E1331

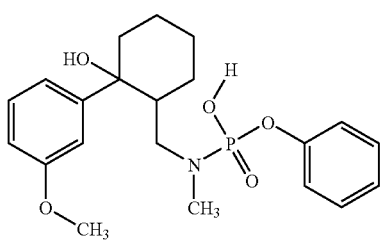
E1332

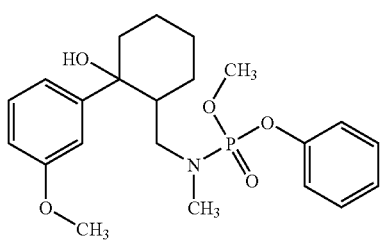
E1333

| Venlafaxine (Effexor ®) | | | | | |
|---|---|---|---|---|---|
| Chemical Structure | | | Active Metabolite Structure | | Hydroxylated Metabolite |

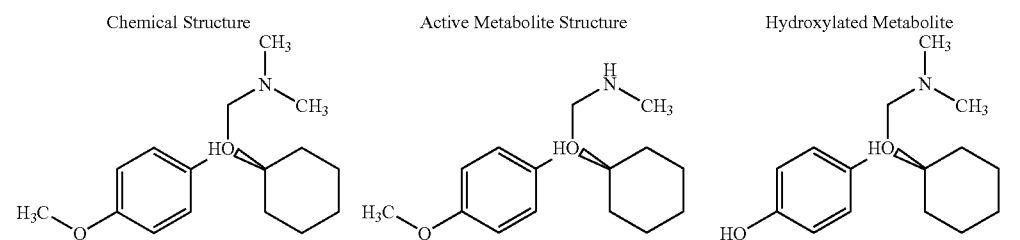

| Compound | R1 | R2 | Chemical Name | Estimated LogP | Estimated pKa |
|---|---|---|---|---|---|
| E1011 | hydrogen | hydrogen | [2-(1-Hydroxy-cyclohexyl)-2-(4-methoxy-phenyl)-eth-yl]-methyl-phosphoramidic acid | 2.88 | 3.22 |
| E1012 | hydrogen | methyl | [2-(1-Hydroxy-cyclohexyl)-2-(4-methoxy-phenyl)-eth-yl]-methyl-phosphoramidic acid monomethyl ester | 2.93 | 4.44 |
| E1013 | methyl | methyl | [3-Hydroxy-2-(4-methoxy-phenyl)-3-propyl-hexyl]-meth-yl-phosphoramidic acid dimethyl ester | 2.99 | 2.84 |
| E1014 | phenyl | hydrogen | [2-(1-Hydroxy-cyclohexyl)-2-(4-methoxy-phenyl)-eth-yl]-methyl-phosphoramidic acid monophenyl ester | 4.70 | 4.02 |
| E1015 | phenyl | methyl | [2-(1-Hydroxy-cyclohexyl)-2-(4-methoxy-phenyl)-eth-yl]-methyl-phosphoramidic acid methyl ester phenyl ester | 4.76 | 3.38 |

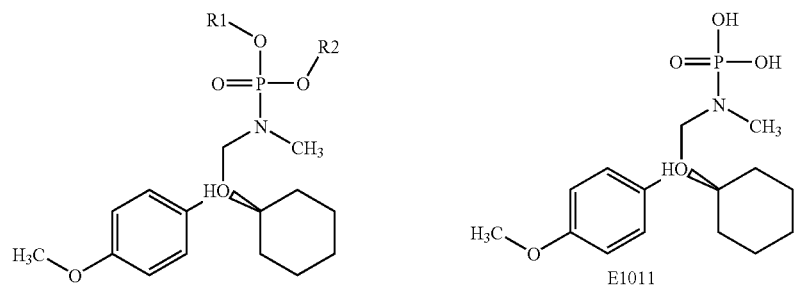

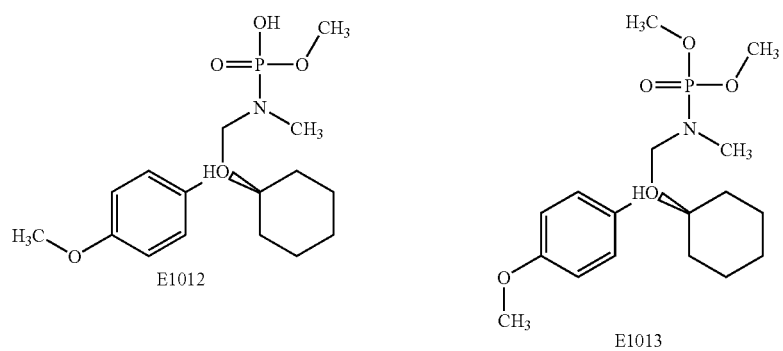

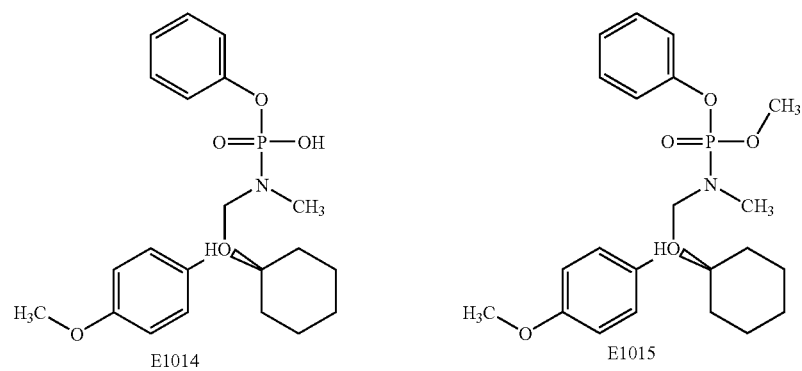

| Zimeldine (Zelmid ®) |
|---|

Chemical Structure      Active Metabolite Structure      Hydroxylated Metabolite

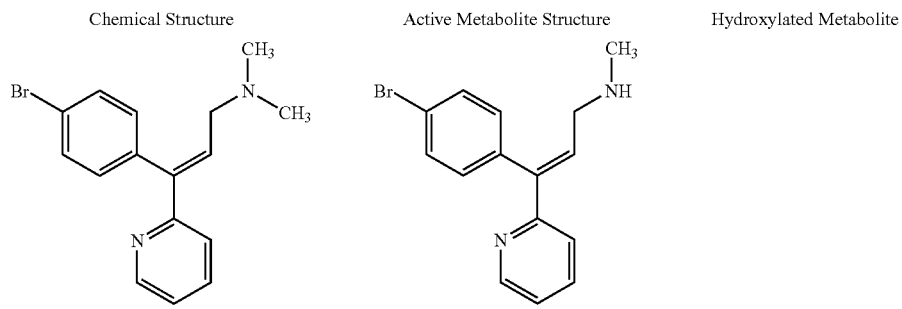

| Compound | R1 | R2 | Chemical Name |
|---|---|---|---|
| E1449 | hydrogen | hydrogen | [3-(4-Bromo-phenyl)-3-pyridin-3-yl-allyl]-methyl-phosphoramidic acid |
| E1450 | hydrogen | methyl | [3-(4-Bromo-phenyl)-3-pyridin-3-yl-allyl]-methyl-phosphoramidic acid monomethyl ester |
| E1451 | methyl | methyl | [3-(4-Bromo-phenyl)-3-pyridin-3-yl-allyl]-methyl-phosphoramidic acid dimethyl ester |
| E1452 | phenyl | hydrogen | [3-(4-Bromo-phenyl)-3-pyridin-3-yl-allyl]-methyl-phosphoramidic acid monophenyl ester |
| E1453 | phenyl | methyl | [3-(4-Bromo-phenyl)-3-pyridin-3-yl-allyl]-methyl-phosphoramidic acid methyl ester phenyl ester |

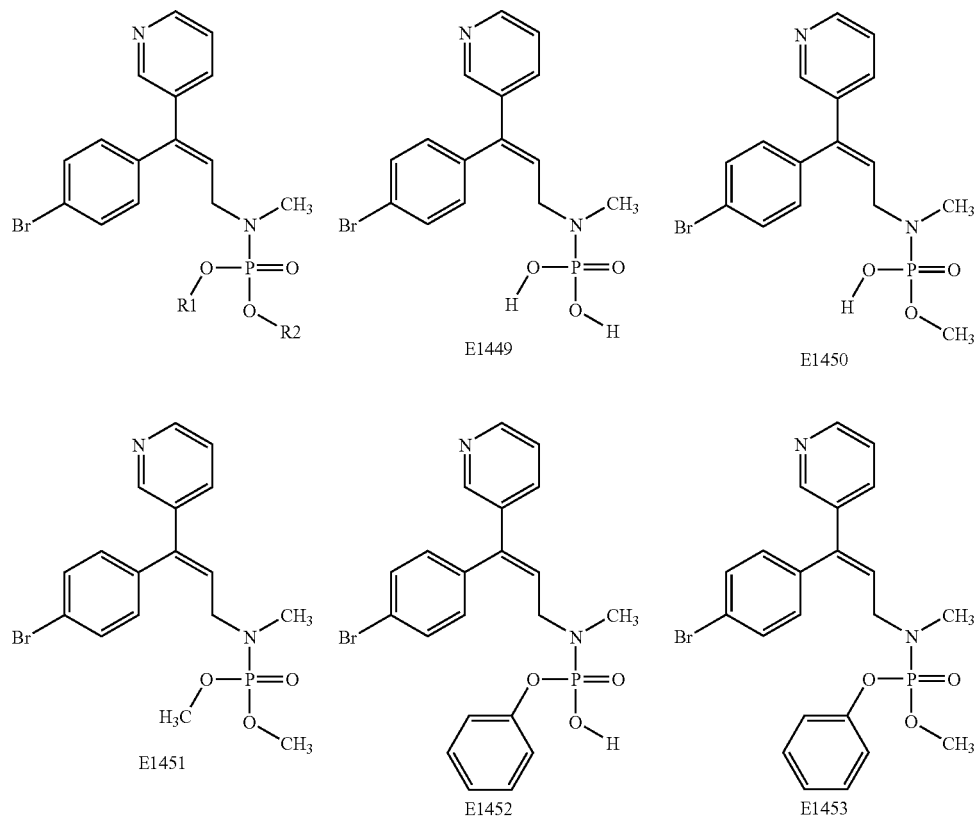

| Zolmitriptan (Zomig ®) |
|---|
| Chemical Structure 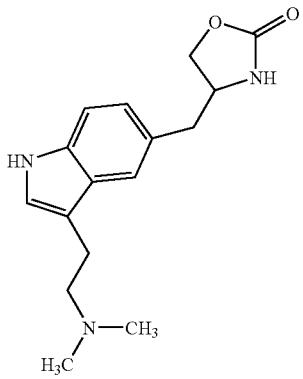 Active Metabolite Structure 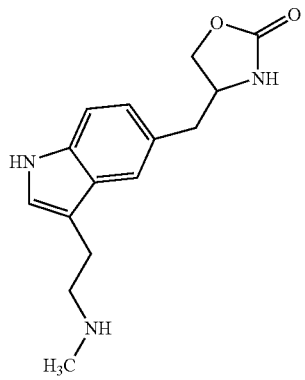 |

| Compound | R1 | R2 | Chemical Name | Estimated LogP | pKa |
|---|---|---|---|---|---|
| E1096 | hydrogen | hydrogen | Methyl-{2-[5-(2-oxo-oxazolidin-4-ylmethyl)-1H-indol-3-yl]-eth-yl}-phosphoramidic acid | 1.65 | 2.59 |
| E1097 | hydrogen | methyl | Methyl-{2-[5-(2-oxo-oxazolidin-4-ylmethyl)-1H-indol-3-yl]-eth-yl}-phosphoramidic acid monomethyl ester | 1.71 | 5.07 |
| E1098 | methyl | methyl | Methyl-{2-[5-(2-oxo-oxazolidin-4-ylmethyl)-1H-indol-3-yl]-eth-yl}-phosphoramidic acid dimethyl ester | 1.76 | 3.93 |
| E1099 | phenyl | hydrogen | Methyl-{2-[5-(2-oxo-oxazolidin-4-ylmethyl)-1H-indol-3-yl]-eth-yl}-phosphoramidic acid monophenyl ester | 3.47 | 4.63 |
| E1100 | phenyl | methyl | Methyl-{2-[5-(2-oxo-oxazolidin-4-ylmethyl)-1H-indol-3-yl]-eth-yl}-phosphoramidic acid methyl ester phenyl ester | 3.53 | 3.49 |

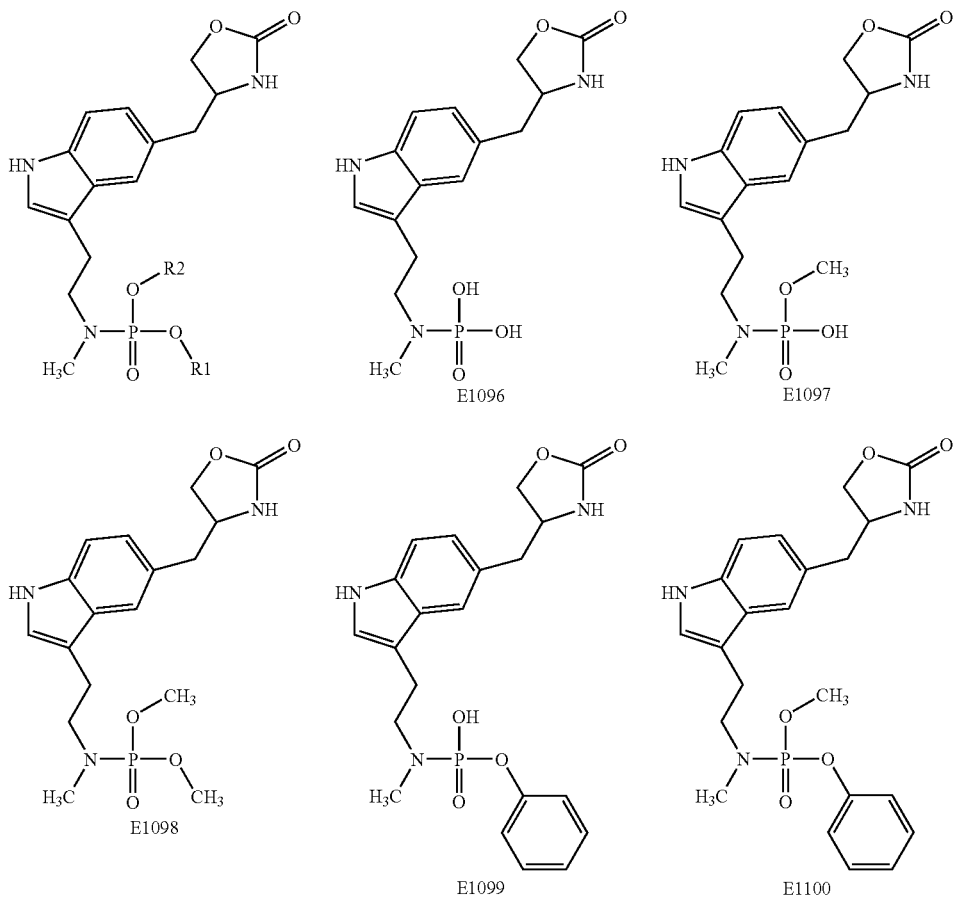

EXAMPLES OF THE INVENTION

Example 1

Synthesis of [3-(10,11-Dihydro-dibenzo[b,f]azepin-5-yl)-propyl]-methyl-phosphoramidic acid diethyl ester Compound Number E1413

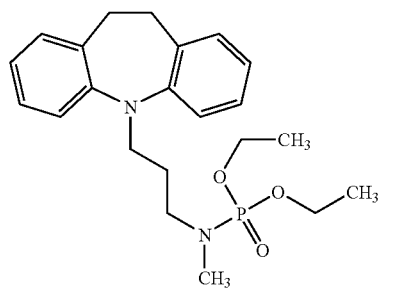

Desipramine hydrochloride (1 equivalent, 0.5 gram) was added drop wise to a stirred solution of potassium carbonate (2 equivalents, 0.456 gram) in dry DMF at 0° C. Diethylchlorophosphate (1.2 equivalents, 0.33 ml) which had been dissolved in dry DMF was added drop wise to this mixture and stirred for 12 hours at room temperature. The reaction mixture was quenched with water, extracted with ethyl acetate, the organic layer separated, washed with brine solution and dried over anhydrous sodium sulfate. The dried material was concentrated and purified by column chromatography to provide a pale yellow liquid (yield: 0.33 gram) and analyzed by HPLC (purity 93.1%). The FTIR, MS and $^1$H NMR spectra were consistent with the assigned with the empirical formula of $C_{22}H_{31}N_2O_3P$.

Example 2

Synthesis of [3-(10,11-Dihydro-dibenzo[b,f]azepin-5-yl)-propyl]-methyl-carbamic acid methyl ester Compound Number E1414

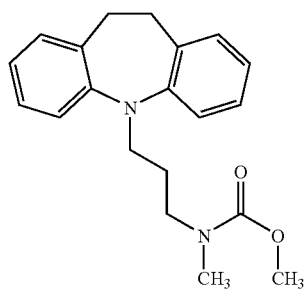

Desipramine hydrochloride (1 equivalent, 0.3 gram) was added drop wise to a stirred solution of potassium carbonate (2 equivalents, 0.27 gram) in dry DMF at 0° C. Methyl chloroform (1.2 equivalents, 0.1 ml) which had been dissolved in dry DMF was added drop wise to this mixture and stirred for 6 hours at room temperature. The reaction mixture was quenched with water, extracted with ethyl acetate, the organic layer separated, washed with brine solution and dried over anhydrous sodium sulfate. The dried material was concentrated and purified by column chromatography to provide a pale yellow liquid (yield: 0.18 gram) and analyzed by HPLC (purity 97.7%). The FTIR, MS and $^1$H NMR spectra were consistent with the assigned with the empirical formula of $C_{20}H_{24}N_2O_2$.

Example 3

Synthesis of [3-(10,11-Dihydro-dibenzo[b,f]azepin-5-yl)-propyl]-methyl-carbamic acid propyl ester Compound Number E1415

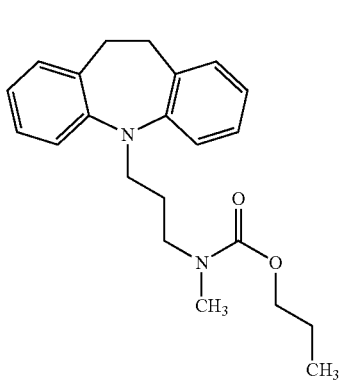

Desipramine hydrochloride (1 equivalent, 0.2 gram) was added drop wise to a stirred solution of potassium carbonate (5 equivalents, 0.45 gram) in dry DMF at 0° C. Propyl chloroform (1.5 equivalents, 0.1 ml) which had been dissolved in dry DMF was added drop wise to this mixture and stirred for 6 hours at room temperature. The reaction mixture was quenched with water, extracted with ethyl acetate, the organic layer separated, washed with brine solution and dried over anhydrous sodium sulfate. The dried material was concentrated and purified by column chromatography to provide a yellow liquid (yield: 0.12 gram) and by HPLC (purity 95.7%). The FTIR, MS and $^1$H NMR spectra were consistent with the assigned structure with the empirical formula of $C_{22}H_{28}N_2O_2$.

Example 4

Synthesis of [3-(10,11-Dihydro-dibenzo[b,f]azepin-5-yl)-propyl]-methyl-carbamic acid isobutyl ester Compound Number E1416

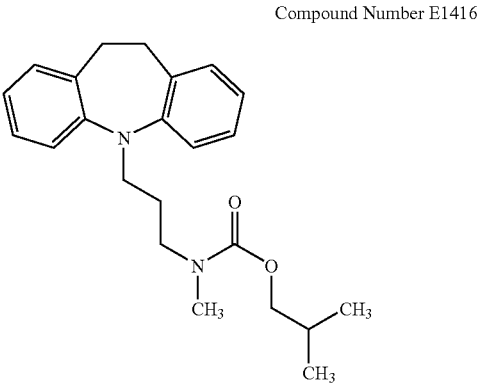

Desipramine hydrochloride (1 equivalent, 0.3 gram) was added drop wise to a stirred solution of potassium carbonate (5 equivalents, 0.68 gram) in dry DMF at 0° C. Isobutyl chloroform (1.5 equivalents, 0.18 ml) which had been dissolved in dry DMF was added drop wise to this mixture and stirred for 6 hours at room temperature. The reaction mixture was quenched with water, extracted with ethyl acetate, the organic layer separated, washed with brine solution and dried over anhydrous sodium sulfate. The dried material was concentrated and purified by column chromatography to provide a pale yellow liquid (yield: 0.18 gram) and analyzed by HPLC (purity 96.4%) The FTIR, MS and $^1$H NMR spectra were consistent with the assigned structure with the empirical formula of $C_{22}H_{28}N_2O_2$.

Example 5

Synthesis of [3-(10,11-Dihydro-dibenzo[b,f]azepin-5-yl)-propyl]-methyl-carbamic acid octyl ester Compound Number E1417

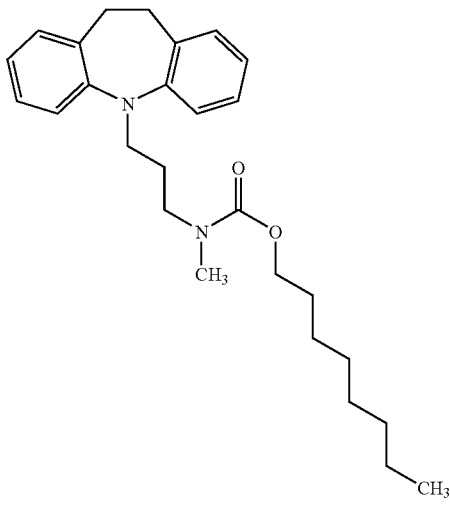

Desipramine hydrochloride (1 equivalent, 0.3 gram) was added drop wise to a stirred solution of potassium carbonate (2.5 equivalents, 0.34 gram) in dry DMF at 0° C. Octyl chloroform (1.5 equivalents, 0.429 grams) which had been dissolved in dry DMF was added drop wise to this mixture and stirred for 12 hours at room temperature. The reaction mixture was quenched with water, extracted with ethyl acetate, the organic layer separated, washed with brine solution and dried over anhydrous sodium sulfate. The dried material was concentrated and purified by column chromatography to provide a pale yellow liquid (yield: 0.12 gram) and analyzed by HPLC (purity 95.3%) The FTIR, MS and $^1$H NMR spectra were consistent with the assigned structure with the empirical formula of $C_{27}H_{38}N_2O_2$.

In the following tables, including Tables 1 and 2 and the tables given in the discussion of Examples 6 through 11, RIC-02 corresponds to the compound of Example 1 (Compound Number E1413), RIC-5a corresponds to the compound of Example 2 (Compound Number E1414), RIC-5b corresponds to the compound of Example 3 (Compound Number E 1415), RIC-5c corresponds to the compound of Example 4 (E1416), RIC-5d corresponds to the compound of Example 5 (E1417).

Example 6

Stability Testing of Prodrugs in Human Plasma

Pooled human plasma was obtained from Bioreclamation (East Meadow, N.Y.) by collection into sodium EDTA as the anticoagulant, and was stored at ca −20° C. prior to use. Prior to use, the plasma defrosted and was spun at ca. 3000 rpm for 5 minutes to remove any precipitate. The pH of the plasma was adjusted to pH 7.4 by careful addition of $NaH_2PO_4$ buffer.

Plasma stability was assessed by incubation of 10 μM of each compound prepared in Examples 1-5 with human plasma, in duplicate, at ca. 37° C. with shaking. Each compound prepared in Examples 1-5 was also incubated at 10 μM in PBS as a control for compound heat stability. Aliquots were removed at 0, 0.5, 1 and 2 hours and stored at −20° C. until analysis.

For analysis, plasma samples were extracted in 1 part acetonitrile and isolation of the supernatant. Analysis of each compound prepared in Examples 1-5 in plasma extracts was conducted by an LC-MS method at each time interval and quantification was achieved by comparison of the response due to the sample to that of a three point standard curve. Appearance of the parent drug the hydroxymetabolites were also monitored at each time interval. The % degradation following incubation at each time point was calculated by comparison of the parent concentration to that at 0 minutes.

The results of the stability testing in human plasma are shown in the following table:

TABLE 1

Stability Testing of Prodrugs in Human Plasma

| Incubation Time (min) | Loss of parent compound in human plasma (%) | | | | |
|---|---|---|---|---|---|
| | RIC-02 | RIC-5a | RIC-5b | RIC-5c | RIC-5d |
| 0 | 0.00 | 0.00 | 0.00 | 0.00 | 0.00 |
| 30 | −.43 | 5.47 | 7.15 | 5.11 | −32.74 |
| 60 | 9.94 | 15.80 | 6.85 | −1.48 | −1.44 |
| 120 | 7.93 | 26.22 | 21.06 | 25.82 | 49.54 |

Example 7

Stability Testing of Prodrugs in Rat Plasma (Elevated Esterase Activity)

Sprague-Dawley rat plasma was obtained by collection into sodium EDTA as the anticoagulant, and was stored at ca −20° C. prior to use. Prior to use, the plasma defrosted and was spun at ca. 3000 rpm for 5 minutes to remove any precipitate. The pH of the plasma was adjusted to pH 7.4 by careful addition of $NaH_2PO_4$ buffer.

Plasma stability was assessed by incubation of 10 μM of each compound prepared in Examples 1-5 with rat plasma, in duplicate, at ca. 37° C. with shaking. Each compound prepared in Examples 1-5 was also incubated at 10 μM in PBS as a control for compound heat stability. Aliquots were removed at 0, 0.5, 1 and 2 hours and stored at −20° C. until analysis.

For analysis, plasma samples were extracted in 1 part acetonitrile and isolation of the supernatant. Analysis of each compound prepared in Examples 1-5 in plasma extracts was conducted by an LC-MS method at each time interval and quantification was achieved by comparison of the response due to the sample to that of a three point standard curve.

Appearance of the parent drug and the hydroxymetabolites were also monitored at each time interval. The % degradation following incubation at each time point was calculated by comparison of the parent concentration to that at 0 minutes.

The results of the stability testing in rat plasma are shown in the following table:

TABLE 2

Stability Testing of Prodrugs in Rat Plasma

| Incubation | Loss of parent compound in rat plasma (%) | | | | |
|---|---|---|---|---|---|
| Time (min) | RIC-02 | RIC-5a | RIC-5b | RIC-5c | RIC-5d |
| 0 | 0.00 | 0.00 | 0.00 | 0.00 | 0.00 |
| 30 | 4.67 | 8.81 | 7.17 | −14.69 | −8.16 |
| 60 | 11.01 | 23.43 | 8.34 | −2.88 | 41.70 |
| 120 | 9.02 | 45.85 | 23.42 | 33.40 | 73.48 |

Example 8

Stability Testing of Prodrugs in the Stomach and Intestine

The stability of each compound prepared in Examples 1-5 was assessed in both simulated gastric fluids and intestinal fluids alone and intestinal fluids spiked with alkaline phosphatase to approximate the enzymatic activity of the intestinal wall.

The stability of each compound prepared in Examples 1-5 was assessed in duplicate by incubation of 10 μM of each compound at ca. 37° C. and shaking with each of the following: simulated gastric fluids (saline pH approximately 1, plus pepsin); simulated intestinal fluids (phosphate pH 6 with pepsin); and alkaline phosphatase enhanced simulated intestinal fluids (phosphate pH 6 with pepsin and ± alkaline phosphatase). Aliquots were removed at 0, 0.5, 1 and 2 hours, extracted with one volume of organic solvent and stored at −20° C. until analysis.

Analysis of each compound prepared in Examples XXXX in gastric fluid and intestinal fluid extracts was conducted by an LC-MS method at each time interval and quantification was achieved by comparison of the response due to the sample to that of a three point standard curve. Appearance of the parent drug and the hydroxymetabolites were also monitored at each time interval. The % degradation following incubation at each time point was calculated by comparison of the parent concentration to that at 0 minutes.

The results of the stability testing in simulated gastric fluids are shown in the following table:

| Incubation | Loss of parent compound in simulated gastric fluid (%) | | | | |
|---|---|---|---|---|---|
| Time (min) | RIC-02 | RIC-5a | RIC-5b | RIC-5c | RIC-5d |
| 0 | 0.00 | 0.00 | 0.00 | 0.00 | 0.00 |
| 30 | 49.94 | 13.93 | 58.72 | 70.64 | 13.84 |
| 60 | 74.67 | 31.78 | 26.67 | 82.77 | |
| 120 | 93.12 | 81.43 | 94.37 | 98.11 | |

The results of the stability testing in simulated intestinal fluids are shown in the following table:

| Incubation | Loss of parent compound in simulated intestinal fluid (%) | | | | |
|---|---|---|---|---|---|
| Time (min) | RIC-02 | RIC-5a | RIC-5b | RIC-5c | RIC-5d |
| 0 | 0.00 | 0.00 | 0.00 | 0.00 | 0.00 |
| 30 | 11.65 | 16.75 | 6.73 | 1.05 | 7.73 |
| 60 | 7.83 | 22.88 | 13.57 | 12.68 | −8.72 |
| 120 | 9.29 | 35.18 | 25.61 | 21.78 | 4.23 |

No further loss of RIC-02 in simulated intestinal fluids enhanced with alkaline phosphatase was observed up to 120 minute incubation.

Example 9

Metabolic Stability Testing of Prodrugs—Microsomal Incubations

The metabolic stability of each compound prepared in Examples 1-5 was assessed in microsomal preparations obtained from BD Gentest (Woburn, Mass.).

The metabolic stability of each compound prepared in Examples 1-5 was assessed in duplicate by incubation of 10 μM compound with 0.5 mg/mL microsomal protein, 1 mM in 0.1 M phosphate buffer, pH 7.4 in the presence and absence of a CYP3A4 inhibitor (ketoconazole). The reaction mixture was pre-incubated, in the absence of the microsomes, at ca. 37° C. for 5 minutes, followed by initiation of the incubation by the addition of microsomal protein and maintained at ca. 37° C. for a further 0, 30 and 60 minutes. After the appropriate incubation time, the mixtures were quenched by the addition of one volume of acetonitrile and the supernatant was isolated by centrifugation. Positive control incubations (7-ethoxycoumarin) were performed in the same manner as the compounds from Examples 1-5 and quenched after 0 and 30 minutes. In addition, negative control incubations were performed for 60 minutes in the absence of NADPH to assess chemical stability.

Analysis of supernatants from each time interval was conducted for each compound prepared in Examples 1-5 by LC-MS analysis. Quantification of the disappearance on the parent drug was achieved by comparison of the sample response to that of a suitable standard curve constructed in 0.1 M phosphate buffer, pH 7.4. The standard curve ranged between ≦1% up to ≧100% of the dosing concentration.

The % turnover following 60 minutes of incubation was calculated by comparison of the parent concentration to that at 0 minutes. The % degradation was calculated in the same manner from the negative control incubations. Appearance of the parent drug and the hydroxymetabolites were also monitored at each time interval.

The results of the metabolic testing in microsomes without inhibitor are shown in the following table:

| Incubation | Loss of parent compound with no ketoconazole (%) | | | | |
|---|---|---|---|---|---|
| Time (min) | RIC-02 | RIC-5a | RIC-5b | RIC-5c | RIC-5d |
| 30 | 76.17 | 70.94 | 64.76 | 54.01 | 59.12 |
| 60 | 91.40 | 87.25 | 82.29 | 76.36 | 74.17 |

The results of the metabolic testing in microsomes with ketoconazole inhibitor are shown in the following table:

| Incubation | Loss of parent compound with ketoconazole (%) | | | | |
|---|---|---|---|---|---|
| Time (min) | RIC-02 | RIC-5a | RIC-5b | RIC-5c | RIC-5d |
| 30 | −17.26 | 27.65 | 31.69 | 6.36 | 15.18 |
| 60 | 11.04 | 62.37 | 50.21 | 19.49 | 55.88 |

Example 10

Metabolic Stability of the Prodrugs—CYP3A4 and 2D6 Incubations

The metabolic stability of each compound prepared in Examples 1-5 was assessed in the presence of CYP2D6 and CYP3A4 obtained from BD Gentest (Woburn, Mass.).

The metabolic stability of each compound prepared in Examples 1-5 was assessed in duplicate by incubation of 10 μm compound with recombinant human CYP2D6 and 3A4 using similar conditions to those in Example 9. Samples were removed for analysis at 0, 30 and 60 minutes and extracted with one volume of organic solvent. Appropriate controls were included. Quantification of the disappearance of the prodrug was conducted LC-MS. Appearance of metabolites was also monitored.

The results of the metabolic testing in the presence of CYP3A4 isozyme are shown in the following table:

| Incubation | Loss of parent compound with CYP3A4 isozyme (%) | | | | |
|---|---|---|---|---|---|
| Time (min) | RIC-02 | RIC-5a | RIC-5b | RIC-5c | RIC-5d |
| 0 | 0.00 | 0.00 | 0.00 | 0.00 | 0.00 |
| 30 | 97.05 | 91.32 | 92.32 | 72.07 | 33.66 |
| 60 | 98.62 | 97.96 | 95.20 | 90.69 | 60.64 |

The results of the metabolic testing in the presence of CYP2D6 isozyme are shown in the following table:

| Incubation | Loss of parent compound with CYP2D6 isozyme (%) | | | | |
|---|---|---|---|---|---|
| Time (min) | RIC-02 | RIC-5a | RIC-5b | RIC-5c | RIC-5d |
| 0 | 0.00 | 0.00 | 0.00 | 0.00 | 0.00 |
| 30 | 13.19 | 73.91 | 19.21 | 43.71 | 18.68 |
| 60 | 37.11 | 83.13 | 28.01 | 70.07 | |

Example 11

Metabolic Stability Testing—Hepatocyte Incubations

The metabolic stability of each compound prepared in Examples 1-5 was assessed in human hepatocytes obtained from In Vitro Technologies (Baltimore, Md.).

The metabolic stability of each compound prepared in Examples 1-5 was assessed in duplicate by incubation of 10 μM compound with human hepatocytes after thawing of cryopreserved suspensions. The hepatocytes were maintained in Modified Williams' E medium (HMM, Clonetics, MD) supplemented with 0.1 μM dexamethasone, 0.1 μM insulin and 0.05 % gentamicin immediately after thawing.

Each compound prepared in Examples 1-5 was tested by incubation in duplicate with the hepatocyte suspensions (1.0× $10^6$ viable cells/mL HHM media) and incubated for 0, 1, 2 and 4 hours at 37° C. at 5% $CO_2$. Incubations were terminated by the addition of two volumes of ice-cold methanol, cell debris was removed by centrifugation and the supernatant was stored at approximately −70° C. prior to analysis.

Negative and positive control incubations were performed in duplicate under the same conditions as described for the prodrugs. Negative control incubations: An incubation of each compound prepared in Examples 1-5 in Modified Williams' E media (HHM media), in the absence of hepatocytes was performed alongside the hepatocyte incubations. Positive control incubations: Incubations with a positive control (7-ethoxycoumarin; 100 μM) was performed with hepatocytes from each species for 1 hour alongside the prodrug incubations. Analysis of metabolic turnover was performed by HPLC. Quantification of the parent compound was achieved by comparison of the sample response to that of a suitable standard curve. The standard curve ranged between $\leq$1% up to $\geq$100% of the dosing concentration. The % turnover following 1, 2 and 4 hours of incubation was calculated by comparison of the parent concentration to that at 0 minutes.

The present invention has been described in specific detail and with particular reference to its preferred embodiments; however, it will be obvious to those having skill in the art that modifications and changes can be made thereto without departing from the spirit and scope of the invention.

I claim:

1. A pharmaceutical composition comprising a compound having the formula

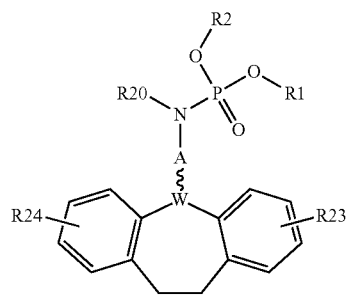

or

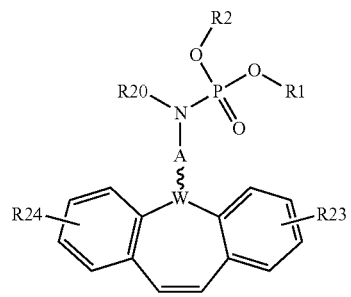

where $R_1$ and $R_2$ are independently hydrogen, alkyl having from 1 to about 7 carbon atoms, aryl, aralkyl, or cycloalkyl having from 3 to about 6 carbon atoms, A is a lower alkyl, lower heteroalkyl or cycloalkyl, $R_{20}$ is hydrogen, phenyl or lower alkyl, W is carbon or nitrogen, $R_{23}$ and $R_{24}$ are independently hydrogen, halogen, alkyl or alkoxy, and pharmaceutically acceptable salts thereof in combination with a pharmaceutically acceptable excipient, diluent or carrier suitable for delayed release oral administration.

2. A pharmaceutical composition comprising a compound having the formula

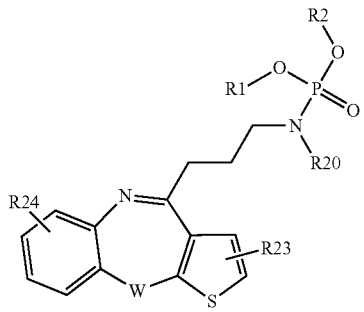

where $R_1$ and $R_2$ are independently hydrogen, alkyl having from 1 to about 7 carbon atoms, aryl, aralkyl, or cycloalkyl having from 3 to about 6 carbon atoms, $R_{20}$ is hydrogen, phenyl or lower alkyl, W is carbon or nitrogen, $R_{23}$ and $R_{24}$ are independently hydrogen, halogen, alkyl or alkoxy, and pharmaceutically acceptable salts thereof in combination with a pharmaceutically acceptable excipient, diluent or carrier suitable for delayed release oral administration.

3. A pharmaceutical composition comprising a compound having the formula

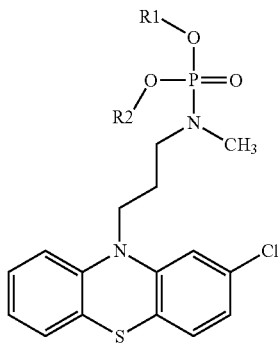

where $R_1$ and $R_2$ are independently hydrogen, alkyl having from 1 to about 7 carbon atoms, aryl, aralkyl, or cycloalkyl having from 3 to about 6 carbon atoms, and pharmaceutically acceptable salts thereof in combination with a pharmaceutically acceptable excipient, diluent or carrier suitable for delayed release oral administration.

4. A pharmaceutical composition comprising a compound having the formula

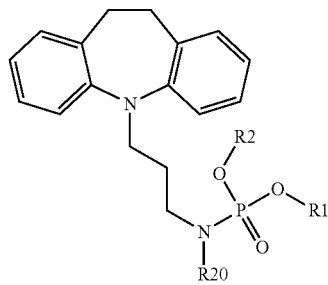

where $R_1$ and $R_2$ are independently hydrogen, alkyl having from 1 to about 7 carbon atoms, aryl, aralkyl, or cycloalkyl having from 3 to about 6 carbon atoms, $R_{20}$ is hydrogen, phenyl or lower alkyl and pharmaceutically acceptable salts thereof in combination with a pharmaceutically acceptable excipient, diluent or carrier suitable for delayed release oral administration.

5. The pharmaceutical composition of claim 4 where $R_1$ and $R_2$ are independently hydrogen and alkyl having from 1 to about 2 carbon atoms and $R_{20}$ is hydrogen or lower alkyl.

6. The pharmaceutical composition of claim 5 where $R_{20}$ is hydrogen or methyl.

7. A pharmaceutical composition comprising a compound having the formula

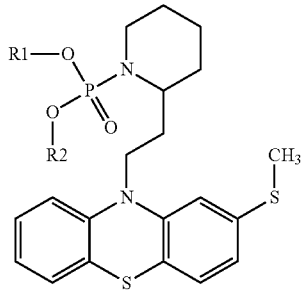

where $R_1$ and $R_2$ are independently hydrogen, alkyl having from 1 to about 7 carbon atoms, aryl, aralky, or cycloalkyl having from 3 to about 6 carbon atoms, and pharmaceutically acceptable salts thereof in combination with a pharmaceutically acceptable excipient, diluent or carrier suitable for delayed release oral administration.

* * * * *